US012329975B2

(12) United States Patent
Mangual-Soto et al.

(10) Patent No.: US 12,329,975 B2
(45) Date of Patent: Jun. 17, 2025

(54) SYSTEMS AND METHODS FOR IMPROVED HIS BUNDLE AND BACKUP PACING TIMING

(71) Applicant: Pacesetter, Inc., Sylmar, CA (US)

(72) Inventors: Jan O. Mangual-Soto, Rho (IT); Yun Qiao, Valencia, CA (US); Wenwen Li, San Jose, CA (US); Xiaoyi Min, Santa Rosa, CA (US); Luke C. McSpadden, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 654 days.

(21) Appl. No.: 16/871,166

(22) Filed: May 11, 2020

(65) Prior Publication Data

US 2021/0016097 A1 Jan. 21, 2021

Related U.S. Application Data

(60) Provisional application No. 62/875,863, filed on Jul. 18, 2019, provisional application No. 62/948,047, filed on Dec. 13, 2019.

(51) Int. Cl.
*A61N 1/37* (2006.01)
*A61N 1/36* (2006.01)
*A61N 1/365* (2006.01)

(52) U.S. Cl.
CPC ....... *A61N 1/3712* (2013.01); *A61N 1/36167* (2013.01); *A61N 1/36592* (2013.01)

(58) Field of Classification Search
CPC .... A61N 1/36167; A61N 1/362; A61N 1/371; A61N 1/3712
See application file for complete search history.

(56) References Cited

U.S. PATENT DOCUMENTS

| 7,006,869 B2 | 2/2006 | Bradley |
| 7,920,920 B1 | 4/2011 | Williamson |
| 2003/0208241 A1* | 11/2003 | Bradley ............... A61N 1/3712 607/27 |
| 2011/0264158 A1 | 10/2011 | Dong et al. |
| 2019/0126050 A1* | 5/2019 | Shuros .................. A61N 1/362 |

OTHER PUBLICATIONS

Day et al. "S-LBCT03 Late-Breaking Clinical Trials Session III: Late Breaking Science" Heart Rhythm 2019 (4 pages).
Cantu et al. "Validation of Criteria for Selective HIS Bundle and Para-Hisian Permanent Pacing" The Authors, Journal Compilation; 2006 (9 pages).

* cited by examiner

Primary Examiner — Allen Porter
(74) Attorney, Agent, or Firm — Dean D. Small; The Small Patent Law Group, LLC.

(57) ABSTRACT

Methods and systems for dynamically modifying pacing timing and backup pacing delivery in cardiac stimulation devices include applying pacing impulses, measuring corresponding responses, and, based on such responses, automatically modifying timing or operational settings of the stimulation device to improve pacing functionality. Among other things, the approaches described herein reduce unnecessary backup pacing impulses in HIS bundle pacing applications, facilitate fusion in bundle branch block applications, and automatically enable or disable backup pacing in response to achieving QRS complex correction.

16 Claims, 42 Drawing Sheets

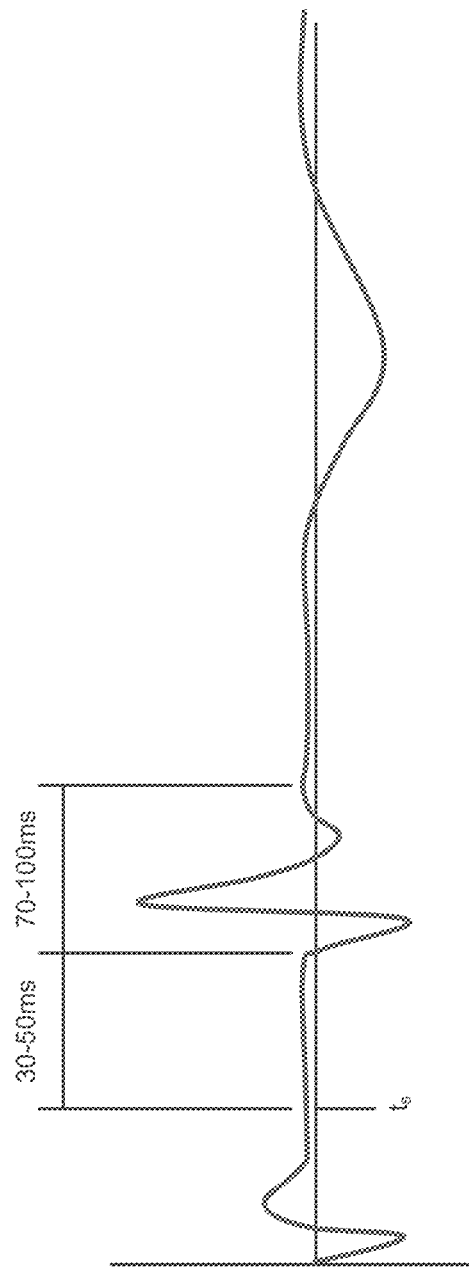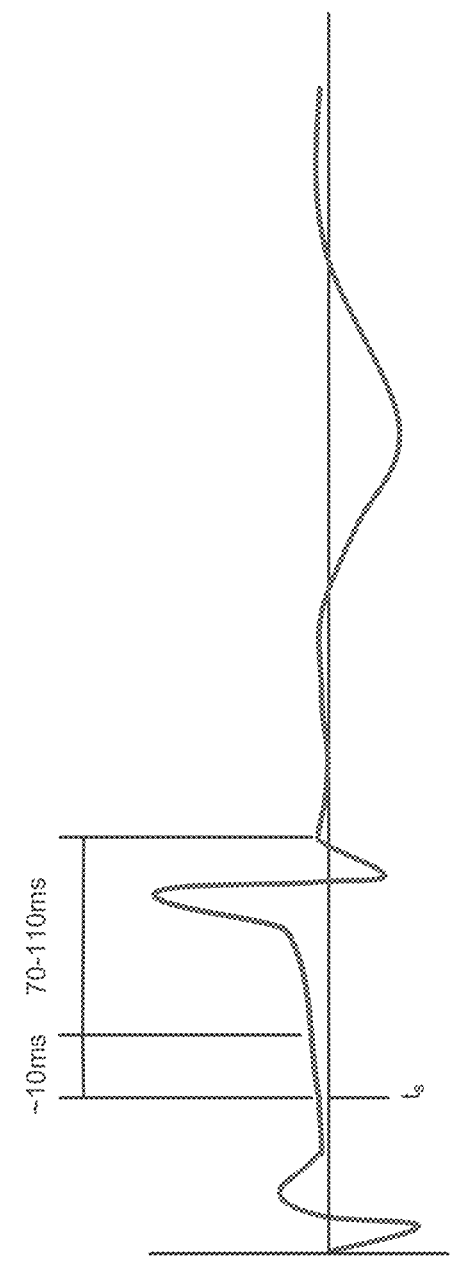

| His Ring to Can | | | | | |
|---|---|---|---|---|---|
| A Ring to Can | | | | | |
| His pace to RV sense interval | HP VS | HP VS | HP VS | HPVS | HPVS |
| A sense/pace to RV sense interval | AS / VS | AS / VS | AS / VS | AS / VS | AS / VS |
| RV Bipolar morphology | | | | | |
| AH interval (ms) | 40 | 70 | 100 | 130 | 160 |

*FIG. 20*

SYSTEMS AND METHODS FOR IMPROVED HIS BUNDLE AND BACKUP PACING TIMING

RELATED APPLICATIONS

The present application claims priority to U.S. Provisional Application No. 62/875,863, Titled "SYSTEMS AND METHODS FOR IMPROVED HIS BUNDLE AND BACKUP PACING TIMING" which was filed on Jul. 18, 2019, and to U.S. Provisional Application No. 62/948,047, Titled "AUTOMATIC PACING IMPULSE CALIBRATION USING PACING RESPONSE TRANSITIONS" which was filed on Dec. 13, 2019, the complete subject matter of which are expressly incorporated herein by reference in their entireties.

FIELD

This disclosure relates generally to implantable cardiac stimulating devices. More specifically, the present disclosure is directed to a cardiac stimulation device that includes a lead for HIS bundle pacing and that includes logic for automatically identifying and implementing settings of the cardiac stimulation device for delivering HIS bundle pacing. This disclosure further relates to a method for identifying and implementing cardiac stimulating device settings for HIS bundle pacing. This disclosure relates generally to implantable cardiac stimulating devices for use in providing His bundle pacing. More specifically, the present disclosure is directed to a cardiac stimulation device for providing His bundle pacing and associated methods for automatically identifying and implementing settings of the cardiac stimulation device to deliver His bundle pacing.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of HIS (also referred to as the HIS bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. To the extent the electrical pulses are sufficient to induce depolarization of the associated heart tissue, the heart tissue is said to be captured and the minimum electrical pulse resulting in capture is generally referred to as the capture threshold.

In the majority of individuals, the most effective heartbeat is triggered by the patient's own natural pacing physiology. Implantable cardiac stimulation devices are intended to fill in when the natural pacing functionality of the patient's heart fails or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the HIS bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the HIS bundle has been found to provide hemodynamic improvement for various patients including those suffering from dilated cardiomyopathy but having normal ventricular activation. Other examples of patients that may benefit from direct stimulation of the HIS bundle include those with atrioventricular junction (AVJ) ablation or third-degree AV block that require permanent ventricular pacing. Accordingly, the natural conduction system, when intact, can provide hemodynamically optimal depolarization timing of the heart chambers.

What is needed, therefore, is a cardiac stimulation device capable of identifying electrical pulses for inducing HIS bundle capture and self-configuring output settings of the cardiac stimulation device to output such electrical pulses. To improve efficiency and operational life of the cardiac stimulation device, it would be desirable that the cardiac stimulation device identify the minimum power and rate necessary to induce HIS bundle capture and subsequent ventricular depolarization.

The His bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the His bundle and a subsequent depolarization of the ventricles in response to the excitation is generally on the order of approximately 30-50 milliseconds (ms) and the resulting QRS complex generally has a duration of approximately 70-100 ms.

Disruption of the natural pacemaking and conduction system of the heart as a result of aging or disease can be successfully treated by artificial cardiac pacing using implantable cardiac stimulation devices, including pacemakers and implantable defibrillators. Such devices deliver rhythmic electrical impulses at particular energies and rates or provide other anti-arrhythmia therapies to the heart via electrodes implanted in contact with the heart tissue. To the extent the electrical impulses are sufficient to induce depolarization of the associated heart tissue, the heart tissue is said to be captured. The minimum electrical impulse energy resulting in capture is generally referred to as the capture threshold for the heart tissue.

In the majority of individuals, the most effective heartbeat is triggered by the patient's own natural pacing physiology. Implantable cardiac stimulation devices are intended to fill in when the natural pacing functionality of the patient's heart fails or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the His bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the His bundle has been found to provide hemodynamic improvement for various patients including those suffering from dilated cardiomyopathy but having otherwise normal ventricular activation. Other examples of patients that may benefit from direct stimulation of the His bundle include those with atrioventricular junction (AVJ) ablation or third-degree AV block, which may require permanent ventricular pacing. Accordingly, the natural conduction system, when intact, can provide hemodynamically optimal depolarization timing of the heart chambers.

What is needed, therefore, is a cardiac stimulation device capable of efficiently identifying electrical impulses settings for inducing His bundle capture for a particular patient and self-configuring output settings of the cardiac stimulation device to output such electrical impulses. It is further desirable to identify the minimum power necessary to induce His bundle capture and subsequent ventricular depolarization, thereby improving efficiency and operational life (e.g., battery life) of the cardiac stimulation device. Moreover, due to variability of patients, it is further desirable that such devices and associated methods provide configurations that are patient-specific without relying on empirical data that may not accurately reflect an individual patient's physiology or condition.

It is with the foregoing in mind that the following aspects of the present disclosure, among others, were conceived.

BRIEF SUMMARY OF THE DISCLOSURE

In one aspect of the present disclosure a method of controlling backup pacing of a patient heart using a stimulation system in HIS bundle pacing applications is provided. The stimulation system includes a memory, a pulse generator, a stimulating electrode in proximity to the HIS bundle, a backup pacing electrode in proximity to a ventricle of the patent heart, and at least one sensing electrode adapted to sense electrical activity of the patient heart. The method includes setting a first delay of the stimulation system between pacing of the HIS bundle and backup pacing of the ventricle ($H_P$-$V_P$) to be greater than a conduction time between the HIS bundle and the ventricle. The method further includes applying, using the pulse generator, an impulse through the stimulating electrode and measuring, using the sensing electrode, a response of the patient heart to application of the impulse. The method also includes inhibiting backup pacing of the ventricle when the time between application of the impulse and onset of the measured response is less than the first delay.

In certain implementations, the method further includes measuring the conduction time between the HIS bundle and the ventricle. In such implementations, measuring the conduction time between the HIS bundle and the ventricle may include measuring the conduction time between the HIS bundle and the ventricle for multiple capture types.

In other implementations, the method may further include setting a second delay of the stimulation system between sensing an event of an atrium and pacing of the HIS bundle (A-$H_P$) to be less than a conduction time between the atrium and HIS bundle. In such implementations, the method may further include calculating the conduction time between the atrium and HIS bundle based on each of the conduction time between the HIS bundle and the ventricle and a conduction time between an atrial event and depolarization of the ventricle. Such implementations may further include measuring each of the conduction time between the HIS bundle and the ventricle and the conduction time between an atrial event and depolarization of the ventricle In still other implementations, the method may include applying a backup pacing impulse to the ventricle when the time between application of the impulse and onset of the measured response is greater than the first delay. In such implementation, the method may further include incrementing a backup pacing counter in response to applying the backup pacing impulse. The method may further include recalibrating the stimulation device in response to the backup pacing counter exceeding a threshold value. Such recalibration may include, but is not limited to, initiating a capture threshold test.

In another aspect of the present disclosure, a cardiac stimulation system adapted to deliver impulses for pacing a HIS bundle of a patient heart and for backup pacing of a ventricle of the patient heart is provided. The cardiac stimulation system includes a pulse generator adapted to generate electrical impulses for each of pacing the HIS bundle and providing backup pacing of the ventricle, a processor communicatively coupled to the pulse generator and adapted to receive response characteristics from one or more sensing electrodes in response to pacing the HIS bundle and a memory. The memory is communicatively coupled to the processor and includes instructions executable by the processor. When executed by the processor, the instructions cause the processor to set a first delay of the pulse generator between pacing of the HIS bundle and backup pacing of the ventricle ($H_P$-$V_P$) to be greater than a conduction time between the HIS bundle and the ventricle. The instructions further cause the processor to apply, using the pulse generator, an impulse through the stimulating electrode and measure, using the one or more sensing electrode, a response of the patient heart to application of the impulse. The instructions also cause the processor to inhibit backup pacing of the ventricle when the time between application of the impulse and onset of the measured response is less than the first delay.

In certain implementations, the instructions further cause the processor to measure the conduction time between the HIS bundle and the ventricle. In such implementations, the instructions may further cause the processor to measure the conduction time between the HIS bundle and the ventricle for multiple capture types.

In other implementations, the instructions further cause the process to set a second delay for the pulse generator between sensing an event of an atrium and pacing of the HIS bundle (A-$H_P$) to be less than a conduction time between the atrium and HIS bundle. In such implementations, setting the second delay may include calculating the conduction time between the atrium and HIS bundle based on each of the conduction time between the HIS bundle and the ventricle and a conduction time between an atrial event and depolarization of the ventricle. Setting the second delay may also include measuring each of the conduction time between the HIS bundle and the ventricle and the conduction time between an atrial event and depolarization of the ventricle.

In still other implementations the instructions further cause the process to cause the pulse generator to generate a backup pacing impulse when the time between application of the impulse and onset of the measured response is greater than the first delay. In such implementations, the instructions may further cause the process to increment a backup pacing counter in response to the pulse generator generating the backup pacing impulse. The instructions may further cause the processor to recalibrate the stimulation device in response to the backup pacing counter exceeding a threshold value. Such recalibration may include, but is not limited to, initiating a capture threshold test.

In another aspect of the present disclosure a method of pacing a patient heart with bundle branch block using a stimulation system is provided. The stimulation system includes a memory, a pulse generator, a stimulating electrode distal the bundle branch block, and at least one sensing electrode adapted to sense electrical activity of the patient heart. The method includes applying pacing impulses using the stimulating electrode at a plurality of different pacing delays, the pacing delays being delays from detection of an atrial event. The method further includes measuring, using the at least one sensing electrode and for each of the plurality of pacing delays, a respective response of the patient heart to application of the pacing impulse and determining, based on the responses, a pacing delay resulting in fusion. The method further includes setting an atrial event-to-pacing (A-H) timing parameter of the stimulation system to be equal to the pacing delay resulting in fusion, the A-H timing parameter of the stimulation system corresponding to a delay between the stimulation system identifying atrial events and applying a pacing impulse using the stimulating electrode.

In one implementation, determining the pacing delay resulting in fusion includes analyzing at least one of morphologies of the responses to the pacing impulses or QRS complex durations of the responses to the pacing impulses.

In another implementation, the response to application of the pacing impulses includes a unipolar intracardiac electrogram (IEGM), and the pacing delay resulting in fusion is the pacing delay of the plurality of pacing delays having the narrowest unipolar IEGM width.

In still another implementation, the response to application of the pacing impulses includes a bipolar morphology, and the pacing delay resulting in fusion is the shortest pacing delay of the plurality of pacing delays resulting in monophasic morphology.

In yet another implementation the response to application of the pacing impulses includes an interval between pacing and sensing depolarization of a ventricle, and the pacing delay resulting in fusion being the shortest pacing delay of the plurality of pacing delays for which the interval shortens.

In another implementation, the response to application of the pacing impulses includes an interval between the atrial event and sensing depolarization of a ventricle, and the pacing delay resulting in fusion is the shortest pacing delay of the plurality of pacing delays for which the interval lengthens.

In yet another implementation the stimulating electrode is implanted in the left branch bundle and applying the pacing impulses comprises applying pacing impulses to the left branch bundle. Alternatively, the stimulating electrode is implanted in the right branch bundle and applying the pacing impulses comprises applying pacing impulses to the right branch bundle.

In still another implementation measuring the respective responses comprises obtaining an intracardiac electrogram (IEGM). In such implementations, the IEGM may be obtained using at least one vector selected from a group of vectors consisting of: (1) a tip electrode of a lead further including the stimulating electrode and a housing of the pulse generator; (2) an electrode of an atrial lead and a housing of the pulse generator; (3) an electrode of a lead further including the stimulating electrode and an electrode of a ventricular lead; (4) an electrode of an atrial lead and an electrode of a ventricular lead; (5) different electrodes of a bipolar ventricular lead; (6) a coil of a ventricular lead and a housing of the pulse generator; or (7) a superior vena cava coil and a coil of a ventricular lead.

In another implementation, the method further includes applying a second pacing impulse using the stimulating electrode, the second pacing impulse applied according to the A-H timing parameter, measuring a response to the second pacing impulse, and determining the response does not meet a fusion criteria, and, in response to determining the response does not meet the fusion criteria, modifying the A-H timing parameter. In such implementations, determining the response does not meet the fusion criteria may include determining the duration of a QRS complex of the response exceeds a predetermined threshold.

In still another aspect of the present disclosure a cardiac stimulation system adapted to deliver impulses for pacing a branch bundle of a patient heart is provided. The cardiac stimulation system includes a pulse generator adapted to generate electrical impulses for pacing the branch bundle, a processor communicatively coupled to the pulse generator and adapted to receive response characteristics from at least one sensing electrodes in response to pacing the branch bundle, and a memory communicatively coupled to the processor. The memory includes instructions executable by the processor that, when executed by the processor, cause the processor to apply pacing impulses to the branch bundle using a stimulating electrode connected to the pulse generator at a plurality of different pacing delays, the pacing delays being delays from detection of an atrial event. The instructions further cause the processor to measure, using the at least one sensing electrode and for each of the plurality of pacing delays, a respective response of the patient heart to application of the pacing impulse and determine, based on the responses, a pacing delay resulting in fusion. The instructions also cause the processor to set an atrial event-to-pacing (A-H) timing parameter to be equal to the pacing delay resulting in fusion, the A-H timing parameter being a delay between identification of atrial events and application of a corresponding pacing impulse using the stimulating electrode.

In certain implementations the instructions further cause the processor to determine the pacing delay resulting in fusion comprises analyzing at least one of morphologies of the responses to the pacing impulses or QRS complex durations of the responses to the pacing impulses.

In other implementations the response to application of the pacing impulses includes a unipolar intracardiac electrogram (IEGM), and the instructions cause the processor to determine the pacing delay resulting in fusion by identifying the pacing delay of the plurality of pacing delays having the narrowest unipolar IEGM width.

In still other implementations the response to application of the pacing impulses includes a bipolar morphology, and the instructions cause the processor to determine the pacing delay resulting in fusion by identifying a shortest pacing delay of the plurality of pacing delays resulting in monophasic morphology.

In another implementation the response to application of the pacing impulses includes an interval between pacing and sensing depolarization of a ventricle, and the instructions cause the processor to determine the pacing delay resulting in fusion by identifying a shortest pacing delay of the plurality of pacing delays for which the interval shortens.

In yet another implementation the response to application of the pacing impulses includes an interval between the atrial event and sensing depolarization of a ventricle, and the instructions cause the processor to determine the pacing delay resulting in fusion by identifying a shortest pacing delay of the plurality of pacing delays for which the interval lengthens.

In another implementation, the instructions cause the processor to measure the responses to the pacing delays by obtaining an intracardiac electrogram (IEGM).

In still another implementation, the instructions further cause the processor to apply a second pacing impulse using the stimulating electrode, the second pacing impulse applied according to the A-H timing parameter; measure a response to the second pacing impulse; determine the response does not meet a fusion criteria, the fusion criteria being one of a QRS duration and a QRS morphology; and, in response to determining the response does not meet the fusion criteria, modify the A-H timing parameter.

In yet another aspect of the present disclosure a method of controlling backup pacing of a patient heart using a stimulation system in HIS bundle pacing applications is provided. The stimulation system includes a memory, a pulse generator, a stimulating electrode in proximity to the HIS bundle of the patient heart, a backup pacing electrode in proximity to a ventricle of the patent heart, and at least one sensing electrode adapted to sense electrical activity of the patient heart. The method includes applying, using the pulse generator, an impulse through the stimulating electrode; measuring, using the sensing electrode, a response of the patient heart to application of the impulse; and determining, based on the response, whether the pacing impulse resulted in QRS correction. The method further includes operating the stimulation system in a first mode in which backup pacing is disabled when QRS correction has not occurred and operating the stimulation system in a second mode in which backup pacing is enabled if QRS correction has occurred.

In certain implementations, the method further includes obtaining a baseline QRS duration for the patient heart and determining whether the pacing impulse resulted in QRS correction includes determining whether a QRS duration of the response is less than the baseline QRS duration. In one specific implementation, the reduction is about 20%.

In another implementation, wherein determining whether the pacing impulse resulted in QRS correction comprises determining whether a QRS duration of the response is less than a threshold QRS duration. In one specific implementation the threshold QRS duration is about 120 ms.

In still another implementation determining whether the pacing impulse resulted in QRS correction includes identifying a change in one or more conduction time through the patient heart.

In another implementation the method further includes determining an atrial event-to-His pacing (A-H) delay for applying the impulse and the impulse is applied according to the A-H delay. In such implementations, determining the A-H delay may include directly measuring a conduction delay between an atrial event and corresponding depolarization of the HIS bundle. In another such implementation, determining the A-H delay may include measuring a delay between pacing of the HIS bundle and depolarization of a ventricle. Determining the A-H delay in such cases may further include calculating the A-H delay by subtracting the delay between pacing of the HIS bundle and depolarization of a ventricle from one of (1) the conduction time between an atrial event and depolarization of the ventricle; (2) a predetermined maximum conduction time; or (3) an intra-atrial conduction delay.

In still another implementation the method further includes, when operating in the second mode in which backup pacing is enabled, determining an interval between pacing of the HIS bundle and a resulting QRS peak ($H_P$-peak interval), applying a pacing impulse to the HIS bundle, and determining whether onset of a response to the pacing impulse to the HIS bundle occurs within the $H_P$-peak interval. In such implementations, the method may further include applying a backup impulse, in response to determining onset of the response does not occur within the $H_P$-peak interval. Alternatively, the method may also include inhibiting a backup impulse in response to determining onset of the response occurs within the $H_P$-peak interval.

In another aspect of the present disclosure, a stimulation system adapted to deliver impulses for pacing a HIS bundle of a patient heart and for backup pacing of a ventricle of the patient heart is provided. The stimulation system includes a pulse generator adapted to generate electrical impulses for each of pacing the HIS bundle and providing backup pacing of the ventricle, a processor communicatively coupled to the pulse generator and adapted to receive response characteristics from one or more sensing electrodes in response to pacing the HIS bundle, and a memory communicatively coupled to the processor. The memory includes instructions executable by the processor that, when executed by the processor, cause the processor to apply, using the pulse generator, an impulse through the stimulating electrode to the HIS bundle, measure, using the sensing electrode, a response of the patient heart to application of the impulse, and determine, based on the response, whether the pacing impulse resulted in QRS correction. The instructions further cause the processor to operate the stimulation system in a first mode in which backup pacing of the ventricle is disabled when QRS correction has not occurred and operate the stimulation system in a second mode in which backup pacing of the ventricle is enabled if QRS correction has occurred.

In certain implementations, the instructions further cause the processor to obtain a baseline QRS duration for the patient heart and to determine whether the pacing impulse resulted in QRS correction by determining whether a QRS duration of the response is less than the baseline QRS duration.

In other implementations the instructions cause the processor to determine whether the pacing impulse resulted in QRS correction by determining whether a QRS duration of the response is less than a threshold QRS duration.

In still other implementations the instructions cause the processor to determine whether the pacing impulse resulted in QRS correction by identifying a change in one or more conduction time through the patient heart.

In other implementations, the instructions further cause the processor to set an atrial event-to-His pacing (A-H) delay for applying the impulse. In such implementations the instructions may further cause the processor to set the A-H delay by directly measuring a conduction delay between an atrial event and corresponding depolarization of the HIS bundle. In other such implementations, the instructions further cause the processor to set the A-H delay by measuring a delay between pacing of the HIS bundle and depolarization of a ventricle and subtracting the delay between pacing of the HIS bundle and depolarization of a ventricle from one of the conduction time between an atrial event and depolarization of the ventricle, a predetermined maximum conduction time, or an intra-atrial conduction delay.

In another implementation, the instructions further cause the processor to, when operating in the second mode in which backup pacing is enabled, determine an interval between pacing of the HIS bundle and a resulting QRS peak ($H_P$-peak interval), apply a pacing impulse to the HIS bundle, and determine whether onset of a response to the pacing impulse to the HIS bundle occurs within the $H_P$-peak interval. In such implementations, the instructions may further cause the process to apply a backup impulse in response to determining onset of the response does not occur within the $H_P$-peak interval. Alternatively, the instructions may further cause the processor to inhibit a backup impulse in response to determining onset of the response occurs within the $H_P$-peak interval.

In accordance with embodiments herein, a cardiac stimulation system is provided that comprises a pulse generator adapted to generate electrical impulses for pacing a HIS bundle; a processor communicatively coupled to the pulse generator and adapted to receive response characteristics from one or more sensing electrodes in response to pacing the HIS bundle; and a memory communicatively coupled to the processor, the memory including instructions executable by the processor that, when executed by the processor, cause the processor to: apply, using the pulse generator, a HIS bundle pacing (HBP) impulse through the stimulating electrode; measure, using the one or more sensing electrode, a response of the patient heart to application of the HBP impulse; analyze a first segment of the response to identify an evoked response (ER) characteristic of interest (COI); analyze a second segment of the response to identify a QRS COI; determine an activation time based on the HBP impulse and the QRS COI; utilize at least one of the ER COI or activation time to apply a capture class (cc) discriminator to distinguish between first and second capture classes, were at least one of the first and second capture classes includes two or more capture types; and utilize at least another of the ER COI or activation time to apply a feature discriminator to distinguish between first and second capture types within one of the at least first and second capture classes.

Additionally or alternatively, the first segment is positioned to closely follow the HBP impulse and the second segment is spaced apart from the HBP by an interval sufficient to avoid atrial activity over sensing. Additionally or alternatively, the capture types include selective capture, nonselective capture, loss of capture, and myocardial only capture, and wherein the activation time is utilized as the CC discriminator to distinguish between i) the first capture class that includes selective capture and nonselective capture and ii) the second capture class that includes myocardial only capture and loss of capture. Additionally or alternatively, the ER COI is utilized as the feature discriminator to distinguish between the selective capture and nonselective capture in the first capture class and to distinguish between the myocardial only capture and loss of capture in the second capture class. Additionally or alternatively, the capture types include selective capture, nonselective capture, loss of capture, and myocardial only capture, and wherein the ER COI is utilized as the CC discriminator to distinguish between i) the first capture class that includes selective capture and loss of capture and ii) the second capture class that includes myocardial only capture and nonselective capture. Additionally or alternatively, the activation time is utilized as the feature discriminator to distinguish between the selective capture and loss of capture in the first capture class and to distinguish between the myocardial only capture and nonselective capture in the second capture class. Additionally or alternatively, the QRS COI represents an end of the QRS complex such that the activation time extends between a time of the HBP impulse and a time of the end of the QRS complex.

Additionally or alternatively, the QRS COI represents a maximum slope of the QRS complex such as the activation time extends between a time of the HBP impulse at the time of the maximum slope of the QRS complex. Additionally or alternatively, the ER COI correspond to at least one of a total energy within an evoked response, an ER peak amplitude, or an ER maximum slope. Additionally or alternatively, the CC discriminator distinguishes between the first capture class that includes selective and nonselective capture with QRS correction and the second capture class that includes selective and nonselective capture without QRS correction.

In accordance with embodiments herein, the method is provided for controlling a stimulation system in HIS bundle pacing applications, the stimulation system having a memory, a pulse generator, a stimulating electrode in proximity to the HIS bundle of the patient heart, and at least one sensing electrode adapted to sense electrical activity of the patient heart, the method comprising: applying a HIS bundle pacing (HBP) impulse through the stimulating electrode; measuring, using the one or more sensing electrode, a response of the patient heart to application of the HBP impulse; analyzing a first segment of the response to identify an evoked response (ER) characteristic of interest (COI); analyzing a second segment of the response to identify a QRS COI; determine an activation time based on the HBP impulse and the QRS COI; utilizing at least one of the ER COI or activation time to apply a capture class (cc) discriminator to distinguish between first and second capture classes, were at least one of the first and second capture classes includes two or more capture types; and utilizing at least another of the ER COI or activation time to apply a feature discriminator to distinguish between first and second capture types within one of the at least first and second capture classes. Additionally or alternatively, the first segment is positioned to closely follow the HBP impulse and the second segment is spaced apart from the HBP by an interval sufficient to avoid atrial activity over sensing. Additionally or alternatively, the capture types include selective capture, nonselective capture, loss of capture, and myocardial only capture, and wherein the activation time is utilized as the CC discriminator to distinguish between i) the first capture class that includes selective capture and nonselective capture and ii) the second capture class that includes myocardial only capture and loss of capture. Additionally or alternatively, the ER COI is utilized as the feature discriminator to distinguish between the selective capture and nonselective capture in the first capture class and to distinguish between the myocardial only capture and loss of capture in the second capture class. Additionally or alternatively, the capture types include selective capture, nonselective capture, loss of capture, and myocardial only capture, and wherein the ER COI is utilized as the CC discriminator to distinguish between i) the first capture class that includes selective capture and loss of capture and ii) the second capture class that includes myocardial only capture and nonselective capture. Additionally or alternatively, the activation time is utilized as the feature discriminator to distinguish between the selective capture and loss of capture in the first capture class and to distinguish between the myocardial only capture and nonselective capture in the second capture class. Additionally or alternatively, the QRS COI represents an end of the QRS complex such that the activation time extends between a time of the HBP impulse and a time of the end of the QRS complex. Additionally or alternatively, the QRS COI represents a maximum slope of the QRS complex such as the activation time extends between a time of the HBP impulse at the time of the maximum slope of the QRS complex. Additionally or alternatively, the ER COI correspond to at least one of a total energy within an evoked response, an ER peak amplitude, or an ER maximum slope. Additionally or alternatively, the CC discriminator distinguishes between the first capture class that includes selective and nonselective capture with QRS correction and the second capture class that includes selective and nonselective capture without QRS correction.

In one aspect of the present disclosure, a method of identifying pacing thresholds and programming a stimulation device for His bundle pacing is provided. The stimulation device includes a pulse generator, a stimulating electrode in proximity to a His bundle of a patient heart, at least one sensing electrode adapted to sense electrical activity of the patient heart, a processor, and a memory. The method includes applying, using the pulse generator and stimulating electrode, a first pacing impulse having a first pacing impulse energy to the His bundle and, in response to applying the first pacing impulse, collecting first response data using the at least one sensing electrode. The method further includes applying, using the pulse generator and stimulating electrode, a second pacing impulse having a second pacing impulse energy to the His bundle, the second pacing impulse energy being different than the first pacing impulse energy and, in response to applying the second pacing impulse, collecting second response data using the at least one sensing electrode. The method also includes identifying a change in one or more response characteristics between the first response data and the second response data, the response characteristics indicative of a change from a first capture type for the first pacing impulse energy and a second capture type for the second pacing impulse energy and, in response to identifying the change in the one or more response characteristics, setting a pacing impulse energy setting of the stimulation device to the first pacing impulse energy.

In certain implementations, the first response data includes a first unipolar electrogram (EGM) and the second response data includes a second unipolar EGM. In such implementations, the response characteristics may include unipolar stim-to-onset time and unipolar width.

In other implementations, the first response data includes a first bipolar EGM and the second response data includes a second bipolar EGM.

In still other implementations, wherein the first response data includes each of a first unipolar electrogram (EGM) and a first bipolar EGM, the second response data includes each of a second unipolar EGM and a second bipolar EGM, and the response characteristics include each of bipolar stim-to-peak and unipolar width.

In yet other implementations, the response characteristics include at least one of bipolar stim-to-peak, unipolar width, unipolar stim-to-onset time, and unipolar maximum positive slope.

In other implementations, the response characteristics include a first response characteristic corresponding to total ventricular activation time and a second response characteristic corresponding to time between pacing and activation.

In certain implementations, the first capture type indicates capture of the His bundle and the second capture type indicates a loss of capture of the His bundle.

In still other implementations, the first capture type indicates correction of a branch bundle block and the second capture type indicates a loss of branch bundle block correction.

In another aspect of the present disclosure, a cardiac stimulation system adapted to deliver impulses for pacing the His bundle of a patient heart is provided. The system includes a pulse generator adapted to generate electrical impulses, a processor communicatively coupled to the pulse generator and adapted to measure responses of the patient heart using at least one sensing electrode, and a memory communicatively coupled to the processor including instructions executable by the processor. The instructions cause the processor to apply, using the pulse generator and a stimulating electrode, a first pacing impulse having a first pacing impulse energy to the His bundle and, in response to applying the first pacing impulse, to collect first response data using a sensing electrode. The instructions further cause the process to apply, using the pulse generator and the stimulating electrode, a second pacing impulse having second pacing impulse energy to the His bundle, the second pacing impulse energy being different than the first pacing impulse energy and, in response to applying the second pacing impulse, to collect second response data using the at least one sensing electrode. The instructions also cause the processor to identify a change in one or more response characteristics between the first response data and the second response data, the response characteristics indicative of a change from a first capture type for the first pacing impulse energy and a second capture type for the second pacing impulse energy. The instructions further cause the process to set a pacing impulse energy setting of the stimulation device to the first pacing impulse energy in response to identifying the change in the one or more response characteristics.

In certain implementations, the first response data includes a first unipolar electrogram (EGM) and the second response data includes a second unipolar EGM. In other implementations, the first response data includes a first bipolar EGM and the second response data includes a second bipolar EGM. In still other implementations, the response characteristics include at least one of bipolar stim-to-peak, unipolar width, unipolar stim-to-onset time, and unipolar maximum positive slope. In other implementations, the response characteristics include a first response characteristic corresponding to total ventricular activation time and a second response characteristic corresponding to time between pacing and activation. In still other implementation, the first capture type indicates capture of the His bundle and the second capture type indicates a loss of capture of the His bundle. In other implementations, the first capture type indicates correction of a branch bundle block and the second capture type indicates a loss of branch bundle block correction.

In yet another aspect of the present disclosure, a method of identifying pacing thresholds and programming a stimulation device for His bundle pacing is provided. The stimulation device includes a pulse generator, a stimulating electrode in proximity to a His bundle of a patient heart, and at least one sensing electrode adapted to sense electrical activity of the patient heart. The method includes collecting a first response data set for a first pacing impulse energy. Collecting the first response data set includes applying, using the pulse generator and stimulating electrode, a plurality of first pacing impulses having the first pacing impulse energy to the His bundle and measuring a response to each of the plurality of first pacing impulses using the at least one sensing electrode. The method further includes collecting a second response data set for a second pacing impulse energy different than the first pacing impulse energy. Collecting the second response data set includes applying, using the pulse generator and stimulating electrode, a plurality of second pacing impulses having the second pacing impulse energy to the His bundle and measuring a response to each of the plurality of second pacing impulses using the at least one sensing electrode. Subsequent to determining a variance of the responses of the first response data set is below a variance value, the method includes identifying a change in one or more response characteristics between the first set of response data and the second set of response data, the response characteristics indicative of a change from a first capture type for the first pacing impulse energy and a second capture type for the second pacing impulse energy. The method further includes, in response to identifying the change in the one or more response characteristic, setting a pacing impulse energy setting of the stimulation device to the first pacing impulse energy.

In certain implementations, each response of the first response data set and each response of the second response data set includes a unipolar electrogram (EGM). In other implementations, each response of the first response data set and each response of the second response data set includes a unipolar electrogram (EGM). In still other implementations, the one or more response characteristics include a first response characteristic corresponding to total ventricular activation time and a second response characteristic corresponding to time between pacing and activation.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIGS. 1A and 1B are example electrocardiograms illustrating selective and non-selective HIS bundle capture, respectively;

FIG. 20 is a table illustrating changes to measurements obtained from various IEGM vectors for different HIS pacing intervals.

DETAILED DESCRIPTION

Figure 2:
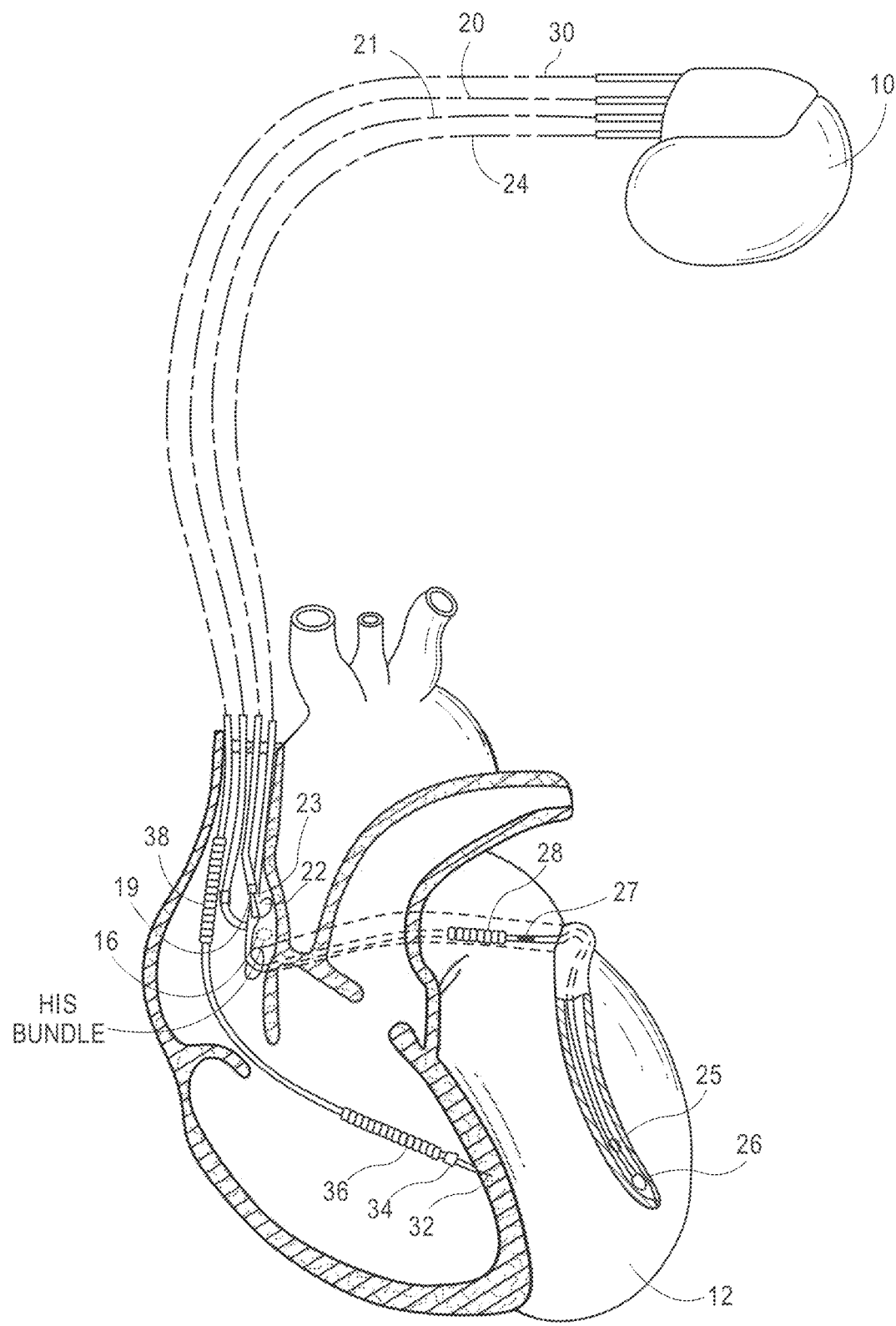
FIG. 2 is a simplified, partly cutaway view illustrating an implantable stimulation device in electrical communication with at least four leads, including a HIS Bundle lead, implanted into a patient's heart for delivering multi-chamber stimulation and shock therapy.

The present disclosure is directed to various aspects of stimulation devices and corresponding methods related to HIS bundle pacing. Among other things, the present disclosure provides methods and devices for automatic determination of HIS bundle capture thresholds, for configuring stimulation devices based on determined capture thresholds, for identifying different capture types in response to application of pacing impulses, and other related features and functions. Aspects of the present disclosure may be implemented in either a dual chamber or multi-chamber cardiac stimulation device. For example, the present disclosure may be implemented in multi-chamber cardiac stimulation device such as the stimulation device 10 depicted in FIG. 2.

Certain cardiac pacemakers and defibrillators incorporate a pacing lead in the right ventricle and may also include a second lead in the right atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. HIS bundle pacing (HBP) may restore physiological activation patterns by utilizing a patient's intrinsic conduction system and may do so even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown most effective for patients exhibiting a wide QRS complex and left bundle branch block. HBP has also been shown to be effective at narrowing the QRS complex in patients with left bundle branch block, likely due to restoration of conduction through HIS and Purkinje, which includes right and left bundle fibers that are longitudinally dissociated. Therefore, what is thought of as left bundle branch block, can be a result of a proximal blockage within the HIS bundle that eventually branches to the left bundle. As a result, by pacing the HIS bundle distal to the blockage, a normalized QRS complex can be achieved in some patients. Theoretically, this pacing mode may provide even better results than known CRT treatments, as activation propagates rapidly through natural conduction pathways.

The HIS bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the HIS bundle and a subsequent depolarization of the ventricles in response to the excitation is generally on the order of approximately 30-50 milliseconds (ms) and the resulting QRS complex generally has a duration of approximately 70-100 ms.

Depending on electrode position, pacing leads targeted for the HIS bundle may achieve either non-selective or selective HBP. Non-selective HIS bundle pacing (nsHBP) refers to pacing of the HIS bundle in which both the HIS bundle and the local myocardium surrounding the HIS bundle are captured. Capture occurs when an electrical stimulus applied to the heart is of sufficient energy to depolarize the cardiac tissue near stimulation electrodes and propagate, thereby causing the heart muscle to contract. As a result of the simultaneous depolarization of multiple areas of cardiac tissue, the sequential electrical responses typically observed during normal heart activity may be combined or condensed. HIS bundle capture resulting in such a response is often characterized by the stimulus to ventricular depolarization duration being short, on the order of 20 ms, because the myocardial depolarization propagates immediately without exclusively traveling through the His-Purkinje system. Because the HIS bundle is stimulated and captured, the QRS duration is similar to the native QRS duration but may be slightly longer due to the myocardial excitation (e.g., 70-120 ms). In contrast, selective HIS bundle pacing (sHBP) refers to exclusive capture of the HIS bundle without stimulating surrounding myocardial tissue. With sHBP, the stimulus to ventricular depolarization interval is virtually the same as the native delay between HIS bundle stimulation and subsequent ventricular depolarization and the QRS duration is essentially identical to the native QRS duration.

Overview of HBP System and Components

To further illustrate the foregoing, FIGS. 1A and 1B are example electrocardiograms corresponding to selective and non-selective HIS bundle capture, respectively. In each of FIGS. 1A and 1B, a stimulus is applied at a predetermined time ($t_s$) following an atrial event. In FIG. 1A, selective HIS bundle capture occurs, i.e., only the HIS bundle is captured and the myocardium is not excited by the stimulus applied at L. As a result, while the delay between application of the stimulus and onset of the QRS complex may vary for a given patient, it is generally in the range of approximately 30 to 50 ms, which is generally consistent with normal heart function. The resulting QRS may be narrowed, but is typically between 70 and 100 ms in duration. The example electrocardiogram of FIG. 1B, in contrast, illustrates non-selective HIS bundle capture in which the stimulus applied at is results in simultaneous capture of both the HIS bundle and the myocardium. With non-selective capture the delay between application of the stimulus and the onset of the QRS complex is reduced (typically less than 10 ms) and the QRS duration generally remains between 70 and 120 ms. As further illustrated in FIG. 1B, non-selective HIS bundle capture may also result in the occurrence of a delta wave, which is generally a slurred upstroke in the QRS complex resulting from local excitation of the ventricles near a HIS lead.

Because sHBP more closely approximates native heart function, it is generally preferred to nsHBP. However, due to the complexity and dynamic nature of certain cardiomyopathies and cardiac anatomies, sHBP may not be possible or, if possible at one time, may no longer be possible as a patient's condition changes. Moreover, a patient's condition may also change to the point where HBP is generally unsuitable as a pacing method and ventricular pacing is required.

In light of the foregoing, this disclosure describes methods and apparatuses directed to optimizing HBP of a patient's heart. More specifically, this disclosure describes stimulation devices capable of HBP and processes that may be implemented by such stimulation devices to initialize and dynamically modify settings of the stimulation devices to provide HBP. To do so, the stimulation devices are generally capable of identifying and dynamically modifying one or more capture thresholds associated with HBP. As discussed below in more details, FIGS. 2-7 generally describe the components and functionality of stimulation devices in accordance with this disclosure while the remaining figures illustrate various processes that may be implemented by such stimulation devices to provide HBP and associated data.

With reference to FIG. 2, the stimulation device 10 is shown in electrical communication with a patient's heart 12 by way of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 illustrated in FIG. 2 is generally configured as an implantable cardioverter-defibrillator (ICD) and generally includes functionality for pacing, sensing, and providing defibrillation to a patient heart. It should be appreciated however, that the ICD illustrated in FIG. 2 is just one example stimulation device that may implement aspects of the present disclosure. Other configurations and types of implantable stimulation devices incorporating aspects of the present disclosure are also contemplated. For example and without limitation, in at least one implementation, the stimulation device 10 of FIG. 2 may instead be configured as a pacemaker without defibrillation functionality and, in particular, a pacemaker configured to provide cardiac resynchronization therapy (CRT). In such implementations, some or all of the defibrillation coils illustrated on the various leads of FIG. 2 and their associated circuitry within the stimulation device 10 may be omitted. It should also be appreciated that the specific configuration of leads and placement of leads illustrated in FIG. 2 is intended merely as an example and other configurations are possible. For example, in one specific implementation, the coronary sinus lead 24 may instead be replaced with a left ventricle lead that extends and is implanted within the left ventricle for pacing and/or sensing of the left ventricle. More generally, implementations of the present disclosure are generally applicable to any suitable stimulation devices currently known or later developed that provide HIS bundle pacing.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a HIS bundle lead 21 having a HIS tip electrode 16, such as a helical active fixation device, and a HIS ring electrode 19 located proximal from the HIS tip electrode 16. In certain implementations, the HIS ring electrode 19 is located approximately 10 mm proximal the HIS tip electrode 16. The HIS bundle lead 21 may be transvenously inserted into the heart 12 so that the HIS tip electrode 16 is positioned in the tissue of the HIS bundle. Accordingly, the HIS bundle lead 21 is capable of receiving depolarization signals propagated in the HIS bundle and exiting the Purkinje fibers to the myocardium or delivering stimulation to the HIS bundle, creating a depolarization that can be propagated through the lower conductive pathways of the right and left ventricles (i.e., the right and left bundle branches and Purkinje fibers).

The HIS bundle lead 21 will be described in greater detail in conjunction with FIGS. 5 and 6.

Figure 3:
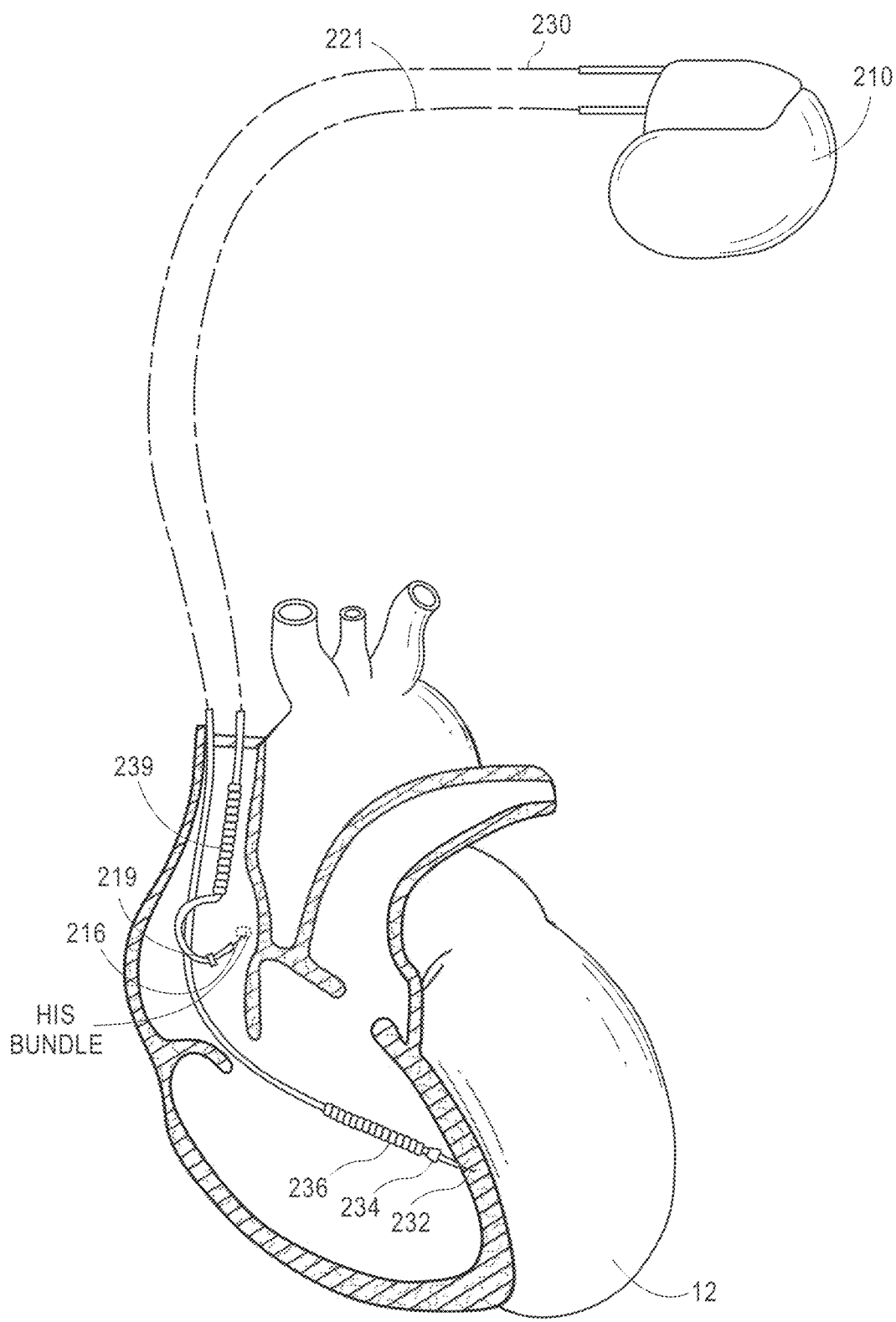
FIG. 3 is a simplified, partly cutaway view illustrating an alternative design of an implantable stimulation device, shown implanted into the right chambers of the patient's heart for delivering dual-chamber stimulation and shock therapy.

An alternative embodiment of the present disclosure is shown in FIG. 3 in which a dual chamber stimulation device 210 is in communication with one atrium, one ventricle, and the HIS bundle. Though not explicitly illustrated in FIG. 3, a right atrial lead 20 (shown in FIG. 2) can be optionally included. In such implementations, the stimulation device 210 maintains communication with the right atrium of the heart 12 via a right atrial lead 20 having at least an atrial tip electrode 22 and an atrial ring electrode 23 (which may be implanted in the patient's right atrial appendage as described earlier in connection with FIG. 2), and an SVC coil electrode 239

A HIS bundle lead 221, having a HIS tip electrode 216 and a HIS ring electrode 219, is positioned such that the HIS tip electrode 216 is proximate the HIS bundle tissue. The stimulation device 210 is shown in FIG. 3 in electrical communication with the patient's heart 12 by way of a right ventricular lead 230 including a right ventricular tip electrode 232, a right ventricular ring electrode 234, and a right ventricular coil electrode 236.

Figure 4:
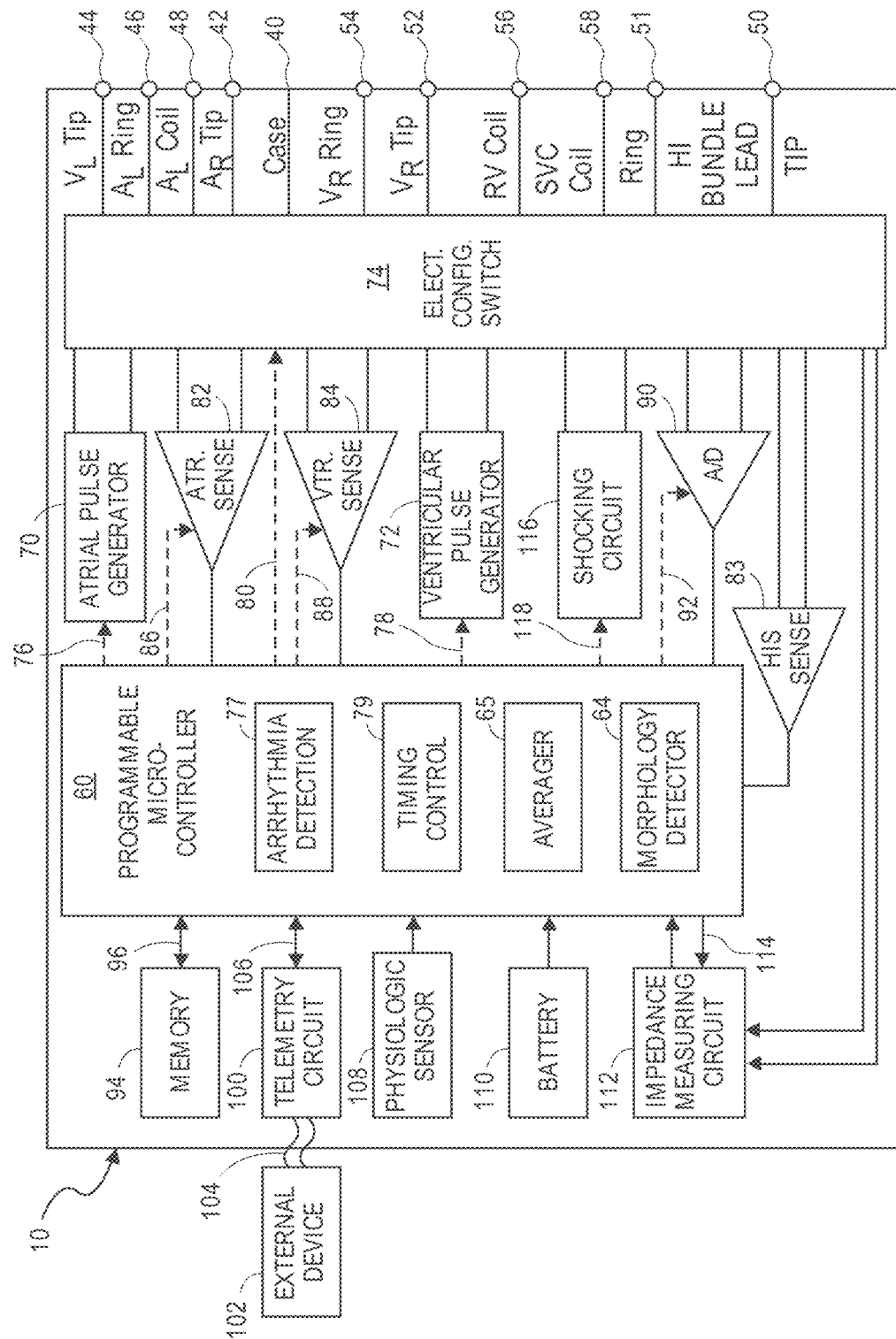
FIG. 4 is a functional block diagram of the multi-chamber implantable stimulation device of FIG. 2, illustrating the basic elements that provide pacing stimulation, cardioversion, and defibrillation in four chambers of the heart.

Referring now to FIG. 4, there is illustrated a simplified block diagram of the multi-chamber implantable stimulation device 10 of FIG. 2, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 2) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 2).

To achieve left chamber sensing, pacing, and defibrillation (in applications in which the stimulation device 10 is an ICD), the connector includes at least a left ventricular tip terminal (VL TIP) 44, a left atrial ring terminal (AL RING) 46, and a left atrial shocking terminal (AL COIL) 48, which are adapted for connection to the left ventricular tip electrode 26, the left atrial ring electrode 27, and the left atrial coil electrode 28, respectively (each shown in FIG. 2).

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 2).

To achieve HIS bundle sensing, or sensing and stimulation, the connector further includes a HIS bundle lead tip terminal 50 and a HIS bundle lead ring terminal 51 which are adapted for connection to the HIS tip electrode 16 and the HIS ring electrode 19, respectively (each shown in FIG. 2).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 4, an atrial pulse generator 70 and a ventricular pulse generator 72 generate pacing stimulation pulses for delivery by the right atrial lead 20, the right ventricular lead 30, the coronary sinus lead 24, and/or the HIS bundle lead 21 via an electrode configuration switch 74. As previously noted, in certain applications, the coronary sinus lead 24 may instead be substituted with a left ventricle lead. It is understood that in order to provide stimulation therapy in each of the chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present disclosure, timing control circuitry 79 also controls the onset and duration of a HIS signal sensing window during which a depolarization signal conducted through the AV node to the HIS bundle can be detected. Timing control circuitry 79 also controls a timing delay provided after a detected HIS signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24 (or left ventricle lead), and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one implementation of the present disclosure, a HIS sensing circuit 83 is selectively coupled to the HIS bundle lead 21 (shown in FIG. 2) for detecting the presence of a conducted depolarization arising in the atria and conducted through the HIS bundle via the AV node. As used herein, each of the atrial sensing circuit 82, the ventricular sensing circuit 84, and the HIS sensing circuit 83, includes a discriminator, which is a circuit that senses and can indicate or discriminate the origin of a cardiac signal in each of the cardiac chambers.

As illustrated in FIG. 4, the HIS sensing circuit 83 is shown as a dedicated circuit within the stimulation device 10. However, it should be appreciated that in certain implementations, His-related functionality may instead be provided by repurposing other pacing and sensing channels and circuitry of the stimulation device 10. For example, the stimulation device 10 may be reprogrammed such that a pacing channel, a sensing channel, and associated circuitry initially programmed for use in sensing and pacing one of the atria or ventricles may instead be reconfigured to pace and sense the HIS bundle.

Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart.

The atrial and ventricular sensing circuits 82, 84, in turn, receive control signals over signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AID) data acquisition system 90 represented by an A/D converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the HIS bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the HIS bundle signal. In one embodiment, an averager 65 is used to determine a sliding average of the HIS bundle signal during a HIS signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed at least once a day during at least the acute phase (e.g., the first 30 days following device implant) and less frequently thereafter. A capture threshold search would begin at a desired starting point (either a high energy level or the level at which capture is currently occurring) and decrease the energy level until capture is lost. The minimum energy at which capture is consistently obtained is known as the capture threshold. Thereafter, a safety margin can be automatically or programmably added to the capture threshold.

Capture detection and threshold testing may also be performed for purposes of HIS bundle pacing. The process of performing capture threshold testing for HIS bundle pacing and configuring the stimulation device 10 based on the results of such testing are described in more detail below in the context of FIGS. 8A, 8B, and 9.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In certain implementations, the stimulation device 10 may further include a physiologic sensor 108, commonly referred to as a "rate-responsive" sensor to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate, and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 10 additionally includes a battery 110 which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 is shown in FIG. 4 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

According to one implementation of the present disclosure, the HIS tip electrode 16 and HIS ring electrode 19 may be selectively coupled via switch 74 to the impedance measuring circuit 112 for performing a tissue impedance measurement. The tissue impedance measurement may be made to determine the location of the HIS bundle as the HIS tip electrode 16 or mapping collar 418 as shown in FIG. 5, or sensing electrodes 520-523 (shown in FIG. 6) are advanced along the endocardial surface of the right atrium. A method for performing this tissue impedance measurement using the HIS bundle lead 21 will be described further in conjunction with FIG. 7. In other implementations of the present disclosure, alternative approaches for mapping the intrinsic conduction signals of the HIS bundle and associated tissue may be used. For example and without limitation, in at least one implementation an electrophysiology (EP) catheter may be used to identify a location for the HIS tip electrode 16.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode). As previously noted, the implementation illustrated in FIG. 2 is provided as an example and other configurations are possible. For example, in other implementations, the high voltage coils for both RV coil and SVC coil may be disposed on the right ventricle lead as opposed to the RA lead.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 5:
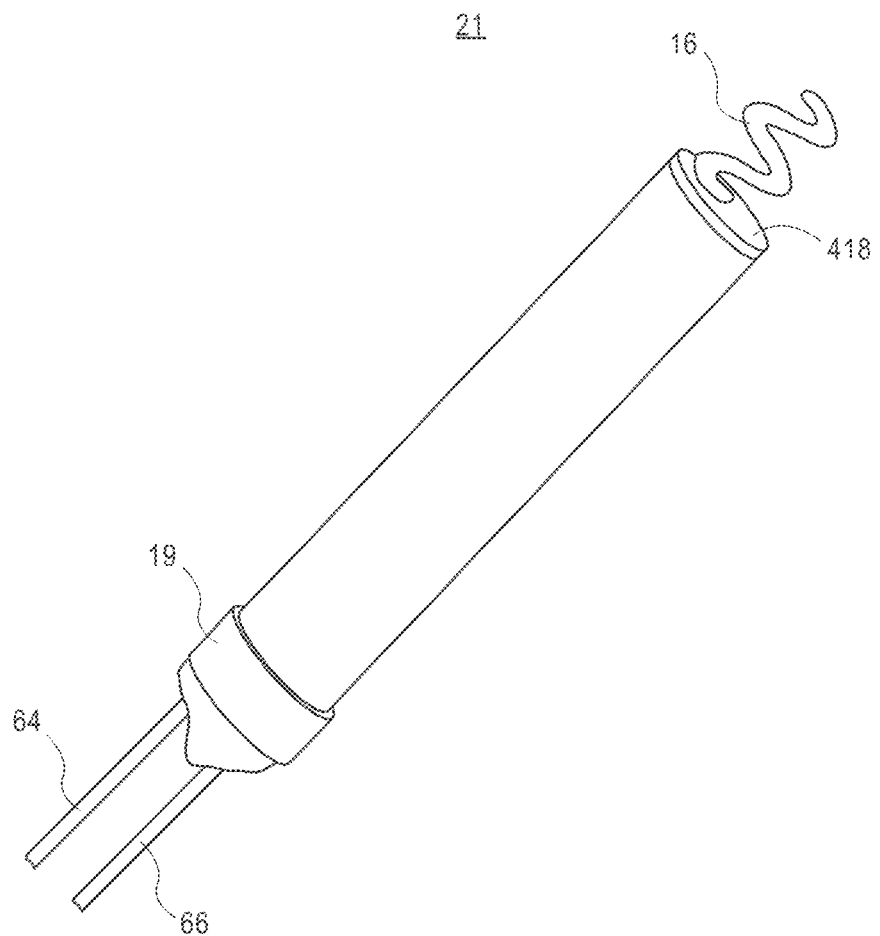
FIG. 5 is a partly fragmentary illustration of the distal end of the HIS bundle lead for use with the stimulation device of FIG. 4, depicting a tip electrode with an active fixation device and a non-traumatic conductive surface, and a ring electrode.

A more detailed illustration of the HIS bundle lead 21 is shown in FIG. 5. At the distal end of the lead 21 is the HIS bundle tip electrode 16. The HIS bundle tip electrode 16 is, or includes, an active fixation device, such as a helical, "screw-in," device that allows stable fixation of the electrode in the HIS bundle tissue.

The distal end of the HIS bundle lead 21 is further provided with a non-traumatic conductive surface (also referred to herein interchangeably as a mapping collar) 418. The non-traumatic conductive surface 418 is advantageously used to make electrical measurements that indicate the location of the HIS bundle without having to anchor the HIS bundle tip electrode 16 into the endocardial tissue. The non-traumatic conductive surface 418 and the HIS bundle tip electrode 16 are electrically coupled within the lead body of the HIS bundle lead 21 and together form one conductive element for the purposes of sensing, stimulation, and impedance measurements.

The HIS bundle lead 21 is also provided with a HIS ring electrode 19. The HIS ring electrode 19 is preferably spaced between approximately 2 mm and 30 mm, but preferably 10 mm, from the HIS tip electrode 16. The HIS ring electrode 19 may function as the return electrode during bipolar sensing, stimulation or impedance measurement operations.

The HIS tip electrode 16 and the HIS ring electrode 19 are each connected to flexible conductors 64, 66, respectively, which may run the entire length of the HIS bundle lead 21. The flexible conductor 64 is connected to the HIS tip electrode 16 and is electrically insulated from the flexible conductor 66 by a layer of insulation. The conductor 66 is connected to the HIS ring electrode 19. The flexible conductors 64, 66 serve to electrically couple the HIS ring electrode 19 and the HIS tip electrode 16 to the HIS ring electrode terminal 51 and the HIS tip electrode terminal 50, respectively. One embodiment of the HIS bundle lead 21 is available from St. Jude Medical CRMD as lead model No. 2088T.

Figure 6:
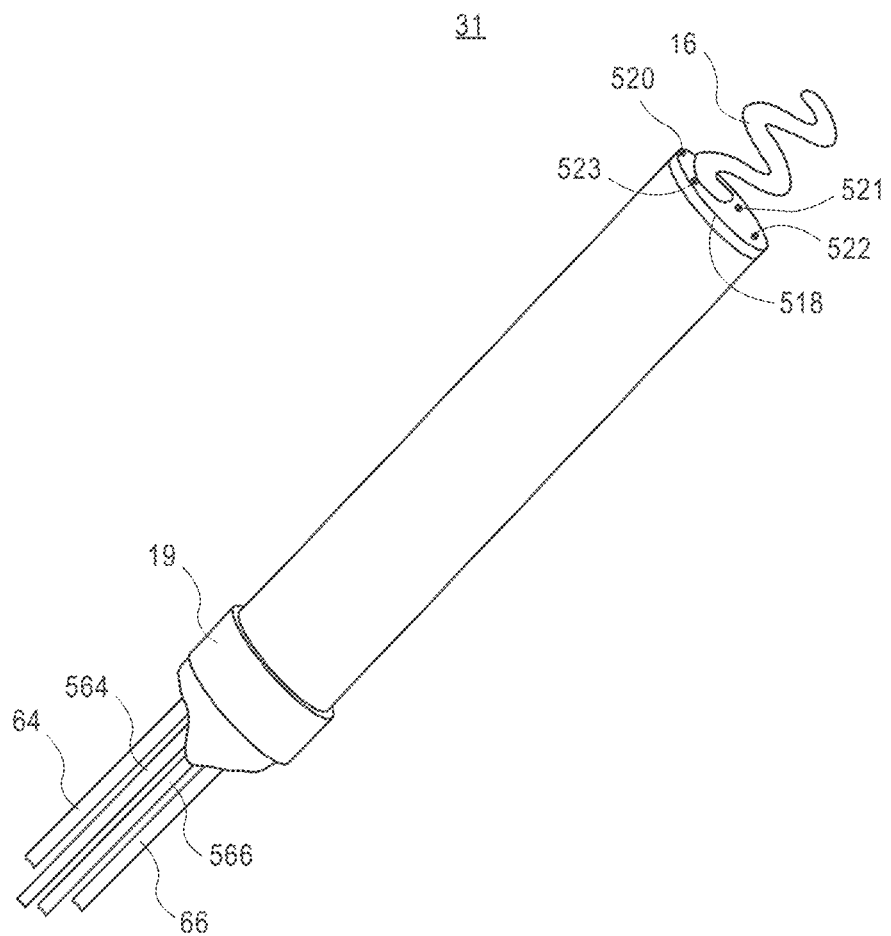
FIG. 6 is a partly fragmentary illustration of the distal end of another HIS bundle lead for use with the stimulation device of FIG. 4, depicting a tip electrode with an active fixation device and a non-traumatic conductive surface, a ring electrode, and four conductive sensing electrodes.

FIG. 6 illustrates an alternative HIS lead 31 that is generally similar in function and design to the HIS lead 21 shown in FIG. 5. The HIS lead 31 is provided with a HIS tip electrode 16 that includes multiple, round, closely-spaced conductive surfaces 520-523 that are arranged on a distal face 518 of the lead 31, directly facing the HIS bundle tissue. Though four round conductive surfaces 520-523 are shown as being uniformly distributed around the HIS tip electrode 16 and are electrically separated from each other by insulating material, it should be clear that a different number of conductive surfaces may alternatively be selected.

In one embodiment, a conductive surface, e.g. 520 is connected to a flexible conductor, e.g. 564 that extends along the length of the HIS bundle lead 31. The remaining conductive surfaces 521-523 are electrically connected together and are also connected to a flexible conductor 566 that extends along the length of the HIS bundle lead 31. The flexible conductors, e.g. 564, 566 are insulated from each other.

In the embodiment of FIG. 6 and with reference to FIG. 4, the device 10 includes two separate connection terminals, one for each of the two flexible conductors 564, 566 that are further connected to switch 74. The two flexible conductors 564, 566 can then be selectively connected as desired to the HIS sensing circuit 83, ventricular pulse generator 72, or impedance measuring circuit 112 for sensing, stimulating, and measuring tissue impedance at the site of the HIS bundle.

Using the lead 31, it is possible to effect stimulation with the HIS tip electrode 16 and the HIS ring electrode 19, and to effect sensing with the conductive surfaces 520-523. According to another design, the sensing is effected by the conductive surfaces 520-523 and stimulation is effected by means of the leads other than the HIS lead 31, for example the right atrial lead 20. For more details regarding a heart electrode equipped with multiple conductive surfaces, reference is made to U.S. Pat. Nos. 5,306,292 and 5,645,580, which are incorporated herein by reference.

During the implantation procedure, the HIS bundle lead 21 of FIG. 5 (or the HIS bundle lead 31 of FIG. 6) is introduced transvenously into the right atrium or below the valve inside RV. It is then gradually advanced with the HIS tip electrode 16 in contact with the endocardial tissue. Electrical measurements may be made continuously as the HIS tip electrode 16 is advanced to determine the location of the HIS bundle. The non-traumatic conductive surface 418 (helix not extended) advantageously provides electrical contact with the endocardial tissue thereby allowing electrical measurements to be performed without having to fix the HIS tip electrode 16 into the endocardial tissue using the HIS bundle tip electrode 16.

Figure 7:
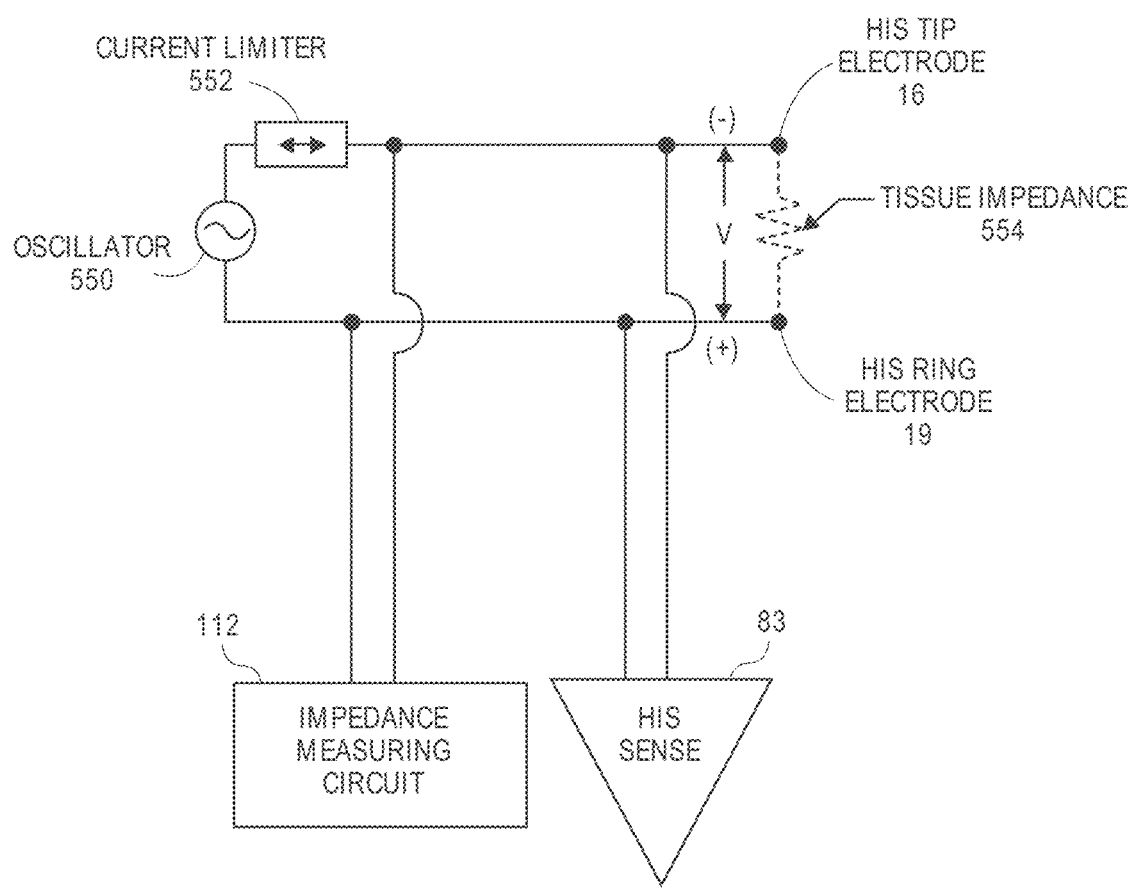
FIG. 7 is an equivalent circuit diagram illustrating a tissue impedance measurement method using the lead of FIG. 5 and the stimulation device of FIG. 4 for locating the HIS Bundle.

In one embodiment, a map of HIS signals and tissue impedance measurements are made in order to locate the HIS bundle. The equivalent circuit diagram depicted in FIG. 7 represents a model by which HIS signals and a tissue impedance measurement can be made using the HIS bundle lead 21 of FIG. 5. An excitation current is applied through the HIS tip electrode 16. A voltage signal can then be measured between the HIS tip electrode 16 (or the non-traumatic conductive surface 418) and the HIS ring electrode 19 in a bipolar fashion. The voltage signal is related to the supplied current and the tissue impedance 554 associated with the tissue in contact with the HIS tip electrode 16. Thus, the measured voltage signal is processed by the impedance measuring circuit 112 to determine the impedance of the tissue in contact with HIS tip electrode 16. The impedance equals the voltage divided by the current.

The HIS tip electrode 16 may then be secured in the HIS bundle thereby anchoring the HIS tip electrode 16 in contact with the HIS bundle tissue. The electrogram signal arising from the HIS bundle can then be received by the HIS sensing circuit 83. A bypass filter (not shown) that allows signals ranging from 30-200 Hz to be received may be used to block the high frequency alternating current excitation signal produced by the oscillator 550.

It should be appreciated that the HIS bundle leads and associated components illustrated in each of FIGS. 5 and 6 are provided merely as examples and should not be viewed as limiting this disclosure to requiring any particular type of lead. Rather, aspects of the present current disclosure may be implemented using any suitable HIS bundle lead capable of being implanted at or near the HIS bundle and providing pacing impulses to the HIS bundle.

Capture Threshold Testing

Stimulation devices in accordance with this disclosure may be configured to perform a capture threshold test to classify electrical impulses generated by the stimulation device based on characteristics of the response elicited by applying the electrical impulses to a patient's heart. Based on the classification, the stimulation device may then initiate and/or adjust its settings to provide optimal HBP.

Figure 8A:
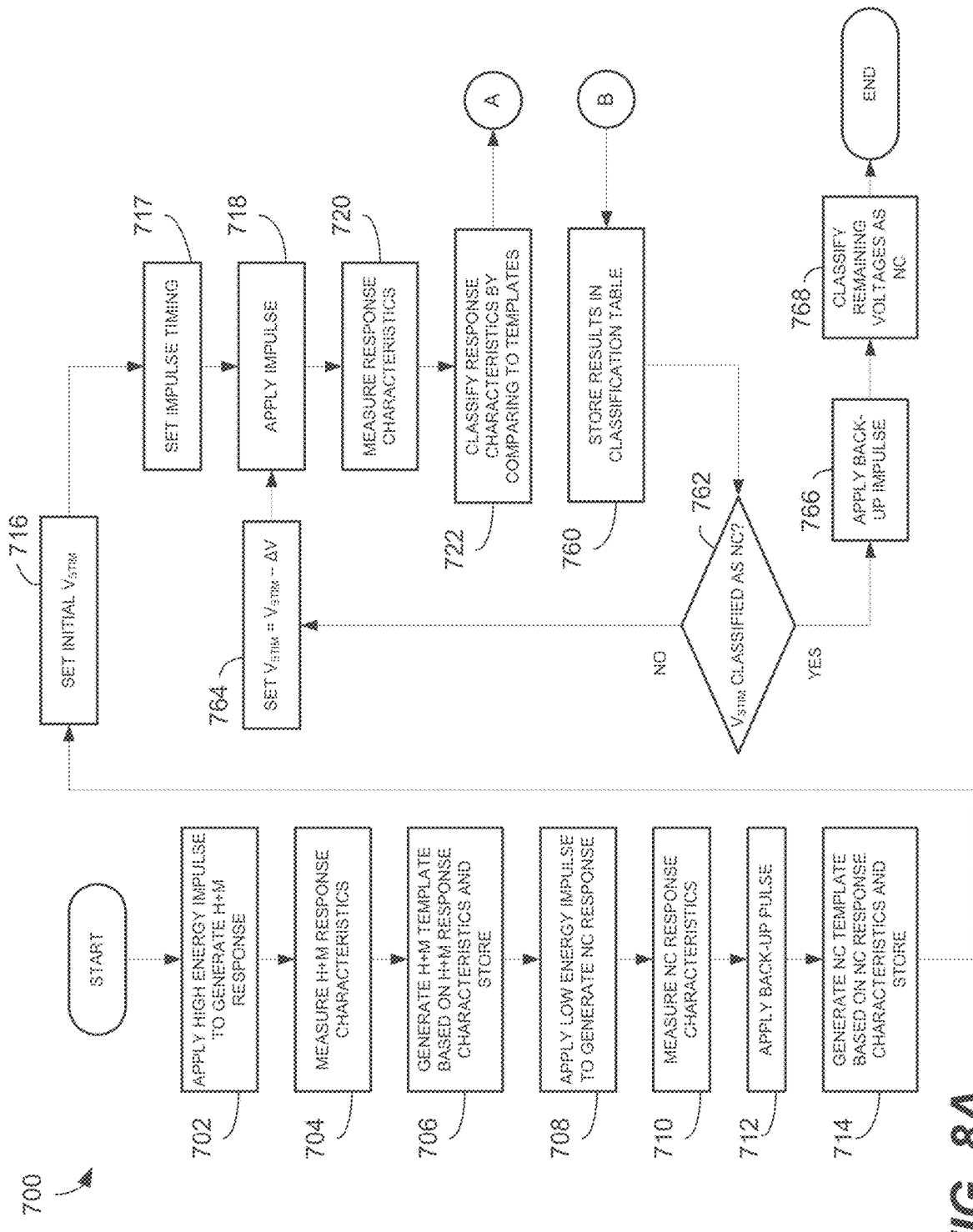
FIGS. 8A and 8B are a flow chart illustrating a method of performing a capture threshold test that may be implemented using the stimulation device of FIG. 2.
Figure 8B:
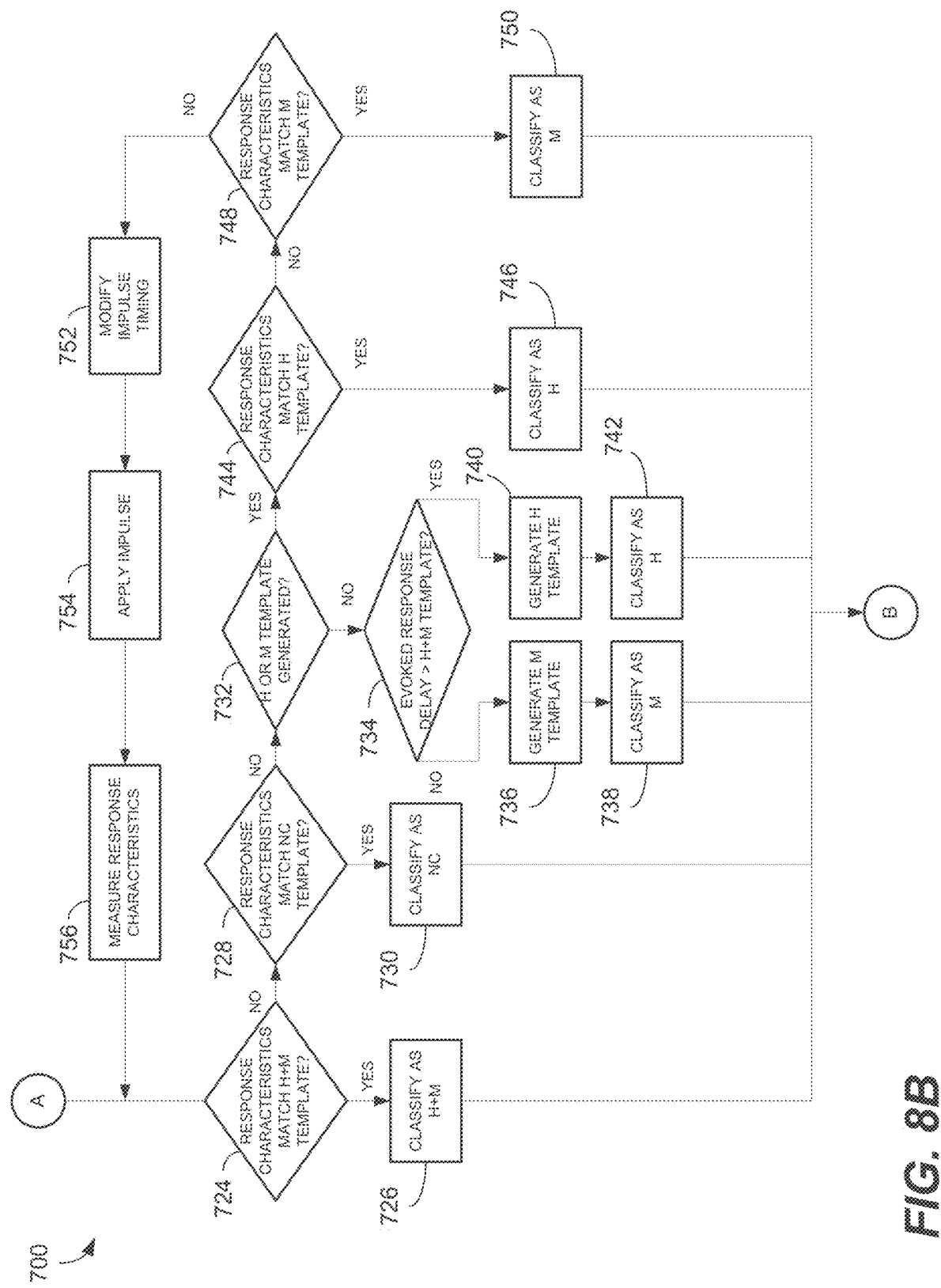

FIGS. 8A and 8B include a flow chart illustrating a method 700 for conducting a capture threshold test using a stimulation device, such as the stimulation device 10 of FIG. 4. The capture threshold test comprises applying a series of electrical impulses to the HIS bundle via a HIS tip electrode, such as the HIS tip electrode 16, and classifying the electrical impulses based on characteristics of the response of the heart tissue to the electrical impulse. Such response characteristics may be analyzed to determine if the applied electrical impulse resulted in capture of one or more of the HIS bundle and the right ventricle. In certain implementations, the capture threshold test illustrated in FIGS. 8A and 8B may be conducted manually by a physician, technician, or similar medical personnel that issues commands to the stimulation device 10, for example through the telemetry circuit 100 (shown in FIG. 4). In other embodiments, the capture threshold test may be implemented as a series of instructions stored within the memory 94 of the stimulation device 10 and executable by the programmable microcontroller 60 (also shown in FIG. 4).

Manual and automatic capture threshold testing may be performed at various times. For example, either of manual and automatic capture threshold testing in accordance with FIGS. 8A and 8B may be performed as part of one or more of implantation, implantation follow-up, and troubleshooting of the stimulation device 10. Automatic capture threshold testing may also be performed by the stimulation device 10 according to a predetermined schedule. For example, in certain implementations, automatic capture threshold testing may be performed by the stimulation device 10 at a regular frequency during times when the patient is asleep or otherwise inactive, such as on a daily basis during the late evening or early morning. The stimulation device 10 may also initiate automatic capture threshold testing in response to detecting specific events. For example, during regular operation, the stimulation device 10 may measure response characteristics of impulses delivered by the stimulation device 10 to determine whether the current settings result in HIS bundle capture. If not, the stimulation device 10 may initiate or schedule an automatic capture threshold test. In other implementations, the automatic capture threshold test may instead be initiated after a certain number of impulses fail to capture the HIS bundle or after similar criteria are met.

As discussed below in more detail below, the method 700 generally includes applying an impulse having a predetermined voltage and duration using the stimulation device 10, measuring response characteristics of the heart, and determining whether the response characteristics indicate capture of one, both, or neither of the HIS bundle and myocardium. The response characteristics may include, without limitation, the time between application of the impulse and onset of a corresponding QRS complex (referred to herein as the "evoked response delay") and the duration of the induced QRS complex. In certain implementations, the stimulation device 10 may generate and store one or more templates including values or ranges of values for response characteristics that are indicative of particular cardiac tissue being captured. For example, the stimulation device 10 may store templates corresponding to one or more of non-selective HBP (an "H+M" template), selective HBP (an "H" template), capture of the myocardium only (an "M" template), and non-capture of either the HIS bundle or right ventricle (an "NC" template).

The term "template" is used herein to refer to one or more values, sets or values, ranges, and the like, that may be used to identify or describe a particular type of capture. For example, a template may include one or more values or ranges of values for characteristics of a response to a pacing impulse. The template may also include values, ranges of values, series of values, etc., that more generally describe the shape or morphology of a given capture type. For example, the template may include a series of time and amplitude pairs derived from an electrogram or other measured response corresponding to a particular capture type. More generally, however, for purposes of this disclosure a template includes data to which a measured response to a pacing impulse may be compared for purposes of identifying a capture type.

Performing capture threshold testing generally includes each of sensing and pacing of heart tissues. For the purposes of the method 700, sensing includes sensing electrical activity of each of the HIS bundle and the myocardium. Such sensing may be accomplished using various electrode configurations and sensing vectors. Referring to FIG. 2, sensing vectors that may be used to measure electrical responses for the purposes of capture threshold testing may include, without limitation, those extending between the following pairs of electrodes: (i) the atrial tip electrode 22 and the stimulation device 10; (ii) the right atrial ring electrode 23 and the stimulation device 10; (iii) the right atrial tip electrode 22 and the right atrial ring electrode 23; (iv) the right ventricle coil electrode 36 and the stimulation device 10; (v) the SVC electrode 38 and the stimulation device 10; and (vi) the right ventricle coil electrode 36 and the SVC electrode 38. In implementations in which a left ventricular lead is present, additional possible sensing vectors include those extending between: (i) the right ventricle coil electrode 36 and a coil electrode of the left ventricular lead; (ii) the SVC coil electrode 38 and the left ventricle coil electrode; and (iii) the right ventricular tip electrode 32 and a ventricular tip electrode of the left ventricular lead. Similarly, application of pacing impulses to the HIS bundle may be accomplished in various ways depending on the particular configuration of the pacemaker or defibrillation device. For example, HIS bundle pacing may be achieved along a vector defined between any of the following pairs of electrodes: (i) the HIS tip electrode 16 and the stimulation device 10; (ii) the HIS ring electrode 19 and the stimulation device 10; and (iii) the HIS tip electrode 16 and the HIS ring electrode 19.

Referring now to FIG. 8A, the method 700 includes first generating each of an H+M template and an NC template, corresponding to non-selective HIS bundle capture and non-capture, respectively. Generation of the H+M template may include applying a high energy impulse predetermined to induce non-selective HIS bundle capture (operation 702), measuring characteristics of the corresponding response (operation 704), and generating and storing an H+M template based on the measured response characteristics (operation 706). As previously noted, the H+M template may include values or ranges of values corresponding to each of an evoked response delay and a QRS complex duration.

A similar series of steps may also be performed to generate the NC template. More specifically, a low energy impulse predetermined not to induce capture of either the HIS bundle or myocardium may be applied (operation 708) and the resulting response characteristics may be measured (operation 710). A back-up impulse may then be applied (operation 712). The back-up impulse is generally of a sufficient voltage and duration to capture at least the right ventricle, thereby facilitating beating of the heart despite the lack of capture during application of stimulation. After the back-up impulse is applied, the NC template may be generated and stored (operation 714).

FIG. 8A illustrates generation of each of the H+M and NC templates based on a single set of response characteristics obtained after a respective impulse is applied by the stimulation device 10. In other implementations, the H+M and NC templates may be generated by collecting multiple sets of response characteristics following multiple applications of high and/or low energy impulses, respectively. The collected sets of response characteristics may then be combined to generate each of the H+M and NC templates. Accordingly, the values or ranges of values for particular response characteristics stored within the H+M and NC templates may be based on one or more measurements and may include, without limitation, averages, ranges, and similar statistical values derived from multiple response characteristic measurements.

Following generation and storage of the H+M and NC templates, the stimulation device 10 applies impulses having different stimulation voltages. The resulting responses for each impulse are then measured, analyzed, and classified based on the cardiac tissue captured as a result of each impulse. For example, in the implementation illustrated in FIG. 8A, initial impulse stimulation voltage ($V_{STIM}$) and impulse timing are each set (operations 716, 717).

The initial $V_{STIM}$ is generally set to a high starting voltage from which classification is to begin. In certain implementations, the initial voltage value may be, without limitation, one of the maximum output voltage of the stimulation device 10, the voltage previously used to generate the H+M template in operations 702-706, and a voltage that is a predetermined step below the voltage used to generate the H+M template.

The initial impulse timing may vary based on the configuration and mode of the pacemaker or defibrillator device used. For example, in the presence of an atrial lead and ventricular tracking (e.g., "DDD" pacing), the HIS capture threshold test may be run with an AV delay short enough to prevent competition with intrinsic conduction. This can be achieved, for example, by first lengthening the atrial sensing-to-ventricular pacing delay (for example, to 200 ms) to determine the intrinsic conduction duration. If there is an inhibition of ventricular pacing then the atrial sensing-to-ventricular pacing delay may be shortened (for example to 100 ms) and tested again. If ventricular sensing occurs, then the atrial sensing-to-ventricular pacing delay may be further shortened, for example, to 50 ms. A similar procedure can be followed for ODD devices in which atrial pacing is implemented.

If the implemented device does not include atrial lead or is otherwise programmed to operate in a single chamber mode, such as a "WI" mode, the capture test should generally be performed at a rate that is faster than the underlying heart rate. This may be done by setting the base rate to a programmed base rate plus a predetermined rate increase (e.g., 10 ppm) for a predetermined time period (e.g., 30 seconds) and measuring the underlying rate. For example, measuring the underlying rate may be performed by calculating R-R intervals for heartbeats measured during the predetermined time period. If there is no inhibition of ventricular pacing due to ventricular sensing, then the base rate may be set at the programmed base rate plus the predetermined rate increase. In alternative implementations, each of an average R-R interval and standard deviation may be determined over a predetermined time period and the base rate may be calculated based on a heart rate calculated from the R-R interval plus a factor based on the standard deviation. For example, in certain implementations, a heart rate may be calculated using the formula $HR_{AV}=60000/(R-R\ interval)$, where the R-R interval is measured in milliseconds. The ventricular pacing rate may then be set to $HR_{AV}+3*$standard deviation (ppm). In certain implementations, the process of determining the base rate may be repeated to eliminate spurious results caused by fusion.

After establishing the initial impulse timing and $V_{STIM}$ settings, the stimulation device 10 then initiates the capture test by applying an impulse (operation 718) and measuring the resulting response characteristics (operation 720).

Referring to FIG. 8B, the impulse is then classified by analyzing the response characteristics measured during operation 720. In general, the process of classifying the response characteristics includes comparing the response characteristics to values or ranges of values to determine whether the response characteristics indicate capture of one or more of the HIS bundle and the right ventricle. For example, in certain implementations, the response characteristics are compared to templates stored within the stimulation device 10, such as the H+M and NC templates generated during operations 706 and 714, respectively. In instances when the template includes a range of values, determining whether a particular measured response characteristic indicates capture of certain cardiac tissue generally includes determining whether the measured response characteristic falls within the range of values. In contrast, when the template includes a single value, determining whether the measure response characteristic indicates capture may include determining whether the measured response characteristic falls within a certain tolerance of the stored value. For example, a match may be considered to occur when the measured response characteristic is within one or more of an absolute tolerance, a percentage-based tolerance, and a particular number of standard deviations (if the stored value was obtained from multiple measurements).

As shown in FIG. 8B, the response characteristics may first be compared to the H+M template (operation 724) to determine whether the response characteristics correspond to non-selective capture of the HIS bundle (e.g., capture of both the HIS bundle and the myocardium). If so, $V_{STIM}$ is classified as inducing non-selective capture ("H+M") (operation 726) and the classification is stored or otherwise recorded (operation 760), such as in a classification table maintained in the memory 94 of the stimulation device 10.

For purposes of this disclosure, a classification table refers to a table or similar data structure maintained within the memory 94 of the stimulation device 10. The classification table includes multiple classification table entries that include a stimulation voltage and data corresponding to the stimulation voltage. The data may include, without limitation, one or more of a classification assigned during the automatic threshold capture test for the particular stimulation voltage and response characteristics generated by application of the particular stimulation voltage. Entries within the classification table may further be based on particular combinations of stimulation voltages and pulse durations such that each entry within the classification table corresponds to a unique combination of impulse voltage and duration. For ease of searching and analysis, the classification table may be organized or indexed in an ascending or descending order based on voltage/power. As described further in the context of FIG. 9, the classification table may be accessed by the microcontroller 60 of the stimulation device 10 to determine and change control output settings of the stimulation device 10.

If the response characteristics do not correspond to the H+M template, they are then compared to the NC template (operation 728). If the response characteristics correspond to those of the NC template, $V_{STIM}$ is classified as resulting in non-capture ("NC") (operation 730) and the classification results are stored in the classification table (operation 760). In certain implementations, an additional check may be performed to determine whether $V_{STIM}$ resulted in non-capture (operation 762). If capture occurred, $V_{STIM}$ may be updated (operation 764) and the process of applying an impulse using the updated $V_{STIM}$ and classifying the resulting response may be repeated. In the implementation illustrated in FIGS. 8A and 8B, for example, $V_{STIM}$ is decreased by a predetermined voltage change (AV). AV may be any suitable increment by which the output of the stimulation device 10 may be changed. Using a higher value for AV generally leads to a faster capture threshold test as fewer voltage levels of the stimulation device 10 are required to be tested. In contrast, a more granular AV may be used to increase the precision of the capture threshold test and, as a result, more accurately determine the voltage levels at which capture of particular cardiac tissues occur or are lost.

If application of an impulse at a particular $V_{STIM}$ results in non-capture, a back-up impulse may be applied (operation 766). Also, because any subsequent lower voltages are also likely to result in non-capture, any remaining voltage levels yet to be tested that are below $V_{STIM}$ may automatically be classified as NC within the classification table (operation 768).

Referring back to FIG. 8B, in certain instances, the response characteristics may not correspond to values representative of either of the H+M template and the NC template. In such instances, the response characteristics may be further analyzed to determine whether they indicate the occurrence of selective HBP, in which only the HIS bundle is captured, or ventricular pacing, in which only the right ventricle is captured. To do so, the response characteristics may be compared to values or ranges of values, which may be stored as additional templates and, more specifically, as a selective HBP ("H") template and a myocardium only ("M") template. Accordingly, and as illustrated in FIG. 8B, a check may be performed to determine whether either of an H template or an M template has been generated (operation 732). If so, the response characteristics may be compared to the H or M templates (operations 744 and 748, respectively) and, if a match exists, the current $V_{STIM}$ may be classified accordingly (operations 746 and 750, respectively). The classification may then be stored in the classification table (operation 760).

If an H or M template does not currently exist, the response characteristics may be analyzed to determine whether they correspond to either selective HBP or to ventricular pacing and an H or M template may be generated. To do so, the QRS duration and the evoked response delay of the response characteristics may be compared to those of the H+M template. If the QRS duration is longer than that of the H+M template but the evoked response delay is approximately equal to that of the H+M template, it is likely that the current response characteristics are indicative of ventricular capture. Alternatively, if the QRS duration is approximately equal to that of the H+M template and the evoked response delay is longer, it is likely that the response characteristics correspond to selective HBP. In FIG. 8B, this process is simplified by determining whether the evoked response delay exceeds that of the H+M template. Accordingly, based on the outcome of the comparison, either a myocardium only capture (M) template or a selective HBP template (H) may be generated based on the response characteristics (operations 736, 740) and the response characteristics may be classified accordingly (operations 738, 742). The resulting classification may then be stored in the classification table (operation 760).

Due to various factors, which may include the physiology of the heart and the location of stimulating electrodes, the method 700 may generate only one of the H and the M template. More specifically, heart physiology generally dictates one of two capture sequences as impulse energy is reduced. In the first sequence, high energy impulses result in non-selective HBP in which both of the HIS bundle and right ventricle are captured. As impulse energy is reduced, selective HBP occurs resulting from capture of the HIS bundle only. As impulse energy is further reduced, neither the HIS bundle or the right ventricle is captured. In the second sequence, high energy impulses similarly result in non-selective HBP. However, as impulse energy is reduced, only the right ventricle is captured and, as impulse energy is further reduced, non-capture results. As a result, if the physiology of the patient's heart conforms to the first sequence, only an H template is likely to be generated and if the physiology of the patient's heart results in the second capture sequence, a V template will be generated.

A number of scenarios may occur where the response characteristics do not match any of the generated templates. Such situations may include what are referred to herein as fusion, pseudo-fusion, and hemi-capture. Fusion occurs when conduction resulting from the impulse delivered during operation 718 coincides with the intrinsic conduction of the patient's heart. In contrast, pseudo-fusion occurs when an ineffective impulse is delivered during the absolute refractory period. In each of fusion and pseudo-fusion, the response characteristics resulting specifically from the impulse cannot be readily distinguished from the intrinsic response of the heart. Finally, hemi-capture occurs when the impulse results in capture of only one of the right bundle fibers and the left bundle fibers of the HIS bundle, leading to incomplete electrical communication between the HIS bundle and the ventricles.

To discriminate between fusion, pseudo-fusion, and hemi-capture, the timing of the impulse may be varied (operation 752). More specifically, the delay between sensing electrical activity and delivering an impulse to the HIS bundle is varied from the timing implemented during operation 718. For example, in implementations including each of an atrial lead and a HIS bundle lead, the timing between sensing electrical activity of the atrium (e.g., by observing a P wave) and applying an impulse to the HIS bundle may be increased or decreased by a predetermined interval. The impulse is reapplied using the new timing (operation 754) and a new set of response characteristics are measured (operation 756). The process of classifying the new response characteristics then proceeds to determine whether the new timing has resolved the inability to classify the original response characteristics. Subsequent storage of a classification table entry in the classification table (during operation 760) may further include storing the modified timing.

In certain implementations, the new response characteristics obtained using the modified timing are compared with the response characteristics originally obtained during operation 720 to provide further information and, more specifically, to identify whether the inability to classify the original impulse was the result of fusion, pseudo-fusion, or hemi-capture. If the response characteristics obtained using the modified timing are consistent with the originally obtained response characteristics, hemi-capture is likely. More specifically, if the evoked response delays and/or QRS complex morphology are consistent, it is likely that electrical impulses are unable to properly proceed through one of the left and right HIS bundle fibers. Similarly, comparison of the new and original response characteristics may identify the occurrence of pseudo-fusion and/or fusion. For example, if the timing between atrial sensing and HIS bundle pacing is increased, and the resulting response characteristics indicate consistent QRS morphology but a reduced evoked response delay, pseudo-fusion likely occurred. In contrast, if QRS morphology differs between the modified and original timing, fusion likely occurred.

Data corresponding to the identification and detection of fusion, pseudo-fusion, and hemi-capture may be stored within the memory 94 of the stimulation device 10 for later retrieval and diagnostic analysis. For example, in certain implementations, the stimulation device 10 may generate and store a log in which data corresponding to fusion, pseudo-fusion, hemi-capture, and similar events is recorded. Such data may include, without limitation, a date/time stamp, the response characteristics corresponding to the event, the stimulation device settings that resulted in the event, and the stimulation device settings that circumvented the event.

If response characteristics obtained using modified impulse timing is still unable to be classified, the impulse timing may be further modified and another set of response characteristics may be obtained and analyzed to determine whether classification is possible. In certain implementations, the number of times that the impulse timing is modified may be limited such that after the limit is exceeded, the current $V_{STIM}$ is classified as resulting in non-capture. Also, to the extent the response characteristics measured during operation 756 indicate non-capture of a portion of the heart tissue, a back-up impulse may be delivered.

Initialization of Stimulation Devices for HBP

Figure 9:
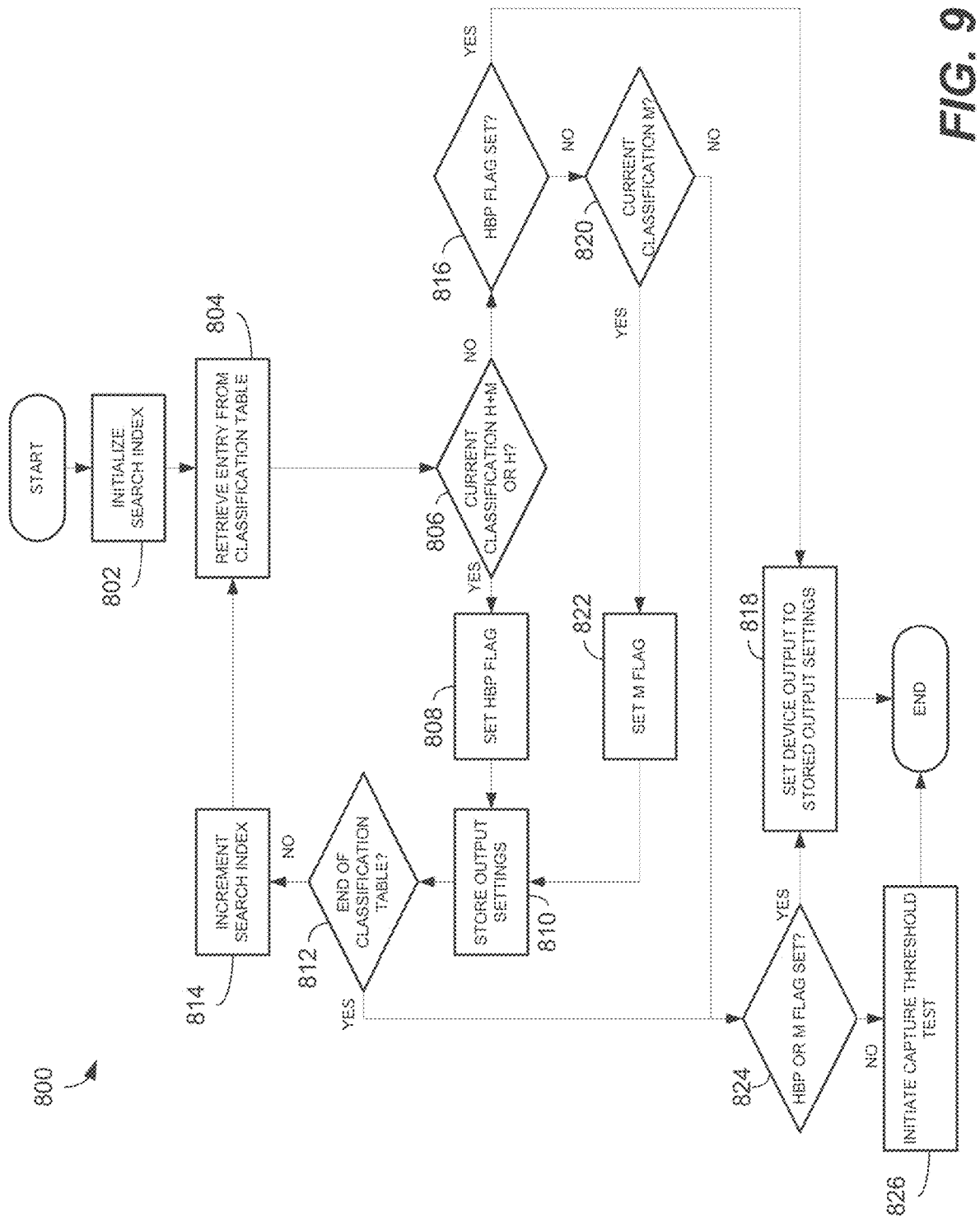
FIG. 9 is a flow chart illustrating a method for initializing a stimulation device, such as the stimulation device of FIG. 2.

FIG. 9 is a flow chart illustrating a method 800 of initializing output settings of a stimulation device, such as the stimulation device 10. In certain implementations, initialization of the stimulation device 10 includes identifying the lowest energy impulse capable of capturing the HIS bundle, regardless of whether capture of the HIS bundle is selective or non-selective. In the event that HIS bundle capture is not possible, initialization further includes identifying the lowest energy impulse capable of capturing the myocardium. If such capture is not possible, backup pacing may be applied and a capture threshold test may be initiated.

During initialization, the stimulation device 10 and, more specifically, the microprocessor 60 of the stimulation device 10, determines and applies initial output settings. In certain implementations, the microprocessor 60 may search or otherwise analyze data stored in the memory 94 of the stimulation device 10 to determine the initial output settings. For example, the memory 94 may store a classification table including entries that form a list of possible output settings of the stimulation device 10 and corresponding classifications for the responses generated by applying an impulse according to the output settings. For purposes of the method 800, the output settings generally correspond to a HIS bundle electrode adapted to provide pacing of the HIS bundle, however, in configurations in which other pacing electrodes are implemented, additional output settings for pacing of other heart tissue may further be loaded by the stimulation device 10 during the initialization process.

The method 800 assumes that a classification table has been created that includes an ordered list of output settings arranged by output energy and that each entry in the classification table is associated with an index. The method 800 further assumes that the classification table is arranged or indexed such that as the search index is incremented, the classification table entries that are retrieved and analyzed correspond to progressively lower output settings. Accordingly, the method 800 includes initializing a search index (operation 802) and retrieving an entry corresponding to the index from the classification table (operation 804).

The retrieved record is then analyzed to determine whether the entry corresponds to settings that were previously classified (such as during the threshold capture test illustrated in FIGS. 8A and 8B) as evoking either non-selective (H+M) or selective (H) HIS bundle capture (operation 806). If the output settings of the current classification table entry resulted in HIS bundle capture, a flag (HBP flag) is set indicating that an HBP-suitable setting has been identified (operation 808) and the output settings are stored as potential output settings of the stimulation device 10 (operation 810). If the current index does not correspond to the end of the classification table (operation 812), the search index is incremented (operation 814), and the process of retrieving and analyzing the corresponding classification table entry is repeated. To the extent subsequent classification table entries are also classified as either H or H+M, the temporarily stored settings will continue to be updated to reflect the lowest power settings for which HIS bundle capture was identified.

If the current classification table entry is not classified as either H or H+M, a check is performed to determine whether the HBP flag has been set (operation 816). In other words, a check is performed to determine whether output settings are currently stored that result in capture of the HIS bundle. If the HBP flag is set, the stored settings are applied to the stimulation device 10 (operation 818) and the initialization process ends. In certain implementations, application of the stored settings to the stimulation device 10 includes setting the output setting of the stimulation device 10 to match the stored output settings. In other implementations, the output settings of the stimulation device 10 may correspond to the stored output settings augmented by a safety factor. The safety factor may include, without limitation, one or more of a quantity added to one or more of the stored output settings or a factor by which one or more of the stored output settings are multiplied.

If, on the other hand, the HBP flag has not been set, the implication is that no output settings were identified that resulted in HIS bundle capture. A check is then performed on the current classification table entry to determine whether it has been classified as resulting in myocardium-only capture (M) (operation 820). If so, a corresponding flag (M flag) is set (operation 822), the output settings corresponding to the current classification table entry are stored (operation 810), and the search index is incremented (operation 814). To the extent any subsequent classification table entries are also classified as M, the stored output settings will be updated such that the stored output settings reflect the lowest output settings capable of ventricular capture.

When the end of the classification table is reached (as determined by operation 812) or the current classification table entry is not classified as any of H, H+M, or M (as determined by operation 820), a check is performed to determine whether either of the HBP or M flags have been set (operation 824), thereby checking whether output settings have been stored. If so, the output settings of the stimulation device 10 (operation 818) are set to the stored output settings and the initialization process ends.

If neither of the HBP or the M flag has been set, then the initialization process failed to identify any settings capable of capturing either the HIS bundle or ventricle and remedial measures may be initiated. For example, in the method 800, a capture threshold test, such as the capture threshold test illustrated in FIGS. 8A and 8B, may be initiated to generate an updated classification table. In certain implementations, capture threshold testing may also be initiated upon determining that the classification table does not include any entries classified as resulting in HIS bundle capture (i.e., H+M or H).

Operation of Stimulation Devices for HIS Bundle Pacing

Figure 10:
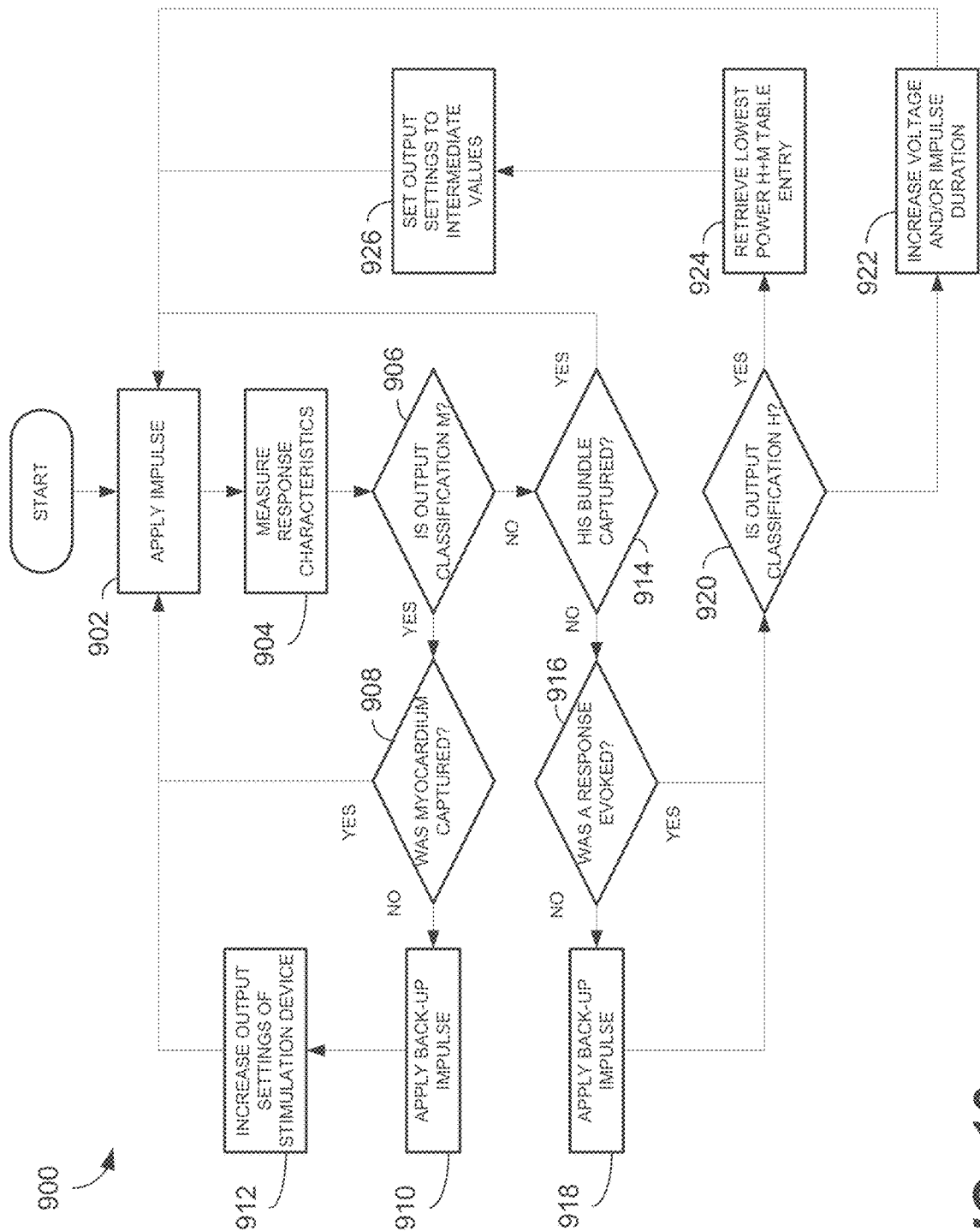
FIG. 10 is a flow chart illustrating a method for operating a stimulation device, such as the stimulation device of FIG. 2.

FIG. 10 illustrates a method 900 of operating a stimulation device 10 subsequent to the initialization process illustrated in FIG. 9. In general, operation of the stimulation device 10 includes applying an impulse based on the current output settings of the stimulation device 10, measuring response characteristics resulting from application of the impulse, and determining whether the response characteristics are consistent with the classification associated with the output settings of the stimulation device 10. To the extent the response characteristics are inconsistent with the classification, the output settings of the stimulation device 10 are modified for the subsequent impulse. The method 900 presumes that the output settings of the stimulation device 10 have been initialized. Initialization of the output settings may include executing an initialization process, such as that illustrated in FIG. 9, or may include loading previously stored output settings.

The method 900 includes applying an impulse (operation 902) according to the settings applied during initialization and measuring the corresponding response characteristics (operation 904). Following measurement of the response characteristics, a check is performed to determine whether the current output settings were previously classified as inducing myocardium-only capture (M) (operation 906). If so, a subsequent evaluation of the response characteristics is performed to determine whether the myocardium was capture (operation 908). Evaluation of the response characteristics may include comparison of the response characteristics to one or more templates including values or ranges of values indicative of myocardium-only capture. Such templates may, for example, be generated as part of a capture threshold test, such as the capture threshold test illustrated in FIGS. 8A and 8B.

If the response characteristics are consistent with myocardium-only capture, the operational loop is reinitiated by applying a subsequent impulse using the existing output settings. If, on the other hand, the myocardium was not captured, a back-up impulse may be applied (operation 910) and the output settings of the stimulation device 10 may be increased (operation 912). Increasing the output settings of the stimulation device 10 may include, without limitation, increasing one or both of the output voltage and pulse duration settings of the stimulation device 10. Increasing an output setting may include, without limitation, one or more of increasing the output setting by a predetermined amount, multiplying the output setting by a predetermined factor, or modifying the output setting based on settings data stored within a classification table. In implementations in which the output settings are modified based on a classification table, such modification may include identifying the next highest output setting classified as resulting in myocardium-only capture and setting the output settings of the stimulation device 10 to the next highest output setting. Alternatively, the output settings of the stimulation device 10 may be set to an average or weighted average of the current and next highest output settings.

If the output settings of the stimulation device 10 are not classified as myocardium-only capture, a subsequent check may be performed to determine if the impulse resulted in capture of the HIS bundle (operation 914). If the HIS bundle was captured, the operational loop may be reinitiated. Alternatively, a check may be conducted to determine whether the impulse evoked a response (operation 916), such as a QRS complex, by analyzing the response characteristics. In the event the impulse did not produce a response, a back-up impulse may be applied to ensure a heartbeat (operation 918).

Whether a response was evoked by the original impulse or the back-up impulse, the original impulse is then modified in an attempt to adjust the output settings to result in HIS bundle capture. Generally, modifying the output settings involves increasing at least one of the output voltage or impulse duration, thereby increasing the overall energy of the impulse. As previously discussed in the context of myocardium-only capture, modification of the output settings of the stimulation device 10 may include, without limitation, one or more of increasing an output setting of the stimulation device 10 by a predetermined amount, multiplying the output setting by a predetermined factor, or modifying the output setting based on settings data stored within a classification table.

In certain implementations, the type of modification applied to the output settings may vary based on the classification assigned to the original output settings of the stimulation device 10. For example, in the method 900 a check is performed to determine whether the initial output settings were classified as resulting in selective HIS bundle capture (H) (operation 920). If not, the method 900 assumes the original classification corresponded to non-selective HIS bundle capture (H+M) and one of the voltage and impulse duration is increased by a predetermined amount (operation 922). If, on the other hand, the original output settings were classified as H, a more complex modification is undertaken. Specifically, the lowest power entry in the classification table resulting in non-selective HIS bundle capture is identified and retrieved (operation 924). The output settings of the stimulation device 10 are then changed to an intermediate value between the current output settings and those corresponding to the lowest power H+M table entry (operation 926).

In certain implementations, the stimulation device 10 may be configured to initiate a capture threshold test if certain one or more criteria are met. For example, in one implementation, the stimulation device 10 may initiate a capture threshold test instead of increasing the output setting (i.e., replace operation 912 with a capture threshold test). In other implementations, the stimulation device 10 may count or evaluate the number of loss of capture events or applied backup impulses and initiate a capture threshold test when the number of loss of capture events exceeds a predetermined quantity. In still other implementations, the capture threshold test may be initiated based on changes to the output setting of the stimulation device 10. For example, a capture threshold test may be initiated when the output settings have been increased a predetermined number of times or cumulatively increased by more than a predetermined amount.

After modification of the output of the stimulation device 10, the process of applying an impulse based on the current settings of the stimulation device 10, measuring corresponding response characteristics, and analyzing the response characteristics to determine if they are consistent with the output setting classification are repeated. In certain implementations, failure to capture the HIS bundle may automatically trigger initiation of a capture threshold test, such as the capture threshold test illustrated in FIGS. 8A and 8B.

The methods illustrated in FIGS. 8A and 8B are example methods in which sensing and stimulation are applied primarily to the HIS bundle and the right ventricle. In other implementations in accordance with this disclosure, other heart tissue may be sensed and stimulated instead of or in addition to the right ventricle. Such heart tissue may include, without limitation, one or more of the right atrium, the left atrium, and the left ventricle. For example and with reference to FIGS. 8A and 8B, in certain implementations, the "M" template may correspond to a response of any of the left ventricle, the right atrium, the left atrium, or portion of the myocardium corresponding to tissue other than that of the right ventricle. Alternatively, in addition to the "M" template corresponding to a response of the myocardium of the right ventricle, additional templates may be generated for the myocardium of one or more of the left ventricle, the right atrium, and the left atrium. In either case, the templates corresponding to the left ventricle, the right atrium, and the left atrium may be used instead of or in conjunction with a template corresponding to the right ventricle for purposes of classifying impulses (for example, as illustrated in FIGS. 8A and 8B) and dynamically controlling an implantable cardiac stimulating device (for example, as illustrated in FIG. 10).

Implantable cardiac stimulating devices in accordance with this disclosure may also store data related to their operation and may make such data available for retrieval and analysis. For example, and referring to the stimulation device 10 depicted in FIGS. 2 and 4, data may be collected and stored by in the memory 94 and made available to one or more external devices, such as the external device 102, using the telemetry circuit 100. In certain implementations, data made available from the stimulation device 10 may include, without limitation, any templates generated and/or stored within the stimulation device for classifying impulse responses, classification tables used to initialize settings of the stimulation device 10, and one or more logs used to record one or both of device activity and cardiac activity. Such data may be recorded over time to facilitate identifying trends that may correspond to changes in the stimulation device 10 or components thereof or the cardiac tissue to which the stimulation device 10 is coupled. For example, such trend data may include a summary diagnostic that may include a count or percentage of selective and non-selective HIS bundle pacing events over a period of time. As another example, such data may include measurements of the capture threshold over time, which may be used to identify improvement or degeneration of heart tissue based on whether the capture threshold is decreasing or increasing over time, respectively.

Determination of QRS Duration

In implementations in accordance with this disclosure, the stimulation device 10 captures and analyzes electrical activity of the heart for various purposes. For example, in the method 700 of FIGS. 8A and 8B, response characteristics produced by applying an impulse to the heart are measured during various operations (for example, each of operations 704, 710, and 720). One characteristic that may be determined and used to evaluate whether HIS bundle capture has occurred and whether the capture is selective of non-selective is the duration of the QRS complex produced subsequent to the application of an impulse by the stimulation device 10. Accordingly, stimulation devices in accordance with this disclosure may be able to determine the duration of a QRS complex using various methods.

Figure 11:
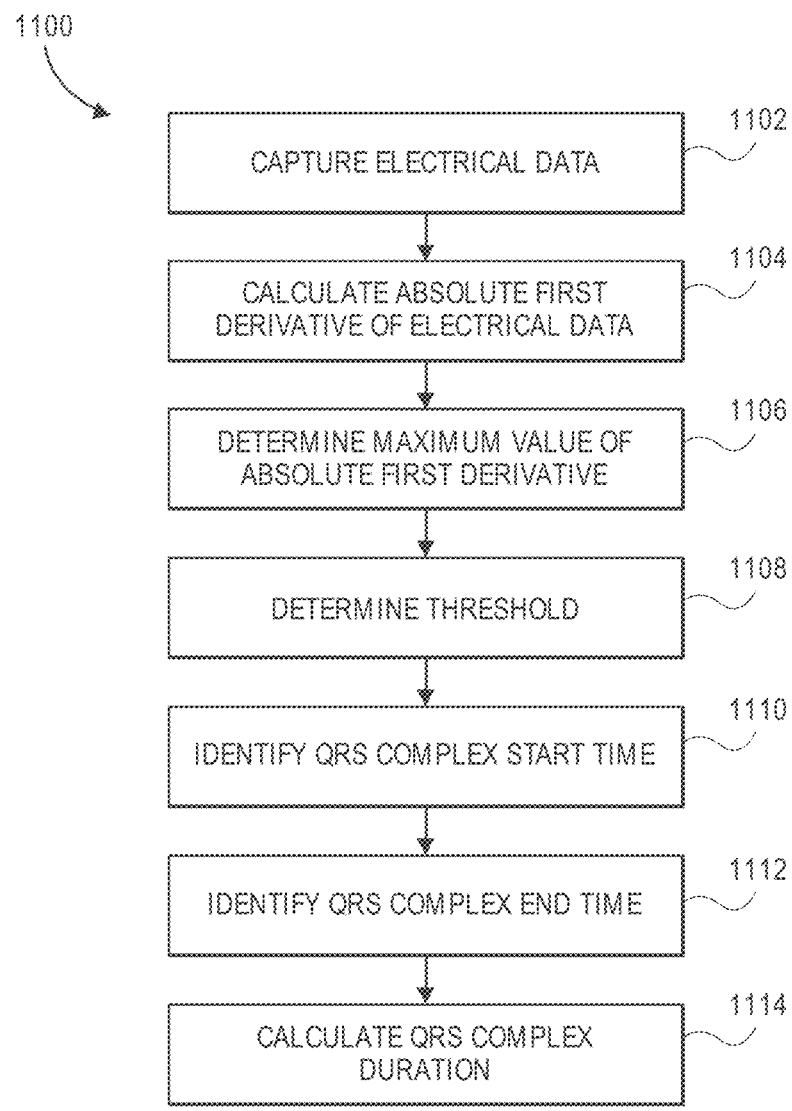
FIG. 11 is a flow chart illustrating a method for determining QRS complex duration.
Figure 12A:
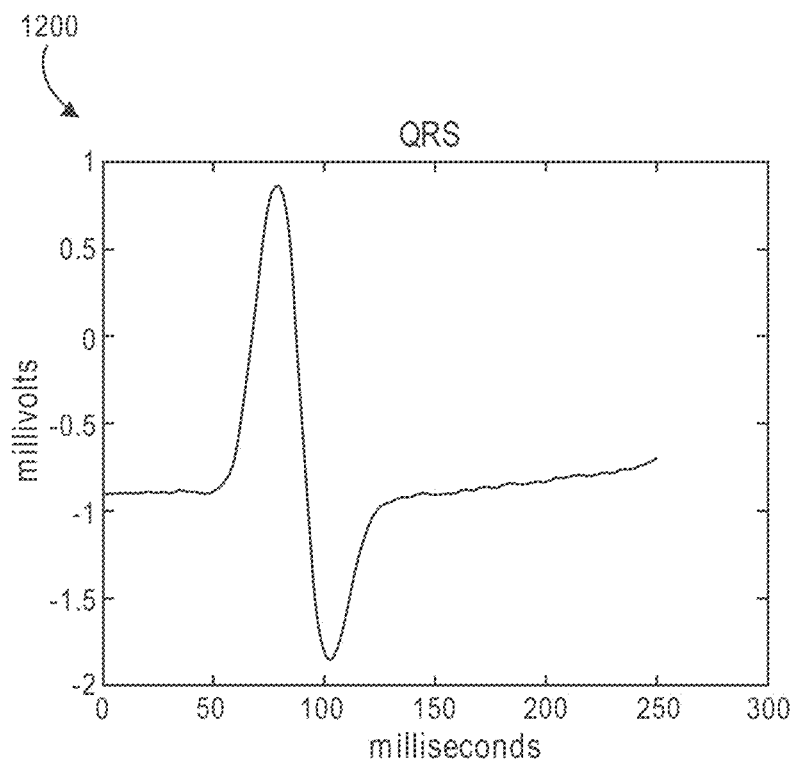
FIGS. 12A and 12B are graphs of example electrical data for illustrating the method of FIG. 11.

FIG. 11 is a flow chart describing an example method 1100 for determining QRS complex duration. Generally, the method 1100 involves identifying each of a start time and end time of the QRS complex and then determining the length of the interval between the start and end times. To do so, the method 1100 includes capturing electrical data (operation 1102), the electrical data corresponding to a cardiac response, such as a QRS complex, following application of an electrical impulse from a stimulation device. For example, the stimulation device may be configured to sample signals from sensing electrodes for a predetermined time period (e.g., 300 ms) following application of an impulse by the stimulation device and to store the sampled data. An example of such collected data is illustrated in FIG. 12A, which depicts a graph 1200 including millivolt readings over time corresponding to a QRS complex following application of an electrical impulse to cardiac tissue.

Figure 12B:
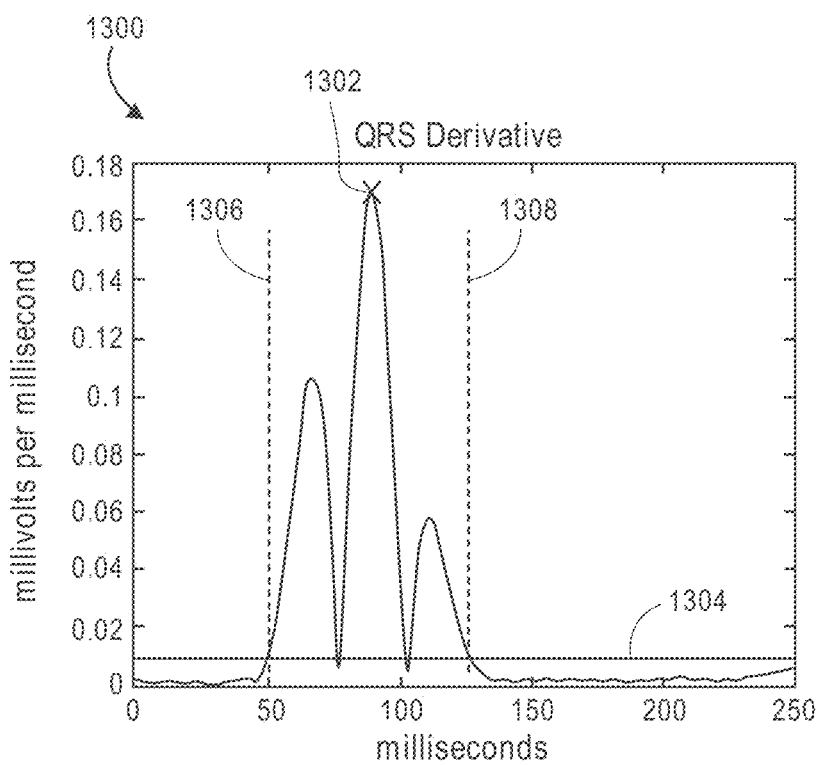

After receiving the electrical data, the data may be processed and analyzed to determine the duration of the QRS complex. In the method 1100, for example, the absolute value of the first derivative of the electrical data is taken (operation 1104) such that an absolute rate of change of the electrical readings may be determined. The graph of FIG. 12B is a graph 1300 of the absolute first derivative of the electrical data of FIG. 12A and, as a result, depicts the absolute rate of change of the electrical activity (in millivolts (mV)/ms) over time.

The duration of the QRS complex may be determined from the absolute first derivative data in various ways. For example, in certain implementations, the maximum value of the absolute first derivative is identified (operation 1106). In the example data of FIGS. 12A and 12B, the maximum absolute first derivative is 0.17 mV/ms and occurs at approximately 90 ms and is indicated by an "X" 1302. Next, a threshold value may be calculated based on the maximum value (operation 1108). The threshold value is generally selected to distinguish between possible noise or similar transients in the electrical signal and the actual electrical response of the cardiac tissue to the impulse and, as a result, may vary from application to application. In the current example, however, the threshold value is calculated as 5% of the maximum absolute first derivative, or approximately 0.0085 mV/ms, which is indicated in the graph 1300 by a threshold line 1304.

After establishing the threshold, the start time of the QRS complex is determined (operation 1110). In the current example, the absolute first derivative values are compared to the threshold beginning at the time the impulse was applied (t=0ms). The start time of the QRS complex is then identified as the time at which the absolute first derivative value first crosses the threshold 1304. In the example illustrated in FIG. 12B, this occurs at approximately 50 ms and is indicated by a first dashed line 1306. The end time of the QRS complex may then be determined in a similar process (operation 1112). More specifically, the absolute first derivative values are compared to the threshold beginning at the end of the sampled data (i.e., t=250 ms). The end time of the QRS complex is then identified as the time at which the absolute first derivative value of the electrical signal crosses the threshold 1304, which is indicated in the graph 1300 with a second dashed line 1308. Referring again to the example in FIG. 12B, the QRS complex end time occurs at approximately t=127 ms. The QRS duration may then be calculated (operation 1114), for example, by determining the difference between the QRS complex start time and the QRS complex end time and which in the example is approximately 77 ms. The calculated QRS complex duration may then be used to perform various evaluations and analyses as previously described herein including, but not limited to, the creation of templates and classification of impulse responses.

Beat-to-Beat HIS Bundle Pacing Using Time Domain Analysis

As previously noted, pacing of the HIS bundle may result in different responses identified by the particular tissue activated by the pacing impulse. For example, selective capture refers to when pacing of the HIS bundle results in capture of the HIS bundle only and propagation of the pacing impulse occurs using the heart's natural pathways. In contrast, non-selective capture refers to capture of both the HIS bundle and local myocardium. Finally, myocardium-only capture occurs when pacing of the HIS bundle captures only the myocardium surrounding the HIS bundle but not the HIS bundle itself. Such capture generally results in the impulse propagating down the septum and to the ventricles at a relatively slow velocity as compared to the other types of capture which involve activation of faster, intrinsic conduction paths of the heart associated with the His-Purkinje system. It should also be appreciated that a pacing impulse may fail to capture either of the HIS bundle or the surrounding myocardium, resulting in what is generally referred to herein as non-capture or loss-of-capture. In such cases, the intrinsic beat of the heart may be measured or otherwise come through.

In light of the foregoing, measuring and analyzing the response of the heart to pacing of the HIS bundle can enable identification of the particular type of capture (or non-capture) resulting from the applied pacing impulses. In response to identifying certain responses, the stimulation device may also be configured to recalibrate (e.g., by conducting a threshold search, such as that described in FIGS. 8A-9) or otherwise adjust one or more operational parameters. For example, an intracardiac electrogram (IEGM) may be captured in conjunction with application of a pacing impulse to the HIS bundle. Characteristics of the IEGM may then be measured to determine the type of capture (if any) resulting from the pacing impulse. In certain implementations of the present disclosure, such analysis may be conducted in the time-domain, e.g., by identifying and measuring characteristics of the response as indicated in the IEGM over time.

As described below in further detail, analysis of the time-domain characteristics of the heart's response to a pacing impulse (e.g., as recorded as an IEGM) can be used to determine what type of capture, if any, has occurred in response to the pacing impulse. Such analysis may be based on characteristics of the total response (e.g., the overall shape and duration of the complete IEGM waveform resulting from the impulse), select portions of the response (e.g., time intervals between certain identifiable events in the response), or combinations thereof. It should also be appreciated that in certain implementations, narrowing the response to a particular capture type may require analysis of multiple characteristics. For example, a first characteristic may be analyzed to distinguish between selective capture and non-selective and myocardium-only capture and a second characteristic may be analyzed to further distinguish between non-selective and myocardium-only capture after selective capture has been effectively eliminated as a consideration.

Although various measurements of the response to a pacing impulse may be used to determine capture and capture type, Table 1 below provides a summary of various measurements and qualitative characteristics of such measurements as they pertain to the different types of capture. Certain of the measurements listed in Table 1 are further explored below.

amplitude. The stimulation device may then correlate the template to the response data based on a pacing time (or other point common to each of the template and response data) and compare the subsequent points by cross-correlation. Based on such a comparison a score or similar metric, such as a cross-correlation coefficient, describing the "fit" of the response to the template may be calculated. If the comparison metric exceeds a threshold (e.g., an 80% match, a cross-correlation coefficient of 0.8, etc.), the template and response may be considered a match and the response may be classified accordingly. If the score falls below the threshold, additional comparisons of the response to other templates may be performed or the response may be classified as non-capture/loss-of-capture or undefined. Alternatively,

TABLE 1

Qualitative Comparison of Capture Types

| Measurement | Capture Type | | | |
| --- | --- | --- | --- | --- |
| | Selective | Non-Selective | Myocardium-Only | Non-Capture |
| Morphology | Similar to natural sinus rhythm | Narrower than natural sinus rhythm | Narrower than natural sinus rhythm | Long delay between impulse and onset of QRS complex, if any No change when AV delay shortened high R-to-R variability |
| Stimulation to unipolar peak | Similar across all capture types | | | |
| Simulation to Bipolar Peak | Long | Short | Short | Longer than selective capture |
| Stim to unipolar max(−dV/dt) | Long | Short | Short | Long |
| IEGM QRS width | Narrow | Wide | Wide | Narrow |
| Unipolar Peak to Peak width (−ve to +ve peak) | Short | Short | Long | Short |
| Stimulation to last peak | Short | Short | Long | Long |
| Stimulation to end of dV/dt peak | Short | Short | Long | Long |
| Unipolar amplitude | Small | Large | Large | Small |
| Unipolar downstroke/upstroke slope | Steep | Steep | Less steep | Steep |
| IEGM QRS integral | Small | Intermediate | Large | Small |

Morphology generally refers to the overall size and shape of the IEGM waveform. As previously discussed in this disclosure, analyzing morphology of an IEGM waveform may include comparing the IEGM waveform to one or more templates representative of different capture types. For example, templates for each of selective, non-selective, and myocardium only capture may be stored within the stimulation device. Each template may in turn include a series of points, such as ordered pairs of time and signal amplitude, defining a model waveform corresponding to the particular type of capture.

In conjunction with pacing of the HIS bundle, the stimulation device may collect and store responsive EGM data and compare such data to the templates. Similar to the template, the response data may be collected and stored as a series of points, such as ordered pairs of time and signal the specific way in which the response deviates from the template may be used to identify the type of capture or non-capture.

IEGM or similar templates for the different types of capture may be dynamically generated and stored during an in-office visit following implantation of the stimulation device (e.g., a post-operative visit or other follow up office visit). Alternatively or in addition to such initial setup, the templates may be generated during an automatic configuration and calibration routine executed by the stimulation device. In either case, prior to generation of the IEGM templates, an initial threshold search/test may be conducted to determine impulse parameters for each type of capture, as described in FIGS. 8A and 8B. Impulses may then be applied according to the results of the threshold test and the corresponding response may be recorded and stored as a template. A template may correspond to a single response or may be an average or other mathematical combination of multiple responses. In addition to templates for each type of capture, a template corresponding to the heart's intrinsic response/natural sinus rhythm may also be generated and stored.

Comparison of a measured response to the stored templates may facilitate identifying what, if any, capture has occurred. For example, as noted in Table 1, while a response resulting from selective capture will generally appear similar to an intrinsic response/sinus rhythm, deviation from sinus rhythm may be indicative of either non-selective or myocardium-only capture. For example, such deviation may appear as a relative narrowing of the response waveform as compared to that of sinus rhythm or selective capture due to premature stimulation of the myocardium.

Other metrics that may be used to identify what type of capture has occurred may be based on the timing between stimulation and particular characteristics of the resulting response. In certain specific implementations and without limitation, the time interval between application of a pacing impulse and any of a bipolar peak, a unipolar maximum rate of voltage change (dV/dt), or a last peak of the QRS complex may be measured and used to identify capture type. Each of these metrics provides an indication of how rapidly the QRS complex arises following application of a pacing impulse and indirectly indicates activation time of the ventricles and QRS width. To the extent the interval is relatively short, non-selective or myocardium-only capture is likely. More specifically, during selective capture, a longer delay (as compared to non-selective or myocardium-only capture) is observable between pacing of the HIS bundle and initiation of the QRS complex due to the impulse having to propagate through the heart's intrinsic electrical pathways. In contrast, in each of non-selective and myocardium-only capture the pacing impulse at least partially bypasses such intrinsic pathways and local propagation occurs around the stimulus, resulting in the QRS complex arising sooner than in the case of selective capture.

In light of the foregoing, measuring the delay between application of a pacing impulse and the occurrence of portions of the QRS complex having particular characteristics may be used to determine a type of capture. For example, values, ranges of values, or templates for some or all of the different capture scenarios may be stored in memory of the stimulation device. Following application of a pacing impulse, a measured response (e.g., an IEGM) to the impulse may be analyzed relative to the stored information. Such analysis may generally include identifying each of the application of the pacing impulse, the relevant characteristics of the QRS complex of the response, and the delay therebetween and then comparing the delay to the stored delay information. Based on the comparison, the stimulation device may determine what, if any, type of capture has occurred.

In still other implementations of the present disclosure, characteristics of the QRS complex independent of the pacing impulse may be used to determine what type of capture has occurred. For example, conduction velocity through the heart generally indicates capture type with each of selective and non-selective capture resulting in faster conduction than myocardium-only capture. In light of this observation, one example metric indicative of conduction velocity is the peak-to-peak interval of the QRS complex and, in particular, the negative-to-positive peak-to-peak interval between the Q and R points of the QRS complex. More generally, however, the interval between any two portions of the QRS complex may be used to determine capture type.

As another example, the total QRS duration may also be used to determine capture type. More generally, because conduction through the HIS bundle and intrinsic pathways tends to be faster than through the myocardium, each of selective and non-selective capture results in shorter activation and, as a result, a narrower QRS complex than myocardium-only capture. As previously discussed in the context of FIGS. 12A-12B, determining total QRS duration may include first calculating a derivative of the QRS complex, which may facilitate identification of the start and end of the QRS complex. As yet another example metric, the integral the QRS complex (or a rectified version thereof) may also be used to determine capture type.

The foregoing examples should be regarded as a non-limiting list of characteristics that may be used to distinguish between capture types and, as a result, other distinguishing characteristics of the response data may be considered.

As previously mentioned, Table 1 provides qualitative differences between various measurements as they relate to each capture type. Although specific values for the foregoing example metrics may vary from patient-to-patient, Table 2, below, provides a summary of quantitative values obtained experimentally for at least some of the measurements.

TABLE 2

Experimental Results for Metrics Indicating Capture Type (mean ± standard deviation from 25 patients)

| Measurement | Capture Type | | | |
| --- | --- | --- | --- | --- |
| | Selective | Non-Selective | Myocardium-Only | Intrinsic |
| Stimulation to unipolar peak (ms) | 88 | 88 | 86 | N/A |
| Stimulation to bipolar peak (ms) | 120 ± 17 | 59 ± 17 | 53 ± 11 | 182 ± 95 |
| Stimulation to unipolar max dV/dt (ms) | 75 | 29 | 45 | N/A |
| Peak to peak interval (ms) | 25 | 39 | 90 | 41 |
| Stimulation to last peak (ms) | 121 | 137 | 176 | N/A |
| Stimulation to end of dV/dt peak | 125 | 140 | 180 | N/A |
| Unipolar width (Tip-Can) | 67 ± 24 | 91 ± 15 | 102 ± 10 | 71 ± 25 |
| Unipolar width (Ring-Can) | 66 ± 15 | 98 ± 25 | 104 ± 12 | 65 ± 26 |
| Integral of Rectified QRS | 27 | 242 | N/A | 29.7 |

The values included in Table 2 should be considered as examples only and are provided primarily as examples of the variation between capture types for the measurements listed. As previously noted, specific values for each capture type may vary between patients. So, for example, the time delay between application of a stimulation impulse and the bipolar peak may generally indicate selective capture when it exceeds about 70 ms or loss of capture when it exceeds 140 ms. Similarly, the peak-to-peak interval, the time delay between application of the impulse and a last peak of the response, and the time delay between application of the impulse and the end of the peak slope of the response may generally indicate myocardium-only capture when they exceed about 60 ms, about 150 ms, and about 150 ms, respectively. Moreover, while specific values of measurements are included in Table 2, it should be appreciated that, in most cases, inherent variability in the structure and function of the heart may result in variability from beat-to-beat for the listed measurements. Accordingly, while indicated as individual values, in at least certain implementations of the present disclosure, the values may instead correspond to an average or similar statistical measure corresponding to multiple beats. It should be appreciated that the values provided in Table 2 are merely examples from a relatively small set of patients. The specific values for the characteristics in Table 2 can vary from patient to patient. As a result, in at least some implementations of the present disclosure, one or more metrics used to determine capture type may be specifically measured or derived for a given patient.

Based on the foregoing examples of response characteristics and their corresponding use in determining capture type, stimulation devices in accordance with the present disclosure may apply pacing impulses, analyze the resulting responses to determine capture type, and, if an undesirable or suboptimal response is detected, modify operational characteristics of the stimulation device accordingly.

Figure 13A:
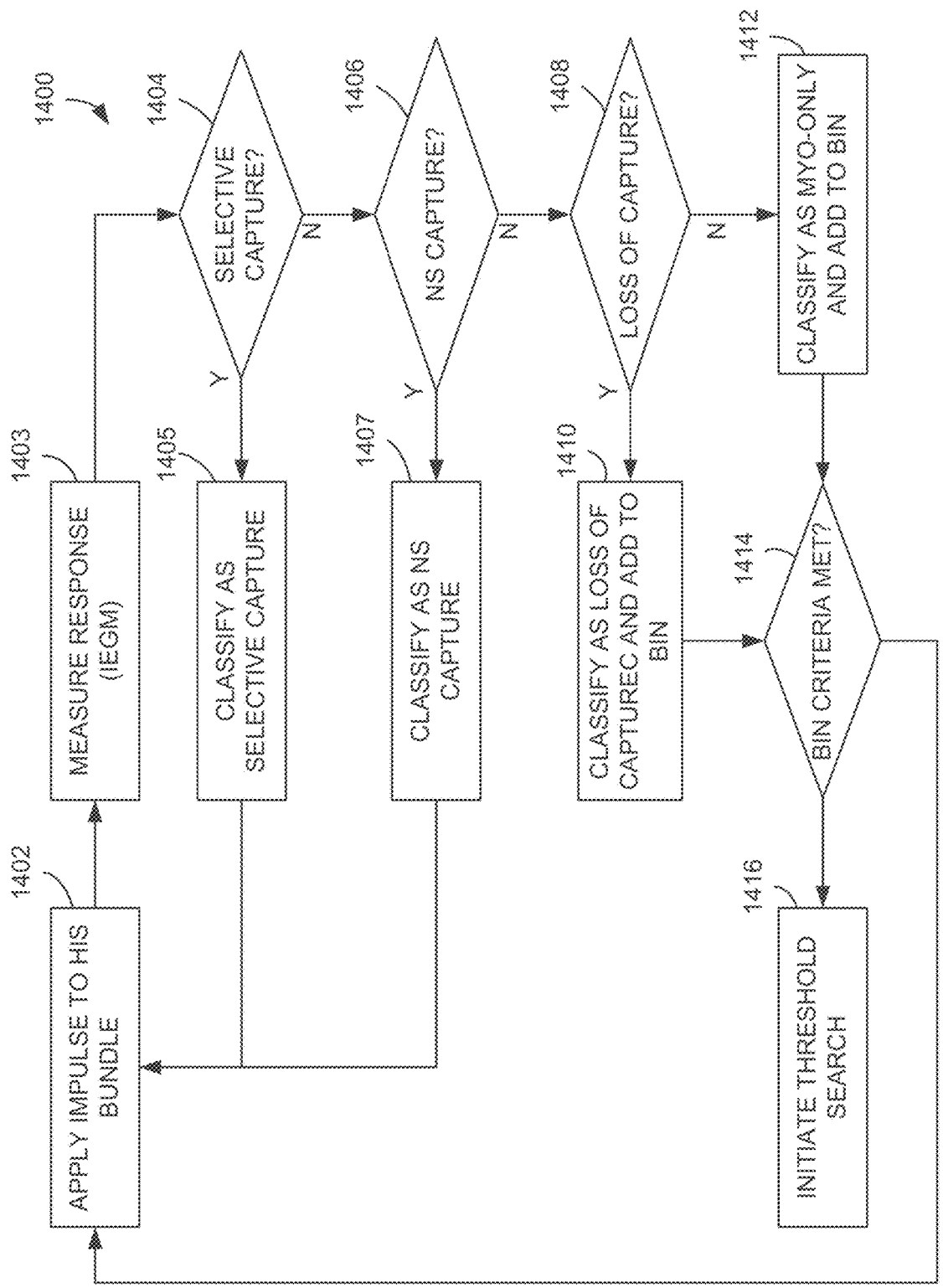
FIG. 13A is a flow chart illustrating a method for identifying capture types based on time-domain characteristics of a response to a pacing impulse.

FIG. 13A is a flow chart illustrating a method 1400 for performing HIS bundle pacing and may be executable by a stimulation device in accordance with the present disclosure. In general and as described below in further detail, the method 1400 includes applying a pacing impulse to the HIS bundle, measuring the corresponding response of the heart, and evaluating the response to determine what, if any, capture has occurred. Due to similarities in responses between different capture types, the method 1400 specifically includes an elimination approach in which the measured response is first evaluated to determine whether it corresponds to selective capture. More specifically, the response is first analyzed to determine if it has characteristics indicative of selective capture only. If not, subsequent analysis is performed to determine whether the response corresponds to myocardium only or non-selective capture. As a result, the process of distinguishing between myocardium only and non-selective capture can rely on metrics for which values may overlap for selective capture. In the event of myocardium only or non-capture, the method also includes taking various remedial steps, including initiating a threshold search.

At operation 1402, a stimulation/pacing impulse is applied to the HIS bundle and, at operation 1403, the corresponding response of the heart is measured, such as by using an intracardiac electrogram (IEGM). Although operation 1403 is indicated in FIG. 13 as occurring after operation 1402, it should be appreciated that the stimulation device may monitoring/measure electrical activity of the heart constantly or may begin recording data prior to application of the stimulation/pacing impulse at operation 1402. By doing so, the application of the impulse may also be measured and identified and, as a result, used in determining the type of capture resulting from the application of the impulse at operation 1403.

The stimulation device may first analyze the response obtained in operation 1403 to determine whether the pacing impulse resulted in selective capture (operation 1404). Such a determination may be conducted in various ways, however, as indicated in Table 1, selective capture may generally result in a response that is distinguishable from each of non-selective and myocardium-only capture with respect to one or more of: (1) overall morphology; (2) time between stimulation and bipolar peak; (3) time between stimulation and unipolar maximum slope; (4) QRS width; (5) unipolar amplitude; and (6) QRS integral. Accordingly operation 1406 may generally include identifying one of the foregoing characteristics and comparing the characteristic to a corresponding stored value, range of values, or template for selective capture. If selective capture is detected, the stimulation device classifies the response as selective capture (operation 1405) and may proceed to generate an impulse for and analyze the next heartbeat (operations 1402, 1403).

If, on the other hand, the stimulation device determines that selective capture has not occurred, the stimulation device may further analyze the response obtained in operation 1403 to determine whether the pacing impulse resulted in non-selective capture (operation 1406). Similar to the previous analysis for determining selective capture, non-selective capture may be determined in various ways. However, as indicated in Table 1, similar to selective capture, non-selective capture may be distinguished by one or more of: (1) overall morphology; (2) time between stimulation and bipolar peak; (3) time between stimulation and unipolar maximum slope; (4) QRS width; (5) unipolar amplitude; and (6) QRS integral. Accordingly operation 1406 may generally include identifying one of the foregoing characteristics and comparing the characteristic to a corresponding stored value, range of values, or template for selective capture. If non-selective capture is detected, the stimulation device classifies the response as non-selective capture (operation 1407) and may proceed to generate an impulse for and analyze the next heartbeat (operations 1402, 1403).

If neither selective nor non-selective capture is detected, the stimulation device may determine whether loss of capture has occurred (operation 1408). Again, such a determination may be conducted in various ways, however, as indicated in Table 1, loss of capture may generally result in a response that is distinguishable from other capture types with respect to one or more of: (1) overall morphology; (2) time between stimulation and bipolar peak; (3) time between stimulation and unipolar maximum slope; (4) QRS width; (5) unipolar amplitude; and (6) QRS integral. Accordingly operation 1408 may generally include identifying one of the foregoing characteristics and comparing the characteristic to a corresponding stored value, range of values, or template for loss of capture/non-capture.

If the response is identified as being indicative of loss of capture in operation 1408, the stimulation device may classify the response as loss of capture and may generate a "bin" entry, log entry, or similar record for purposes of tracking loss of capture events (operation 1410). If, on the other hand, the response is not indicative of loss of capture, the response may be classified as myocardium-only capture and a corresponding bin entry may be generated (operation 1412).

It should be appreciated that instead of testing for loss of capture, the stimulation device may instead test for myocardium-only capture instead. To do so, the stimulation device may further analyze one or more of: (1) the peak-to-peak time interval (PPI); (2) the stimulation to last peak time interval; and (3) the stimulation to an end of the dV/dt peak. With respect to the peak-to-peak time interval, for example, myocardium only capture generally results in significantly greater peak-to-peak time intervals (e.g., ~90 ms versus ~40 ms or less), stimulation to last peak time intervals (e.g., ~175 ms versus ~140 ms or less), and stimulation to end of dV/dt peak intervals as compared to non-selective (or selective) capture.

As previously noted, whether the response is identified as being indicative of loss of capture or myocardium-only capture, the stimulation device may generate a corresponding log or "bin" entry. In certain implementations, such an entry may simply indicate that loss of capture or myocardium-only capture occurred and provide a tally of the number of loss of capture or myocardium-only capture events. In other implementations, each entry may further contain information regarding the pacing impulse (e.g., energy and duration) that may be subsequently used to perform a threshold search.

As indicated in the method 1400, such a threshold search may be initiated in response to the log/bin meeting certain criteria (operation 1414). Such criteria may include, among other things, the number of log/bin entries (i.e., a certain number of myocardium-only captures or loss of capture events) being generated, a certain number of consecutive beats for which myocardium-only capture or loss of capture has occurred (e.g., five consecutive beats), a certain proportion of beats being myocardium-only capture or loss of capture (e.g., five out of the last ten beats), or any other similar criteria. If such criteria are met, the stimulation device may initiate a threshold search (operation 1416) to recalibrate the stimulation device and, in particular, the pacing impulse parameters to increase the likelihood of non-selective or selective capture. If the criteria is not met, the stimulation device may simply move on to providing an impulse for and analyzing the next heartbeat (i.e., operations 1402, 1403). Notably, in certain implementations separate bins/logs for myocardium-only capture and loss of capture may be maintained and separate criteria may be applied to each such bin to determine when to initiate a threshold search.

It should also be appreciated, however, that the specific order of tests for capture type implemented by the stimulation device may vary. More specifically, the stimulation device may test the response data for any of selective capture, non-selective capture, myocardium-only capture, or loss of capture in any order. In one implementation, loss of capture may be identified in conjunction with determining whether selective or non-selective capture has occurred. For example, subsequent to a positive result in operation 1404, the stimulation device may determine whether the response is actually indicative of a loss of capture due to shared response characteristics between selective capture and loss of capture. Although various characteristics of the response may be analyzed to do so, in at least one specific instance the stimulation device may analyze a time between application of the impulse and the resulting bipolar peak as such time is generally shorter in the loss of capture case than in the selective capture case. Similar analysis may be conducted in combination with the other capture types by analyzing response characteristics that differ between the particular capture case (e.g., non-selective or myocardium only capture) and loss of capture/non-capture. Non-limiting examples of such characteristics are provided above in Table 1.

In certain implementations, if the stimulation device identifies the response as indicating loss of capture, a loss of capture routine may be initiated. The loss of capture routine generally includes one or more steps directed to addressing a loss of capture event and may include, among other things, delivery of a backup impulse, generation of a bin of log entry for tracking loss of capture events, evaluation of a log or bin to determine whether a capture threshold test (or similar recalibration) is required, and initiating a capture threshold test (or similar recalibration). Although the specific details of the loss of capture routine may vary, one example loss of capture routine is discussed in further detail below in the context of FIG. 13B.

Figure 13B:
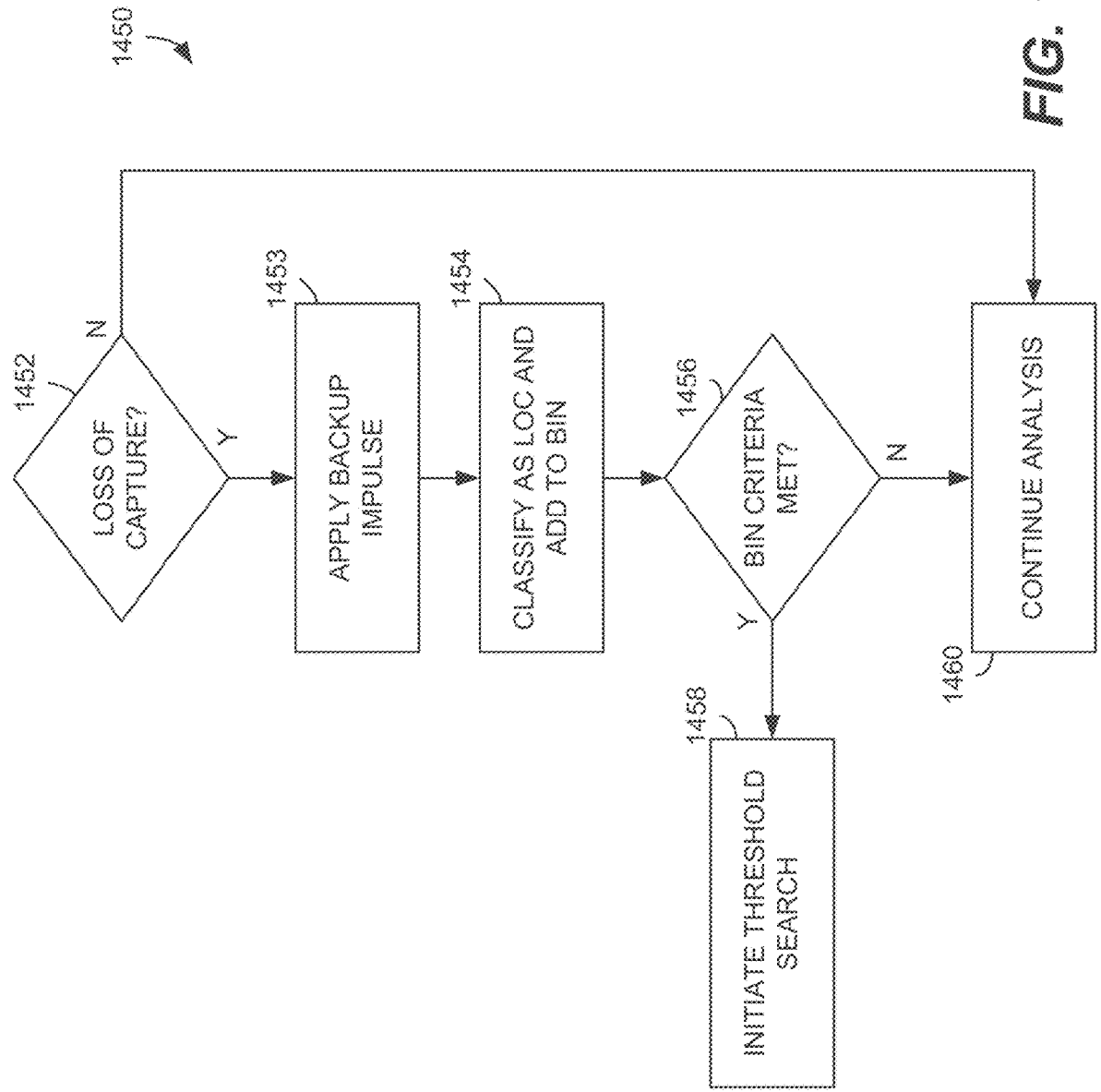
FIG. 13B is a flow chart illustrating a method for addressing loss of capture in the context of the method of FIG. 13A.

As noted, FIG. 13B is a flow chart illustrating an example method 1452 of identifying and processing loss of capture events. The method 1452 may be implemented at various locations during the broader operational cycle of stimulation devices according to the present disclosure.

At operation 1452, the stimulation device performs an initial analysis on previously obtained response data (e.g., response data obtained in operation 1403 of FIG. 13A). Similar to operations 1406 and 1408 of FIG. 13A, such an analysis may include identifying one or more characteristics of the response data indicative of loss of capture by comparing the response data to one or more templates or similar data stored in memory of the stimulation device.

If loss of capture has not occurred, analysis of the response data continues (operation 1460). If, on the other hand, loss of capture is identified, a backup impulse is applied (operation 1453) and the response data is classified as indicating loss of capture and a corresponding log or "bin" entry may be generated (operation 1454). In certain implementations, such an entry may simply indicate that loss of capture occurred and may provide a tally of the number of loss of capture events. In other implementations, each entry may further contain information regarding the pacing impulse (e.g., energy and duration) that may be subsequently used to perform a threshold search.

The threshold search may be initiated in response to the log/bin meeting certain criteria (operation 1456). Such criteria may include, among other things, the number of log/bin entries (i.e., a certain number of myocardium-only captures) being generated, a certain number of consecutive beats for which myocardium-only capture has occurred (e.g., five consecutive beats), a certain proportion of beats resulting in loss of capture (e.g., five out of the last ten beats), or any other similar criteria. As noted above, if such criteria are met, the stimulation device may initiate a threshold search (operation 1458) to recalibrate the stimulation device and, in particular, the pacing impulse parameters to increase the likelihood of non-selective or selective capture. If the criteria are not met, the stimulation device may simply move on to continue analysis of the measured response data (operation 1460). In certain implementations, the log/bin used for purposes of tracking loss of capture may be shared with a log/bin used for purposes of capturing myocardium-only capture events (e.g., the log discussed above in the context of FIG. 13A). Alternatively, separate logs/bins may be maintained for each type of event. It should also be appreciated that in at least some implementations a threshold search may occur automatically in response to a single loss of capture event such that analysis of the bin criteria at operation 1456 is unnecessary.

Beat-to-Beat HIS Bundle Pacing Using Frequency Domain Analysis

The foregoing section of the pending application was directed to systems and methods for identifying capture type based on a response to a pacing impulse delivered to the HIS bundle. In general, the foregoing approach included delivering the pacing impulse, measuring the response (e.g., in the form of an intracardiac electrogram (IEGM)), and analyzing various characteristics of the response as compared to templates, ranges, or similar values associated with various capture types (i.e., selective capture, non-selective capture, myocardium-only capture, and non-capture/loss of capture).

The various characteristics of the response considered in the foregoing approach for identifying capture type were primarily in the time-domain. In other words, the particular characteristics considered were based on voltage measurements over time and included, among other things, delays between particular peaks, delays between application of the pacing impulse and features of the corresponding QRS complex, and the like. The voltage measurements further included derivatives and integrals of voltage measurements with respect to time.

In addition to or as an alternative to such time-domain analysis, implementations of the present disclosure may further take into account frequency characteristics of the IEGM (or other response) data to differentiate between different types of capture. More specifically, when examined in the frequency domain, each of the different types of capture exhibit particular characteristics such that the frequency response to applying a pacing impulse may be used to identify which type of capture has occurred.

For example, since propagation through the HIS bundle and associated intrinsic pathways occurs much faster than through myocardium (e.g., on the order of 4 m/s versus 0.5 m/s), the frequency response for selective capture generally exhibits greater high frequency components than the responses of either non-selective or myocardium-only capture. Accordingly, by determining the presence or amplitude of high frequency components in a response to a pacing impulse, selective capture may be distinguished from non-selective or myocardium-only capture. Similarly, non-selective capture has been experimentally shown to include a greater proportion of median frequency components as compared to myocardium-only capture.

In light of the foregoing, various frequency-based approaches may be applied to determine capture type in the context of HIS bundle pacing. In general, such approaches include applying a pacing impulse to the HIS bundle and measuring a corresponding response, such as in the form of an IEGM. In one implementation of the present disclosure, the response data is then transformed into the frequency domain (e.g., by using a fast Fourier transform). The frequency response may then be analyzed to determine what type of capture, if any, has occurred. For example, such analysis may include determining whether certain frequencies are present in the response and/or the relative dominance of various frequency bands. Such characteristics of the response may then be compared to values, ranges of values, templates, or similar criteria stored in the stimulation device for each of the capture types.

Instead of transforming the response data into the frequency domain, other implementations of the present disclosure include applying one or more filters designed according to previously obtained frequency spectra to the response to generate sets of filtered response data. The applied filters may include any of low-pass, high-pass, or band-pass filters corresponding to particular frequencies or frequency bands associated with different capture types. The resulting filtered response may then be analyzed to determine whether it indicates a particular capture type. For example, as previously noted, selective capture generally results in a response including a greater amount of high frequency components as compared to non-selective or myocardium-only capture. Accordingly, a high pass filter may be applied to the response to generate a filtered response isolating the high frequency components. To the extent the amplitude (or other characteristic) of the filtered response meets a particular criteria, the response may be categorized as indicating selective capture. A similar approach may also be used to identify each of non-selective or myocardium-only capture. In at least one implementation, the filters may be programmed during initial testing and calibration of the stimulation device. For example, during an initial threshold (or similar) test, a technician or physician may analyze responses corresponding to the different capture types and configure one or more filters of the stimulation device based on the frequency characteristics of the responses.

Figure 14:
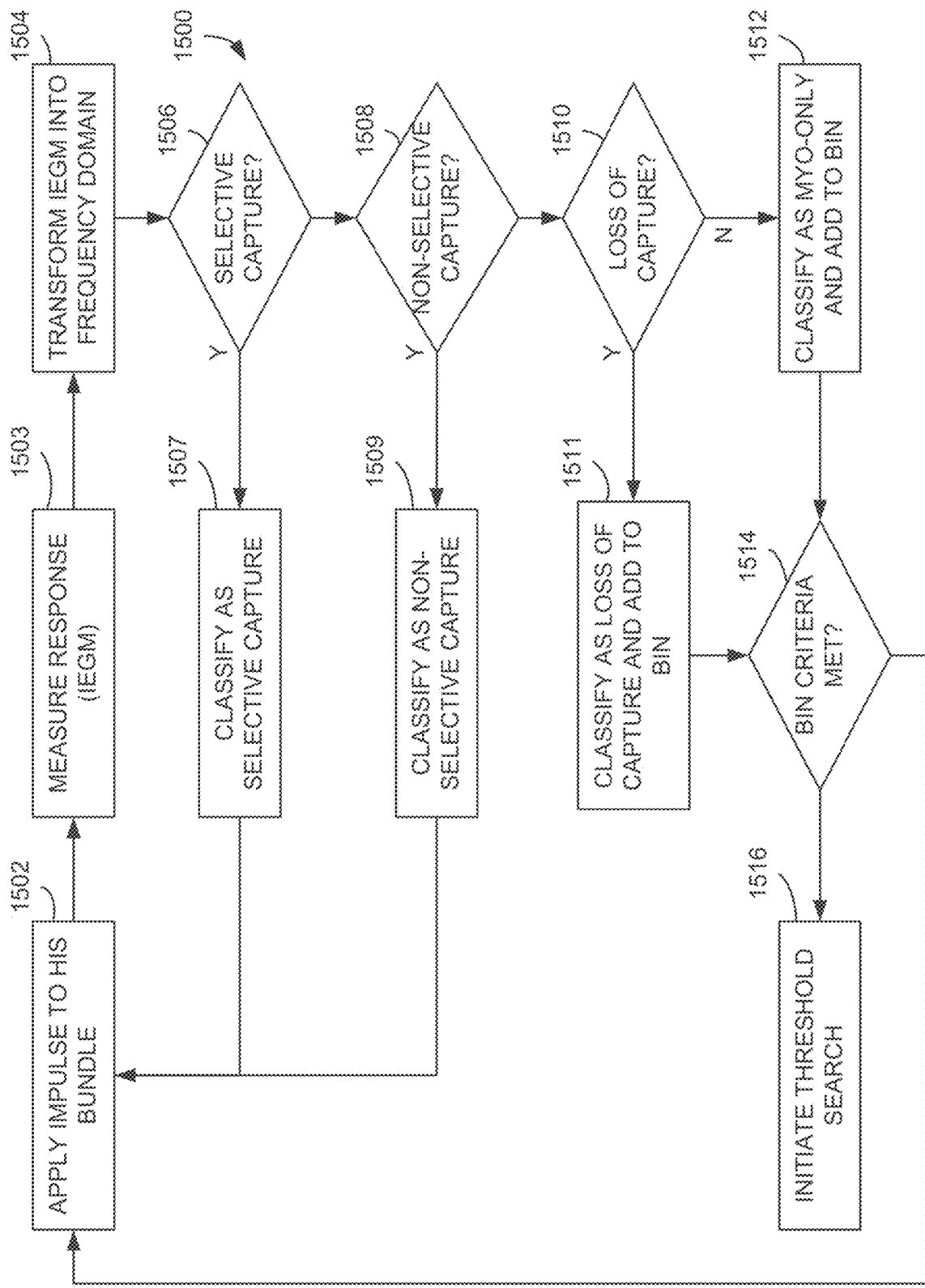
FIG. 14 is a flow chart illustrating a method for identifying capture types based on frequency spectrum characteristics of a response to a pacing impulse.
Figure 15A:
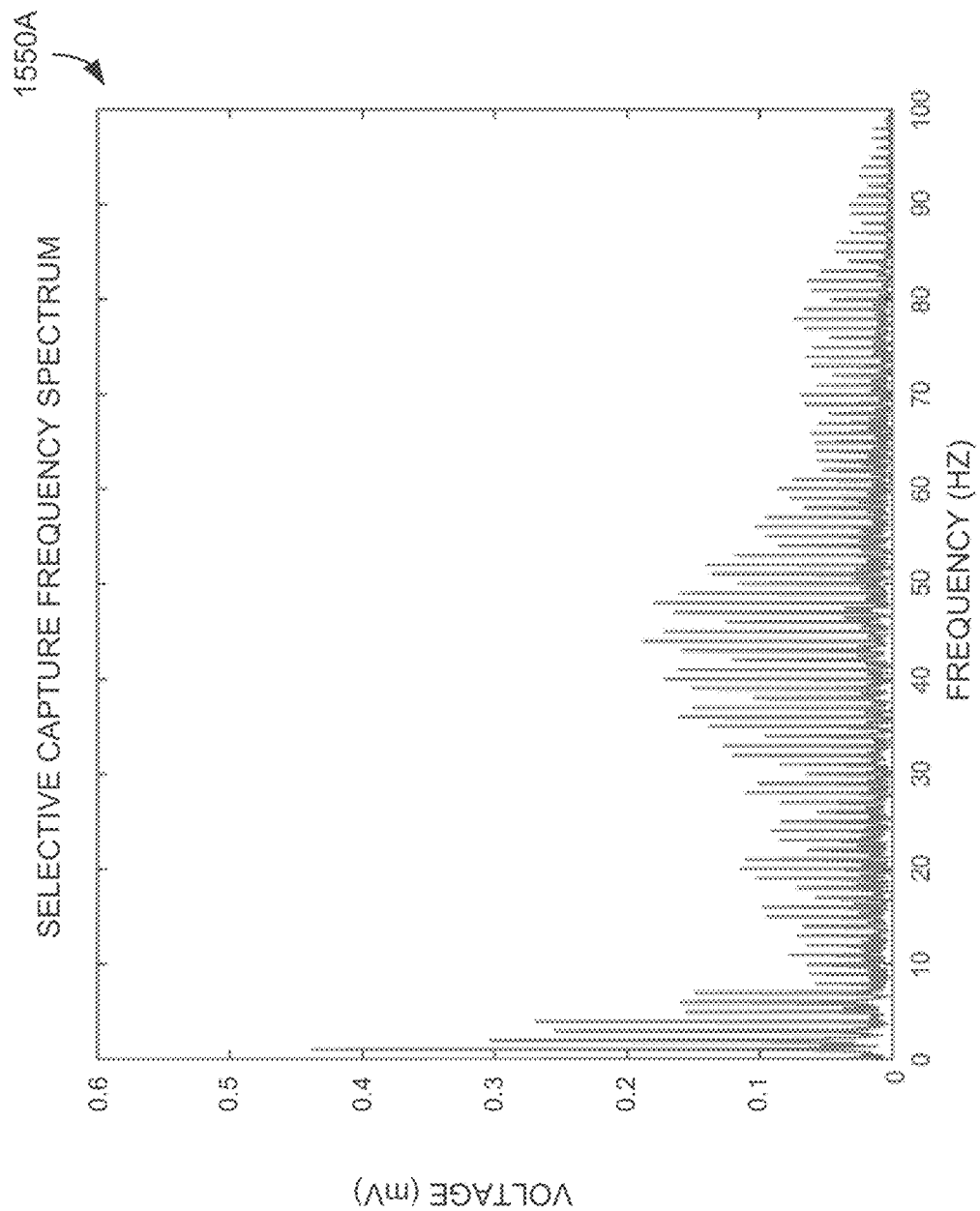
FIGS. 15A-15C are example frequency spectra for selective, non-selective, and myocardium-only capture with bipolar sensing.
Figure 15B:
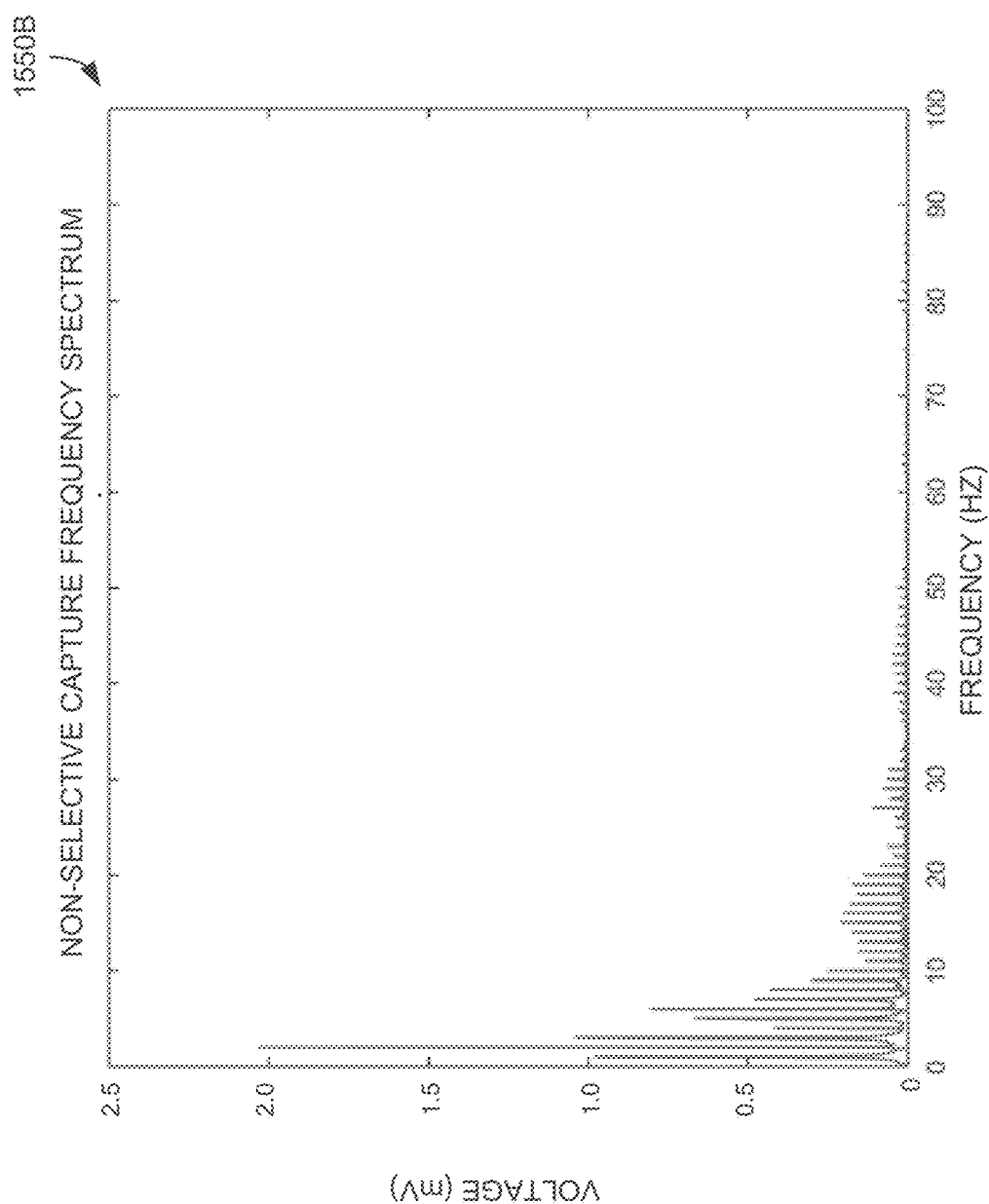
Figure 15C:
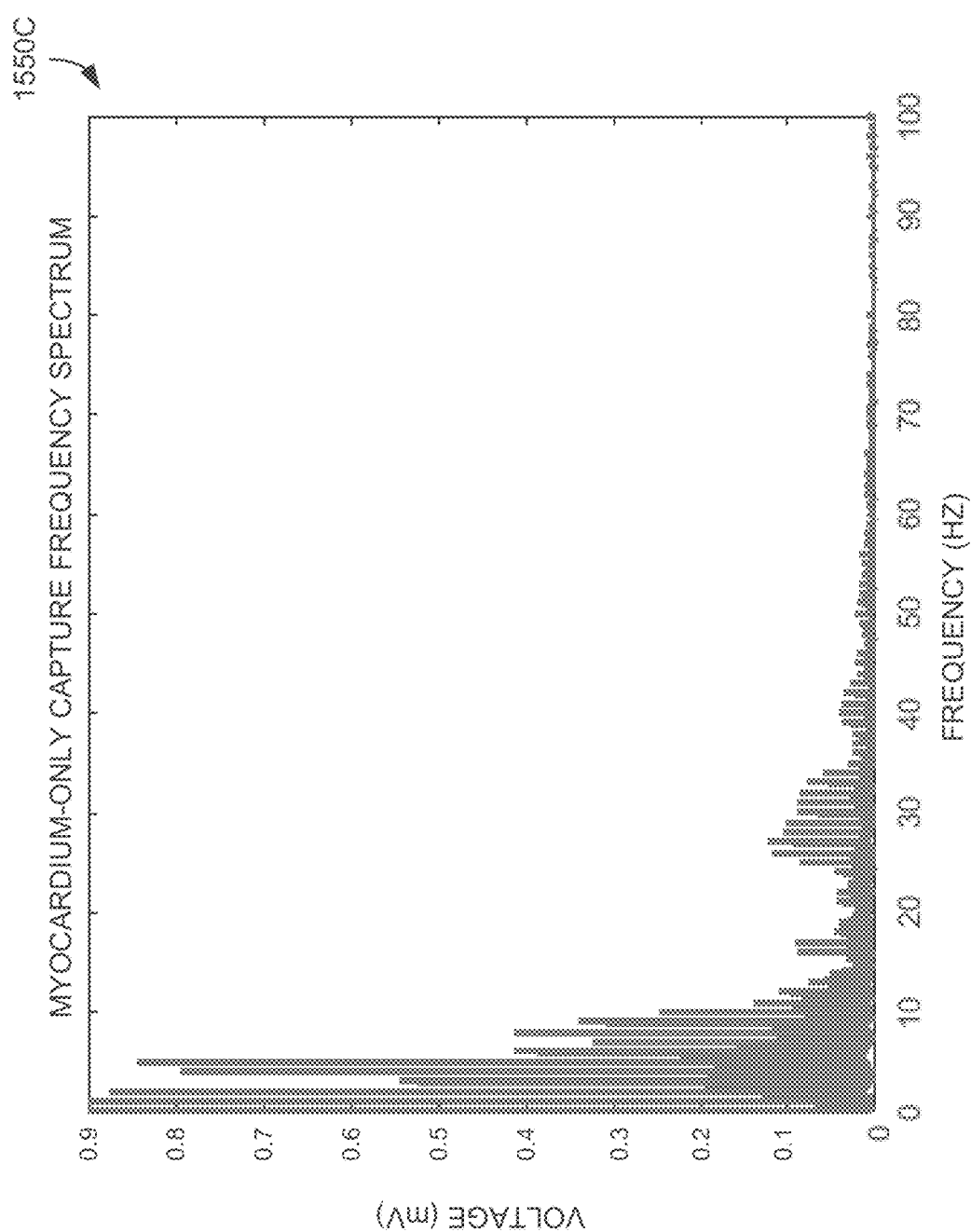

FIG. 14 is a flow chart illustrating a method 1500 for performing HIS bundle pacing and may be executable by a stimulation device in accordance with the present disclosure. To provide additional context for the following discussion, FIGS. 15A-15C are provided. Each of FIGS. 15A-15C includes a respective frequency spectrum 1550A-C for each of selective capture, non-selective capture, and myocardium-only capture, respectively.

In general and as described below in further detail, the method 1500 includes applying a pacing impulse to the HIS bundle and measuring the corresponding response of the heart. The measured response is then transformed into the frequency domain to produce a frequency spectrum of the response. The stimulation device then evaluates the frequency spectrum to determine what, if any, capture has occurred. To do so, the stimulation device may compare the frequency spectrum to templates, values, ranges, or similar response characteristics for the different capture types. For example, to identify selective capture, which generally includes a high-frequency component not present in other capture types, the stimulation device may determine the amplitude and/or proportion of frequencies within the frequency spectrum.

Due to similarities in responses between different capture types, the method 1500 specifically includes an elimination approach in which the measured response is first evaluated to determine whether it corresponds to selective capture. More specifically, the response is first analyzed to determine if it has characteristics indicative of selective capture only. If not, subsequent analysis is performed to determine whether the response corresponds to myocardium only or non-selective capture. As a result, the process of distinguishing between myocardium only and non-selective capture can rely on metrics for which values may overlap for selective capture. In the event of myocardium only or non-capture, the method also includes taking various remedial steps, including initiating a threshold search.

At operation 1502, a stimulation/pacing impulse is applied to the HIS bundle and, at operation 1503, the corresponding response of the heart is measured, such as by using an intracardiac electrogram (IEGM). Although operation 1503 is indicated in FIG. 14 as occurring after operation 1502, it should be appreciated that the stimulation device may monitoring/measure electrical activity of the heart constantly or may begin recording data prior to application of the stimulation/pacing impulse at operation 1502. By doing so, the application of the impulse may also be measured and identified and, as a result, used in determining the type of capture resulting from the application of the impulse at operation 1503.

At operation 1504, the stimulation device transforms the time-based response data into a frequency response. Although various transformations may be applied to the response data, in at least one implementation of the present disclosure, the transformation of the time-based response data into a frequency response is achieved by applying a fast Fourier transform (FFT) to the time-based response data. Accordingly, the time-based response (which generally indicates voltage over time) is transformed into a corresponding data set in which the time-based response is expressed as a series of sinusoids and their respective amplitudes.

The frequency response is then analyzed to determine what type of capture, if any, has occurred in response to application of the impulse at operation 1502. In one implementation, the stimulation device may then analyze the frequency response data to determine whether selective capture has occurred (operation 1506). To do so, the stimulation device generally analyzes the frequency response to determine if it contains high frequency components indicative of selective capture. Such analysis may be conducted in various ways; however, in one implementation (and as illustrated in the frequency spectrum 1550A of FIG. 15A as compared to frequency spectrums 1550B and 1550C of FIGS. 15B and 15C, respectively) the stimulation device may identify selective capture by determining the frequency response/frequency spectrum includes one or more components greater than approximately 30 Hz that exceed a certain threshold (e.g., 0.05 mV). In another implementation, the stimulation device may determine selective capture if an average amplitude for a frequency band (e.g., 30-60 Hz) exceeds a predetermined threshold. If selective capture is detected, the stimulation device may classify the response as selective (operation 1507) and proceed to generate an impulse for and analyze the next heartbeat (operations 1502, 1503).

If, on the other hand, the stimulation device determines that selective capture has not occurred, the stimulation device may further analyze the measured response to determine if it is indicative of non-selective capture (operation 1508). To do so, the stimulation device may further analyze the frequency response to determine if frequency components indicative of non-selective capture are present. In one specific example and as illustrated by comparing the frequency spectrums of FIGS. 15B and 15C, the stimulation device analyzes a median frequency band (e.g., 10-30 Hz) and determines the signal strength within the median band. Similar to operation 1506, such analysis may include, among other things, determining whether certain frequency components within the median frequency band exceed a particular threshold, whether the band as a whole has average amplitude above a certain threshold, identifying the presence of certain harmonics in the response data, or any other similar metric. Similar to the selective capture case, if non-selective capture is detected, the stimulation device may classify the response as non-selective capture (operation 1509) and proceed to generate an impulse for and analyze the next heartbeat (operations 1502, 1503).

If operation 1510 does not indicate non-selective capture, the stimulation device may next analyze the frequency response data to determine whether a loss of capture (non-capture) has occurred (operation 1510). In at least some implementations, a check for loss of capture may include measuring a time between the application of the impulse at operation 1502 and the onset of a corresponding QRS complex (if any) as measured in operation 1503 or separately monitored. To the extent such a delay exceeds a predetermined threshold, the stimulation device may classify the response as non-capture or loss of capture.

Similar to the method 1400 of FIG. 13, when loss of capture is identified, the response may be classified as loss of capture and a log or "bin" entry may be generated indicating the occurrence of myocardium-only capture (operation 1511). Alternatively, if loss of capture is not identified, the response may be classified as myocardium only capture and a corresponding bin entry may be generated (operation 1512). When the entries of the log or bin meet a particular threshold (e.g., number of entries) (operation 1514), a threshold search may be initiated (operation 1516) to recalibrate the stimulation device. It should be understood that the test at operation 1510 may instead determine whether myocardium-only capture has occurred with substantially similar results.

It should be appreciated, however, that the specific order in which the various capture type tests are applied may vary. More specifically, the stimulation device may test the response data for nay of selective capture, non-selective capture, myocardium-only capture, or loss of capture in any order. For example, loss of capture may be identified at various points during analysis and processing of response data obtained following application of the impulse to the HIS bundle (e.g., following operations 1502-1504) and is not limited to being identified immediately after conversion of the response data into the frequency domain.

For example, the test for loss of capture may occur at any point in the method 1500 following application of the pacing impulse and measurement of the corresponding response (i.e., operations 1502, 1503). In one specific implementation, operation 1512 may instead involve testing to see if myocardium-only capture has occurred. To do so, the frequency response may be further analyzed to determine if it includes substantial low-frequency components indicative of capture of the myocardium. Notably, such low-frequency components may also be present in cases of non-selective capture; however, due to the elimination of non-selective capture as a candidate in operation 1508, analysis of low frequency components of the response may be used to distinguish between myocardium-only capture and loss of capture.

In certain implementations and instead of operations 1511, 1514, and 1516, the stimulation device may initiate a loss of capture routine in response to identifying loss of capture. Similar to previously discussed loss of capture routines, the loss of capture routine may include one or more steps directed to addressing a loss of capture event and may include, among other things, delivery of a backup impulse, generation of a bin of log entry for tracking loss of capture events, evaluation of a log or bin to determine whether a capture threshold test (or similar recalibration) is required, and initiating a capture threshold test (or similar recalibration). As previously noted, the specific details of the loss of capture routine may vary, but one example loss of capture routine is discussed in further detail above in the context of FIG. 13B, albeit in the context of time-domain response data. It should be appreciated that the same routine or steps of the routine are generally applicable in the frequency-domain context as well. In other words, the general process of identifying loss of capture (operation 1452) and taking subsequent remedial action (e.g., applying a backup impulse (operation 1454), classifying and binning/logging the results (operations 1454-1456), and initiating a threshold test if necessary (operation 1458)) may be similarly applied to the frequency-domain based approach of FIG. 14, with the primary difference being that identification of loss of capture is based on analysis of a frequency spectra of the measured response.

Figure 16A:
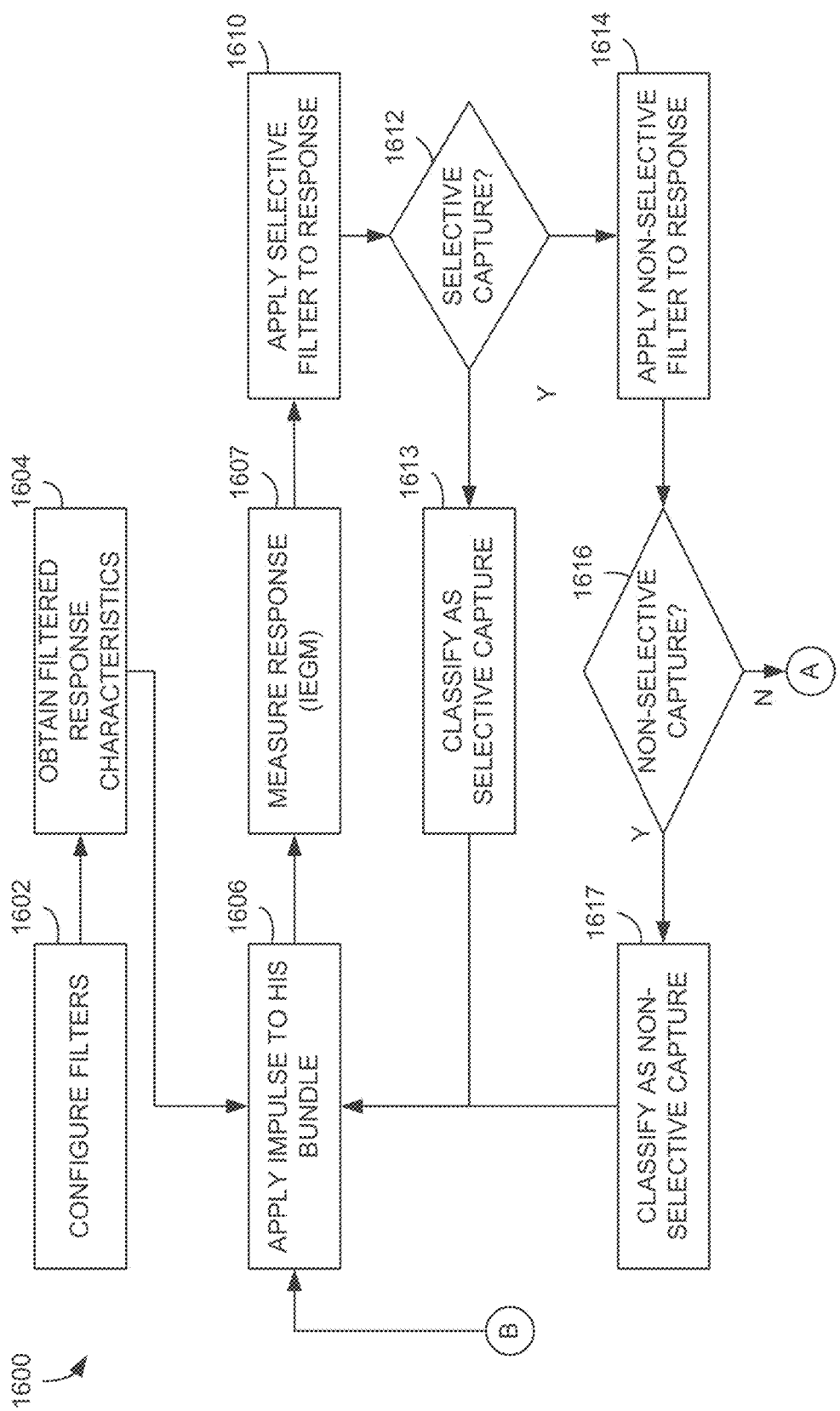
FIGS. 16A and 16B are a flow chart illustrating a method for identifying capture types by filtering responses to pacing impulses.
Figure 16B:
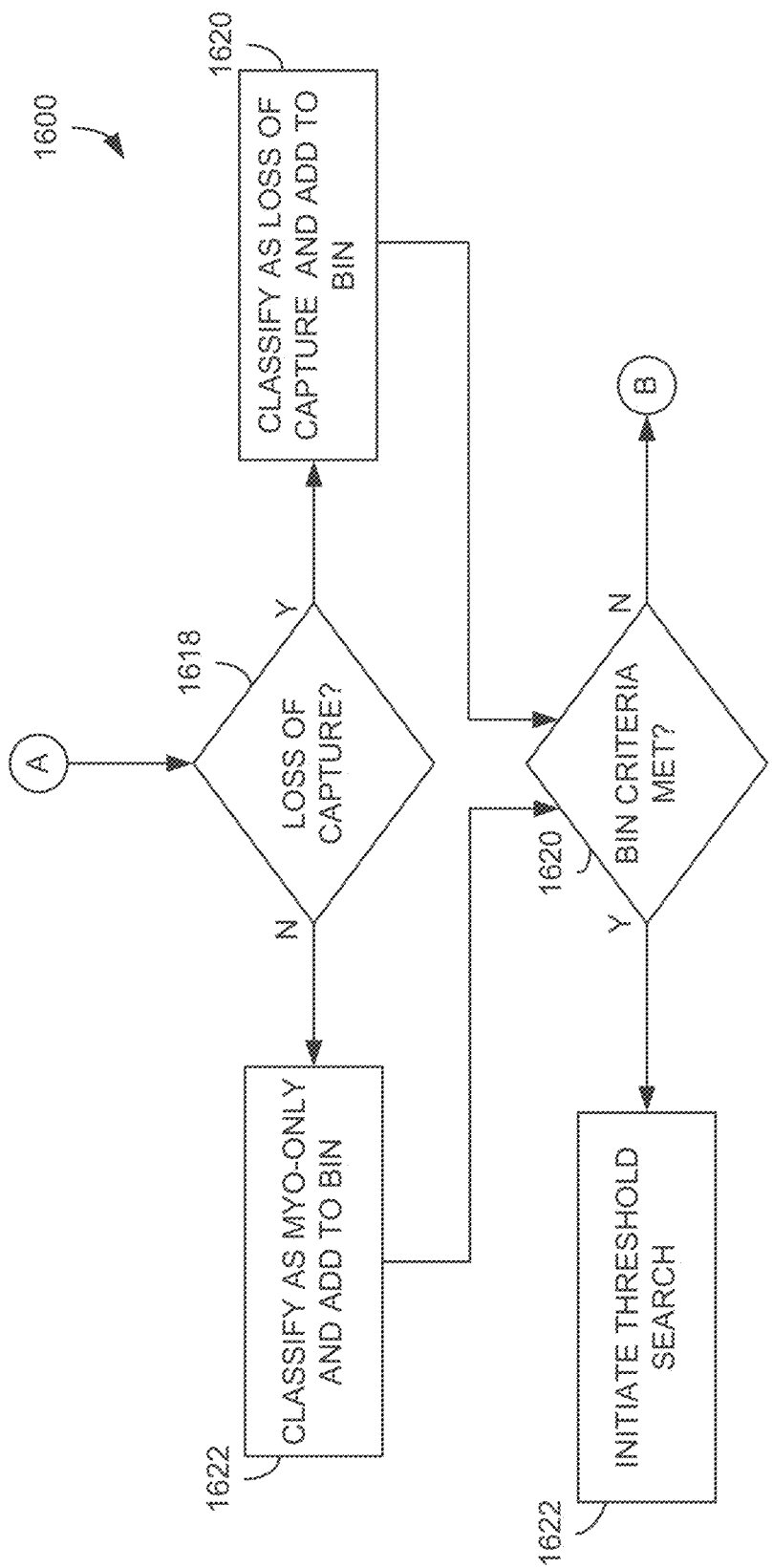

The example method 1500 generally relies on transforming response data into the frequency domain and analyzing the resulting frequency response data. FIGS. 16A and 16B provide an alternative frequency-based method 1600 for determining capture type that relies instead on the application of one or more filters to the response data to generate filtered response data. The filtered response data is then analyzed to determine what type of capture has occurred, if any.

At operation 1602, one or more filters of the stimulation device are configured for use in subsequent filtering of IEGM or similar response data collected following delivery of an impulse by the stimulation device. Although the exact configuration of the filters may vary in different applications of the present disclosure, configuration of the filters may generally include selecting one or more of a frequency response, a type of filter, a filter order, a stopband attenuation, and one or more cutoff frequencies. With respect to frequency response, for example, each filter may be configured as a high-pass filter, a band-pass filter, a low-pass filter, a band-stop/band-reject filter, a notch filter, a comb filter, or to have any other suitable frequency response. As another example, each filter may be further specified to be an elliptical filter, a Butterworth filter, a Chebyshev filter (type I or type II), a Bessel filter, or any other suitable filter type. In implementations in which multiple cascaded filters are implemented, configuration of the filters may also include establishing a filter order, such as by specifying inputs for each filter (which may include outputs from one or more other filters).

Configuration of the filters may occur during initial calibration and testing of the stimulation device. For example, following implantation of the stimulation device a physician or technician may conduct an initial threshold search to determine how different pacing impulses result in different capture scenarios. During such testing, IEGM or other data may be collected and analyzed to determine the particular frequency characteristics of the patient and, as a result, to determine the particular settings to be used for the filters of the stimulation device. In one specific implementation, a physician or technician may collect multiple waveforms for one or more capture types (e.g., selective capture) and analyze the waveforms in the frequency domain (e.g., by applying a FFT or similar transform to the waveform data). Based on the frequency response, the physician or technician may then determine different how best to configure the filters of the stimulation device.

In one specific example, the physician or technician may determine a cutoff frequency for identifying selective capture. As previously discussed, selective capture is generally indicated and distinguished from other capture types by the presence of relatively high frequency components. Accordingly, by observing the frequency at which such components begin in the frequency response, a physician or technician may select a cutoff frequency for a low-pass filter to isolate such components for purposes of identifying the occurrence of selective capture. A similar process may be repeated for filters configured to distinguish other capture types, as discussed below in further detail.

Although described above as a substantially manual process conducted by a physician or technician, it should be appreciated that at least a portion of the filter configuration process may also be automated. For example, the stimulation device or a system configured to calibrate the stimulation device may collect response data during a threshold search or similar test and conduct various analyses of the frequency responses for different capture types. Based on such analysis, the stimulation device or calibration system may automatically determine some or all filter parameters to be used in identifying the different capture types. In yet another approach, filter parameters may be set in the device hardware based on previously obtained clinical data or testing data obtained during testing and development of the stimulation device design.

At operation 1604, filtered response characteristics are obtained for the various capture types. In one implementation, doing so involves applying the filters configured in operation 1602 to response data for a known capture type. Characteristics and corresponding values of the resulting filtered response are then identified and stored in memory. As described below, the stored characteristics are subsequently used to analyze filtered response data to determine whether the filtered response data is indicative of a particular capture type. In general, any of the characteristics previously discussed in the context of time-domain analysis may be used to determine capture type. For example and without limitation, such characteristics may include: (1) waveform morphology; (2) waveform width; (3) time between stimulation and the onset of the response waveform; (4) time between stimulation and a particular peak; (5) amplitude (e.g., maximum/minimum amplitude, amplitude of a particular peak, etc.); (6) integral value of the waveform; (7) peak-to-peak slopes; (8) peak-to-peak times; and/or (9) the presence of particular harmonics in the filtered data. In certain implementations, combinations of characteristics may be stored as a template for some or all of the various capture types.

Following the calibration processes of operations 1602 and 1604, the stimulation device may begin normal operation. More specifically, at operation 1606 a stimulation/pacing impulse is applied to the HIS bundle and, at operation 1607, the corresponding response of the heart is measured, such as by using an IEGM. Although operation 1607 is indicated in FIG. 16A as occurring after operation 1606, it should be appreciated that the stimulation device may monitoring/measure electrical activity of the heart constantly or may begin recording data prior to application of the stimulation/pacing impulse at operation 1606. By doing so, the application of the impulse may also be measured and identified and, as a result, used in determining the type of capture resulting from the application of the impulse at operation 1607.

The response measured in operation 1607 may then be filtered by applying one or more of the filters configured in operation 1602. In the method 1600, for example, a first filter is applied to the response data at operation 1610 to isolate high frequency components of the response. Although other filters may be implemented and variation may exist between patients, in at least one implementations the first filter may be one of a band pass or low pass filter having a lower cutoff frequency of approximately 10 Hz. In implementations including a band pass filter, the band pass filter may also have an upper cutoff frequency of about 30 Hz or 60 Hz, although other upper cutoff frequencies may also be used.

The resulting filtered response is then analyzed to determine if it is indicative of selective capture (operation 1612). As previously discussed, during calibration of the stimulation device, various characteristics for different capture types and their respective values (or ranges of values) may be identified and stored in memory of the stimulation device. Accordingly, operation 1612 generally includes identifying the same characteristics in the filtered response data and comparing the values for such characteristics to the stored characteristic data for selective capture. To the extent the characteristics of the filtered response data correspond to or match the stored characteristic data for selective capture, the stimulation device may conclude that selective capture has occurred. In one specific and non-limiting example, the response data may be passed through a low pass filter with a cutoff frequency of 10 Hz and the resulting filtered response may be considered to be indicative of selective capture if the peak-to-peak amplitude is less than 1 mV. The stimulation device may then classify the current response as selective (operation 1613) and proceed to generate an impulse for and analyze the next heartbeat (operations 1606, 1607).

If, on the other hand, the stimulation device determines that selective capture has not occurred, the stimulation device may apply a second filter to the response data to generate a second filtered response (operation 1614). In the example method 1600, the second filter applied to the response data is specifically configured to facilitate distinction between non-selective and myocardium-only capture. For example, the second filter may be a band pass filter configured to isolate median frequency components (e.g., frequency components in the 10-30 Hz range) of the response, which tend to be more prevalent for non-selective versus myocardium-only capture.

The second filtered response generated during operation 1614 may then be analyzed to determine whether it is indicative of either non-selective or myocardium-only capture (operation 1616). Similar to operation 1610, the analysis of operation 1616 may include comparison of characteristics of the second filtered response to those stored in memory of the stimulation device and corresponding to non-selective or myocardium-only capture. In one specific implementation, however, at least one of peak-to-peak slope or peak-to-peak interval of the second filtered response is used to distinguish between non-selective and myocardium-only capture. For example, peak-to-peak interval generally provides an indication of conduction velocity and is therefore greater when the intrinsic conduction pathways are recruited (e.g., during non-selective capture).

Although such values may differ in specific applications, during testing of aspects of the present disclosure, it was observed that the peak-to-peak time for filtered response data (using a 10-30 Hz band pass filter) was substantially shorter for non-selective capture (~35 ms) as compared to myocardium-only capture (~90 ms). Accordingly, in one specific implementation of the present disclosure, the stimulation device may determine whether the second filtered response indicates non-selective capture by evaluating whether the peak-to-peak time interval is less than approximately 40 ms.

The response obtained at operation 1607 may then be analyzed to determine whether a loss of capture (non-capture) has occurred (operation 1618). Identifying the response as being indicative of loss of capture may include analyzing the raw response data in the time-domain, analyzing either of the filtered responses generated in operations 1610 and 1614, or applying a third filter to the response data, the third filter configured to isolate or attenuate specific frequencies indicative of loss of capture. If the response is identified as being indicative of loss of capture in operation 1618, the stimulation device may classify the response as loss of capture and may generate a "bin" entry, log entry, or similar record for purposes of tracking loss of capture events (operation 1620). If, on the other hand, the response is not indicative of loss of capture, the response may be classified as myocardium-only capture and a corresponding bin entry may be generated (operation 1622).

It should be appreciated that operation 1618 may instead involve testing for myocardium-only capture with substantially the same outcome. Similar to testing for loss of capture, testing for myocardium only capture may include analyzing the raw response data in the time-domain, analyzing either of the filtered responses generated in operations 1610 and 1614, or applying a third filter to the response data, the third filter configured to isolate or attenuate specific frequencies indicative of myocardium-only capture. Similar to the previous methods when the entries of the log or bin meet a particular threshold (e.g., number of entries) (operation 1620), a threshold search may be initiated (operation 1622) to recalibrate the stimulation device.

Figure 17A:
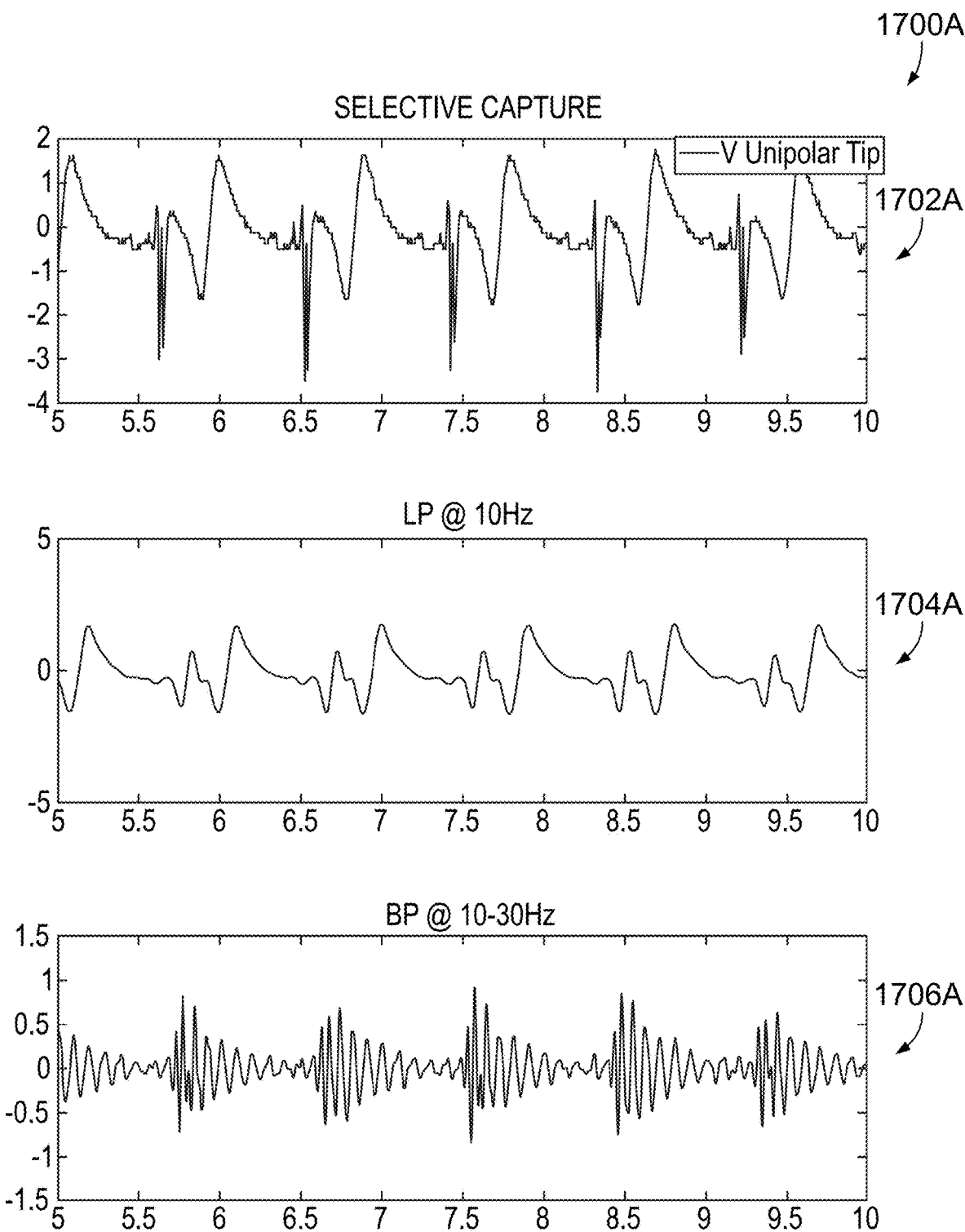
FIGS. 17A-17C are example graphs illustrating example responses (unfiltered and filtered) for selective, non-selective, and myocardium-only capture, respectively.
Figure 17B:
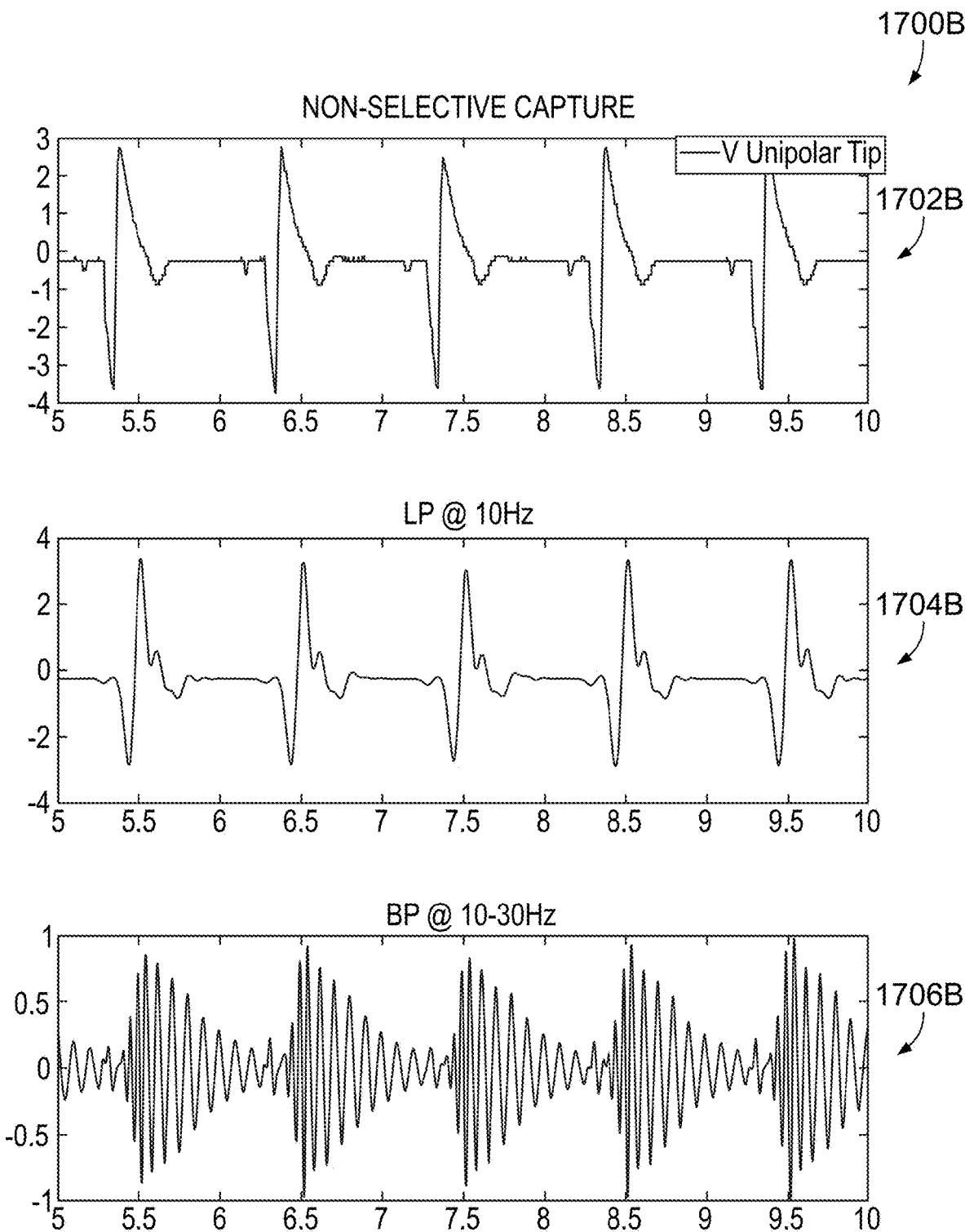
Figure 17C:
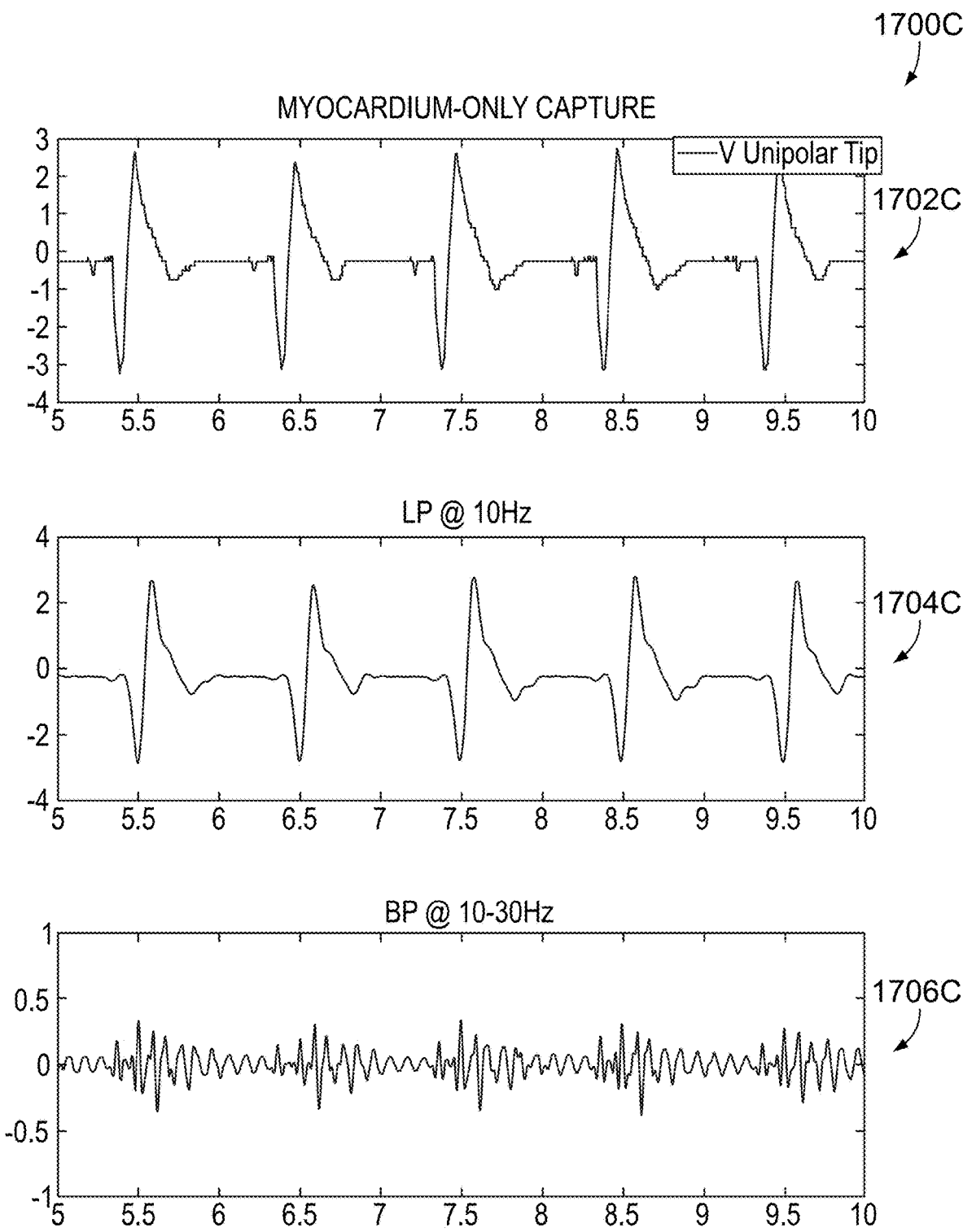

FIGS. 17A-17C are example graphs provided to illustrate the differences between responses for different types of capture when subjected to different filters and, more specifically, each of a 10 Hz low pass filter and a 10-30 Hz band pass filter. More specifically, FIG. 17A illustrates each of unfiltered 1702A, low pass filtered 1704A, and band pass filtered 1706A response data during selective capture; FIG. 17B illustrates each of unfiltered 1702B, low pass filtered 1704B, and band pass filtered 1706B response data during non-selective capture; and FIG. 17C illustrates each of unfiltered 1702C, low pass filtered 1704B, and band pass filtered 1706C response data for during myocardium only capture. Although other differences exist between the data represented in each of FIGS. 17A-17C, the response data for selective capture is distinguishable from selective and myocardium only capture at least by its relatively low amplitude when subjected to the low pass filter. Similarly, the response data for myocardium only capture is distinguishable from non-selective capture by a relatively low amplitude response when subjected to the band pass filter.

The foregoing approaches to determining capture type are applicable to both unipolar and bipolar sensing and pacing. However, in certain implementations, it may be preferable to use bipolar sensing signals for local HIS bundle activity.

Example Approaches to Threshold Searching

As previously noted, threshold searching refers to the process of identifying particular impulse characteristics at which different types of capture occur. In general, such processes include applying a pacing impulse at a starting voltage, measuring the corresponding response (e.g., by IEGM), determining what type of capture (if any) has occurred, and, based on the type of capture, modifying the voltage. The process of applying an impulse, measuring and classifying the response, and adjusting the voltage for a subsequent impulse is repeated to eventually converge on an optimal voltage setting. As described below in further detail, different approaches to setting the starting voltage, modifying the voltage, and conducting other aspects of the threshold test may be varied.

Figure 18:
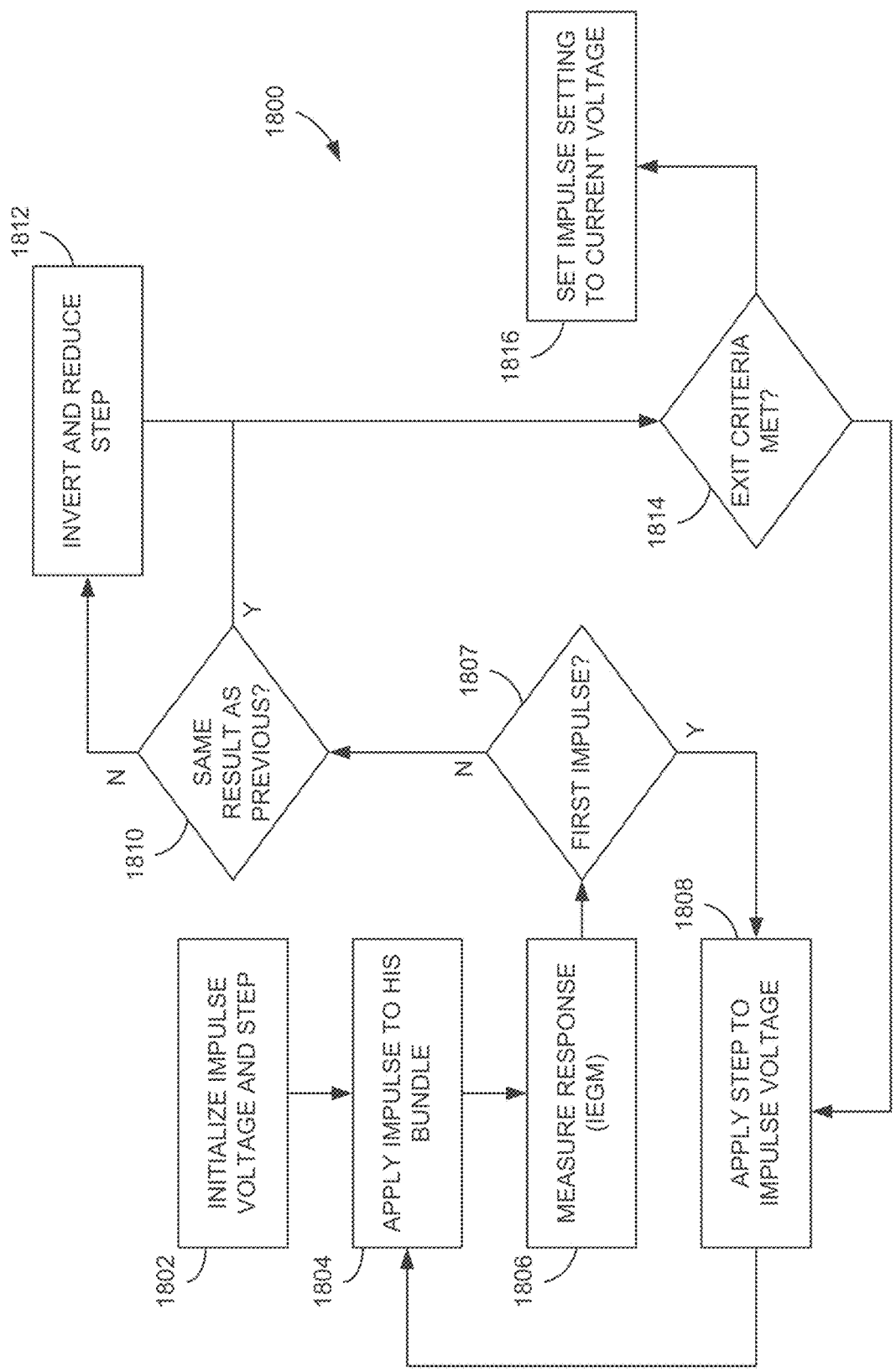
FIG. 18 is a method for performing a threshold search with a step down scheme.

FIG. 18 is a flow chart illustrating an example method 1800 for performing a threshold search. In general, the approach illustrated in FIG. 18 may be viewed as a first "step-up/step-down" approach to threshold searching. In particular, the method 1800 relies on applying a first impulse that achieves non-selective capture and reducing the voltage until capture of the HIS bundle is lost. The step size is then decreased and the step is inverted such that the voltage is increased until capture is regained. This process repeats with progressively smaller step sizes until a final impulse voltage is reached.

At operation 1802, the impulse voltage is set to a relatively high initial value (e.g., 5V) and a relatively large negative step size (e.g., -0.5V). At operations 1804 and 1806, a pacing impulse is delivered and the corresponding response is measured and classified to determine if the HIS bundle has been captured.

If the impulse applied at 1804 is the first impulse of the threshold search (operation 1807), the step is applied (operation 1808) to the impulse voltage and a subsequent iteration of applying an impulse and classifying the corresponding response (i.e., operations 1802 and 1804) is initiated.

The foregoing approach assumes that the initial impulse voltage is sufficient to capture the HIS bundle. However it should be appreciated that in certain implementations, capture of the HIS bundle using the initial impulse voltage may be confirmed from the measurements obtained during operation 1806. In the event capture does not occur, the impulse voltage may be increased until capture is achieved or the stimulation device determines capture cannot be achieved (e.g., if the devices maximum voltage is reached).

If the impulse is not the first impulse of the threshold search, the result of the current iteration and previous iteration are compared (operation 1810). If the result is the same (i.e., both of the previous and current iterations resulted in capture or non-capture of the HIS bundle), the step remains unchanged. However, if the previous and current iteration differ in their result (i.e., the previous iteration resulted in capture and the current iteration resulted in non-capture, or vice versa), the step is inverted and the step size is reduced (operation 1812). In one example implementation, the step size is inverted and halved (e.g., from −0.5V to +0.25V). Regardless of whether the step is modified in operation 1812 and provided one or more exit criteria are not met, the step is applied to the current impulse voltage (operation 1808) and the process of applying the impulse and evaluating the corresponding response is reiterated.

As noted, following operation 1810 (and possible adjustment of the step at operation 1812), one or more exit criteria may be evaluated (operation 1814). When the exit criteria are met, the threshold search effectively ends and an impulse voltage setting of the stimulation device is set to the current impulse voltage (operation 1816). The specific exit criteria used to trigger implemented may vary. For example, in one implementation, the exit criteria may include the step size reaching some minimum resolution. In another implementation, the exit criteria may include a predetermined number of iterations. In yet another implementation, the exit criteria may include when application of the current step would result in a previously tested value. Although illustrated as occurring after operation 1810 or 1812, it should be appreciated that the exit criteria may be evaluated at other times during execution of the method 1800.

In one specific example, suppose application of an initial 5V impulse results in non-selective capture of the HIS bundle. A −0.5V step is then applied such that the impulse voltage is changed to 4.5V. The subsequent 4.5V impulse again results in capture of the HIS bundle, so the −0.5V step is applied again. This process may be repeated until the impulse results in myocardium-only capture. For purposes of this example, it is assumed that a 3.5V impulse results in myocardium-only capture (i.e., loss of capture of the HIS bundle). In response to the change to myocardium-only capture, the step size is inverted and halved (i.e., set to +0.25V) and applied such that the new voltage is 3.75V. The 3.75V impulse regains non-selective capture of the HIS bundle, causing the step to be inverted and halved again (i.e., set to −0.125V). The step is again applied to the current impulse voltage, resulting in an impulse voltage of 3.625V. The 3.625V impulse again results in non-selective capture of the HIS bundle and the threshold test is concluded with a non-selective threshold of 3.625V (as applying the 0.125V step would result in the previously applied voltage of 1.5V).

The foregoing search approach can be further applied to identify thresholds for any or all types of capture associated with a patient. For example, after the non-selective capture threshold is found in the above example, the impulse voltage may be set to 3.5V (or other voltage identified as resulting in myocardium-only capture) and the step value may be reset to −0.5V. The foregoing iterative process of identifying when a change in capture type occurs, inverting and reducing the step size, and applying the new step size may then be repeated to identify the threshold between myocardium-only capture and loss of capture. By doing so, thresholds may be identified between non-selective and myocardium-only capture and between myocardium-only and loss of capture.

It should be appreciated that the foregoing approach may be inverted such that the initial voltage is set at a relatively low value to cause myocardium-only or loss of capture and increased until capture occurs. For example, suppose an initial 1.0V impulse results in capture of the myocardium only. A +0.5V step is then applied such that an impulse voltage of 1.5V is used to deliver a subsequent impulse. The 1.5V impulse again results in capture of the myocardium only, so the +0.5V step reapplied. The steps are repeated until the resulting 2.5V impulse then results in capture of the HIS bundle (i.e., selective or non-selective capture). In response, the step size is inverted and halved (i.e., set to −0.25V) and applied such that the new impulse voltage becomes 2.25V. The 2.25V impulse maintains capture of the HIS bundle and the −0.125V step is applied. The resulting 2.125V impulse results in loss of capture such that 2.125 V is identified as the threshold for selective capture.

It should be appreciated that the foregoing method may also be modified such that the threshold search is implemented as a binary search. To do so, the initial impulse value may be set without intending to specifically result in HIS capture or non-capture. If capture of the HIS bundle occurs, the sign of the step may be set to negative (i.e., the voltage of the impulse for the subsequent search iteration may be reduced). Alternatively, if non-capture occurs, the sign of the step may be set to positive (i.e., the voltage of the impulse for the subsequent search iteration may be increased). Subsequent iterations may then include reducing and inverting the step as described in the previous examples.

In one specific example of this alternative approach, the initial impulse voltage may be set to 1.5V and the initial step voltage may be 0.5V. In response to the 1.5V impulse resulting in myocardium-only capture, the impulse voltage may be increased to 2.0V (i.e., the sign of the step voltage may be set to positive). Applying the 2.0V impulse results in capture of the HIS bundle (i.e., selective or non-selective capture). In response, the sign of the step is inverted and the step size is reduced such that the step becomes −0.25V and the subsequent impulse becomes 1.75V. The 1.75V impulse again results in capture of the HIS bundle; however, instead of applying the −0.25V step (resulting in the previously tested 1.5V value), the step size is instead reduced such that the step becomes-0.125V. The subsequently applied voltage of 1.625V results in capture and is set as the impulse voltage.

It should be appreciated that the foregoing threshold search method is provided merely as an example search method that may be used in implementations of the present disclosure. Moreover, to the extent any specific values are included in the foregoing description (e.g., for the initial voltage, initial step size, and the like), such values are included only as examples and should not be viewed as limiting.

Backup Pacing for HIS Bundle Pacing Applications

Atrioventricular node (AVN) ablation and permanent right ventricular (RV) pacing have been previously shown to improve quality of life for patients suffering from symptomatic permanent atrial fibrillation (AF) refractory to optimal medical therapy. However, long term apical RV pacing can increase the risk of death and heart failure hospitalization.

If intact, the His-Purkinje conduction system allows electrical stimulation to rapidly propagate into both right and left ventricles, ensuring synchronized ventricular contraction. Studies have demonstrated that distal HIS bundle pacing (HBP) could normalize bundle branch block and QRS morphology. For example, at least one study has demonstrated in a small number of patients with AF and dilated cardiomyopathy that HBP improved left ventricle (LV) dimensions and cardiac function. Accordingly, HBP may provide physiological activation and avoid ventricular dyssynchrony (i.e., separate LV and RV pacing) associated with RV pacing, thereby preserving ventricular function.

For patients with complete AV node block, a back-up lead is commonly placed in the RV apex in addition to the HBP lead such that RV backup pacing is available when HBP loses capture. In such applications, a cardiac resynchronization therapy pacemaker (CRT-P) device may be used to deliver pacing pulses through each of the atrial lead, RV lead, and HBP lead. Although other configurations may be possible, in at least some cases, the HBP lead may be connected to the LV port of the CRT-P device (as opposed to a dedicated HBP port/channel) in at least some applications.

Although necessary when capture is lost, RV backup pacing is energy intensive and can reduce battery life and operational life of the impulse generator. Such reduced operational life can contribute to higher rates of lead revisions and generator changes in HBP devices as compared to conventional RV apical pacing devices. Accordingly, to preserve operational and battery life, it is desirable to avoid unnecessary application of RV backup pacing impulses in HBP applications.

In at least some stimulation devices, the delay between an atrial event (sensing or pacing) and that of the ventricle (referred to herein as the "A-V" delay) is programmed significantly shorter than the nominal A-V interval such that the HIS bundle is preemptively paced. The device may further be programmed to provide LV pacing followed by RV pacing after an LV-RV delay that is significantly longer than the nominal LV-RV interval (which, in certain applications may be the maximum LV-RV delay of the device) such that back-up pacing is provided in the event of loss of capture, HBP lead dislodgment in patients with complete AV block, or similar events. Notably, certain devices may not allow RV sensing or RV pacing inhibition after an LV pacing impulse is delivered. As a result, in such cases, the backup RV pacing impulse may always be delivered regardless of whether HIS bundle capture has occurred. This cause unnecessary wastage of the device battery and might lead to higher rates of generator change.

To address the foregoing issues, among others, the present disclosure includes stimulation devices (such as, but not limited to, CRT-P devices) and methods of operating such stimulation devices that evaluate timing between various pacing and sensing events to promote HIS bundle capture and avoid unnecessary backup pacing.

In one implementation of the present disclosure, the stimulation device measures and evaluates conduction time between the atrium and HIS bundle (referred to herein as "A-H delay" or the "A-H interval") and HIS bundle capture type. In at least one implementation, HIS capture type is determined based on the delay between pacing of the HIS bundle ($H_P$) and sensing in the RV ($RV_S$). The A-H delay and H-RV delay may be measured during initial setup of the stimulation device (e.g., during in-office testing and configuration) or during operation of the stimulation device (e.g., in device-based implementations). During operation, HIS bundle capture type may be continuously evaluated. If the HIS bundle is not effectively captured, then backup RV pacing is delivered. A diagnostic test (e.g., A-H delay test, capture threshold test, etc.) may also be performed in the event of a failure to capture the HIS bundle.

Figure 19A:
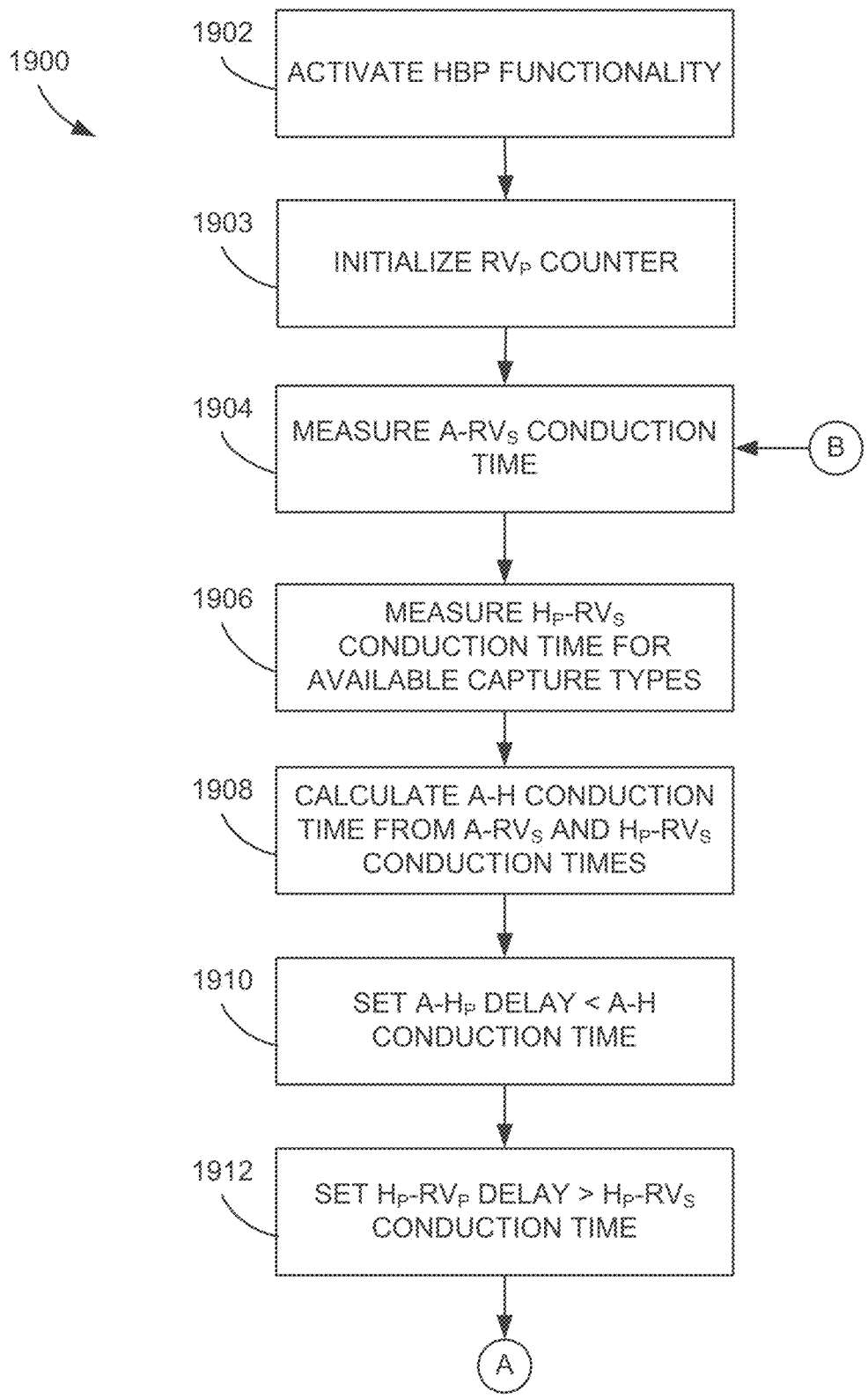
FIGS. 19A and 19B are a flow chart illustrating a method for controlling delivery of backup impulses in HIS bundle pacing applications.
Figure 19B:
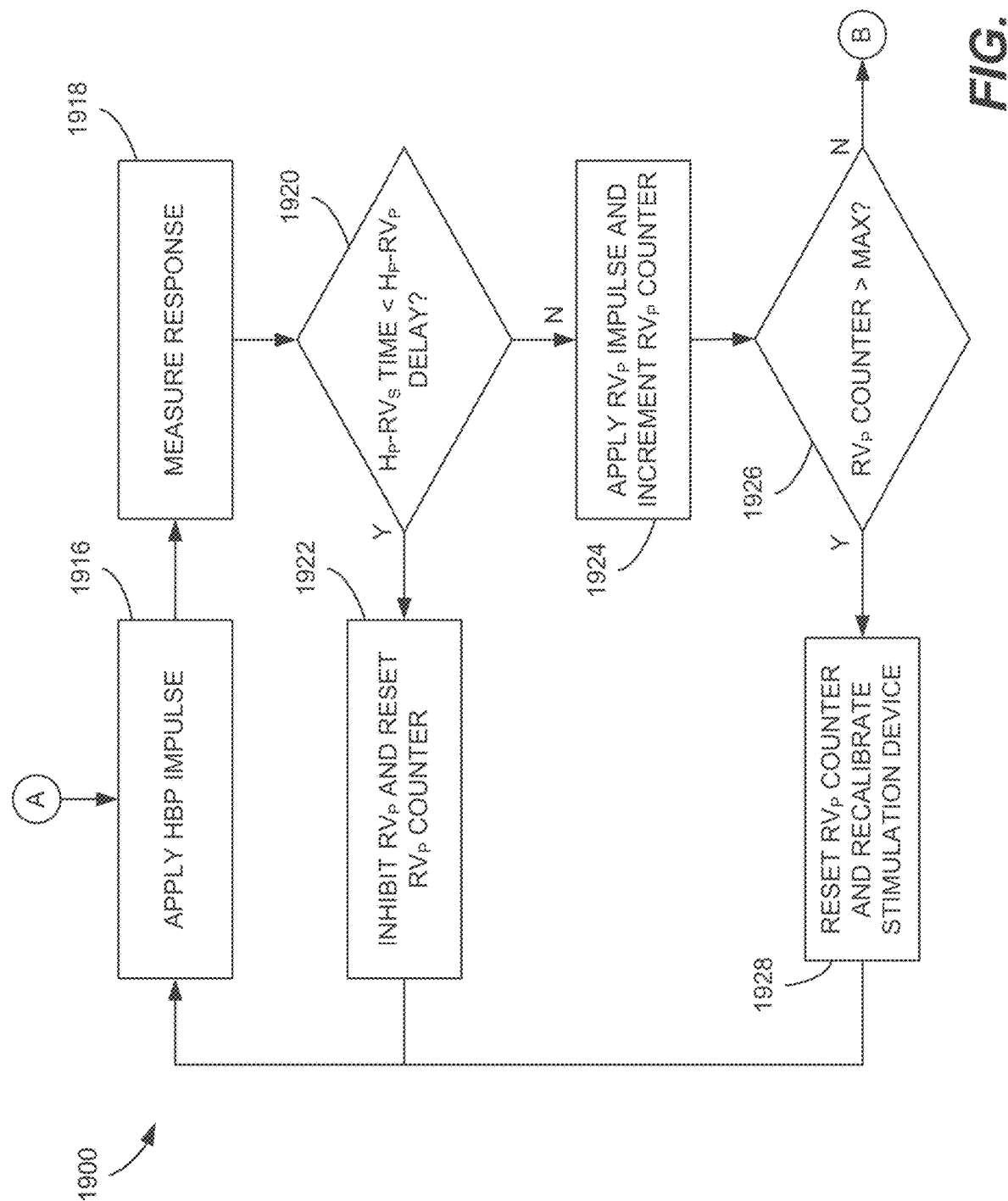

FIGS. 19A and 19B are a flow chart illustrating a method 1900 for controlling delivery of backup impulses during HIS bundle pacing (HBP). The method 1900 may be implemented in a stimulation device that generally includes at least each of an atrial lead, a HIS bundle lead, and a ventricular lead. For the specific example of FIG. 19, the ventricular lead is considered to be a RV lead, but implementations of the present disclosure may be modified to provide LV pacing using an LV lead instead. In certain implementations, the stimulation device may be a CRT-P device, however the method 1900 may more generally be implemented by any stimulation device configured to provide HBP.

At operation 1902, HBP functionality is activated in the stimulation device. As previously discussed, HBP functionality may be implemented in CRT-P or other stimulation devices that may not be initially designed for HBP functionality. Accordingly, in at least some implementations, activating HBP functionality may include programming such functionality into the stimulation device and activating the programmed functionality, e.g., by changing operational modes to a HBP mode. In certain implementations, the stimulation device may internally count, log, or otherwise track backup impulses. Accordingly, after activating HBP functionality, a right ventricle pacing ($RV_P$) (or similar backup impulse) counter (or other tracker) of the stimulation device may be initialized (e.g., set to zero) at operation 1903.

Subsequent to activation of HBP functionality, initial conduction times are measured and corresponding pacing delays are set. More specifically, at operation 1904, the time between an atrial event and a corresponding response of the RV (referred to herein as the $A-RV_S$ conduction time) is measured. The atrial event may be either sensing of activation of the atrium ($A_S$, e.g., as measured using a sensing electrode of the atrial lead) or atrial pacing ($A_P$, e.g., as delivered by a pacing electrode of the atrial lead). The response of the right ventricle ($RV_S$), on the other hand, corresponds to activation of the right ventricle following a given atrial event (e.g., as measured using a sensing electrode of the RV lead following either pacing of the atrium or sensing of atrial activation).

In addition to measuring the $A-RV_S$ conduction time at operation 1904, one or more delays between HBP and activation of the RV (referred to herein as the "$H_P$-$RV_S$" delay) are also measured at operation 1906 and, more specifically, measured for one or more available capture type. In one implementation, doing so may include delivering multiple impulses previously identified as eliciting particular types of capture and measuring the corresponding time between application of such impulses to the HIS bundle and the resulting depolarization of the RV.

To the extent such data is unavailable, operation 1906 may further include first performing a threshold capture test or similar test to determine what capture types are available for the patient and the corresponding impulse levels required for the capture types. In at least one such test, differentiation may be made between capture of the HIS bundle (either non-selective or selective) and myocardium-only capture based on the $H_P$-$RV_S$ time. More specifically, each of non-selective and selective $H_P$-$RV_S$ time is generally shorter than $H_P$-$RV_S$ conduction when myocardium-only capture occurs. In such implementations, two $H_P$-$RV_S$ conduction times may be identified; one corresponding to non-selective/selective capture and the other corresponding to myocardium only capture. Notably, this approach does not distinguish between selective and non-selective capture, but rather distinguishes between capture of the HIS bundle and capture of the myocardium only.

Having obtained each of the A-RV$_S$ and H$_P$-RV$_S$ conduction times in operations 1904 and 1906, an A-H conduction time is calculated at operation 1908. In at least one implementation, A-H conduction time is calculated as the difference between the A-RV$_S$ conduction time and the H$_P$-RV$_S$ conduction time for a particular capture type. In implementations in which selective capture is specifically available, it is generally preferred to use the H$_P$-RV$_S$ conduction time obtained in operation 1906 for selective capture to determine the A-H conduction time. Otherwise, the H$_P$-RV$_S$ conduction time for non-selective capture may be used to calculate the A-H conduction time. In yet another implementation, if the foregoing example approach is used in which a distinction is not specifically made between selective and non-selective capture, the H$_P$-RV$_S$ conduction time indicative of general HIS bundle capture may be used.

In general, if neither selective nor non-selective HIS bundle capture is available during initialization of the stimulation device, additional actions may be required. Among other things, an additional capture threshold test or similar calibration routine may be executed to try to identify pacing parameters capable of achieving selective or non-selective capture. Otherwise, a physician may be required to reevaluate whether HBP is appropriate for the particular patient and may opt for other approaches for addressing the patient's particular condition.

At operation 1910, the delay between an atrial event and pacing of the HIS bundle (referred to herein as the "A-H$_P$ delay") for the stimulation device is set. More specifically, the A-H$_P$ delay is set to be less than the A-H conduction time calculated in operation 1908 such that the HIS bundle is preemptively paced following an atrial event (i.e., pacing or sensing). In at least one specific implementation, the A-H$_P$ delay is set approximately 10 ms shorter than the A-H conduction time. In other words, the stimulation device is configured to pace the HIS bundle 10 ms ahead of when the HIS bundle would otherwise be naturally activated in response to an atrial event.

As described below in further detail, the stimulation device may be configured with an A-H$_P$ delay corresponding to selective and/or non-selective capture but may subsequently result in myocardium-only or loss of capture. In such cases, the A-H$_P$ delay previously calculated A-H$_P$ delay may be maintained, at least for a predetermined number of beats before the stimulation device undergoes recalibration.

At operation 1912, the delay between pacing of the HIS bundle and pacing of the RV (referred to herein as the "H$_P$-RV$_P$ delay") is set. In methods according to the present disclosure, the RV is paced only when a backup impulse is required. Accordingly, the H$_P$-RV$_P$ delay is generally set to exceed the H$_P$-RV$_S$ conduction time (obtained in operation 1906 (i.e., the natural conduction time between pacing of the HIS bundle and a resulting response in the RV). In at least one specific implementation, the H$_P$-RV$_P$ delay is set approximately 10 ms longer than the H$_P$-RV$_S$ conduction time. In other words, the stimulation device is configured to pace the RV 10 ms after when the RV would otherwise naturally activated in response to pacing of the HIS bundle.

Once configured, the stimulation device operates by applying an impulse to the HIS bundle (operation 1916) and measuring the corresponding response (operation 1918), each of which may be performed according to any approach discussed herein. The response is subsequently analyzed to determine whether the measured time between pacing of the HIS bundle and a corresponding response of the RV falls within the H$_P$-RV$_P$ delay. In other words, the stimulation device applies an impulse to the HIS bundle and determines whether the RV naturally activates within the window identified in operation 1912.

In one specific example, a timer is started when the pacing impulse is applied to the HIS bundle and is configured to stop when either activation of the RV is identified or the timer exceeds the H$_P$-RV$_P$ delay. In the former case, backup pacing of the RV (i.e., RV$_P$) is inhibited because the RV activated within the prescribed window of time and the backup impulse/RV$_P$ counter is reset (operation 1922). Normal operation of the stimulation device then resumes. If, on the other hand, the timer expires before activation of the RV occurs, myocardium-only or loss of capture has occurred. Accordingly, at operation 1924, a backup impulse is applied and the backup impulse/RV$_P$ counter is incremented (or a log entry, bin entry, etc. is made if a log is used instead of a counter).

Following application of the backup impulse at operation 1924, the counter, log, bin, etc. is evaluated to determine whether it meets certain criteria to initiate recalibration of the stimulation device (operation 1926). In the specific implementation method 1900 of FIGS. 19A and 19B, the criteria is whether the RV$_P$ counter exceeds a maximum (e.g., three); however, any other suitable criteria may be used in other implementations. If the criteria is met, the RV$_P$ counter is reset and the stimulation device is recalibrated (e.g., using a threshold capture or similar test) (operation 1928).

If, on the hand, the RV$_P$ counter is below the maximum, the stimulation device may adjust the A-H$_P$ and H$_P$-RV$_P$ delays by reexecuting operations 1904-1912 using the measured response data obtained in operation 1918. More specifically, the A-RV$_S$ conduction time and H$_P$-RV$_S$ conduction time identified in operations 1904 and 1906 may instead be based on the actual response data obtained in operation 1918 such that the delay values subsequently set in operation 1910 and 1912 reflect actual performance characteristics of the heart.

The foregoing method may be applied during operation of a stimulation device such that the A-H$_P$ delay and H$_P$-RV$_P$ delay values are substantially continuously reevaluated and adjusted by the stimulation device. With respect to the A-H$_P$ delay, such continuous monitoring enables the stimulation device to reliably deliver pacing impulses that preempt natural activation of the HIS bundle in response to atrial events. Similarly, continuous monitoring of the H$_P$-RV$_P$ delay ensures that backup impulses are provided only when necessary, thereby conserving energy and extending the operation life of the stimulation device.

By applying the foregoing method, the timing of HBP impulses and the delivery of backup impulses are improved.

It should be appreciated that the foregoing method for controlling backup impulses is provided merely as an example that may be used in implementations of the present disclosure. Moreover, to the extent any specific values are included in the foregoing description, such values are included only as examples and should not be viewed as limiting.

Atrium-to-his Bundle Delay in Bundle Branch Pacing Applications

Permanent HIS bundle pacing (HBP) was initially demonstrated to improve cardiac function in heart failure patients with atrial fibrillation. Since then, HBP has also been investigated as a means for correcting other cardiac conditions. Among other conditions, conventional HBP (e.g., using a permanently implanted pacemaker and HIS bundle lead implanted at the HIS bundle) has been shown to be effective in improving cardiac function in a high proportion of patients with bundle branch block (BBB). BBB generally refers to a condition in which a blockage occurs in one of the left branch bundle (LBB) or right branch bundle (RBB) that bifurcate from the HIS bundle into the endocardium of the ventricular septum. The BBB can occur in either branch bundle, resulting in what are commonly referred to as right branch bundle block (RBBB) and left branch bundle block (LBBB), respectively. In general, in each of RBBB and LBBB, the BBB slows conduction (or fully inhibits conduction in severe cases) through the corresponding bundle branch, resulting in ventricular dyssynchrony, among other effects.

With respect to certain BBB cases where conventional HBP is ineffective, at least one theory is that such patients may have a more severe and/or more distal conduction block that cannot be corrected by applying an impulse at the HIS bundle at reasonable pacing outputs. One approach to addressing such cases is to implant the HIS bundle into the blocked branch bundle distal the BBB such that delivered impulses are not affected by the BBB. In such approaches, conduction through the unblocked branch bundle may generally occur through natural conduction. Such a pacing approach has been shown to enable achievement of substantially normal conduction through the His-Purkinje conduction system.

Nevertheless, a significant issue in achieving synchrony (e.g., A-V synchrony or V-V synchrony) is identifying and implementing a proper delay between an atrial event and delivery of the subsequent pacing impulse. For purposes of the following discussion the terms atrial-His delay/"A-H delay" and/or A-H interval are used to refer to this delay, however it should be appreciated that the actual delay or interval is between an atrial event (i.e., sensing or pacing) and subsequent pacing of the blocked bundle branch.

In patients without atrioventricular block (AVB), the A-H delay has direct and significant influence on the QRS morphology and duration. For example, Table 3, below, shows the general effects of different A-H delays in patients with LBBB and for which pacing is applied to the LBB. As noted, if the A-H delay is configured to be relatively short (e.g., less than approximately 70 ms), the LBB will generally be captured. However, the resulting QRS morphology and duration will generally be consistent with that of patients with RBBB. More specifically, because the LBB is paced ahead of intrinsic conduction through the RBB, the result is conduction through the RBB "lagging" conduction through the LBB, as is similar with RBBB. If, on the other hand, the A-H delay is configured to be relatively long (e.g., greater than approximately 120 ms), the response will not differ substantially from the LBBB. In other words, with such delays, the LBB may be paced too late to correct the LBBB and the resulting QRS morphology and duration will still be consistent with LBBB.

If the A-H delay is set optimally (e.g., in the range of approximately 70 ms to approximately 120 ms), substantial fusion of the RBB and LBB may occur. In other words, when pacing is applied with a proper A-H delay, the RBB and LBB will function in a substantially normal way, the dyssynchrony caused by the LBBB will be substantially corrected, and the resulting QRS morphology and duration will be substantially normal (i.e., as if the conduction delay resulting from the LBBB was substantially attenuated or eliminated).

Table 4, below provides a similar summary of the effects of A-H delay as Table 3, but in the RBB pacing context. As indicated, a short A-H interval generally results in QRS morphology and duration similar to those of LBBB, a long A-H interval results in QRS morphology and duration consistent with RBBB, and an optimal A-H interval results in QRS morphology and duration consistent with the dyssynchrony caused by the RBBB being at least partially attenuated.

TABLE 3

General Effects of Different A-H Intervals in LBB Pacing

| A-H Interval | Source of Response | QRS Morphology | QRS Duration |
|---|---|---|---|
| Short (<~70 ms) | LBB capture | RBBB | Long |
| Optimal (~70 ms-~120 ms) | RBB + LBB fusion | Normal | Normal |
| Long (>~120 ms) | Intrinsic RBB conduction | LBBB | Very long |

TABLE 4

General Effects of Different A-H Intervals in RBB Pacing

| A-H Interval | Source of Response | QRS Morphology | QRS Duration |
|---|---|---|---|
| Short (<~70 ms) | RBB capture | LBBB | Very Long |
| Optimal (~70 ms-~120 ms) | RBB + LBB fusion | Normal | Normal |
| Long (>~120 ms) | Intrinsic LBB conduction | RBBB | Long |

In light of the foregoing, implementations of the present disclosure are directed to a device-based method for obtaining an A-H interval to achieve fusion in bundle branch pacing applications. Among other things, the method includes indirectly detecting using various methods for estimating QRS duration and recognizing BBB. It should be appreciated that the proposed method can be modified to apply to either LBB pacing applications for patients with LBBB or RBB pacing applications for patients with RBBB; however, for purposes of the example LBB pacing and a patient with LBBB are assumed.

As previously noted, changing the A-H interval in bundle branch pacing applications may result in significant changes in the QRS complex. Accordingly, to obtain an optimal A-H interval (i.e., an A-H interval that substantially results in fusion), implementations of the present disclosure include obtaining QRS morphology and/or measuring QRS duration using IEGM. Since LBB pacing can be performed using a wide range of simulation devices (including, without limitation, DR pacemakers, CRT-P devices, and CRT-D devices) different IEGM vectors can be used to record the heart's response to an applied impulse and to measure or estimate the corresponding QRS morphology and/or duration. A summary of such approaches is provided below in Table 5, which lists various IEGM vectors and potential methods for assessing either QRS morphology or duration. As noted in the table, in at least some implementations, the width of a unipolar IEGM signal may be used as a surrogate for QRS duration. In certain implementations, QRS width/duration may also be determined using the derivative of the IEGM signals, such as described above in FIGS. 11-12B.

TABLE 5

Example IEGM Vectors and Corresponding Methods for Identifying Fusion

| IEGM Vector | Non-Limiting List of Example Devices | Fusion Identification Method |
|---|---|---|
| His* Tip/ Ring-to-Can | CRT-P devices CRT-D devices DR Pacemakers | Estimate QRS duration from unipolar width. |
| A Tip/ Ring-to-Can | CRT-P devices CRT-D devices DR Pacemakers | Estimate QRS duration from high-passed V far field in the unipolar signal |
| His* bipolar-to-RV bipolar interval | CRT-P devices CRT-D devices DR pacemaker (for paroxysmal atrial fibrillation patients) | Measure delay between the two channels. Lengthening the A-H interval generally shortens the delay between the two channels due to increased contribution from the RBB to RV activation. |
| A bipolar-to-RV bipolar interval | CRT-P devices CRT-D devices | Measure delay between the two channels. The delay between the two channels stops getting longer as the RBB contributes to more RV activation when the A-H interval is lengthened. |
| RV Bipolar | CRT-P devices CRT-D devices DR pacemaker (for paroxysmal atrial fibrillation patients) | Identify morphological change from biphasic to monophasic. |
| RV coil-to-Can | CRT-D devices | Estimate QRS duration from signal. |
| SVC coil-to-RV coil | CRT-D devices (with dual coil leads) | Estimate QRS duration from signal |

*The term "His" as used in this table refers to the lead implanted at either LBB or RBB, which, in at least some implementations, corresponds to the HIS channel of the stimulation device.

FIG. 20 is a table illustrating other changes to measurements obtained from various IEGM vectors for differing A-H intervals. For purposes of FIG. 20, it is assumed that the optimal A-H interval for the patient is 100 ms; however, the specific optimal A-H interval may vary from patient-to-patient. Accordingly, the changes illustrated in FIG. 20 for different A-H intervals should be regarded only as examples.

Figure 21:
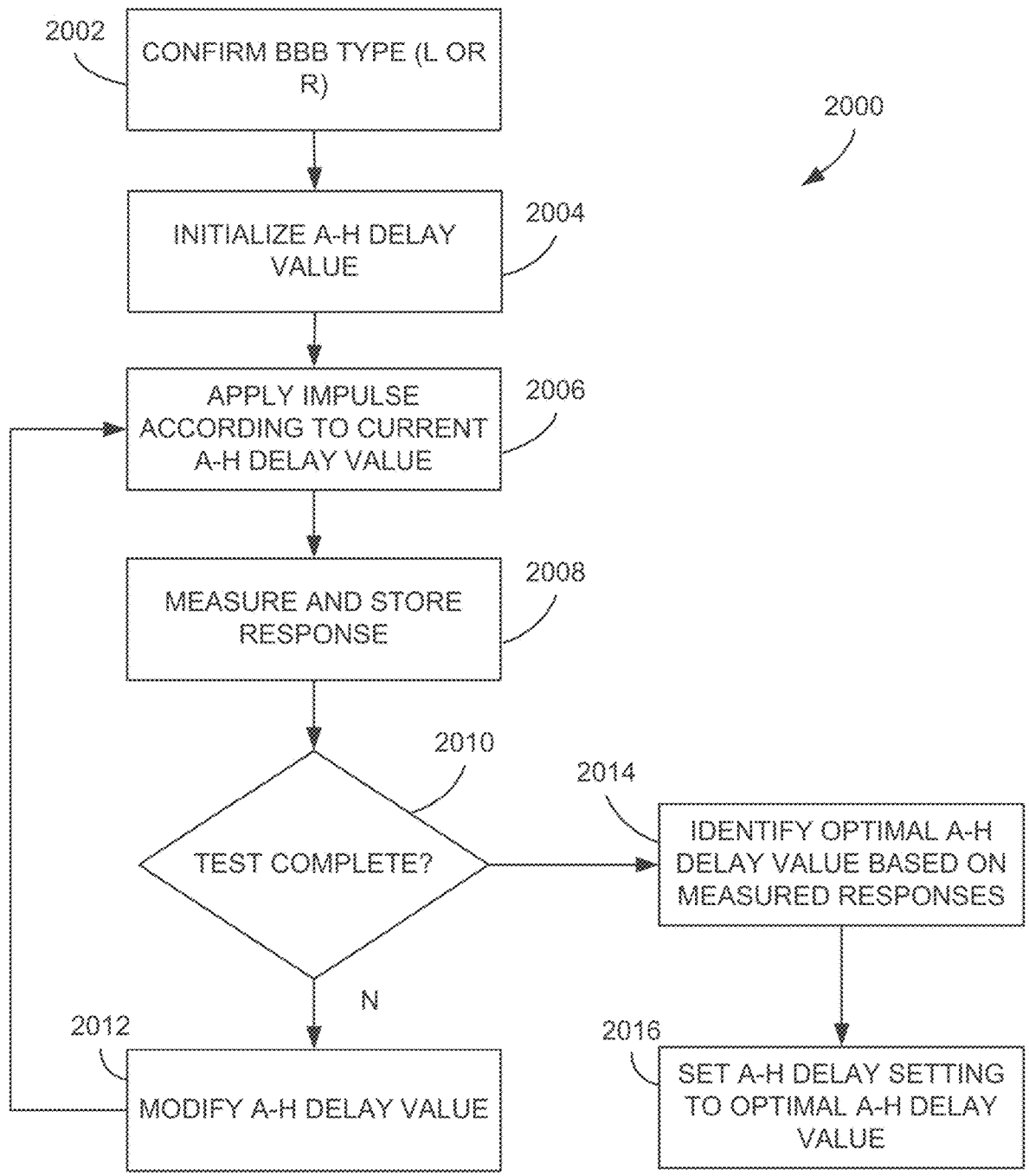
FIG. 21 is a flow chart illustrating an example method for setting HIS pacing delays in stimulation devices configured to provide pacing for patients with branch bundle block.

FIG. 21 is a flow chart illustrating an example method 2000 for setting A-H delay in stimulation devices configured to provide BBB pacing. As previously noted, the specific type of stimulation device used may vary; however, in general, such devices include a lead including an electrode for applying a pacing impulse to a bundle branch and components configured to measure a response of the heart to the pacing impulse, such as components configured to obtain an IEGM in conjunction with application of the pacing impulse. Accordingly, the stimulation device may at least conform to any stimulation device discussed herein or otherwise known and capable of performing the foregoing functions. As indicated in Table 5, the specific approach or vector for obtaining the IEGM may vary depending on the type and configuration of the device being used. Nevertheless, it should be appreciated that the specific approaches provided herein are intended merely as examples and any suitable way of obtaining a measurement of cardiac activity may be used.

At operation 2002, the type of BBB (e.g., RBBB or LBBB) is confirmed. In one specific implementation, confirmation is performed at or following implantation of the stimulation device and generally includes programming or configuring the stimulation device to perform the specific type of BBB pacing. In one specific example, a physician, technician, or similar personnel confirms the BBB type during post-operative testing and calibration of the stimulation device.

In addition to confirming the type of BBB pacing, initial setup of the stimulation device may also include initializing an A-H delay value (operation 2004). The initial value of the A-H delay may vary based on various factors including, without limitation, the patient's specific physiology, conduction times obtained from testing, clinical data for similar patients, and the like. Among other approaches, initializing the A-H delay value may include programming of the A-H delay value (e.g., by a physician, technician, or similar personnel during post-operative testing and calibration of the stimulation device) or automatically setting the A-H delay value to a predetermined value.

Following initialization of the A-H delay, the stimulation device begins testing to determine which A-H delay results in an optimal response for the patient. As shown in FIG. 20, such testing generally involves applying a pacing impulse according to the current A-H delay value (operation 2006) and measuring and storing the corresponding response (operation 2008).

With respect to operation 2008, measurement of the response may include, but is not necessarily limited to, capturing or recording IEGM data associated with the impulse and corresponding response. Such monitoring may be conducted using various vectors and may depend on the specific type and configuration of the stimulation device, as noted above with respect to Table 5.

Following collection of the response data, a check may be performed to determine whether the test has been completed (operation 2010). If the test is not complete, the A-H delay value may be modified (operation 2012) according to the particular testing protocol. For example, in one specific testing protocol, the A-H delay is initialized to a first, low value at which an impulse is applied and a corresponding response is obtained. The A-H delay may then be increased by a predetermined amount, a subsequent impulse may be applied, and a corresponding response may be recorded. This process may repeat until a maximum A-H delay is reached. In an alternative approach, the A-H delay may be started at a high value and gradually decreased until a minimum A-H delay is reached. The foregoing test protocols are merely examples and any suitable approach for testing various A-H delays may be implemented.

Following testing of various A-H delays, the resulting measurements are analyzed to determine the tested A-H delays resulted in an optimal response (operation 2014) and then the settings of the stimulation device are updated such that the stimulation device applies an impulse after the optimal A-H delay (operation 2016).

The specific approach to identifying the optimal A-H delay may vary in applications of the present disclosure. However, in at least some implementations, the process generally includes analyzing the response data collected for the various tested A-H delay values and determining which meets one or more criteria. For example and without limitation, in a first implementation, the optimal A-H delay value may be considered to be that which resulted in the narrowest unipolar IEGM width. In another implementation, the optimal A-H delay value may be considered to be the shortest A-H delay value with monophasic RV bipolar morphology. In yet another implementation, the optimal A-H delay value may be considered to be the shortest A-H delay value resulting in a shortening of the pacing-to-RV sensing interval. In still another implementation, the optimal A-H delay value may be considered to be the shortest A-H interval at which an atrial event (pacing or sensing)-to-RV sensing interval stops increasing. In another implementation, the response data for each A-H delay value may include data corresponding to a QRS wave and the optimal A-H delay value may be considered that which resulted in a QRS wave that most closely resembles a template (e.g., based on cross-correlating the measured QRS data and the template). Similarly, characteristics of the measured QRS wave data for each A-H delay value may be compared to one or more values and the optimal A-H delay interval may be considered that with characteristics closest to the values. For example, in one specific implementation, the QRS duration for each A-H delay interval may be identified and compared to a fusion QRS duration and the A-H delay value with a QRS duration closest to the fusion QRS duration may be considered optimal. It should be appreciated that the foregoing criteria may be considered alone or in combination. For example, in certain implementations, multiple criteria may be applied with each criterion being associated with a particular score or weight such that the "optimal" A-H interval is that which results in the highest score.

Figure 22:
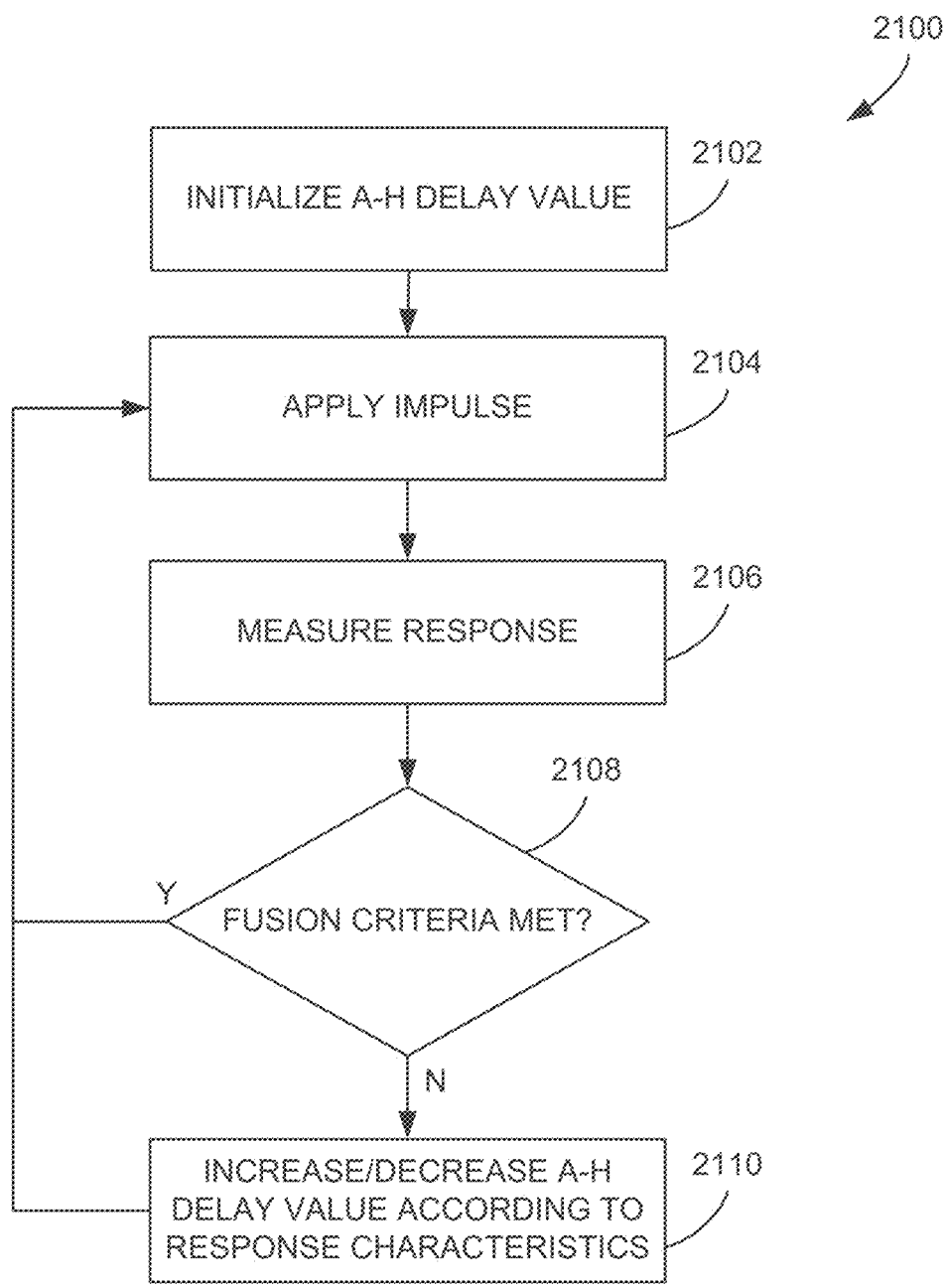
FIG. 22 is a flow chart illustrating an example method for dynamically adjusting the HIS pacing delay during operation of a stimulation device.

The foregoing method was generally described as occurring in the context of initial setup or configuration of the stimulation device. It should be appreciated, however, that a similar approach may be implemented during operation of the stimulation device to dynamically adjust the A-H setting of a stimulation device. FIG. 22, for example, is a flow chart illustrating an example method 2100 for dynamically adjusting the A-H delay of a stimulation device during operation thereof.

As illustrated in FIG. 22, the method 2100 generally includes initializing the A-H delay value (operation 2102). Such initialization may include setting the A-H delay value based on previous testing, such as testing according to the method 2000 of FIG. 21.

Following initialization, the stimulation device initiates a continuous process in which a pacing impulse is applied according to the current A-H delay value (operation 2104) and a corresponding response is measured (operation 2106). The measured response may be in the form of an IEGM, as previously discussed, however, any suitable response measurement may be taken.

The response data is then analyzed to determine whether one or more fusion criteria have been met (operation 2108). In other words, the stimulation device analyzes the measured response data to determine whether it is indicative of fusion. For example and without limitation, in one implementation, the stimulation device determines the QRS duration of the response data and compares the QRS duration to a value or range of values indicative of fusion. To the extent the measured QRS duration is within a threshold of the value or within the range of values, the response data may be said to meet the fusion criteria. In another implementation, the QRS morphology of the response is compared to a fusion template a correlation coefficient or similar fit metric is calculated. If the fit metric is within a threshold range, the QRS morphology may be considered to substantially indicate fusion.

If the stimulation device determines the one or more fusion criteria are met, the stimulation device may proceed to pacing and measuring the next beat. If, on the other hand, the stimulation device determines that fusion has not occurred, the stimulation device may automatically adjust the A-H delay value based on the response characteristics (operation 2110). Such adjustment may include increasing or decreasing the A-H delay. For example and without limitation, either of the QRS duration or QRS morphology may be used to determine whether the A-H delay is too short or too long and should therefore be increased or decreased, respectively. Following adjustment of the A-H delay, a subsequent pacing impulse may be applied and analyzed to determine whether the adjusted A-H delay resulted in fusion (i.e., operations 2104-2108 may be repeated using the adjusted A-H delay).

His Bundle Pacing with Improved Backup Pacing

Cardiac resynchronization therapy with left ventricular pacing is an established therapy for patients with systolic heart failure and intraventricular conduction system delay, particularly left bundle branch block. Despite large-scale randomized trials demonstrating the efficacy of this therapy, clinical and echocardiographic non-response rates remain as high as up to 40%.

His bundle pacing (HBP) has reemerged as a means to provide physiologic resynchronization in patients with bundle branch block by correcting QRS by direct capture of the His-Purkinje system. In these cases, back-up pacing in the right ventricle (RV) or left ventricle (LV) for HBP are needed in cases of loss of capture, especially for patients with AV block.

Programming stimulation devices for HBP may present various challenges as HIS bundle pacing may have specific device configurations and require special considerations for which current implantable pulse generators may not be specifically designed.

In HIS bundle pacing applications (and particularly in pacemaker-dependent patients), backup pacing may be provided by a right ventricle (RV) lead or a left ventricle (LV) lead in the event of loss of capture. While sometimes necessary in loss of capture cases, it is generally preferred to avoid unnecessary ventricular pacing (e.g., applying a backup impulse when loss of capture has not occurred), with the RV lead or LV lead serving only for ventricular sensing.

Although certain stimulation devices may execute algorithms to optimize atrioventricular and/or interventricular delays, such algorithms may not be appropriate for HIS bundle pacing applications and, as a result, may yield suboptimal performance. For instance, certain algorithms adjust the atrioventricular interval (AVI) based on far-field P-wave duration or on intrinsic atrioventricular conduction delay. In such cases, the optimized AVI may be too long (by about 40 to 60 ms in certain specific applications) to be used for HIS bundle pacing applications. In general, such differences arise from conventional AVI algorithms not taking into account the His-to-ventricle interval following the pacing stimulus before ventricular activation in HIS bundle pacing applications.

Furthermore, certain algorithms may propose LV-only pacing for fusion with intrinsic atrioventricular conduction, which may not be desirable in certain situations (e.g., fusion with RV pacing for selective HIS bundle pacing with right branch bundle block). Also, asystole may result in cases of loss of capture in patients with transient complete atrioventricular block (although this may not be an issue in cases of persistent atrioventricular block as such algorithms do not activate LV-only pacing in such instances).

Accordingly, improved stimulation devices and methods for operations such devices to provide backup pacing specifically in HIS bundle pacing applications are needed.

This disclosure introduces an approach for LV backup pacing when necessary by programming the backup pacing delay based on the time between pacing of the HIS bundle and a resulting sensed QRS peak. This approach allows HIS captured beats to reach the LV electrode before delivery of a backup impulse and, as a result, enables inhibition of such backup delays when unnecessary. Accordingly, LV pacing is still provided when loss of capture occurs but is inhibited when HIS captured beats propagate to the ventricles. Also in cases of myocardium-only capture in which conduction time may be longer than the time between pacing of the HIS bundle and a resulting sensed QRS peak, back-up pacing is delivered causing fusion with the septal myocardium propagation wave.

In certain applications, HBP may not result in QRS waveforms with sufficient width reduction. Accordingly, this disclosure further provides approaches to HBP in which fusion of HIS bundle pacing and ventricular pacing (e.g., LV pacing) is used to correct the QRS width.

Although other stimulation devices may be used in applications of the present disclosure, for purposes of the following example, it is assumed that the stimulation device is a CRT device including each of an LV port, an RV port, and an A port. In general, when such CRT devices are used to provide HBP, the HIS lead is connected to either the LV port of the CRT device with (the LV lead connected to the RV port) or to the RV port (with the LV lead connected to LV port). The atrial (A) lead generally remains connected to the A port. This convention is used in the following discussions, however, it should be understood that this convention is used for clarity and should not be viewed as limiting.

As previously noted, certain aspects of the present disclosure are directed to improvements in backup impulse delivery. Accordingly, a new approach to backup pacing is provided that generally avoids back-up pacing of the ventricles when the HIS bundle is paced and captured while also eliminating the risks for any applied back-up pacing impulses occurring during repolarization of the ventricles (e.g., during the T wave).

In general, the methods discussed herein are directed to achieving the foregoing benefits by identifying an appropriate delay between an atrial event (sensing or pacing) and delivery of a pacing impulse to the HIS bundle. For purposes of this portion of the current disclosure, this timing is generally referred to as the A-H delay or A-H interval. Once identified, the stimulation device may be configured to deliver HIS bundle pacing impulses in accordance with the identified A-H delay.

Figure 23:
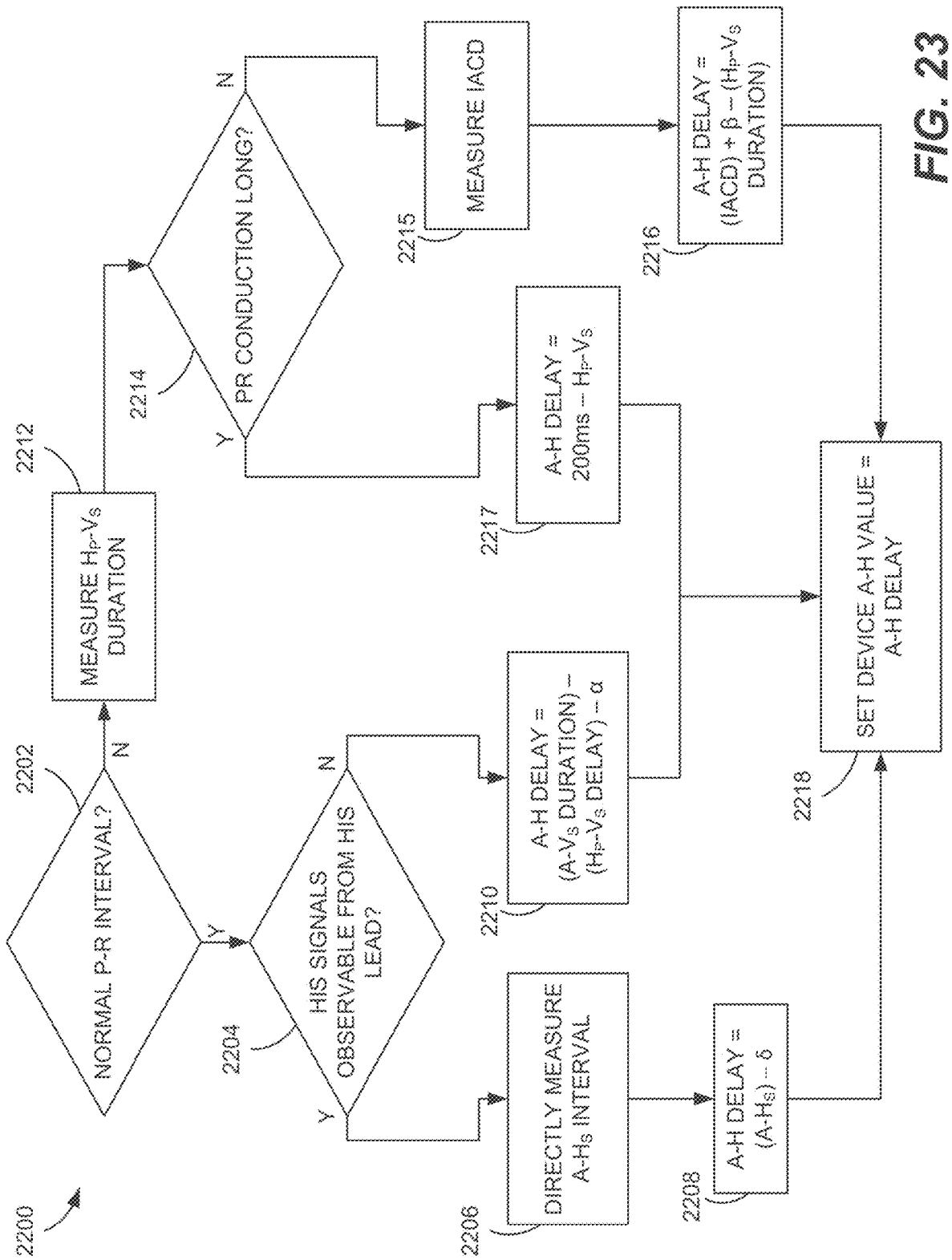
FIG. 23 is a flow chart illustrating an example method for identifying and implementing a HIS pacing delay.

FIG. 23 is a flow chart illustrating a method 2200 for identifying and implementing an A-H delay for a given stimulation device and patient.

Selecting an appropriate A-H delay can be dependent on whether or not the patient in question has a normal atrio-ventricular conduction delay (which is generally from about 120 ms to about 200 ms). Atrio-ventricular delay is also referred to herein as the P-R segment or P-R interval. In certain applications, the P-R interval may be defined as the interval between onset of atrial sensing (the P wave) and onset of the QRS complex. Alternatively, in applications in which the atrium is paced, the P-R interval may be defined as the interval between application of a pacing impulse to the atrium and corresponding onset of the QRS complex. Accordingly, the method 2200 begins with first assessing whether the patient has an intact conduction system, as may be evidenced by a P-R interval in the normal range (operation 2202).

For patients with P-R segments in the normal range (or other measure of an intact conduction system), the calculation of the A-H delay may vary depending on whether the HIS lead includes a sensing electrode that is capable of sensing activation of the HIS bundle in response to an atrial event (i.e., sensing or pacing) (operation 2204). In cases where HIS sensing is observable from the HIS lead, the A-H delay may be determined by measuring a response from the HIS sensing electrode following one of intrinsic activation or pacing of the atrium (operations 2206, 2208). In other words, the A-H delay may be set equal to A-$H_S$-δ where A-$H_S$ is the time between an atrial event and sensed activation of the HIS bundle as measured using the HIS lead and δ is a small delay to account for pacing latency and to ensure pre-emptive HIS pacing.

If, on the other hand, such signals are not available from the HIS lead, the A-H delay may be determined based on various conduction times and correction factors (operation 2210). In one specific implementation each of the A-$V_S$ duration (i.e., the time between an atrial event and sensing of depolarization of the ventricle) and the $H_P$-$V_S$ duration (i.e., the time between pacing/stimulation of the HIS bundle and sensing of depolarization of the ventricle) are measured and a correction factor (α) is applied. In such implementations, the A-H delay for the stimulation device may be calculated according to formula (1), below:

$$A\text{-}H\text{ delay}=(A\text{-}V_S\text{ duration})-(H_P\text{-}V_S\text{ duration})-\alpha \quad (1)$$

The correction factor (α) is used to ensure preemptive pacing of the HIS bundle and, in one example implementation may be approximately 10 ms. It should also be appreciated that in cases of non-selective HIS bundle capture, the duration of the delta wave (e.g., as measured using an IEGM) may also need to be added to the $H_P$-$V_S$ duration if $V_S$ is measured by the onset of the QRS complex from the HIS lead. Alternatively, other landmarks of the QRS complex may be used to eliminate sensing of the onset of the delta wave.

In patients without heart block (e.g., branch bundle block), alternative conduction times and correction factors may be used to calculate an appropriate A-H delay. More specifically, the A-H delay may be calculated and set by first measuring the $H_P$-$V_S$ duration (operation 2212). In certain implementations, different approaches for calculating A-H delay may be used depending on whether the patient exhibits a long P-R interval (operation 2214). In patients without long P-R intervals (e.g., P-R intervals below about 150 ms), the intra-atrial conduction delay (IACD) may also be measured (operation 2215). The A-H delay may then be calculated according to equation (2a), below (operation 2216):

$$A\text{-}H\text{ delay}=(IACD)+\beta-(H_P\text{-}V_S\text{ duration}) \quad (2a)$$

where β is an offset that accounts for electromechanical coupling of the atria and $H_P$-$V_S$ duration is the time between HIS bundle pacing and onset of the sensed depolarization of the ventricle (operation 2216). The specific value of β may vary, but, in general, β is used to account for the delay between electrical activation and the corresponding mechanical movement of the atrium. Among other things, the value of 13 may depend on lead type and placement and the particular sensing vector being used.

Alternatively, in cases where the patient exhibits a long P-R interval, the A-H delay may instead be calculated according to equation (2b), below (operation 2217):

$$A\text{-}H\text{ delay}=200\text{ ms}-(H_P\text{-}V_S\text{ duration}) \quad (2b)$$

As in the previous case, if a delta wave is observed in non-selective capture cases, the duration of delta wave should be added to the $H_P$-$V_S$ duration.

Following determination of the appropriate A-H delay using any of the foregoing approaches, the A-H delay setting of the stimulation device may be set to the determined A-H delay (operation 2218).

Figure 25:
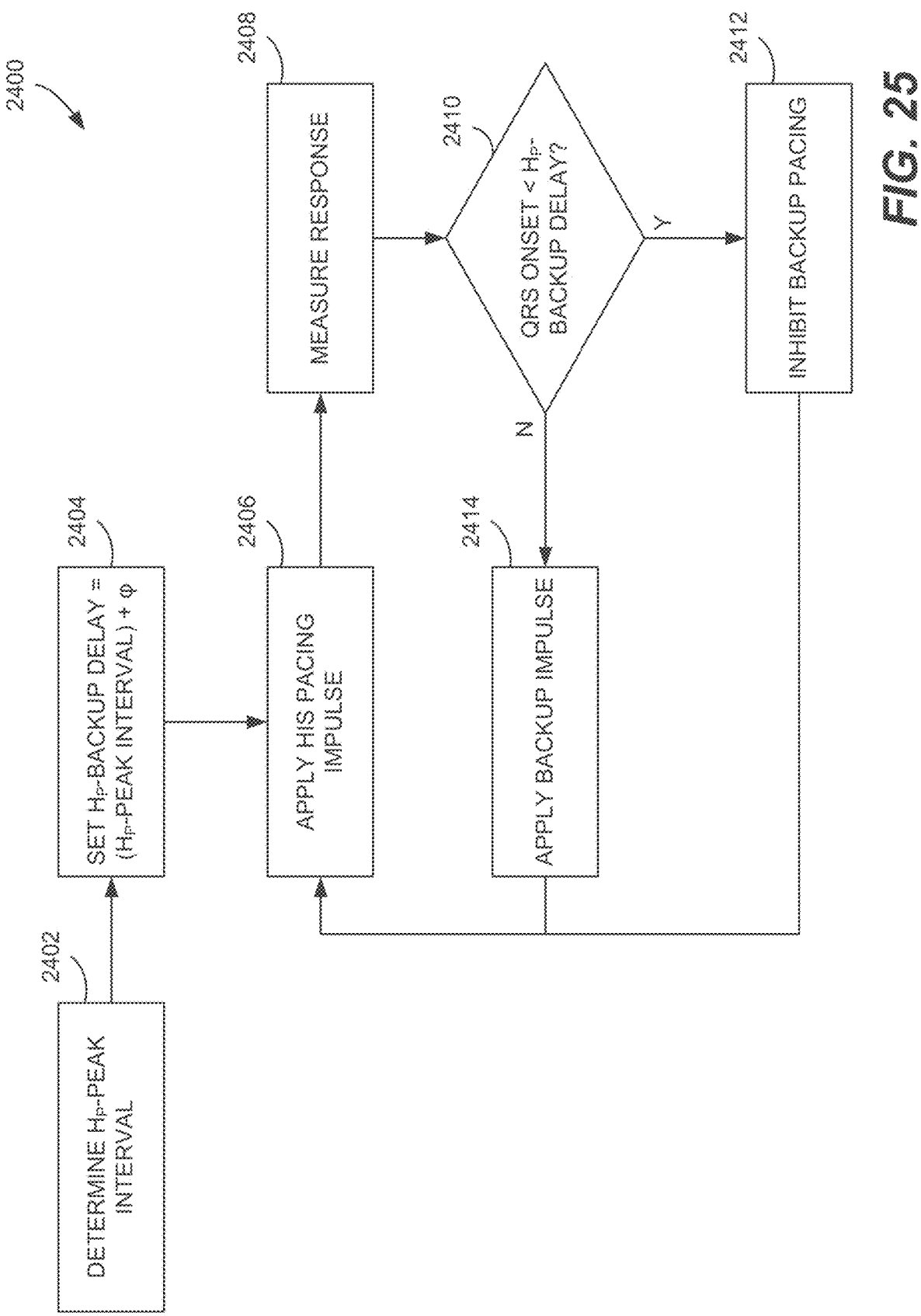
FIG. 25 is a flow chart illustrating a second method for determining whether to apply or inhibit backup pacing.
Figure 26:
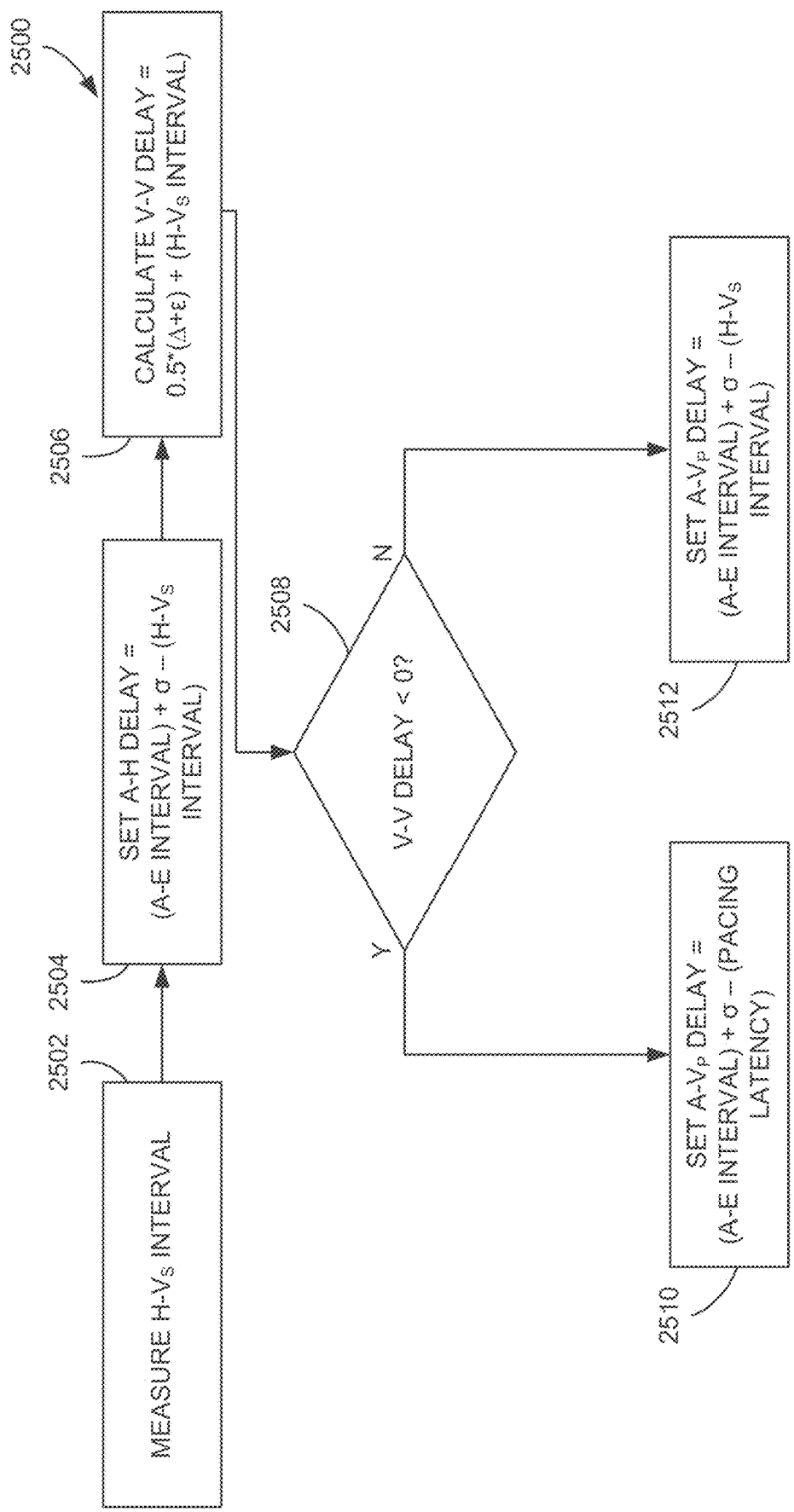
FIG. 26 is a flow chart illustrating a method of configuring a stimulation device for to provide providing fusion-based pacing.

Once the A-H delay is set (either using the foregoing method of FIG. 23 or any other suitable method), the intraventricular pacing delay (referred to herein as the V-V delay) may be determined. Although various approaches may be used, FIGS. 24-26 provide additional example scenarios and approaches for determining whether to apply or inhibit backup pacing.

Figure 24:
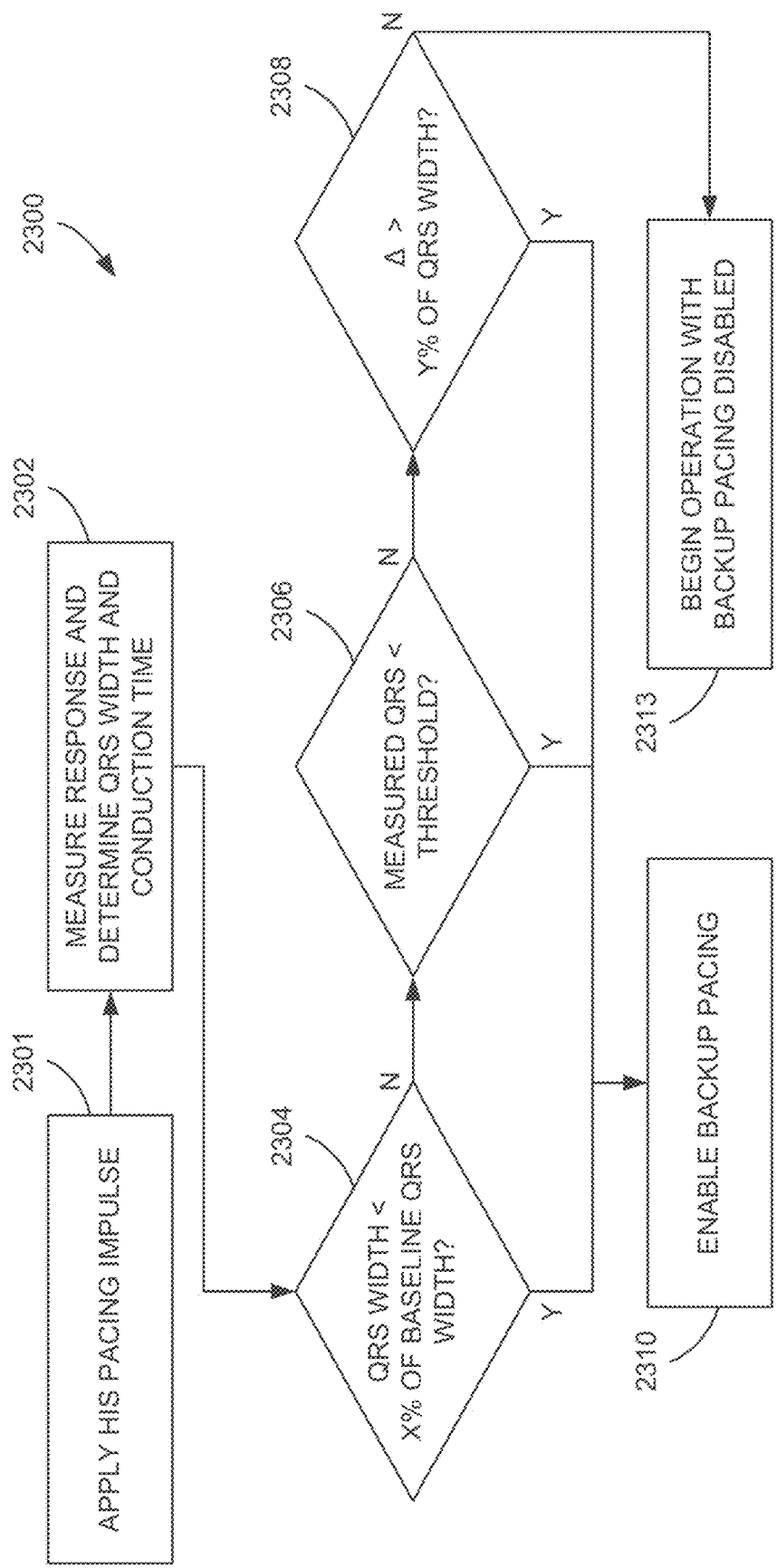
FIG. 24 is a flow chart illustrating a first method for determining whether to apply or inhibit backup pacing.

Referring first to FIG. 24, a flow chart is provided illustrating a first method 2300 for determining whether to apply or inhibit backup pacing. In the method 2300, it is assumed that the stimulation device is a CRT device with a HIS lead in the LV port, a bipolar RV lead in the RV port for providing backup pacing, and an A lead in the A port; however, the following method is readily adaptable to other devices and port configurations. The following method further assumes that the CRT device is programmed to pace the LV port (i.e., the HIS lead) first following a previously set A-H delay.

At operation 2301, a HIS pacing impulse is applied and, at operation 2302, various response characteristics are measured, which may include the intrinsic conduction time between application of the HIS pacing impulse and response of the LV and the QRS width/duration. In certain implementations, the response values may be modified, such as by applying a correction factor, to account for variations in device types, device configurations, and the like. For example, in certain implementations, a correction factor of 5 ms or 10 ms may be applied to any of the measured response characteristics to account for such variations.

The response characteristics obtained in operation 2302 may then be evaluated to determine whether to enable backup pacing. As shown in operations 2304-2308, the method 2300 includes three tests to determine whether backup pacing is necessary. In a first test, the QRS width as measured in operation 2302 is compared to a previously obtained (e.g., during in-clinic testing) baseline (operation 2304). If the measured QRS width is less than a predetermined percentage of the baseline QRS width, pacing of the HIS bundle is considered to have corrected the QRS complex and a backup pacing scheme is enabled in the event capture is later lost (operation 2310). In certain example implementations, the predetermined percentage may be from an including about 15% to and including about 25% and, in one specific implementation, is about 20%. In other words, in such a specific implementation, backup pacing is enabled if the measured QRS width is equal to 80% or less of the baseline QRS width.

In a second test, the measured QRS duration is compared to a threshold value to determine whether the measured QRS duration is less than the threshold value (operation 2306). In certain implementations, the threshold value may generally correspond to an upper limit for a normal/corrected QRS complex. Although values may vary by patient, in at least one implementation, the threshold value may be approximately 120 ms. Accordingly, if the QRS width is less than the threshold, HIS bundle pacing is again considered to have resulted in correction and backup pacing is enabled in the event capture is later lost (operation 2310).

In a third test, various conduction delays may be measured to determine whether correction has occurred. For example, in one implementation, a difference (Δ) between conduction delays measured using different vectors may be calculated. If Δ exceeds a predetermined threshold or a predetermined percentage of another metric (such as a baseline QRS width) (operation 2308), then correction is considered to have occurred and backup pacing is enabled (operation 2310). Δ may be calculated in various ways, however, in one implementation, Δ is calculated according to equation (3), below:

$$\Delta = (H_P - LV_S) - (H - V_S) \tag{3}$$

where $H_P$-$LV_S$ is the delay between pacing of the HIS bundle and sensing at the LV and H-$V_S$ is the delay between pacing of the HIS bundle and peak voltage as identified from a measured QRS complex obtained from the HIS bundle lead. In still other implementations, Δ may instead be calculated based on conduction delays measured relative to pacing or sensing at the atrium. More generally, however, implementations of the present disclosure may include determining whether correction has occurred based on changes in the conduction delay as measured using any suitable approach. In any such case, backup pacing may be enabled if correction has occurred in the event that capture is later lost.

The foregoing tests are merely provided as examples and should not be viewed as limiting. Rather, implementations of the present disclosure more generally include analyzing the response to HIS bundle pacing to determine whether or not correction of the QRS complex has occurred. Such correction may generally be manifested as a reduction in the width of the QRS complex, which in turn may be identified using various approaches.

If backup pacing is not enabled as a result of any of the foregoing tests, the stimulation device begins operation with backup pacing disabled (operation 2313). In the case where backup pacing is enabled, the stimulation device may enter an operational mode in which dynamic analysis is conducted to selectively apply and inhibit backup pacing. Regardless of whether backup pacing is enabled or disabled, the A-$H_P$ delay (i.e., the delay between an atrial event and subsequent pacing of the HIS bundle) may be any suitable value as determined using any of the approaches disclosed herein. When backup pacing is enabled, delay between pacing of the HIS bundle and subsequent backup pacing of the ventricle may also be set according to any suitable method disclosed herein. Notably, in certain implementations in which the HIS bundle is connected to a ventricle port of the stimulation device, the delay between pacing of the HIS bundle and subsequent backup pacing of the ventricle may correspond to a V-V delay (i.e., an intraventricular delay) setting of the stimulation device.

The specific method illustrated in FIG. 24 determines whether to enable or disable backup pacing during subsequent operation of the stimulation device based on the indicated criteria. Although illustrated as relying on a single pacing and response, it should be understood that the method illustrated in FIG. 24 may instead include multiple pacing applications and responses. For example, in one implementation, multiple pacing impulses may be applied and the corresponding responses may be collected and averaged or otherwise combined. The criteria in operations 2304-2308 may then be applied to the combined response data.

As noted above, if backup pacing is enabled in operation 2301, the stimulation device may enter into an operational mode in which backup pacing is automatically applied or inhibited. An example of one such mode is illustrated in FIG. 25, which is a flow chart illustrating a method 2400 for operating with backup pacing enabled. In one specific implementation, the method 2400 may be executed by the stimulation device with the device operating in DDD mode. The method 2400 begins by first determining the interval between pacing of the HIS bundle and the peak of the resulting QRS complex ($H_P$-peak interval) sensed at the electrode for delivering backup pacing (operation 2402). In certain implementations, the $H_P$-peak interval may be determined in-clinic or via an automated test performed by the device; however, any suitable approach for determining the $H_P$-peak interval may be used.

At operation 2404, the delay between pacing of the HIS bundle and application of a backup impulse ($H_P$-backup delay) is set for the stimulation device. In general, the $H_P$-backup delay is set to be equal or greater (e.g., by a small delay ((p)) than the $H_P$-peak interval. In certain implementations in which the HIS lead is connected to a ventricular channel of the stimulation device, the $H_P$-backup delay is set by setting the intraventricular (V-V) delay setting of the stimulation device equal to or greater than the $H_P$-peak interval.

Following setting of the $H_P$-backup delay, the stimulation device paces the HIS bundle (operation 2402) and measures a corresponding response (operation 2404). The stimulation device further determines whether onset of a resulting QRS complex occurs within the "alert" interval corresponding to the $H_P$-backup delay (operation 2410). If so, backup pacing is inhibited (operation 2412). If not and there is a corresponding timeout (e.g., a V-V interval time out), a backup impulse is applied (operation 2414). As described in other aspects of the present disclosure, the stimulation device may also track applied backup impulses and may initiate recalibration of the stimulation device when certain conditions are met (e.g., a predetermined number of backup impulses being delivered).

It should be further understood that in alternative implementations of the methods of FIGS. 24 and 25, the HIS lead may instead be connected to the RV port of the CRT device and the LV lead (which may be a bi- or quadripolar lead) may be connected to LV port. In such implementations, the CRT device may be programmed to pace the RV port first (i.e., where the HIS lead connected) after a previously determined A-H delay. Accordingly, the LV port provides backup pacing. The foregoing description of the method 2300 may then be performed with suitable modifications to account for the change in lead configuration.

In other implementations of the present disclosure, the LV lead may be replaced with a RV lead. In such cases, the V-V delay is instead sensed at the RV lead inside RV such that the V-V delay becomes the interval between stimulation do the HIS bundle and the resulting QRS peak as sensed by the RV lead. The remainder of the foregoing methods otherwise remain substantially the same.

In still other implementations, any of the response characteristics used to determine whether to operate the implantable medical device with or without backup pacing or to apply or inhibit backup pacing when operating with backup packing may vary based on the particular patient in question, the patient's particular cardiac anatomy, the specific type and configuration of the stimulation device and components (e.g., the HIS lead) and the position of the sensing electrode within the ventricle. Nevertheless, the foregoing approaches will reduce the risk of the intraventricular delay being set too long while also avoiding backup pacing during depolarization of the ventricles (i.e. during T waves).

The foregoing methods may also be applied to patients with atrial fibrillation. In such applications, the stimulation device may be configured to enter a mode for non-atrial tracking. In such implementations, the WI for the port with the HIS lead remains the same. The specific response characteristics used to evaluate whether to operate with backup pacing and/or to later apply or inhibit backup pacing may also be the same. For example, in such implementations the foregoing approach in which the delay between application of a HIS pacing impulse resulting in capture and a peak voltage of the resulting QRS complex may still be used.

In general, the stimulation device should also allow a maximum intraventricular pacing delay that is greater than the upper bound of the HIS pacing-ventricular sensing interval. For example, at least some studies show that this interval may be from an including about 80 ms to and including about 110 ms. Moreover, the stimulation device should have a ventricular blanking period that is longer than the HIS pacing-ventricular sensing interval. For example, in at least some implementations, a ventricular blanking period of greater than about 200 ms may be used.

With CRT devices, current algorithms to optimize atrio-ventricular and interventricular delays may be inappropriate for HIS bundle pacing due to extra delays associated with the conduction path between the HIS bundle pacing site to apex of the heart. When HIS pacing corrects QRS width/duration, no paced fusion is required or only backup pacing (of the RV or LV) is needed as previously discussed. However, in at least certain cases, HIS bundle pacing will not sufficiently correct QRS width.

To address the foregoing issues, among others, the present disclosure further proposed using fusion from HIS bundle pacing and ventricular pacing to correct QRS width when HIS bundle pacing alone is insufficient. Doing so requires synchronization between application of the HIS bundle pacing impulse and the impulse applied at the ventricle. Accordingly, the present disclosure provides various approaches to configuring various timing parameter of stimulation devices to provide fusion-based pacing for QRS width correction.

For purposes of the following example, it is assumed that the stimulation device is a CRT device with port configurations for HIS bundle pacing as follows: a HIS lead connected to the RV port, an LV lead connected to the LV port, and an A lead connected to the A port. It should be appreciated that the approach discussed herein may also be applied when the stimulation device is a CRT device with the HIS lead in the LV port, the LV lead in the RV port, and the A lead in the A port. More generally, however, the methods discussed herein are applicable to any stimulation device capable of providing both HIS bundle pacing and ventricular backup pacing.

Referring back to operation 2313 of FIG. 24, the stimulation device may be operated with backup pacing disabled. In such cases, the stimulation device may be further configured to operate to provide fusion-based pacing. An example of such a mode is illustrated in FIG. 26. FIG. 26 is a flow chart illustrating a method 2500 of configuring a stimulation device for purposes of providing fusion-based pacing. More specifically, the method 2500 is intended to identify timing for each of HIS bundle and ventricular pacing such that fusion results, e.g., to achieve QRS width correction. The method 2500 may be implemented at various times. For example, in certain implementations, the method 2500 may be executed, at least in part, during an in-office visit (e.g., a post-operative visit). Alternatively, the following method may be implemented within the stimulation device itself.

To begin, the conduction time between the HIS bundle and ventricle ($H-V_S$ interval) is measured (operation 2502). Notably, in at least some implementations, the conduction time is determined from measurements obtained from the HIS bundle lead and not the RV lead. Doing so ensures that the conduction time approximates the conduction time between the HIS bundle and RV apex as opposed to the HIS bundle and the implantation location of the RV lead. In at least some implementations, the $H$-$V_S$ interval may be estimated from a QRS complex measured using the HIS lead.

In at least some implementations the $H$-$V_S$ interval may be adjusted (e.g., through the use of one or more coefficients) based on the type of HIS bundle capture (selective, non-selective, myocardium-only) achievable for the given patient. For example, such adjustments may be used to adjust the base $H$-$V_S$ interval to correspond to specific "landmarks" or key points of the QRS complex (e.g., the QRS peak or onset of the QRS).

At operation 2504, the A-H delay is set. If the HIS bundle is to paced first, the A-H delay may generally be calculated as follows in equation (4):

$$A\text{-}H\text{ delay} = (A\text{-}E\text{ interval}) + \sigma - (H\text{-}V_S\text{ interval}) \quad (4)$$

where the A-E interval is the intra-atrial conduction delay and σ is an offset to account for electromechanical coupling. While the A-E interval may be measured in various ways, in at least certain implementations, the P-wave duration may be is used for the A-E interval. In such implementations, the offset σ may be chosen based on the P-wave duration. For example, in one specific implementation, if the P-wave duration/A-E interval is less than about 150 ms, then the offset σ may be set to 60 ms. If, on the other hand, the A-E interval is greater than or equal to 150 ms, the offset σ may be set to 30 ms.

With timing of the HIS bundle pacing established (i.e. the A-H delay), the method then continues with determining the proper intraventricular delay (V-V delay) to achieve fusion (operation 2506). In general, the V-V delay indicates that time after which ventricular pacing is to be applied following stimulation of the opposite ventricle. In at least one specific implementation, the V-V delay is calculated according to equation (5), below:

$$V\text{-}V\text{ delay} = 0.5(\Delta + \varepsilon) + (H\text{-}V_S\text{ delay}) \quad (5)$$

where Δ is calculated as described above in the context of equation (3) and ε is a coefficient corresponding to the difference in conduction time between the ventricles. More specifically, ε is calculated as the difference between the time delay from pacing the LV and sensing in the RV and the time delay from pacing in the RV and sensing in the LV. In certain implementations, ε may be determined in an office visit and stored in memory of the stimulation device. Alternatively, provided the stimulation device supports such functionality and proper leads are implanted within the heart, the stimulation device may be configured to execute a basic test to determine ε by stimulating each of the ventricles and measuring the resulting response in the opposite ventricle.

At operation 2508, the V-V delay is evaluated to determine pacing order. More specifically, if the V-V delay calculated using equation (3), above, is less than 0, then the LV should be paced first and the $A$-$V_P$ delay should be set according to equation (6), below (operation 2510):

$$A\text{-}V_P\text{ delay} = (A\text{-}E\text{ interval}) + \sigma - (LV\text{ pacing latency}) \quad (6)$$

If, on the other hand, the V-V delay is greater than 0, then the HIS bundle should be paced first and the $A$-$V_P$ delay should be set according to equation (7), below (operation 2512):

$$A\text{-}V_P\text{ delay} = (A\text{-}E\text{ interval}) + \sigma - (H\text{-}V_S\text{ interval}) \quad (7)$$

At operation 2514, the operational parameters of the stimulation device to reflect the HIS bundle and ventricular pacing intervals previously identified.

As previously noted, in certain implementations, the HIS lead may be connected to the LV port of the stimulation device, the LV lead may be connected to the RV port of the stimulation device, and the A lead may be connected to the A port of the stimulation device. In such cases, while the V-V delay is calculated the same as above in equation (3), interpretation of the V-V delay in operation 2508 is inverted. More specifically, when the V-V delay is less than 0, then the HIS lead should be paced first and the $A$-$V_P$ interval should be set according to equation (5). If, on the other hand, the V-V delay is greater than 0, then the LV should be paced first and the $A$-$V_P$ interval should be set according to equation (4).

As explained in the present application, and elsewhere in the literature, HBP may result in various responses, including LOC, RV capture, nonselective HB capture and selective HB capture. Further, patients may be separated into those who exhibit a wide QRS complex and those who exhibit a narrow QRS complex. A wide QRS complex is common with patients exhibiting bundle branch block (BBB). For patients who exhibit a wide QRS complex, HBP may be further classified into additional capture types that include, nonselective HB capture with QRS correction, nonselective HB capture without QRS correction, selective HB capture with QRS correction and selective HB capture without QRS correction. The terms "QRS correction" and "BBB correction" are used interchangeably throughout.

In order to differentiate the various types of capture, typically, more than one feature discriminator/discrimination is analyzed. Examples of feature discriminators include the time delay between 1) an HBP event and 2) a peak of a sense QRS event, or the time delay between 1) the HBP and 2) a maximum derivative of the sensed QRS event, or the QRS width etc. However, during implantation, certain challenges may be experienced in connection with over sensing atrial signals on a HIS bundle pacing lead. Over sensing atrial signals renders it unduly difficult in separating NS type capture from S type capture by using the delay from the HIS paced event to the ventricular sensed event, as the presence of atrial far field signals can be misinterpreted as a ventricular sensed event, thereby misleading a designation between S and NS types of capture.

In order to simplify the HBP capture discrimination, embodiments herein implement a multi-tiered HBP capture classification process that does not initially differentiate between capture types within certain capture groups. The terms "capture group" and "capture class" shall refer to groups or classes of capture, in which two or more types of capture are grouped are classified together with respect to a corresponding individual feature discriminator/discrimination. Instead, in accordance with new and unique aspects herein, it has been recognized that it may be unnecessary to differentiate between certain capture types, and instead merely differentiate between classes of capture type. For example, it is not always necessary to differentiate between NS and S capture types as a relatively small difference is expected in clinical outcome based on the differentiation between NS and S capture types.

Further, multitiered HBP capture classification processes are described herein that may be applied to patients with a wide QRS complex (e.g., patients who experience BBB), that results in grouping, in one group, the capture types for NS and S with QRS correction, and grouping, in another group, capture types for NS and S without QRS correction, myocardial only and LOC.

Additionally, embodiments herein utilize a myocardial auto capture algorithm in combination with multi-tier HBP classification and beat-to-beat capture determination. Additionally or alternatively, embodiments herein apply different feature discriminators in a cascaded or serial manner, wherein a first capture class discriminator does not necessarily identify a specific individual type of capture, but instead distinguishes between first and second capture groups or capture classes. Embodiments herein apply a first capture class discriminator to distinguish between a first capture group/class that includes both S and NS, and a second capture group/class that includes both myo-only and LOC. Additionally or alternatively, a second capture class discriminator is applied to distinguish between individual capture types within a single capture group/class, such as to distinguish between S and NS (both in the first capture group/class). Optionally, the second capture class discriminator or a third capture class discriminator may be applied to distinguish between the individual capture types for myo-only and LOC (both in the second capture group/class). For patients with a wide QRS, embodiments herein apply a first feature discriminator to distinguish between first and second groups/classes, where the first group includes S and NS with QRS correction and were the second group includes S and NS without QRS correction. Optionally, the second group may also include myocardial only and LOC.

In accordance with new and unique aspects herein, embodiments utilize, as capture class discriminator, a time delay between HBP and the last peak of the QRS or the time delay between HBP and the end of the QRS. In order to simplify the HBP capture algorithm, a first capture class discriminator need not differentiate between NS and S as the distinction is not expected to afford a substantial difference in clinical outcome between patients experiencing NS versus patients experiencing S. Instead, it is expected that conduction in the ventricle would be fast as NS or S capture both lead to conduction through the HIS and Purkinje system. As a result, total activation time in the ventricles for S or non-S should be similar to one another and relatively close to the intrinsic heartbeat activation time, for patients experiencing a narrow QRS complex.

The activation time is identified as the time delay from HBP to the last peak of the QRS or the end of the QRS. The end of the QRS or QRS width can be determined from derivatives of the QRS signals. The activation time (as determined between the HBP and last peak of the QRS) is expected to afford a good indicator, in most patients, for differentiation between the first capture class (S or in S) and the second capture class (maillot only or LOC). Myocardial only capture and LOC are expected to have a longer activation time between HBP and the last peak of the QRS, as compared to the activation time associated with NS or S types of capture.

By utilizing one or more capture class discriminators configured to differentiate groups of capture types, and not individual capture types, a new and useful aspects herein avoids a need to analyze signals within a window of time immediately following the HBP event. The window of time immediately following the HBP event may be generally referred to as an HBP blanking interval, during which the feature discriminators blank out or ignore any sensed signals. By defining an HBP blanking interval, aspects herein avoid the potential of over sensing atrial activity. The advantage of using an HBP blanking interval is especially useful in connection with short AH, as the HBP blanking interval allows a threshold test to also be eliminated.

In certain instances, it would be acceptable clinically if the LOC is undetected. For example, some patients exhibited a normal QRS and an AH duration is close to the intrinsic AH duration, then it is acceptable clinically if the LOC is undetected.

Figure 27:
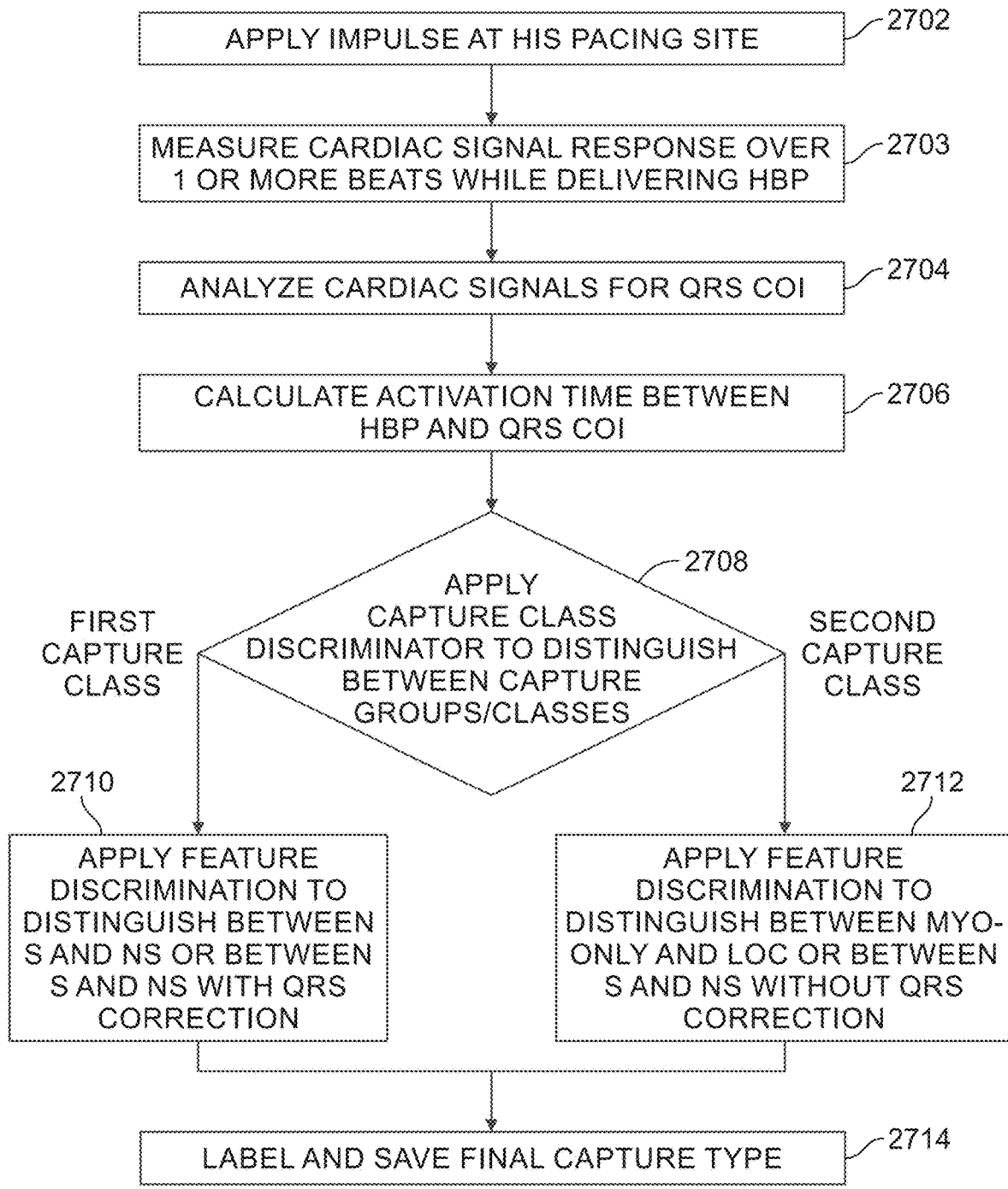
FIG. 27 is a flow chart illustrating an example method for identifying capture types in accordance with an embodiment herein.
Figure 28:
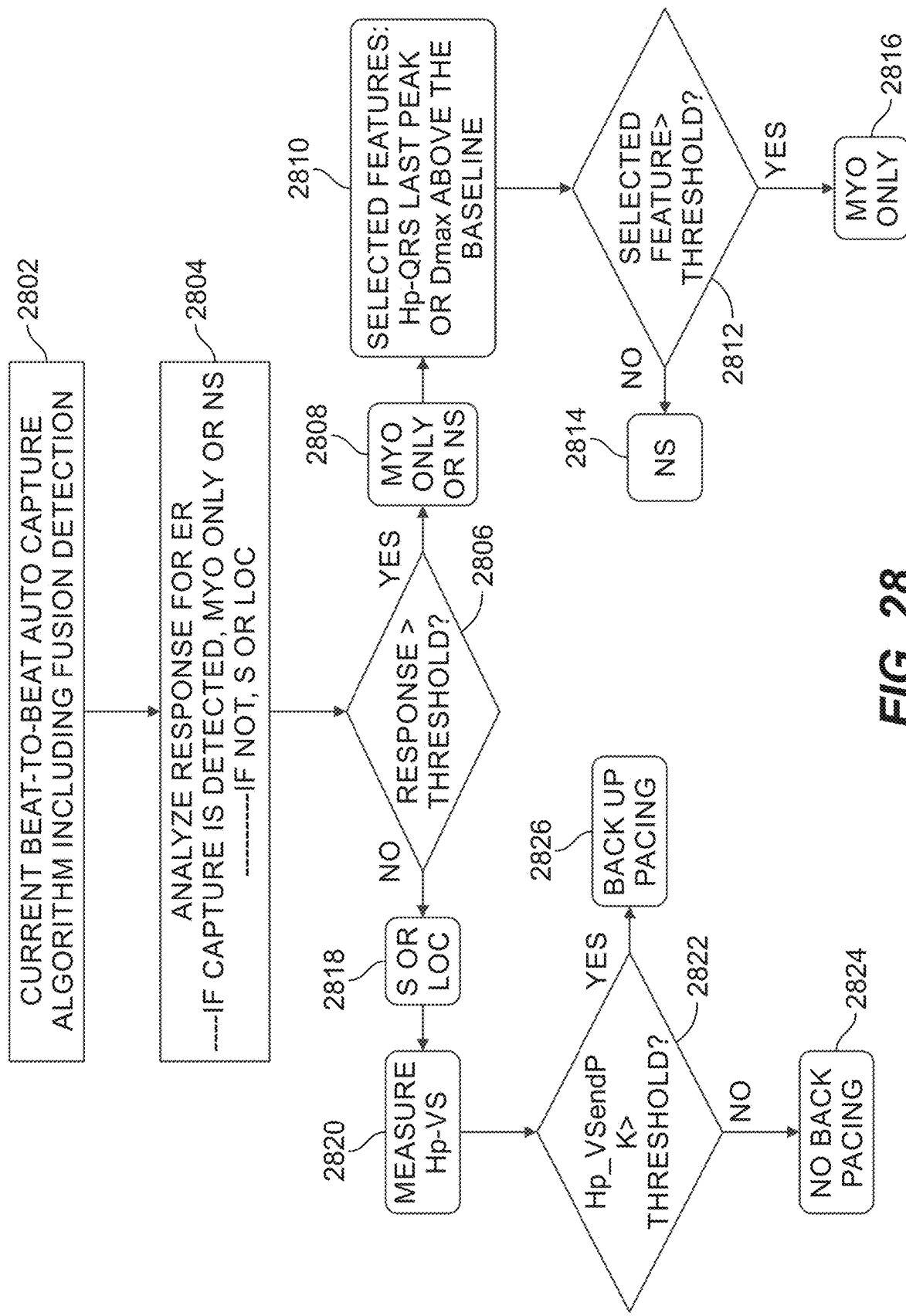
FIG. 28 is a flowchart illustrating an example method for identifying capture types in accordance with an embodiment herein.

FIGS. 27 and 28 illustrate alternative examples for classifying capture types by applying alternative class type classifications, followed by individual feature classifications for corresponding individual capture types.

FIG. 27 is a flow chart illustrating an example method for identifying capture types in accordance with an embodiment herein. The process of FIG. 27 utilizes activation time to distinguish between capture classes, followed by utilization of evoked response COI to distinguish between individual capture types.

At 2702, the one or more processors direct the pulse generator to deliver an impulse at one or more HIS pacing sites as HBP.

At 2703, one or more processors measure a response of cardiac signals in connection with HBP. The one or more processors measure, using the one or more sensing electrode, a response of the patient heart to application of the impulse or impulses of the HBP. For example, the cardiac signals may be collected along the sensing vector that utilizes one or more electrodes on a HIS lead. The electrodes on the HIS lead may be configured in a bipolar or unipolar sensing configuration. During each HIS bundle pacing event, the one or more processors record the point in time at which the HBP was delivered (e.g., with a HBP time stamp). The operations at 2702 and 2703 may be implemented for a single beat or repeated multiple times in connection with a series of beats.

At 2704, the one or more processors analyze a segment of the cardiac signal response that is spaced apart from the HBP by the predetermined interval. For example, the one or more processors align a search window over a segment of the cardiac signal response that is positioned to overlap the QRS complex in the cardiac signal response. The one or more processors analyze the segment of the cardiac signal response within the window to identify a QRS characteristic of interest (COI) within the QRS complex. In accordance with at least one new and unique aspect herein, the QRS COI corresponds to an end of the QRS. The end of the QRS may be determined as the point in time corresponding to a maximum point in the derivative of the QRS complex. Additionally or alternatively, the QRS COI may correspond to a last peak in the QRS complex. The one or more processors may apply a timestamp to the point in time corresponding to the QRS COI. The QRS COI does not occur immediately after delivery of the HBP, but instead occurs at least a predetermined period of time after delivery of the HBP. The portion of the cardiac signal response analyzed at 2704 does not occur immediately after the HBP, but instead occurs at a later point in time spaced apart from the HBP by a time interval sufficient to avoid oversensing atrial activity. For example, the one or more processors may apply a HIS blanking interval immediately following delivery of the HBP, where the HIS blanking interval is positioned immediately following delivery of the HBP and has a duration sufficient to overlap a period of time during which potential atrial activity over sensing may occur.

At 2706, the one or more processors calculate an activation time based on the HBP and the QRS COI. For example, the activation time represents a time delay between the time of the HBP and a time of the QRS COI. The activation time may correspond to the time interval between the HBP and the last peak of the QRS and/or an end of the QRS.

At 2708, the one or more processors apply a first capture class (CC) discriminator that distinguishes between at least first and second capture groups or capture classes. The first capture class discriminator may also be referred to as a group discriminator as it distinguishes between groups or classes of capture types, and not between individual capture types. For example, the first capture class discriminator may correspond to a first timing threshold that is time to such that activation times below the first timing threshold are placed in the first group and activation times above the first timing threshold are placed in the second group. It should be noted that the first timing threshold is not timed to positioned between selective and non-selective capture, but instead to group both selective and nonselective capture in a common class.

At least one of the capture groups or capture classes includes more than one type of capture. For example, the one or more processors may apply a first capture class discriminator to distinguish between a first capture group/class that includes both S and NS, and a second capture group/class that includes both myo-only and LOC. For example, myocardial only capture and LOC will have a longer activation time between the HBP and the last peak of the QRS, as compared to the activation time for S capture and NS capture types.

At least one benefit of the capture class discriminator at 2708 is that embodiments herein avoid the need to apply a detection window in the interval immediately following a HIS bundle pacing event. By avoiding the need for a detection window in the interval immediately following HBP, embodiments herein avoid the risk of atrial over sensing especially with patients who exhibit a short interval between a paced or intrinsic atrial event and a subsequent HIS bundle paced event.

Additionally or alternatively, the one or more processors may apply a wide QRS capture class discriminator that distinguishes between first and second groups or classes, where the first group includes i) S type capture with QRS correction and ii) NS type capture with QRS correction, and where the second group includes i) S type capture without QRS correction, ii) NS type capture without correction, iii) myocardial only and iv) LOC. For example, the wide QRS capture class discriminator may represent a second timing threshold, wherein activation times below the second timing threshold are placed in the first group and activation times above the second timing threshold are placed in the second group. The first timing threshold may be associated with patients exhibiting a normal QRS width, while the second timing threshold is utilized in connection with patients exhibiting a wide QRS width.

Based on the determination at 2708, flow branches in different directions to 2710 or 2712, depending upon which class was identified. At 2710, the one or more processors apply a first feature discriminator to distinguish between capture types within the first capture group. For example, the first feature discriminator may be applied to distinguish between S type capture and NS type capture. By way of example, the first feature discriminator, to distinguish between S and NS may represent an evoked response (ER) COI. Examples of evoked response COIs are explained hereafter in connection with FIG. 28.

For example, as explained below in connection with the operations at 2802-2806, the one or more processors apply a HBP and immediately or shortly thereafter open an ER sensing window to collect a cardiac signal response in connection with sensing for an evoked response within the myocardial tissue surrounding the HIS pacing site. When an HBP has sufficient energy to result in nonselective capture or myocardial only capture, the local myocardial tissue surrounding the HIS pacing site will exhibit a depolarization corresponding to an evoked response. Alternatively, when the HBP does not have sufficient energy to result in nonselective capture or myocardial only capture, the local myocardial tissue surrounding HIS pacing site does not exhibit a depolarization of an evoked response in connection with the HBP. In addition, the one or more processors analyze the cardiac signal response collected during the ER sensing window to identify an ER COI. Based on the ER COI, the one or more processors are able to determine whether the myocardium experienced an evoked response responsive to an HBP event. When an evoked response is detected within the myocardium, following an HBP event, the one or more processors determined that the HBP event captured the myocardium (e.g capture is detected). When the evoked response indicates capture, the potential type of capture would either be myocardial only or nonselective (nonselective with QRS correction or nonselective without QRS correction). Alternatively, the one or more processors may determine that the myocardium does not experience an evoked response responsive to the HBP event. When the cardiac signal response within the sensing window indicates that the myocardium has not experience an ER, the potential type of capture would either be LOC or selective capture (selective with QRS correction or selective without QRS correction). The one or more processors apply a first feature discriminator which may correspond to a total energy within the ER, the ER peak amplitude, the ER maximum slope or another ER characteristic.

Optionally, when used in connection with patients exhibiting a wide QRS (e.g. patients with bundle branch block), the first capture class may represent the capture types for S and NS with QRS correction. Accordingly, the first feature discriminator applied at 2710 may be utilized to distinguish between selective capture with QRS correction and nonselective capture with QRS correction. The first feature discriminator applied to distinguish between selective and nonselective capture with QRS correction may represent an evoked response COI.

At 2712, the one or more processors apply a second feature discriminator to distinguish between capture types within the second capture group. For example, the second feature discriminator may be applied to distinguish between myocardial only type capture and loss of capture. By way of example, the second feature discriminator, to distinguish between myo-only and LOC may represent an evoked response COI.

Optionally, when used in connection with patients exhibiting a wide QRS (e.g. patients with bundle branch block), the second class may correspond to selective and nonselective capture without QRS correction. Accordingly, the second feature discriminator applied at 2712 may be utilized to distinguish between selective capture without QRS correction and nonselective capture without QRS correction. The second feature discriminator applied to distinguish between selective and nonselective capture without QRS correction may represent an evoked response COI.

Additionally or alternatively, embodiments herein apply a first capture class discriminator to distinguish between one capture group/class for S and LOC and a second capture group/class for myo-only and NS, and to apply a second capture class discriminator to distinguish between S and LOC, or between myo-only and NS. For patients with a wide QRS, embodiments herein are able to distinguish between S with QRS correction versus S without QRS correction or LOC. Embodiments are further able to distinguish between NS with QRS correction versus myo-only and NS without QRS correction.

FIG. 28 is a flowchart illustrating an example method for identifying capture types in accordance with an embodiment herein. The process of FIG. 28 utilizes evoked response COI to distinguish between capture classes, followed by utilization of activation time to distinguish between individual capture types.

At 2802, one or more processors apply an automatic capture confirmation process in connection with a current beat. The automatic capture confirmation process applies a HBP and immediately or shortly thereafter opens an ER sensing window to collect a cardiac signal response in connection with sensing for an evoked response within the myocardial tissue surrounding the HIS pacing site. It is recognized that not all HBP cause an evoked response in the local myocardial tissue, such as depending upon the energy delivered within the HBP. When an HBP has sufficient energy to result in nonselective capture or myocardial only capture, the local myocardial tissue surrounding the HIS pacing site will exhibit a depolarization corresponding to an evoked response. Alternatively, when the HBP does not have sufficient energy to result in nonselective capture or myocardial only capture, the local myocardial tissue surrounding HIS pacing site does not exhibit a depolarization of an evoked response in connection with the HBP. Consequently, the presence, shape, amplitude or other characteristics of an ER within the ER sensing window following an HBP may be utilized as a class discriminator (or feature discriminator).

Optionally, the operation at 2802 may also include perfusion detection, in which the one or more processors determine whether the HBP was delivered into a fusion of two or more waveforms.

At 2804, the one or more processors analyze the cardiac signal response collected during the ER sensing window following the HBP to identify an ER COI. Based on the ER COI, the one or more processors are able to determine whether the myocardium experienced an evoked response responsive to an HBP event. When an evoked response is detected within the myocardium, following an HBP event, the one or more processors determined that the HBP event captured the myocardium (e.g capture is detected). When the evoked response indicates capture, the potential type of capture would either be myocardial only or nonselective (nonselective with QRS correction or nonselective without QRS correction). Alternatively, the one or more processors may determine that the myocardium does not experience an evoked response responsive to the HBP event. When the cardiac signal response within the sensing window indicates that the myocardium has not experience an ER, the potential type of capture would either be LOC or selective capture (selective with QRS correction or selective without QRS correction).

At 2806, the one or more processors apply a first capture class (CC) discriminator that distinguishes between at least first and second capture groups or capture classes. For example, the ER COI and first capture class discriminator may correspond to a total energy within the ER, the ER peak amplitude, the ER maximum slope or another ER characteristic. When the cardiac signal response exhibits an ER COI that falls below the first ER threshold, the one or more processors determined that the response corresponds to a first class. When the cardiac signal response exhibits an ER COI that exceeds the first ER threshold, the one or more processors determined that the response corresponds to a second class.

For example, the ER COI may represent a total energy within the ER, which may be calculated by summing an area under the ER curve. As another example, the ER COI may represent a maximum slope within the ER which may be obtained by calculating a derivative of the ER curve. When the decision at 2806 indicates that the myocardium experiences an ER COI that exceeds the ER threshold, flow moves to 2808. Alternatively, when the decision at 2806 indicates that the myocardium experiences an ER COI that falls below the ER threshold, flow moves to 2818.

The branch at 2808-2816 applies a feature discriminator to distinguish between types of capture within the corresponding capture class, such as to distinguish between myocardial only and NS types of capture. The branch at 2818-2826 applies a feature discriminator to distinguish between types of capture within the corresponding capture class, such as to distinguish between S and LOC.

At 2808, the one or more processors recognize that the HBP either achieved myocardial only or NS capture. At 2810, the one or more processors determine an activation time between the HBP and the QRS last peak. For example, the activation time may be determined as explained above in connection with the operations at 2702-2706. Additionally or alternatively, the one or more processors determine the activation time between the HBP and the maximum derivative of the QRS above the baseline.

At 2812, the one or more processors determine whether the activation time exceeds a first activation threshold. The first activation threshold may be preprogrammed or automatically determined, such as during a learning or calibration phase by the implantable medical device. When the first activation time exceeds the threshold, flow moves to 2816 where the event is labeled as a myocardial only capture event. Alternatively, when the activation time does not exceed the threshold, flow moves to 2814 where the event is labeled as a non-selective capture event.

Moving to 2818, the one or more processors recognize that the HBP either achieved selective capture or loss of capture. At 2820, the one or more processors measure a second activation time between the HBP and a ventricular sensed event.

At 2822, the one or more processors determine whether the second activation time exceeds a second activation threshold. The second activation threshold may be preprogrammed or automatically determined, such as during a learning or calibration phase by the implantable medical device. When the second activation time exceeds a second activation threshold, flow moves to 2826. Where the event is labeled as a loss of capture. At 2826, the one or more processors also deliver a backup pacing pulse to the ventricle. At 2822, when the second group activation time does not exceed the second activation threshold, flow moves to 2824 where the one or more processors labels the event as selective capture and determined that no backup pacing is needed.

Optionally, one or both of the processes of FIGS. 27 and 28 may be utilized in connection with patients exhibiting a wide QRS complex. For example, evoked response COI may be utilized as a class discriminator to distinguish between a first class (including selective and LOC) and a second class (including myocardial only and nonselective). Next, the process further divides capture types that have QRS with correction. For example, the process determines the activation time between the HBP and the last peak of a ventricular sensed event (e.g. the end of the QRS). The activation time is utilized as a feature discriminator to distinguish between selective without QRS correction and LOC. Alternatively, the activation time and be utilized as a feature discriminator to distinguish between nonselective without QRS correction and myocardial only capture.

Optionally, the processes of FIGS. 27 and 28, as well as other processes described herein, may be implemented in connection with the methods and systems for automatic pacing impulse calibration as described in U.S. Provisional Application No. 62/948,047 (Docket No. 13653USL1), Titled "AUTOMATIC PACING IMPULSE CALIBRATION USING PACING RESPONSE TRANSITIONS" which was filed on Dec. 13, 2019, the complete subject matter of which is expressly incorporated herein by reference in its entirety.

Automatic Pacing Threshold Testing

The present disclosure is directed to various aspects of stimulation devices and corresponding methods related to His bundle pacing. Among other things, the present disclosure provides methods and devices for automatic determination of His bundle capture thresholds, for configuring stimulation devices based on determined capture thresholds, for identifying different capture types in response to application of pacing impulses of varying energies, and other related features and functions. Aspects of the present disclosure may be implemented in any suitable stimulation device including, but not limited to, implantable dual chamber and multi-chamber cardiac stimulation devices as well as external programming units for such stimulation devices. For example, the present disclosure may be implemented in multi-chamber cardiac stimulation device such as the stimulation device herein.

Certain cardiac pacemakers and defibrillators incorporate a pacing lead in the right ventricle and may also include a second lead in the right atrium. High-burden right ventricle apical pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. His bundle pacing (HBP) has been shown to restore physiological activation patterns by utilizing a patient's intrinsic conduction system, even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown to be most effective for patients exhibiting a wide QRS complex and left bundle branch block. HBP has also been shown to be effective at narrowing the QRS complex in patients with left bundle branch block, likely due to restoration of conduction through the Purkinje fibers, which include right and left bundle fibers that are longitudinally dissociated. Therefore, what is thought of as left bundle branch block, can be a result of a proximal blockage within the His bundle that eventually branches to the left bundle. By pacing the His bundle distal to the blockage, a normalized QRS complex can be achieved in some patients. Theoretically, this pacing mode may provide even better results than known CRT treatments, as activation propagates rapidly through natural conduction pathways.

Depending on electrode position, pacing output, patient physiology, and other factors, pacing impulses delivered to the His bundle may result in capture of different cardiac tissue. As used herein, the term "capture" refers to when a pacing impulse has sufficient energy to depolarize cardiac tissue, thereby causing the depolarized cardiac tissue to contract. In the context of HBP, pacing of the His bundle will generally result in one of four capture scenarios: non-selective His bundle capture, selective His bundle capture, myocardium-only capture, or loss of capture (or non-capture). Non-selective capture refers to when a pacing impulse results in capture of both the His bundle and the local myocardium surrounding the His bundle. Because of the simultaneous depolarization of the His bundle and myocardium, non-selective His bundle capture generally results in a combined or condensed electrical response as compared to normal heart activity in which the His bundle and myocardium are depolarized sequentially. Accordingly, non-selective His bundle capture may be characterized by a shortened delay between application of the pacing impulse and ventricular depolarization (e.g., on the order of 20 ms) because the myocardial depolarization propagates immediately without exclusively traveling through the His-Purkinje system. Nevertheless, because the His bundle is stimulated and captured, the QRS duration is similar to the native QRS duration but may be slightly longer due to the myocardial excitation (e.g., 70-120 ms). In contrast, selective His bundle capture refers to exclusive capture of the His bundle without depolarization of the surrounding myocardial tissue. With selective His bundle capture, the stimulus to ventricular depolarization interval is virtually the same as the native delay between His bundle activation and subsequent ventricular depolarization and the QRS duration is essentially identical to the native QRS duration. In myocardium-only capture, the tissue surrounding the His bundle is captured without capturing the His bundle itself, resulting in slow or delayed signal conduction and activation. Finally, loss of capture generally refers to circumstances in which the applied stimulus is insufficient or otherwise unable to elicit a response. In such cases, backup pacing may be applied. For patients with branch bundle block or similar conduction disorders, the foregoing capture types may be further characterized by whether they result in correction of the conduction disorder. For example, a pacing impulse may result in any of non-selective His bundle capture with correction, non-selective His bundle capture without correction, selective His bundle capture with correction, or selective His bundle capture without correction.

While both selective and non-selective His bundle capture may be used to improve cardiac function, selective His bundle capture is generally preferred as the corresponding response more closely approximates natural heart function. However, due to the complexity and dynamic nature of certain cardiomyopathies and cardiac anatomies, selective His bundle capture may not be possible or, if possible at one time, may no longer be possible as a patient's condition changes over time. Moreover, a patient's condition may also progress such that His bundle capture (whether selective or non-selective) may become unavailable and, as a result, direct ventricular pacing may be required.

In light of the foregoing, this disclosure describes methods and apparatuses directed to optimizing HBP. More specifically, this disclosure describes stimulation devices capable of HBP and processes that may be implemented by such stimulation devices to initialize device settings. To do so, stimulation devices or a programming unit in communication with the stimulation device executes a capture threshold test in which response data is collected for a range of pacing impulse energies (e.g., a range of pacing impulse voltages, pacing impulse pulse widths, or combinations thereof). In certain implementations, the response data may include unipolar, bipolar, or both unipolar and bipolar responses (e.g., electrograms) recorded and stored by the stimulation device or programming unit. Transitions between capture types are then identified by analyzing changes in response characteristics for the various pacing impulse energy settings that were tested. Based on the number of observed transitions, the nature of the changes indicating the transitions (e.g., how the particular response characteristics change), an initial capture type, and/or other similar factors, the capture pacing impulse energies may then be assigned a capture type. The stimulation device or programming unit may then identify capture thresholds based on the pacing impulse energies at which transitions between different capture types occur and calibrate or adjust stimulation device settings to the best available pacing impulse energy (e.g., the lowest energy (the lowest voltage, pulse width, or combination thereof) for which HBP capture is achieved) according to the assigned capture types and/or identified capture thresholds. By relying on response data obtained from the patient, the settings of the stimulation device are specifically tailored to the individual patient and, as a result, improve both pacing reliability and overall life and function of the stimulation device.

The foregoing aspects of the present disclosure are discussed in further detail later in this disclosure; however, FIGS. 29-34 are now provided to generally describe the components and functionality of stimulation devices that may be used to implement aspects of the present disclosure. It should be appreciated that FIGS. 29-34 should be understood to be representative only and are therefore non-limiting. Rather, the methods and techniques described herein may be implemented using any suitable stimulation device capable of pacing the His bundle and obtaining and analyzing corresponding response data to such pacing activities. For example and unless otherwise specifically noted, stimulation devices in accordance with the present disclosure may include any number of leads configured to provide stimulation and/or pacing as described herein and may include either unipolar or bipolar leads. Moreover, it should further be understood that the methods disclosed herein may also be performed, at least in part, by an external testing or programming unit capable of receiving and transmitting data from an implantable stimulation device. Such data may include, without limitation, response data measured by the stimulation device and transmitted to the external unit and configuration data transmitted from the external unit to the stimulation device to configure the stimulation device.

Figure 29:
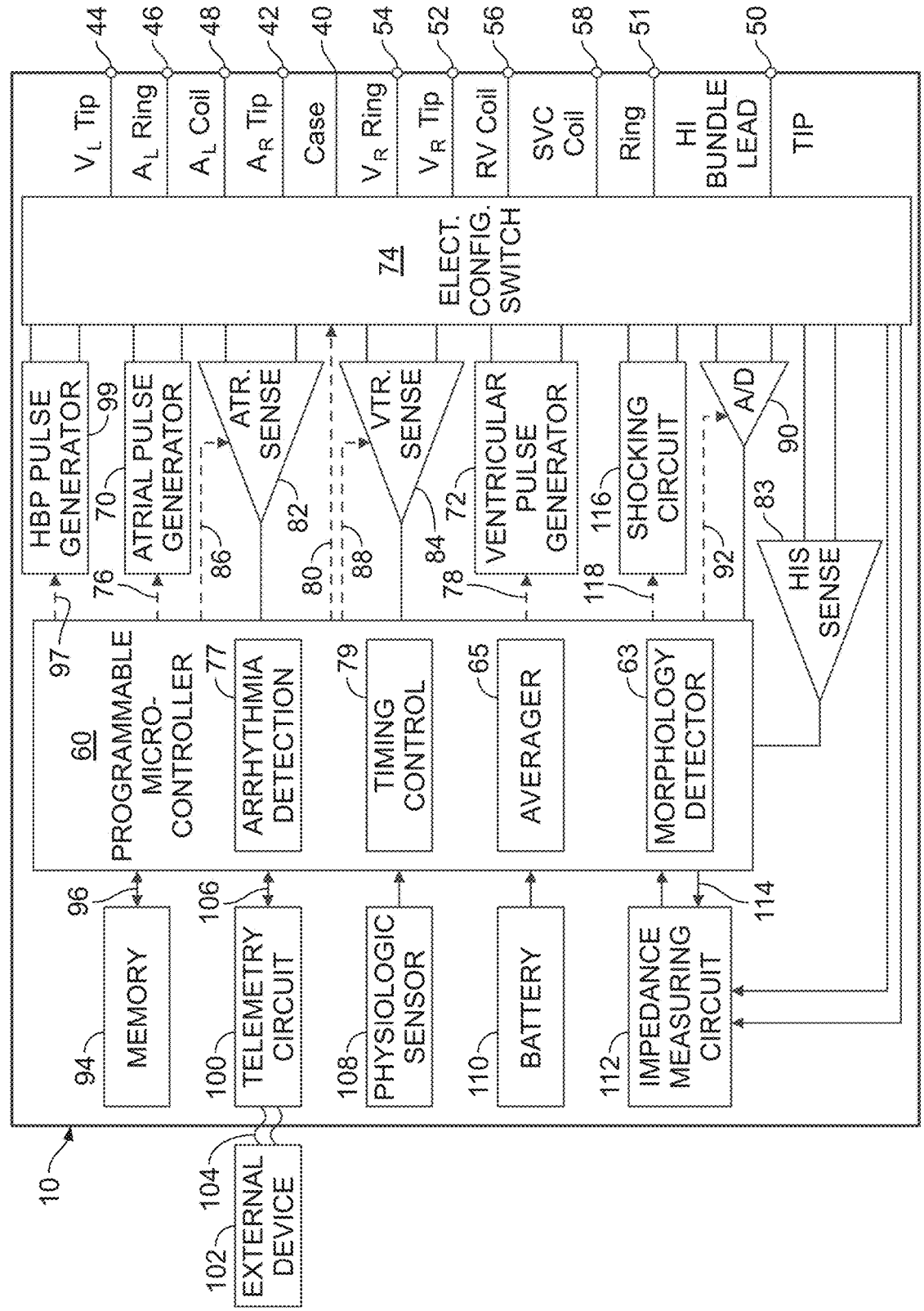
FIG. 29 is a functional block diagram of the multi-chamber implantable stimulation device of FIG. 1, illustrating the basic elements that provide pacing stimulation, cardioversion, and defibrillation in four chambers of the heart.

Referring now to FIG. 29, there is illustrated a simplified block diagram of the multi-chamber implantable stimulation device that substantially resembles the stimulation device described above in connection with FIG. 4. The circuitry and other components that are common to the block diagrams of FIGS. 4 and 29 have been given common reference numerals and are not described hereafter (as the common functionality as discussed above in connection with FIG. 4).

As described below in further detail certain aspects of controlling or configuring the HBP pulse generator 99 may also be based on measurements related to activity of other structures/chambers of the heart. So, for example and without limitation, the HBP pulse generator 99 may also be triggered, inhibited, calibrated, or configured based on outputs from the atrial and ventricular sensing circuits 82-84 or any other similar sensing circuit adapted to measure electrical activity of the heart. The microcontroller 60 manages operation of the HBP pulse generator 99 with control signal 97.

In certain implementations of the present disclosure, the device may be configured to perform beat-by-beat impedance monitoring in conjunction with measuring and monitoring other electrical activity (e.g., generating electrograms (EGMs)) for each beat. In such applications, the measured impedance may generally provide further information regarding the occurrence and potential cause of changes in the electrical activity, including, without limitation, changes in His bundle capture type or capture quality.

Permanent His bundle pacing (HBP) has been proven feasible by delivering pacing stimuli at the His bundle with an implantable pacing lead and pacemaker. HBP activates the heart through the native His-Purkinje conduction system, thus offering the most physiologic pacing approach to correcting electrical dyssynchrony, among other things. HBP has also emerged as a safe alternative to conventional pacemaker therapy by exhibiting a range of clinical and electrophysiological advantages over conventional pacemaker therapy.

In conventional right ventricle (RV) pacing applications, implantable pacemakers may execute algorithms that automatically measure capture thresholds and apply a small safety margin to ensure RV capture. Such pacemakers may also include algorithms that automatically detect loss of capture (LOC). Among other things, such algorithms may provide backup pacing, adjust pacing output to ensure capture, or trigger automatic capture threshold searching when LOC recovery pacing output is too high.

However, conventional pacemaker-based algorithms are generally inappropriate and not readily adaptable for use in HBP applications due to differences in the response of the His bundle and local surrounding myocardium to pacing (as compared to other cardiac tissue) and other related complexities associated with HBP. Therefore, existing automatic capture threshold testing approaches implemented in RV pacing applications generally do not work for HBP applications. Accordingly, a new capture management approach is required for HBP applications. Such an approach should preferably result in HBP with minimal pacing output to improve overall battery and device life, among other things.

Pacing of the His bundle may result in a range of capture scenarios depending on various factors including, among other things, the physiology of the heart, the energy of the pacing impulse, whether the patient has any cardiac conditions affecting conduction, and the like. For example and as previously discussed, for patients with healthy conduction system (e.g., as exhibited by a narrow/normal QRS width), pacing of the His bundle may result in one of four general scenarios. First, selective capture may occur in which only the His bundle is captured. By capturing only the His bundle, subsequent conduction along the His/Purkinje system is the same or substantially similar to normal sinus beats. Second, non-selective capture may occur in which both the His bundle and local myocardium are captured. The resulting ventricular conduction is substantially similar to normal sinus beats, but capture of the local myocardium activation adds a small delta wave prior to the main QRS complex. However, because the conduction speed of His-Purkinje system is much faster than that of the myocardium, there is little to no difference in clinical outcome between selective and non-selective His bundle capture. Third, myocardium-only capture may occur in which the myocardium is captured without capturing this His bundle, resulting in relatively slow/delayed activation of the ventricles. Finally, a loss of capture may occur in which neither the myocardium nor the His bundle is captured. For patients with bundle branch block (BBB) or other similar conduction-related issues (e.g., as exhibited by a wide/long QRS duration), each of the selective and non-selective cases may be further classified as resulting in a response with or without correction of the BBB.

Conventionally, the HBP responses discussed above and the corresponding capture thresholds are identified and diagnosed in-clinic by healthcare professionals using relatively complicated electrocardiogram systems, such as 12-lead surface ECGs. HBP pacing devices are then configured to implement HBP according to the capture thresholds identified during such testing. In addition to such approaches being time-consuming and complicated, if subsequent adjustments to a device's settings are required, a patient typically has to revisit the clinic for the healthcare professional to repeat the capture threshold test. Moreover, to account for changes that may occur between such visits, healthcare professionals may set pacing settings to include a large safety margin, e.g., by adjusting impulse energy settings well above that required to achieve a desired capture result. While such safety margins may be sufficient to account for changes when they occur, such over-stimulation is otherwise inefficient, leading to reduced battery and device life.

Devices and methods are provided herein to address the various issues identified above, among others. More specifically, the present disclosure is directed to methods of performing automatic capture threshold testing for determining efficient settings for stimulation devices for implementing HBP. In certain implementations, the automatic capture threshold testing methods described herein may be executed by the stimulation device itself. Notably, such a device-based approach eliminates or reduces the need for a patient to revisit a clinic or healthcare professional to adjust settings of their stimulation device. Moreover, the device-based approach enables the device to execute the capture threshold test itself (e.g., periodically, in response to a loss or change in capture, etc.) and to dynamically adjust the settings of the stimulation device between clinic visits. By doing so, the need for a significant safety margin is reduced and the stimulation device may be operated in a more efficient manner as compared to conventional pacing approaches.

While the example implementations of the present disclosure focus primarily on implementation in stimulation devices and implementation in the stimulation device carries certain advantages, it should be appreciated that the methods discussed herein may also be implemented by devices capable of communicating with a stimulation device. For example, the process methods of performing automatic capture threshold testing discussed herein may be implemented in programmers or similar devices adapted to monitor, receive data from, and configure stimulation devices.

Systems and methods according to the present disclosure leverage observed changes in the heart's response to different pacing impulse energies resulting to identify capture thresholds and corresponding pacing settings. For example, in one implementation, pacing impulses are applied using a range of pacing impulse energies and one or both of a unipolar and bipolar electrogram (EGM) are measured after each impulse using the His bundle lead. The collected response data is then analyzed to determine changes in characteristics of the measured responses indicative of a change in capture type between pacing impulse energy settings. The stimulation device may then be automatically configured based on the results of the analysis to achieve the best available capture scenario using the lowest pacing impulse energy.

For example, in one implementation, the stimulation device may apply pacing impulses at different energies (e.g., starting at maximum pacing impulse energy and gradually decrementing the pacing impulse energy until a loss of capture occurs) and may record one or both of a unipolar and a bipolar EGM for each pacing impulse energy. The stimulation device may then analyze the data to determine when changes in certain characteristics of the unipolar and bipolar responses have occurred. For example, in one implementation, each of a unipolar width and a bipolar stim-to-peak time (as measured from the unipolar and bipolar EGMs, respectively) may be measured and changes (e.g., a relative change exceeding about 10%) in one or both of the unipolar width and the stim-to-bipolar peak time may be used to identify when a transition between capture types has occurred. As discussed below in further detail, in at least certain implementations of the present disclosure, a capture type may then be associated with each pacing impulse energy based on the number of identified transitions, an initial capture type (e.g., a capture type achievable using a relatively high pacing impulse energy), known information regarding the patient (e.g., whether the patient has a branch bundle block or similar conduction-related condition), and other information. The stimulation system may then select a preferred pacing impulse energy which, in certain cases, is the minimum pacing impulse energy resulting in a particular capture type (e.g., selective capture, if possible, in patients with normal conduction or selective capture with correction in patients exhibiting branch bundle block or similar conduction-related conditions).

Although unipolar width and bipolar stim-to-peak time are used as examples, it should be appreciated that other characteristics of the response may be used to identify transitions between capture types. For example and without limitation, unipolar width may be substituted with another response characteristic indicative of total ventricular activation time. Similarly, bipolar peak-to-stim time may be substituted with any suitable response characteristic indicative of the local activation time relative to pacing of the His bundle. For example, the bipolar peak-to-stim time may be substituted with a metric for stim-to-onset time, such as unipolar stim-to-onset time. Moreover, either of unipolar or bipolar response data may be used for each response characteristic.

Pacing impulse energy is generally used herein to describe the energy of a given pacing impulse. Pacing impulse energy may be determined as a function of the voltage and the duration (e.g., the pulse width) of the pacing impulse. Accordingly, to the extent the present disclosure discusses modifying pacing impulse energy, such modifications can be made by changing one or both of the voltage or the duration of the pacing impulse. For example, in certain implementations, decreasing the pacing impulse energy of the stimulation device may include reducing a pacing impulse voltage setting while maintaining a pulse width setting. Alternatively, decreasing the pacing impulse energy may instead include reducing the pulse width setting while maintaining a constant pacing impulse voltage. In still other implementations, reducing the pacing impulse energy may include reducing both the voltage and pulse width settings of the stimulation device simultaneously, in an alternating fashion (e.g., reducing voltage for a first set of one or more pacing impulses then reducing duration for a second set of one or more pacing impulses), or in any other suitable sequence.

Notably, in conventional approaches to capture threshold testing, empirical/historical data collected from a wide range of patients is often used to generate templates, determine ranges for response characteristics, or otherwise determine capture type for a given pacing impulse energy. Such approaches inherently rely on some universal cutoff applicable to all patients. In contrast, the approaches described herein rely on relative changes exhibited by a specific patient in response to application of pacing impulses of varying energies. As a result, the disclosed approach may be used to identify the best possible pacing settings for a specific patient, taking into account any abnormalities or idiosyncrasies of the patient that may not be fully reflected in available empirical data and that may cause the patient to deviate from any sort of general standard.

The approaches to capture threshold testing and device configuration described herein generally rely on the principle that patients exhibit only a limited number of capture sequences as pacing impulse energy is decreased. In other words, a patient will generally exhibit a first capture type at relatively high pacing impulse energy and will transition to one or more capture types (including loss of capture) as pacing impulse energy is decreased.

For patients with substantially intact conduction systems (e.g., patients exhibiting narrow/normal QRS widths), such transitions are summarized below in Tables 6a and 6b. For purposes of Tables 6a and 6b, nonselective capture is indicated as "NS", selective is indicated as "S", myocardium-only capture is indicated as "M", and loss of capture is indicated as "LOC".

TABLE 6a

Capture Type Transitions for Normal Conduction (Single Transition Cases)

| | Starting Capture Type | After Transition |
|---|---|---|
| 1. | NS | LOC |
| 2. | S | LOC |
| 3. | M | LOC |

TABLE 6b

Capture Type Transitions for Normal Conduction (Two-Transition Cases)

| | Starting Capture Type | After $1^{st}$ Transition | After $2^{nd}$ Transition |
|---|---|---|---|
| 1. | NS | M | LOC |
| 2. | NS | S | LOC |

As illustrated in Table 6a, the single transition cases generally include transitioning from one capture type (non-selective, selective, or myocardium-only) to a loss of capture. In contrast, the two-transition cases are only applicable for patients for which non-selective capture is possible, as each of selective and myocardium-only capture necessarily transition to loss of capture only as pacing impulse energy is decreased. As indicated in Table 6b, the transitions in such cases include transitioning from non-selective capture to one of myocardium-only or selective capture and then subsequently transitioning to loss of capture.

Tables 7a-7c, below, provides a similar summary of possible transitions for patients with conduction issues, such as branch bundle block. In contrast to Tables 6a and 6b, Tables 7a-7c further indicate whether non-selective and selective capture is with or without correction ("w/corr." or "w/o corr.", respectively).

TABLE 7a

Capture Type Transitions for BBB Patients (Single Transition Cases)

| | Starting Capture Type | After Transition |
|---|---|---|
| 1. | S (w/corr.) | LOC |
| 2. | S (w/o corr.) | LOC |
| 3. | NS (w/corr.) | LOC |
| 4. | NS (w/o corr.) | LOC |
| 5. | M | LOC |

TABLE 7b

Capture Type Transitions for BBB Patients (Two-Transition Cases)

| | Starting Capture Type | After $1^{st}$ Transition | After $2^{nd}$ Transition |
|---|---|---|---|
| 1. | S (w/corr.) | S (w/o corr.) | LOC |
| 2. | NS (w/corr.) | S (w/corr.) | LOC |
| 3. | NS (w/corr.) | NS (w/o corr.) | LOC |
| 4. | NS (w/corr.) | S (w/o corr.) | LOC |
| 5. | NS (w/corr.) | M | LOC |
| 6. | NS (w/o corr.) | S (w/o corr.) | LOC |
| 7. | NS (w/o corr.) | M | LOC |

TABLE 7c

Capture Type Transitions for BBB Patients (Three-Transition Cases)

| | Starting Capture Type | After $1^{st}$ Transition | After $2^{nd}$ Transition | After $3^{rd}$ Transition |
|---|---|---|---|---|
| 1. | NS (w/corr.) | S (w/corr.) | S (w/o corr.) | LOC |
| 2. | NS (w/corr.) | NS (w/o corr.) | S (w/o corr.) | LOC |
| 3. | NS (w/corr.) | NS (w/o corr.) | M | LOC |

Similar to Table 6a, the single transitions possible in cases where patients have a conduction-related issue generally include transitioning from one type of capture to a loss of capture. As indicated in Tables 7a and 7b, additional cases in which correction is lost arise in the context of patients with conduction related issues. Notably, once correction is lost, it is generally not regained as pacing impulse energy is further decreased.

Figure 30:
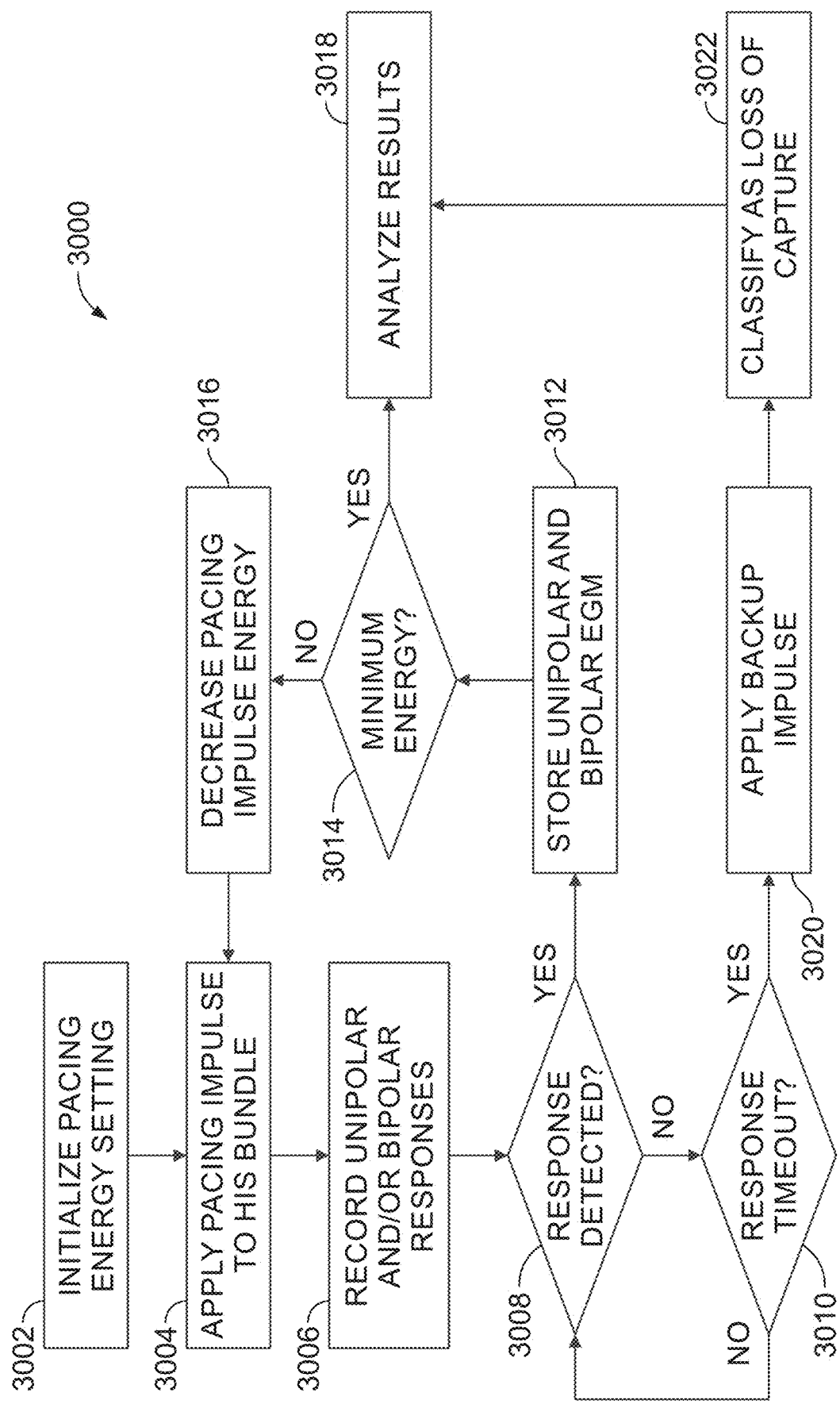
FIG. 30 is a flow chart illustrating a method of response data collection for purposes of subsequent analysis in determining pacing settings for a stimulation device.
Figure 31:
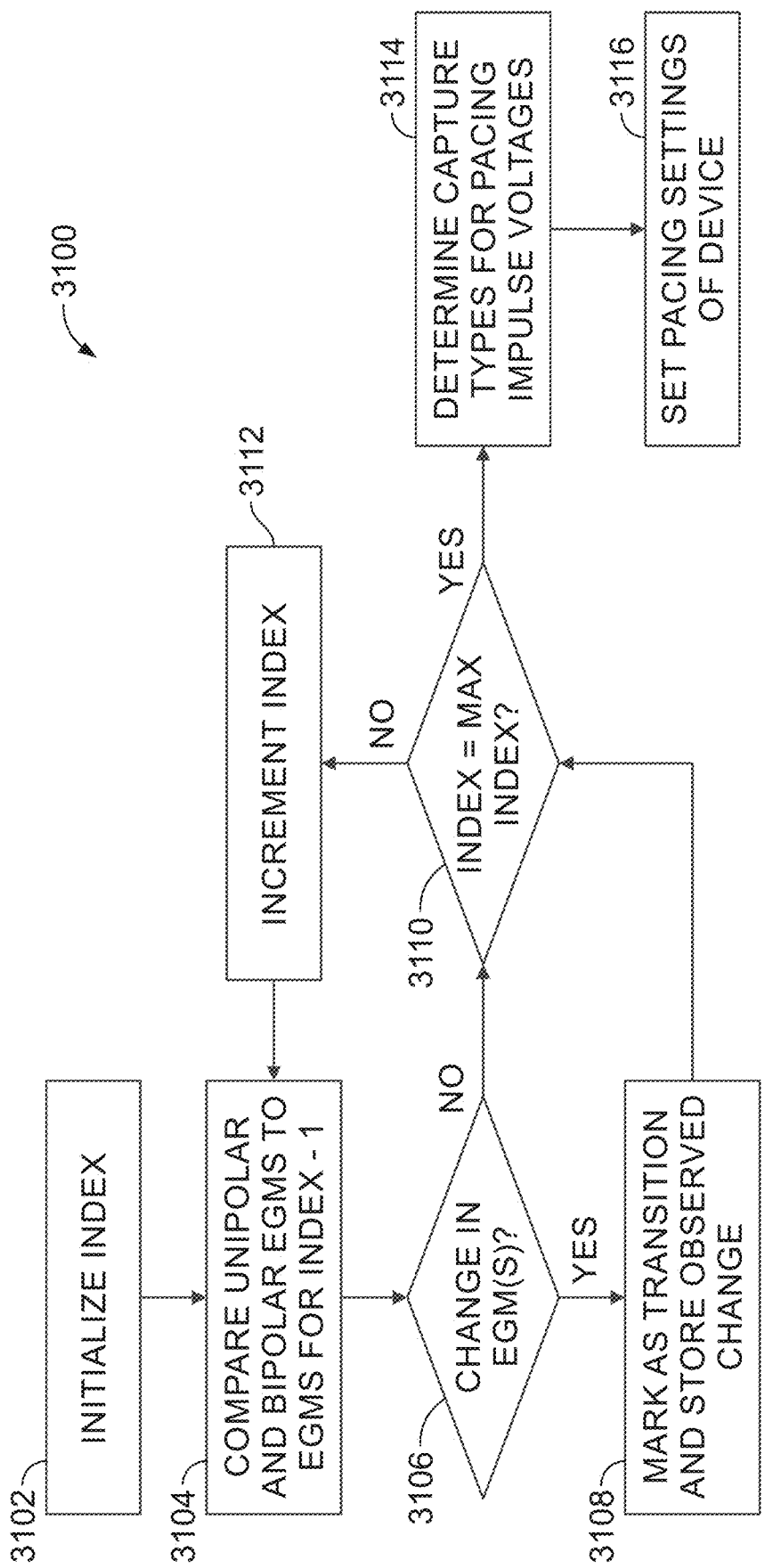
FIG. 31 is a flow chart illustrating a method of analyzing response data, such as obtained in the method of FIG. 30, to determine pacing settings for a stimulation device.

With the foregoing in mind, FIGS. 30 and 31 are flow charts that illustrate methods that may be implemented together to configure a stimulation device for purposes of providing His bundle pacing. More specifically, FIG. 30 illustrates a first method 3000 in which pacing impulses are applied at different energies and corresponding responses are measured and recorded. FIG. 31 illustrates a second method 3100 in which the results, such as those obtained from the method 3000 of FIG. 30, are analyzed and classified to determine pacing settings for the stimulation device.

Referring first to FIG. 30, the method 3000 generally begins with initializing the pacing impulse energy setting of the stimulation device (operation 3002). Although the initial pacing impulse energy setting may vary, in at least certain implementations of the present disclosure, the initial pacing impulse energy setting is the maximum output energy of the stimulation device. For purposes of the following example, pacing impulse energy is controlled based on voltage alone (e.g., by maintaining a constant pulse width) and the initial voltage is assumed to be 7.5V; however, in other implementations and for different devices, the initial pacing impulse energy setting value may differ. In certain implementations, initializing the pacing impulse energy setting of the stimulation device may also include setting an operational mode of the stimulation device. Although specific modes and settings for particular applications may vary, in at least one example implementation, the stimulation device may be set a DDD operational mode with a short A-H delay. In another example implementation, the stimulation device may be set to a WI mode with ventricular overdrive pacing (i.e., pacing of the ventricle occurring at a higher than intrinsic rate).

At operation 3004 a pacing impulse is applied to the His bundle at the current pacing impulse energy setting and a corresponding response is recorded (operation 3006). As indicated in FIG. 30, in at least certain implementations the response includes each of a unipolar and bipolar response, which may be recorded and analyzed as an electrogram (EGM) or similar response data format.

Although the response in FIG. 30 includes both a unipolar and bipolar EGM, in other implementations of the present disclosure, the response data may instead include only one of a unipolar or bipolar response. As discussed below in further detail, subsequent analysis and classification of the response obtained in operation 3004 may vary depending on whether bipolar, unipolar, or both bipolar and unipolar data is available.

During recordation of the unipolar and bipolar responses, the stimulation device may generally monitor for a response to the applied pacing impulse (operation 3008). In certain implementations, detecting the response may include, among other things, detecting the onset of the local myocardium activation resulting from application of the pacing impulse. Such monitoring may continue until either a response is detected or a response timeout occurs (operation 3010).

When a response is detected, the measured response data is stored, e.g., in memory of the stimulation device (operation 3012). If a minimum pacing impulse energy has not yet been reached (operation 3014), the pacing impulse energy of the stimulation device is decreased (operation 3016). For example and without limitation, decreasing the pacing impulse energy may include one or both of reducing the pacing impulse voltage (e.g., by 0.25V or some other predetermined amount), changing the pacing impulse pulse width, or a combination thereof. After decreasing the pacing impulse energy, a subsequent pacing impulse is applied at the new pacing impulse energy, and the foregoing process of detecting and recording each of a unipolar and bipolar response are repeated. If, on the other hand, a response is obtained for a minimum pacing impulse energy (which may be a minimum pacing voltage, a minimum pulse width, minimum combination of voltage and pulse width, or minimum for any other parameter associated with pacing impulse energy for purposes of the capture threshold test), the stimulation device may proceed to analyzing the results of the test (operation 3018).

As previously noted, a timeout may occur when monitoring a response to the pacing impulse applied in operation 3004. In other words, a response to the applied pacing impulse may not be detected within a predetermined period of time. If such a timeout occurs, a backup impulse with higher pacing impulse energy may be applied to ensure a heartbeat (operation 3020) and the current pacing impulse energy may be classified as resulting in loss of capture (operation 3022). In certain implementations, the test may then be terminated and the stimulation device may proceed to analysis of the test results (operation 3018) as further reductions in the pacing impulse energy would be unlikely to result in anything but loss of capture. In other implementations, the test may be terminated in response to detecting loss of capture for a predetermined number of pacing impulse energy settings, e.g., loss of capture for two or more consecutive pacing impulse energy settings.

Analysis of test results, such as those obtained via the method 3000 of FIG. 30, can be conducted in various ways; however, FIG. 31 illustrates one example approach 3100 to analyzing such results to identify and implement patient-specific settings for a stimulation device. In general, the method 3100 is based on an implementation in which the response data includes each of a unipolar and a bipolar response and in which analysis of the response data involves comparing each of the unipolar and bipolar EGM response data for a current pacing impulse energy to those of a next higher pacing impulse energy. If the device identifies a change in one or both of the unipolar or bipolar responses between the different pacing impulse energies, a capture type transition is identified. After such analysis is conducted for each pacing impulse energy, the system classifies each of the pacing impulse energies as resulting in a particular capture type. As discussed below in further detail, such classification may be based on the number of transitions identified, the particular changes indicating the occurrence of the transitions, an initial capture type, and the like. The device may then configure its pacing settings based on the classifications. For example, assuming that one or more pacing impulse energies resulted in selective capture, the device may set its pacing impulse energy to be the lowest energy for which selective capture was achieved.

Referring now to FIG. 31, the method 3100 generally assumes that a collection of pacing response data is available for analysis. As previously discussed in the context of FIG. 30, such data may generally include a range of pacing impulse energies and, for each pacing impulse energy, each of unipolar and bipolar EGM response data. However, in other implementations, the response data may include only one of unipolar or bipolar EGM response data. With such response data available, the method 3100 generally includes initializing an index for purposes of traversing the data (operation 3102). Although other approaches may be implemented, in the specific example of FIG. 31, the index is assumed to be initialized to the second entry of the response data, which in certain implementations may be, the entry corresponding to a pacing impulse energy that is one step below the maximum energy (e.g., the maximum voltage) of the device or a maximum impulse energy used when collecting response data.

At operation 3104, the unipolar and bipolar EGM data for the current pacing energy is compared to that of the next highest energy (e.g., by comparing the unipolar and bipolar EGM data for the current index value to that of the previous index).

At operation 3106, an analysis is conducted to determine whether a change indicative of a transition is reflected by the two sets of unipolar and bipolar EGM data. More specifically, one or more characteristics of the unipolar response data and one or more characteristics of the bipolar response data are compared between the two sets to see if the different pacing impulse energies elicited substantially different responses. In at least certain implementations, the response characteristics may include the activation time of the local ventricular myocardium in the neighborhood of the His bundle and an estimate of the total activation time of the ventricles. Various approaches may be used to measure these characteristics from the collected response data. For example and without limitation, the local activation time of the ventricular myocardium may be measured from any of bipolar stimulation-to-peak time (BSP), bipolar stimulation-to-onset, or unipolar stimulation-to-onset. Similarly and without limitation, total ventricular activation time may be estimated using unipolar width (UW) or differentiated using unipolar maximum positive slope (dv/dt). For purposes of the current example, however, BSP and UW are used as the primary response characteristics for distinguishing between capture types. Nevertheless, it should be appreciated that other implementations of the present disclosure may rely on other response characteristics for distinguishing between capture types, including, but not limited to, any of the other response characteristics noted above or otherwise discussed herein.

The threshold for determining whether a change has occurred in the responses between successive pacing impulse energies may vary between applications and may vary based on the specific response characteristics being compared. The threshold for determining a change may be relative (e.g., a percentage change) or absolute between the responses. Also, depending on the characteristics of interest, a change may be based on any of an increase in the characteristic, a decrease in the characteristic, or any other suitable change.

In at least one specific implementation, a change is considered to have occurred if at least one response characteristic of interest changes between pacing impulse energies by at least about 10% (or an absolute equivalent for the response characteristics of interest). So, for example, in the current example in which BSP and UW are the characteristics of interest, a change of at least about 10% between responses is considered to indicate a change. During testing in conjunction with development of the concepts herein, it was observed that as pacing impulse energies change, BSP either increases or stays relatively constant (e.g., does not change by more than about 10%) while UW may increase, decrease, or stay constant. Accordingly, for the purposes of the current example, a change in response characteristics is considered to have occurred when BSP increases by at least about 10% between responses and/or if UW either increases or decreases by at least about 10% between responses.

Referring back to FIG. 31, if a change is measured, a transition is noted and the observed change may be stored (operation 3108). For example, the stimulation device may generate a flag, record, or similar indicator for purposes of noting that the current pacing impulse energy resulted in a change in one or more response characteristics. The stimulation device may also store data or measurements describing the change in the response characteristics. For example, the stimulation device may generate a record that indicates that the current pacing impulse energy resulted in a change and that includes related information such as the characteristic that changed, the direction of the change (e.g., increase or decrease), the magnitude of the change (measured in absolute or relative terms), or any other aspect of the change that may be used in further characterizing the change.

The foregoing method may be repeated for each pacing impulse energy for which a response was recorded. For example, in one implementation, the stimulation device determines if the current index is the maximum index (e.g., the index corresponding to the lowest tests pacing impulse energy) (operation 3110). If not, the index is incremented (operation 3112) and the process of comparing the response for the pacing impulse energy associated with the current index with the response of the next highest pacing impulse energy and determining whether a change has occurred is repeated.

If, on the other hand, the maximum index is reached, the stimulation device determines the capture type for each pacing impulse energy (operation 3114). As previously discussed, capture types for ranges of pacing impulse energies generally follow a predetermined pattern. In other words, particular capture types tend to transition along a limited number of known transition sequences. As a result, by knowing the number of transitions that occurred, the change in characteristics associated with the transitions, and, in some cases, an initial capture type (e.g., a capture type associated with a relatively high pacing impulse voltage), capture types may be readily assigned to pacing impulse energies.

The following tables provide different transition paths and the various indications by which they may be identified when UW and BSP are the response characteristics of interest. Tables 3a and 3b provide transitions and indications for patients with substantially normal conduction and for which correction is not required. Tables 4a-4c provide transitions and indications for patients with conduction issues, such as branch bundle block. In each of the tables, the capture types include selective capture (S), non-selective capture (NS), myocardium-only capture (M), and loss of capture (LOC). For each of selective and non-selective capture, Tables 4a-4c further indicate whether the given capture type includes correction ("w/corr.") or lacks correction ("w/o corr."). As previously noted, the current example generally relies on bipolar stim-to-peak time (BSP) and unipolar width (UW) as the primary characteristics for identifying transitions. Accordingly, for each of BSP and UW, each transition listed in the tables further includes whether the transition is indicated by each of BSP and UW increasing (+), decreasing (−), or remaining unchanged (=). As previously discussed, an increase or a decrease may, in certain implementations, correspond to a change of at least about 10% in a response characteristic; however, the specific threshold used in identifying a change may vary between applications and patients. In general, it should be understood that for purposes of the present disclosure a characteristic being "unchanged" generally means that any changes to the characteristic fall below the threshold for indicating a change. For example, if a 10% threshold is implemented, any change less than 10% would be considered "unchanged".

TABLE 8a

Transition Indications for Normal Conduction (Single Transition Cases)

| | Transition | Indication |
|---|---|---|
| 1. | NS → LOC | BSP+ UW− |
| 2. | S → LOC | BSP+ UW= |
| 3. | M → LOC | BSP+ UW− |

TABLE 8b

Transition Indications for Normal Conduction (Two-Transition Cases)

| | Transition Progression | $1^{st}$ Indication | $2^{nd}$ Indication |
|---|---|---|---|
| 1. | NS → M → LOC | BSP= UW+ | BSP+ UW− |

TABLE 8b-continued

Transition Indications for Normal Conduction (Two-Transition Cases)

| | Transition Progression | 1st Indication | 2nd Indication |
|---|---|---|---|
| 2. | NS → S → LOC | BSP+ UW− | BSP+ UW= |

TABLE 9a

Transition Indications for BBB Patients (Single Transition Cases)

| | Transition | Indication |
|---|---|---|
| 1. | S (w/corr.) → LOC | BSP+ UW+ |
| 2. | S (w/o corr.) → LOC | BSP+ UW= |
| 3. | NS (w/corr.) → LOC | BSP+ UW+ |
| 4. | NS (w/o corr.) → LOC | BSP+ UW− |
| 5. | M → LOC | BSP+ UW− |

TABLE 9b

Transition Indications for BBB Patients (Two-Transition Cases)

| | Transition Progression | 1st Indication | 2nd Indication |
|---|---|---|---|
| 1. | S (w/corr.) → S (w/o corr.) → LOC | BSP= UW+ | BSP+ UW= |
| 2. | NS (w/corr.) → S (w/corr.) → LOC | BSP+ UW− | BSP+ UW+ |
| 3. | NS (w/corr.) → NS (w/o corr.) → LOC | BSP= UW+ | BSP+ UW− |
| 4. | NS (w/corr.) → S (w/o corr.) → LOC | BSP+ UW+ | BSP+ UW= |
| 5. | NS (w/corr.) → M → LOC | BSP= UW+ | BSP+ UW− |
| 6. | NS (w/o corr.) → S (w/o corr.) → LOC | BSP+ UW− | BSP+ UW= |
| 7. | NS (w/o corr.) → M → LOC | BSP= UW+ | BSP+ UW− |

TABLE 9c

Transition Indications for BBB Patients (Three-Transition Cases)

| | Transition Progression | 1st Indication | 2nd Indication | 3rd Indication |
|---|---|---|---|---|
| 1. | NS (w/corr.) → S (w/corr.) → S (w/o corr.) → LOC | BSP+ UW− | BSP+ UW+ | BSP+ UW= |
| 2. | NS (w/corr.) → NS (w/o corr.) → S (w/o corr.) → LOC | BSP= UW+ | BSP+ UW− | BSP+ UW= |
| 3. | NS (w/corr.) → NS (w/o corr.) → M → LOC | BSP= UW+ | BSP= UW+ | BSP+ UW− |

Referring to Tables 8a-9c, the process of determining capture types for each pacing impulse voltage (operation 3114) may be conducted by first determining the type of patient conduction (e.g., normal or BBB) and determining which table is applicable based on the number of transitions observed during analysis of the response data. For example, if a patient has substantially normal conduction and two transitions were identified during analysis of the response data, the transition and indication information for Table 8b would apply. As another example, if three transitions were identified in a patient known to have BBB, the information in Table 9c would apply.

The specific characteristics of the identified transitions would then be analyzed to determine which transition sequence is applicable. For example, referring to Table 8b, if the transition resulted in an increase in each of BSP and UW, then the transition sequence is most likely NS→S→LOC. Accordingly, all pacing impulse energies above the pacing impulse energy identified as the first transition would be classified as resulting in non-selective capture, all pacing impulse energies from the first transition pacing impulse energy to the second pacing impulse energy would be classified as resulting in selective capture, and all remaining pacing impulse energies would be classified as resulting in loss of capture.

In certain cases, such as the foregoing example, only one transition needs to be analyzed in order to determine the capture types for each pacing impulse energy. However, in other scenarios, analysis of multiple transitions may be required to determine the applicable transition sequence. For example, each of the NS (w/corr.)→S (w/corr.)→LOC sequence and the NS (w/o corr.)→S (w/o corr.)→LOC sequence included in Table 9b share a common indication for their first transition (namely, an increase in BSP and a decrease in UW), but differ in the indication for their second transition (namely, an increase in both BSP and UW for the former and an increase in BSP only for the latter). Accordingly, analysis of multiple transitions may be required to determine the applicable transition sequence.

Certain transition sequences may share all indications and, as a result, may be indistinguishable from each on the basis of the identified transitions alone. In such cases, additional information regarding the patient may be required to determine the applicable transition sequence. For example, in at least one implementation, the capture type corresponding to the maximum pacing impulse energy (or other high pacing impulse energy) may first be identified using any suitable technique. This initial capture type may then be used to identify the correct transition sequence.

In one alternative implementation, the initial capture type may be determined automatically by the stimulation device by conducting a test in which the response elicited by applying the maximum pacing impulse energy (or other high pacing impulse energy) is analyzed in detail, such as by measuring certain characteristics or comparing the response to one or more stored templates to determine its corresponding capture type. Based on this initial capture type, the stimulation device may then be able to distinguish between transition sequences having otherwise similar indications.

In still other instances, neither the transition sequence nor the initial capture type may distinguish between transition sequences. For example, as indicated in Table 9b, the transition sequences NS (w/corr.)→NS (w/o corr.)→LOC and NS (w/corr.)→M→LOC have the same transition indicators and the same initial capture type. In certain implementations, such a result may be addressed by classifying pacing impulse energies between the first and second transitions as resulting in an indeterminate capture type.

Following classification of the pacing impulse energies, the stimulation device identifies a preferred pacing impulse energy setting and sets its pacing settings accordingly (operation 3116). Selection of a pacing impulse energy setting may include identifying the lowest pacing impulse energy resulting in the "best" available capture type. In patients with intact conduction systems, the stimulation device may identify the lowers pacing impulse energy for which selective or non-selective capture was achieved and program the stimulation device's pacing settings accordingly. In patients with branch bundle block or similar conduction issues, corrective results are generally preferred over non-corrective results. Therefore, the stimulation device may identify the lowest pacing energy that leads to capture (either selective or non-selective) and correction and program the stimulation device's pacing settings accordingly.

In certain implementations, a margin of safety may be applied to the selected pacing impulse energy. To do so, the pacing impulse energy setting of the stimulation device may be set higher (e.g., 10-20% higher) than the optimal pacing impulse energy identified based on the response data (e.g., by increasing the voltage and/or the pulse width over that corresponding to the selected pacing impulse energy). In certain implementations, such a margin of safety may be applied when a beat-by-beat capture management mode of the stimulation device is subsequently activated in which pacing is applied and monitored continuously. In general, however, the foregoing approach results in the identification and implementation of pacing settings for optimal heart function for the specific patient while improving overall life and functionality of the stimulation device and its battery by avoiding unnecessary overstimulation.

The foregoing capture threshold test can be run manually in-clinic or periodically out-of-clinic. In certain implementations, the response data and/or any particular response characteristics for each capture type obtained during the capture threshold test may be stored as one or more patient-specific templates. Such templates may then be used when the stimulation device actively provides beat-by-beat pacing and capture management. In one specific implementation, during beat-by-beat pacing and capture management, the stimulation device collects response data (e.g., EGM response data) following application of pacing impulses and analyzes the collected response data.

In one implementation, the stimulation device analyzes the response data collected during beat-by-beat pacing by comparing the collected response data to data collected during the capture threshold test. For example, as noted above, as part of the capture threshold test, the stimulation device may determine and store values or ranges of values of response characteristics that indicate particular capture types. The stimulation device may then compare the response data collected during beat-by-beat pacing to the values identified during the capture threshold test to classify the pacing response, to determine when His bundle capture has been lost (e.g., when myocardium only capture has occurred), and/or when there has been a loss of capture. To the extent a loss of His bundle capture or total loss of capture occurs, the stimulation device may take appropriate recovery actions. Such recovery actions may include, without limitation, increasing the pacing impulse energy to regain capture or delivering one or more back-up pacing impulses.

In one specific example, following initial calibration of a stimulation device, the stimulation device may continuously or periodically measure unipolar and/or bipolar responses resulting from applied pacing impulses. The stimulation device may further determine the resulting capture type for each pacing impulse. If the stimulation device identifies a change in capture type (e.g., from selective or non-selective capture to myocardium only capture of loss of capture), the stimulation device may execute the capture threshold test describe above to identify new pacing impulse energy settings to regain capture. The stimulation device may also be configured to execute the capture threshold test in response to identifying a loss of capture (or predetermined number of loss of capture events).

The example method discussed above generally relies on the use of both unipolar and bipolar EGM characteristics to identify transitions between capture types. More specifically and as illustrated in Tables 3a-4c, the foregoing example relies on changes in unipolar width (UW) and bipolar stim-to-peak time (BSP) to detect changes in capture type. However, as previously discussed, other characteristics may be used to detect changes in capture type.

In certain implementations, capture threshold tests according to the present disclosure may instead rely on characteristics of a unipolar response (e.g., a unipolar EGM) only instead of on a combination of a unipolar and bipolar response. For example and without limitation, instead of BSP and UW, the method may instead be based on unipolar stim-to-onset time (USO) and unipolar width (UW). Similar to Tables 3a-4c, tables 5a-6c list the indications for each transition for a method using USO and UPS TABLE 10a Transition Indications for Normal Conduction
(Single Transition Cases)

| | Transition | Indication |
|---|---|---|
| 1. | NS → LOC | USO+ |
| | | UW− |
| 2. | S → LOC | USO+ |
| | | UW= |
| 3. | M → LOC | USO+ |
| | | UW− |

TABLE 10b

Transition Indications for Normal
Conduction (Two-Transition Cases)

| | Transition Progression | $1^{st}$ Indication | $2^{nd}$ Indication |
|---|---|---|---|
| 1. | NS → M → LOC | USO= | USO+ |
| | | UW+ | UW− |
| 2. | NS → S → LOC | USO+ | USO+ |
| | | UW− | UW= |

TABLE 11a

Transition Indications for BBB Patients (Single Transition Cases)

| | Transition | Indication |
|---|---|---|
| 1. | S (w/corr.) → LOC | USO+ |
| | | UW+ |
| 2. | S (w/o corr.) → LOC | USO+ |
| | | UW= |
| 3. | NS (w/corr.) → LOC | USO+ |
| | | UW+ |
| 4. | NS (w/o corr.) → LOC | USO+ |
| | | UW− |
| 5. | M → LOC | USO+ |
| | | UW− |

TABLE 11b

Transition Indications for BBB Patients (Two-Transition Cases)

| Transition Progression | 1st Indication | 2nd Indication |
|---|---|---|
| 1. S (w/corr.) → S (w/o corr.) → LOC | USO= UW+ | USO+ UW= |
| 2. NS (w/corr.) → S (w/corr.) → LOC | USO+ UW− | USO+ UW+ |
| 3. NS (w/corr.) → NS (w/o corr.) → LOC | USO= UW+ | USO+ UW− |
| 4. NS (w/corr.) → S (w/o corr.) → LOC | USO+ UW+ | USO+ UW= |
| 5. NS (w/corr.) → M → LOC | USO= UW+ | USO+ UW− |
| 6. NS (w/o corr.) → S (w/o corr.) → LOC | USO+ UW− | USO+ UW= |
| 7. NS (w/o corr.) → M → LOC | USO= UW+ | USO+ UW− |

TABLE 11c

Transition Indications for BBB Patients (Three-Transition Cases)

| Transition Progression | 1st Indication | 2nd Indication | 3rd Indication |
|---|---|---|---|
| 1. NS (w/corr.) → S (w/corr.) → S (w/o corr.) → LOC | USO+ UW− | USO+ UW+ | USO+ UW= |
| 2. NS (w/corr.) → NS (w/o corr.) → S (w/o corr.) → LOC | USO= UW+ | USO+ UW− | USO+ UW= |
| 3. NS (w/corr.) → NS (w/o corr.) → M → LOC | USO= UW+ | USO= UW | USO+ UW− |

The methods 3000 of FIG. 30 and 3100 of FIG. 31 provide a relatively complete analysis of pacing impulse energy settings and their respective responses. More specifically, the methods 3000 and 3100 identify the capture type for each pacing impulse energy setting and all transitions between capture types. Nevertheless, it should be appreciated that in certain instances, it may only be necessary to identify a particular transition and to configure the pacing impulse energy settings of the pacing device based on the particular threshold.

In applications for patients with narrow QRS, for example, the systems and methods disclosed herein may be modified to identify the minimum pacing impulse energy below which capture of the His bundle has been lost and to configure the pacing device to deliver pacing impulses at that minimum pacing impulse energy. In other words, the systems and methods may identify the threshold at which the capture type transitions from either of selective or non-selective capture to either of myocardium-only capture or loss of capture and then set the pacing impulse energy of the stimulation device above the energy at which capture of the His bundle is lost. In applications for patients with wide QRS, the systems and methods disclosed herein may be modified to identify the minimum pacing impulse energy below which BBB correction is lost and to configure the pacing device to deliver pacing impulses at that minimum pacing impulse energy. In other words, the systems and methods may identify the threshold at which the capture type transitions from either selective or non-selective capture with correction to a capture type without correction (including any of selective or non-selective capture without correction, myocardium only capture, or loss of capture) and then set the pacing impulse energy of the stimulation device above the energy at which correction is lost.

It should also be understood that while the method 3100 is generally described as occurring after the method 3000, in certain applications, the two methods may be combined. More specifically, in the foregoing example, the unipolar and/or bipolar response data for multiple pacing impulse energies are first collected using the method 3000 of FIG. 30. That response data is then processed to identify transitions using the method 3100 of FIG. 31. In other implementations, certain operations of the method 3100 of FIG. 31 may be performed as pacing impulse response data is collected such that the process of collecting, analyzing, and classifying the response data may be combined.

Figure 32:
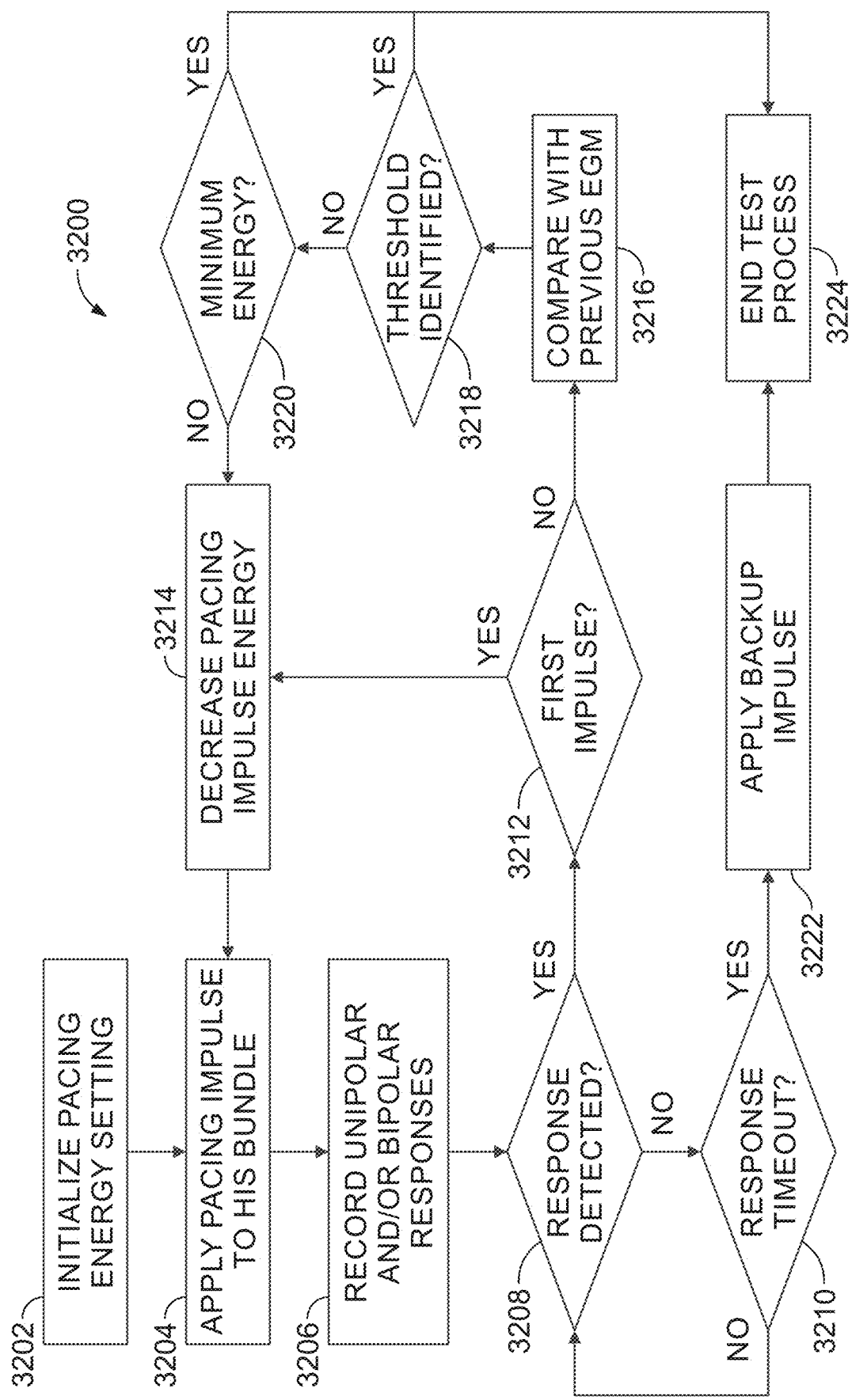
FIG. 32 is a flow chart illustrating a method for collecting and analyzing response data to determine pacing settings for a stimulation device.

FIG. 32, for example, is a flow chart illustrating a method 3200 that combines collection and analysis of response data to configure pacing settings of a stimulation device. Similar to the method 3000 of FIG. 30, the method 3200 of FIG. 32 begins by initializing the pacing energy setting (operation 3202), applying a pacing impulse to the His bundle (operation 3204), and recording corresponding response data (operation 3206), the response data including one or both of unipolar and bipolar responses to the pacing impulse. The method 3200 also similarly includes monitoring for a response to the applied pacing impulse (operation 3208) and determining whether a timeout has occurred (operation 3210). In the event of a timeout (e.g., a timeout caused by a loss of capture), the method includes applying a backup impulse (operation 3222) before terminating the test process (operation 3224). Termination of the test process is discussed below in further detail.

Assuming loss of capture has not occurred and if the pacing impulse applied at operation 3204 is the first pacing impulse of the test (operation 3218), the pacing impulse energy is decreased (operation 3214, e.g., by decreasing the duration and/or amplitude of the impulse as previously discussed in the context of operation 3016). A subsequent pacing impulse is then delivered and the process of recording and identifying a response or identifying loss of capture is repeated such that two sets of response data are available, each corresponding to a respective pacing impulse energy.

If response data is available for two consecutive pacing impulse energies, the response data for the pacing impulses is compared (operation 3218) to determine whether a capture threshold has been identified (operation 3220). The process of comparing consecutive sets of response data generally includes comparing the response data to identify changes indicative of a change in capture type and, more specifically, whether a change in one or more response characteristics between the two response data sets is indicative of a transition between capture types. As discussed in the context of operation 3104 of FIG. 31, in certain implementations, the response data for each pacing impulse energy may include both unipolar and bipolar response data. In such implementations, the response characteristics may include, for example and without limitation, each of bipolar stim-to-peak time and unipolar width. In implementations in which only unipolar response data is collected, the response characteristics may include, for example and without limitation, unipolar stim-to-onset time and unipolar width.

The process of comparing the sets of response data in operation 3216 aims to determine whether a capture threshold has been crossed between the two different pacing impulse energies corresponding to the sets of response data. In applications for patients with narrow QRS, for example, the comparison of operation 3216 may determine whether a loss of His bundle capture occurred between the pacing impulses. To do so, the comparison may include determining whether the response characteristics indicate a transition from either of selective or non-selective capture to myocardium-only or loss of capture occurred in response to reducing the pacing impulse energy (as listed, e.g., in Tables 8a-b for applications including unipolar and bipolar response data or Tables 10a-b for application including unipolar response data only). In applications for patients with BBB, the comparison of operation 3216 may determine whether a loss of BBB correction has occurred. For example, the comparison may include determining whether the response characteristics indicate a transition from a corrective response to a non-corrective response in response to reducing the pacing impulse energy (as listed, e.g., in Tables 9a-c (unipolar/bipolar case) and 11a-c (unipolar only case)).

If a threshold is not identified, a check is performed to determine if the lowest pacing impulse energy has been reached (operation 3220). If not, the pacing impulse energy is decreased and the process of applying a pacing impulse, measuring the corresponding response, and comparing the response to the previously collected response for purposes of identifying a threshold is repeated.

If, on the other hand, a threshold is identified, minimum pacing impulse energy is reached, or (as noted above) loss of capture occurs, the test process is ended (operation 3224). When loss of capture or reaching a minimum pacing impulse energy results in termination of the pacing test, various remedial steps may be initiated including, among other things, generating and transmission of alerts or alarms, restarting of the pacing test, initiation of a backup pacing routine, and the like.

In cases where the test process is terminated in response to identifying a threshold (e.g., a His bundle capture threshold or correction threshold), completing the test process at operation 3224 includes configuring the pacing settings of the stimulation device based on the threshold. In particular, the pacing settings of the stimulation device are configured such that the pacing impulse energy of the stimulation device is the lowest at which the threshold is not crossed. In applications in which the threshold is for His bundle capture or BBB correction, for example, the pacing settings of the stimulation device would be modified to have the lowest pacing energy at which His bundle capture or BBB correction are achieved. As a result, the stimulation device is automatically configured to achieve His bundle capture or correction efficiently by using the minimum pacing impulse energy possible.

In certain applications of the present disclosure, accuracy of the capture threshold test may be improved by capturing multiple sets of response data for each pacing impulse energy and relying on a statistical combination of such responses in identifying thresholds and capture types. For example, FIG. 33 is a flow chart illustrating a method 33000 for collecting multiple sets of response data for each of a range of pacing impulse voltages and FIG. 34 is a flow chart illustrating a method 3400 in which the results obtained from the method 3300 of FIG. 33, are analyzed and classified to determine pacing settings for the stimulation device.

Figure 33:
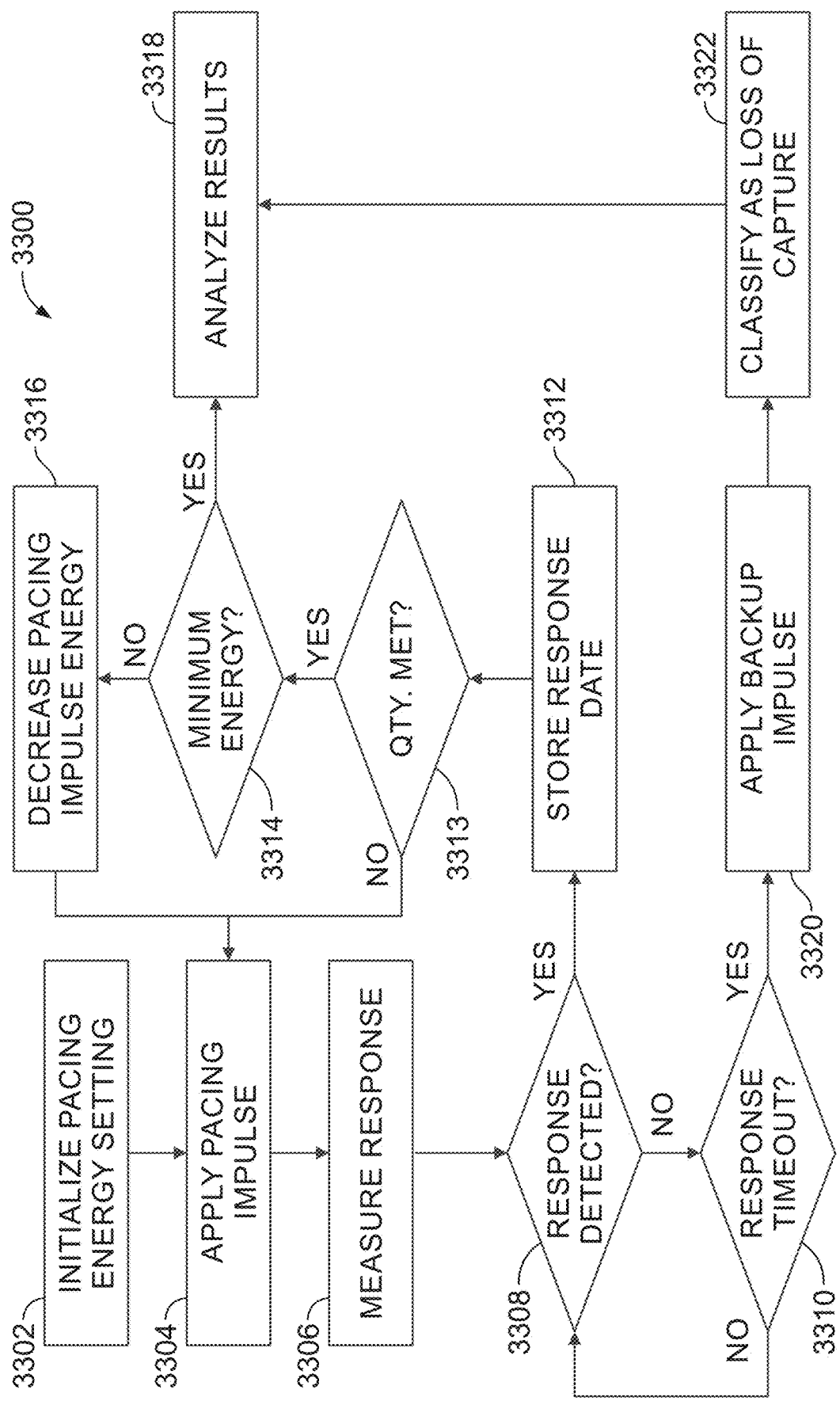
FIG. 33 is a flow chart illustrating a second method of response data collection for purposes of subsequent analysis in determining pacing settings for a stimulation device.
Figure 34:
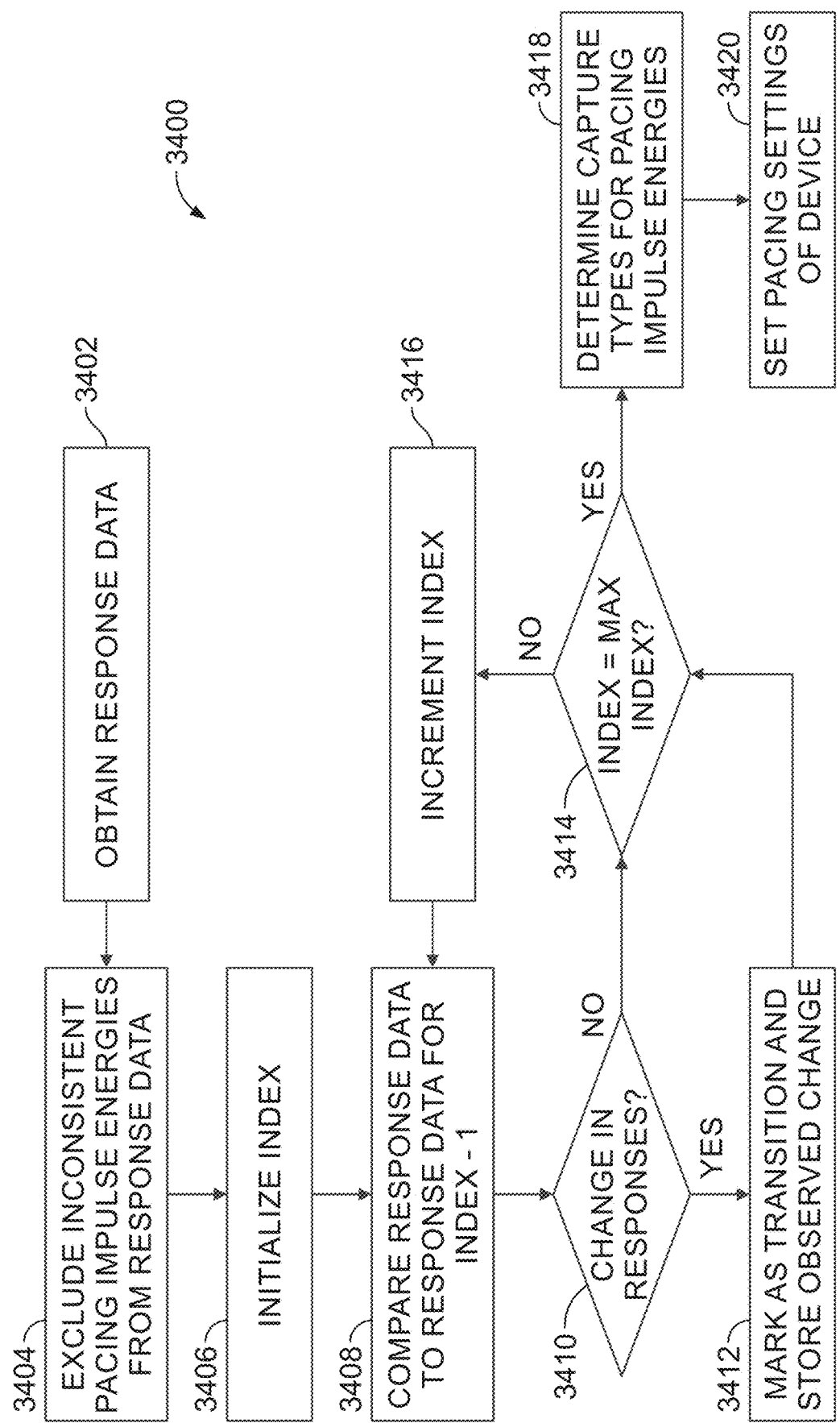
FIG. 34 is a flow chart illustrating a method of analyzing response data, such as obtained in the method of FIG. 33, to determine pacing settings for a stimulation device.

Referring first to FIG. 33, the method 33 generally begins with initializing the pacing impulse energy setting of the stimulation device (operation 3302). Although the initial pacing impulse energy settings may vary, in at least certain implementations of the present disclosure, the initial pacing impulse energy is the maximum output energy of the stimulation device or a similar upper bound value.

At operation 3304 a first pacing impulse at the current pacing impulse energy setting is applied to the His bundle and a first corresponding response is recorded (operation 3306). In at least certain implementations the first response includes one or both of a unipolar response and a bipolar, which may be recorded as an EGM or similar data. During recordation of the response, the stimulation device may generally monitor for a response to the applied pacing impulse (operation 3308) and, if no such response is detected prior to a timeout (operation 3310), a backup impulse may be applied (operation 3320) and the current pacing impulse energy setting may be classified as resulting in loss of capture (operation 3322). In certain implementations, the test may then be terminated (with each subsequent pacing impulse energy similarly being designated as resulting in loss of capture) and the stimulation device may proceed to analyzing of the test results (operation 3318).

When a response is detected, on the other hand, the recorded responses are stored in memory of the stimulation device (operation 3312). The stimulation device then determines whether a required quantity of responses (e.g., three) for the current pacing impulse energy have been collected (operation 3313). If not, another pacing impulse is applied at the current energy and another response is recorded and stored. If, on the other hand, the quantity of recorded responses for the current pacing impulse energy is met, another check is conducted to see if the current pacing impulse energy is a minimum pacing impulse energy (operation 3314). If so, then response collection is complete and analysis begins (operation 3318). If not, the pacing impulse energy is decreased (operation 3316) and response data is collected for the reduced energy.

The method 3300 results in the collection of multiple sets of response data for each of a range of pacing impulse energies. Following such collection, the collected response data may subsequently be analyzed to identify capture thresholds, to identify preferred pacing impulse energy settings for the stimulation device, or perform similar operations.

In one example implementation, analysis of the multiple sets of response data may include averaging or otherwise mathematically combining the response data for each pacing impulse energy. For example, the response data for each pacing impulse energy may be averaged to generate a mean response for each pacing impulse energy. The combined responses may then be analyzed (such as by using the method 3100 of FIG. 31) to identify capture thresholds, capture type transitions, and the like for purposes of determining optimal pacing impulse settings.

In other implementations, analyzing the multiple sets of response data may include identifying pacing impulse energies that resulted in highly variable or otherwise inconsistent responses. To the extent such pacing impulse energies are identified, they may be rejected as potential settings for the pacing impulse energy. In certain implementations, additional analysis may also be conducted to determine whether the inconsistency of the response data for a given pacing impulse energy is a result of poor detection or a result of the pacing impulse energy being at or near a transition energy between two capture types. In the former case, the pacing impulse energy may still be considered a candidate for the optimal pacing impulse energy setting. In the latter case, however, the pacing impulse energy would result in inconsistent and unpredictable capture and would therefore remain rejected as a potential candidate for the optimal pacing impulse energy setting. By way of this process, potentially problematic pacing impulse energy settings (e.g., those that may result in multiple capture types) are avoided and the likelihood that the ultimately selected pacing impulse energy setting will consistently result in the best available capture scenario is increased.

FIGS. 33 and 34 are flow charts of example methods 3300, 3400 for collecting and analyzing response data and identifying an optimal pacing impulse setting for a given patient based on the response data. More specifically, the method 3300 illustrates a method for collecting response data for a patient that includes multiple response data samples for a range of pacing impulse energies. The method 3400, in contrast, illustrates analysis of such response data for purposes of identifying an optimal pacing impulse energy setting for the patient. The methods 3300 and 3400 may be executed by an implanted stimulation device or a programming unit in communication with such an implanted stimulation device.

The method 3400 generally assumes that patient response data is available for analysis. The patient response data generally includes a range of pacing impulse energies and, for each pacing impulse energy, measured responses/samples for each of multiple pacing impulses delivered to the patient at the pacing impulse energy. In certain implementations, each measured response may be stored as one or both of a unipolar or bipolar EGM or as values corresponding to one or both of a unipolar or bipolar EGM.

The method 3400 begins by obtaining response data (operation 3402), such as by executing the response collection method 3300 of FIG. 33. Next, any pacing impulse energies resulting in inconsistent responses are excluded (operation 3404). Although the approach to identifying inconsistent responses may vary, in at least one example implementation, a variance metric is calculated for each pacing impulse energy that indicates the variance between the measured responses for the particular pacing impulse energy. If the variance metric exceeds a threshold (or similar value), the pacing impulse energy is excluded from further consideration as a potential pacing impulse energy setting.

The variance metric may be any suitable measure of variability. However, in certain implementations, the variance metric may correspond to the variance for one or more response characteristics and, in particular, response characteristics that may later be used to identify transitions between capture types. For example, as previously discussed, in certain implementations of the present disclosure, transitions between capture types may be identified based on unipolar width and bipolar stim-to-peak. In such implementations, when evaluating a given pacing impulse energy, the variance metric used to determine whether to exclude the pacing impulse energy, may be based on the variance in unipolar width and/or bipolar stim-to-peak time for the pacing impulse energy. For example, if unipolar width and/or bipolar stim-to-peak time vary by 10% or more for the pacing impulse energy, the pacing impulse energy may be excluded.

In certain implementations, the process of excluding inconsistent pacing impulse energies may include generating updated patient response data that omits the pacing impulse energies having inconsistent responses. In other implementations, each of the inconsistent pacing impulse energies may be marked, flagged, or otherwise noted for exclusion from further consideration and analysis.

After identifying and excluding pacing impulse energies exhibiting high variance, a subsequent analysis of the remaining pacing impulse energy candidates may be conducted to determine an optimal pacing impulse energy setting. Such analysis may vary in implementations of the present disclosure; however, the process of analyzing the updated patient response data generally includes comparing characteristics of the response data for consecutive pacing impulse energies to identify transitions between capture types.

In the specific example of the method 3400, analysis begins by initializing an index for purposes of traversing the updated patient response data (operation 3406). The index of the example method 3400 is assumed to be initialized to the second pacing impulse energy of the updated patient response data, i.e., to the pacing impulse energy that is one step below the maximum pacing impulse energy included in the updated patient response data.

The index of the method 3400 is just one approach to traversing the updated patient response data. More generally, any suitable method for comparing responses for consecutive pacing impulse energies of the updated patient response data may be used in implementations of the present disclosure.

At operation 3408, the response data for the current pacing impulse energy is compared to that of the next highest pacing impulse energy to determine whether a capture type transition has occurred. As previously noted, each pacing impulse energy includes a set of measured responses. Accordingly, comparing the responses of any two pacing impulse energies may first include averaging or otherwise combining the set of measured responses for each of the two pacing impulses. Combining a set of measured responses may include generating an average response from which one or more response characteristics may be determined. So, for example, in implementations in which multiple responses are obtained for each pacing impulse energy and each response includes a bipolar and unipolar EGM, combining the set of measured responses may include generating each of an average bipolar EGM and an average unipolar EGM representative of the set. In other implementations, combining a set of measured responses for a particular pacing impulse energy may include calculating average values for one or more response characteristics for each response in the set and, in particular, for response characteristics that may be used subsequently to identify transitions between capture types. For example, in implementations in which transitions are identified using bipolar stim-to-peak and unipolar width, combining a set of measured responses for a particular pacing impulse energy may include calculating each of an average bipolar stim-to-peak value and an average unipolar width representative of the set.

Regardless of how response data for each pacing impulse energy is combined, operation 3408 generally includes comparing the combined response data for the current pacing impulse energy to that of the next highest pacing impulse energy to determine whether a change in response occurred between the two pacing impulse energies (operation 3410). As previously discussed in the context of FIG. 31, the threshold for determining whether a change in response has occurred may vary between applications and particular patients; however, in at least one implementation, a change may be considered to have occurred if a given response characteristics varies between the combined response data of the current pacing impulse energy and the combined response data of the next highest pacing impulse energy by at least about 10%. If a change is identified in operation 3410, the current pacing impulse energy may be marked, flagged, or otherwise noted as corresponding to a transition (operation 3412).

The foregoing operations may be repeated for each pacing impulse energy included in the updated patient response data. For example, in one implementation, if the current index is not the maximum index (i.e., the index corresponding to the last available voltage) (operation 3414), the index is incremented (operation 3416) and the process of comparing response data to identify a change/transition is repeated for the next consecutive pair of pacing impulse energies included in the updated patient response data.

If, on the other hand, the maximum index is reached, the stimulation device determines the capture type for each pacing impulse voltage (operation 3418) and the stimulation device sets its pacing settings based on the available capture types (operation 3420) using processes substantially similar to those discussed above in the context of FIG. 31. As discussed in the context of FIG. 31, such a process may generally include identifying capture types based on the number of observed transitions, the nature of the changes observed between transitions, and/or an initial capture type for the patient. Based on the identified capture types, the stimulation device may then identify the lowest pacing impulse energy that results in the best available capture type for the particular patient (e.g., the lowest pacing impulse energy that maintains capture of the His bundle or that corrects a branch bundle block). In contrast to the method of FIG. 31, however, such analysis in the context of the method 3400 excludes from consideration any pacing impulse energies identified as potentially resulting in inconsistent pacing responses. By doing so, the stimulation device improves the likelihood that the selected pacing impulse energy setting will result in consistent pacing and capture/correction.

Certain implementations of the current disclosure may also include additional analysis of pacing impulse energies excluded in operation 3404 to determine whether the inconsistent response data for the excluded pacing impulse energy was a result of poor detection during collection of the response data or a result of the pacing impulse energy corresponding to a transition between capture types. In the former case, the pacing impulse energy may be reconsidered as a potential pacing impulse setting while in the latter case, the pacing impulse energy would remain excluded.

One example approach to the foregoing analysis for a pacing impulse energy may include examining the response data and/or capture type for each of the next highest and next lowest pacing impulse energies. If the next highest and next lowest pacing impulse energies resulted in substantially similar response characteristics or otherwise resulted in the same capture type, the inconsistent response data for the pacing impulse energy in question is likely the result of poor detection. In such cases, the pacing impulse energy may be assigned the same capture type as the neighboring pacing impulse energies and may be reconsidered as a candidate for the pacing impulse energy setting of the stimulation device. Alternatively, new response data for the pacing impulse energy may be collected with the goal of obtaining consistent response data. Such new response data may be subsequently analyzed as discussed above. Conversely, if the next highest and next lowest pacing impulse resulted in substantially different response characteristics or otherwise resulted in different capture types, then the inconsistent response data for the pacing impulse energy in question is likely the result of the pacing impulse energy being at or near a transition energy between capture types. Accordingly, to avoid unpredictable pacing results, the pacing impulse energy in question would remain excluded from consideration as a pacing impulse energy setting.

As discussed above, the method 3300 of FIG. 33 and the method 3400 of FIG. 34 provide methods for collecting and then analyzing response data, respectively. According to the methods, a full set of response data is collected and then subsequently analyzed. In other implementations, aspects and operations of the method 3300 of FIG. 33 and the method 3400 of FIG. 34 may be combined such that the process of collecting and analyzing the response data is combined. For example and similar to the method 3200 of FIG. 32, the response data for each pacing impulse energy may be analyzed as it is collected. Such analysis may include, among other things, determining whether the samples of response data for the pacing impulse energy are consistent and whether the response data indicates a transition from a previously applied pacing impulse energy, each of which are discussed above.

In accordance with new and unique aspects herein, a method is provided for identifying pacing thresholds and programming a stimulation device for His bundle pacing, the stimulation device including a pulse generator, a stimulating electrode in proximity to a His bundle of a patient heart, and at least one sensing electrode adapted to sense electrical activity of the patient heart, the method comprising: applying, using the pulse generator and stimulating electrode, a first pacing impulse having a first pacing impulse energy to the His bundle; in response to applying the first pacing impulse, collecting first response data using the at least one sensing electrode; applying, using the pulse generator and stimulating electrode, a second pacing impulse having a second pacing impulse energy to the His bundle, the second pacing impulse energy being different than the first pacing impulse energy; in response to applying the second pacing impulse, collecting second response data using the at least one sensing electrode; identifying a change in one or more response characteristics between the first response data and the second response data, the response characteristics indicative of a change from a first capture type for the first pacing impulse energy and a second capture type for the second pacing impulse energy; and in response to identifying the change in the one or more response characteristics, setting a pacing impulse energy setting of the stimulation device to the first pacing impulse energy.

Additionally or alternatively, the first response data includes a first unipolar electrogram (EGM) and the second response data includes a second unipolar EGM. Additionally or alternatively, the response characteristics include unipolar stim-to-onset time and unipolar width. Additionally or alternatively, the first response data includes a first bipolar EGM and the second response data includes a second bipolar EGM. Additionally or alternatively, the first response data includes each of a first unipolar electrogram (EGM) and a first bipolar EGM, the second response data includes each of a second unipolar EGM and a second bipolar EGM, and the response characteristics include each of bipolar stim-to-peak and unipolar width. Additionally or alternatively, the response characteristics include at least one of: bipolar stim-to-peak; unipolar width; unipolar stim-to-onset time; and unipolar maximum positive slope. Additionally or alternatively, the response characteristics include a first response characteristic corresponding to total ventricular activation time and a second response characteristic corresponding to time between pacing and local ventricular activation time. Additionally or alternatively, the first capture type indicates capture of at least one of the His bundle or myocardium and the second capture type indicates a loss of capture of the at least one of the His bundle or myocardium. Additionally or alternatively, the first capture type indicates correction of a branch bundle block and the second capture type indicates a loss of branch bundle block correction.

In accordance with new and unique aspects herein, a cardiac stimulation system is adapted to deliver impulses for pacing the His bundle of a patient heart, the cardiac stimulation system comprising: a pulse generator adapted to generate electrical impulses; a processor communicatively coupled to the pulse generator and adapted to measure responses of the patient heart using at least one sensing electrode; and a memory communicatively coupled to the processor including instructions executable by the processor that cause the processor to: applying, using the pulse generator and a stimulating electrode, a first pacing impulse having a first pacing impulse energy to the His bundle; and in response to applying the first pacing impulse, collecting first response data using the at least one sensing electrode; applying, using the pulse generator and the stimulating electrode, a second pacing impulse having second pacing impulse energy to the His bundle, the second pacing impulse energy being different than the first pacing impulse energy; in response to applying the second pacing impulse, collecting second response data using the at least one sensing electrode; identifying a change in one or more response characteristics between the first response data and the second response data, the response characteristics indicative of a change from a first capture type for the first pacing impulse energy and a second capture type for the second pacing impulse energy; and in response to identifying the change in the one or more response characteristics, setting a pacing impulse energy setting of the stimulation device to the first pacing impulse energy.

Additionally or alternatively, the first response data includes a first unipolar electrogram (EGM) and the second response data includes a second unipolar EGM. Additionally or alternatively, the first response data includes a first bipolar EGM and the second response data includes a second bipolar EGM. Additionally or alternatively, the response characteristics include at least one of: bipolar stim-to-peak; unipolar width; unipolar stim-to-onset time; and unipolar maximum positive slope.

Additionally or alternatively, the response characteristics include a first response characteristic corresponding to total ventricular activation time and a second response characteristic corresponding to time between pacing and local ventricular activation. Additionally or alternatively, the first capture type indicates capture of at least one of the His bundle or myocardium and the second capture type indicates a loss of capture of the at least one of His bundle or myocardium. Additionally or alternatively, the first capture type indicates correction of a branch bundle block and the second capture type indicates a loss of branch bundle block correction.

In accordance with new and unique aspects herein, a method is provided for identifying pacing thresholds and programming a stimulation device for His bundle pacing, the stimulation device including a pulse generator, a stimulating electrode in proximity to a His bundle of a patient heart, and at least one sensing electrode adapted to sense electrical activity of the patient heart, the method comprising: collecting a first response data set for a first pacing impulse energy, wherein collecting the first response data set comprises: applying, using the pulse generator and stimulating electrode, a plurality of first pacing impulses having the first pacing impulse energy to the His bundle; and measuring a response to each of the plurality of first pacing impulses using the at least one sensing electrode; collecting a second response data set for a second pacing impulse energy different than the first pacing impulse energy, wherein collecting the second response data set comprises: applying, using the pulse generator and stimulating electrode, a plurality of second pacing impulses having the second pacing impulse energy to the His bundle; and measuring a response to each of the plurality of second pacing impulses using the at least one sensing electrode; subsequent to determining a variance of the responses of the first response data set is below a variance value, identifying a change in one or more response characteristics between the first set of response data and the second set of response data, the response characteristics indicative of a change from a first capture type for the first pacing impulse energy and a second capture type for the second pacing impulse energy; and in response to identifying the change in the one or more response characteristic, setting a pacing impulse energy setting of the stimulation device to the first pacing impulse energy.

Additionally or alternatively, each response of the first response data set and each response of the second response data set includes a unipolar electrogram (EGM). Additionally or alternatively, each response of the first response data set and each response of the second response data set includes a unipolar electrogram (EGM). Additionally or alternatively, the one or more response characteristics include a first response characteristic corresponding to total ventricular activation time and a second response characteristic corresponding to time between pacing and local ventricular activation.

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method of controlling backup pacing of a patient heart using a stimulation system in HIS bundle pacing applications, the stimulation system having a memory, a pulse generator, a stimulating electrode in proximity to the HIS bundle, a backup pacing electrode in proximity to a ventricle of the patent heart, and at least one sensing electrode adapted to sense electrical activity of the patient heart, the method comprising:
    measuring a conduction time between the HIS bundle and the ventricle;
    setting a first delay of the stimulation system between pacing of the HIS bundle and backup pacing of the ventricle (HP-VP) to be greater than the conduction time between the HIS bundle and the ventricle;
    applying, using the pulse generator, an impulse through the stimulating electrode;
    measuring, using the at least one sensing electrode, a response of the patient heart to application of the impulse;
    inhibiting backup pacing of the ventricle when the time between application of the impulse and onset of the measured response is less than the first delay;
    in response to applying the backup pacing impulse, incrementing a backup pacing counter; and
    in response to the backup pacing counter exceeding a threshold value, at least one of recalibrating the stimulation device or initiating a capture threshold test.

2. The method of claim 1, wherein measuring the conduction time between the HIS bundle and the ventricle comprises measuring the conduction time between the HIS bundle and the ventricle for multiple capture types.

3. The method of claim 1, further comprising setting a second delay of the stimulation system between sensing an event of an atrium and pacing of the HIS bundle (A-HP) to be less than a conduction time between the atrium and HIS bundle.

4. The method of claim 3, further comprising calculating the conduction time between the atrium and HIS bundle based on each of the conduction time between the HIS bundle and the ventricle and a conduction time between an atrial event and depolarization of the ventricle.

5. The method of claim 4, further comprising measuring each of the conduction time between the HIS bundle and the ventricle and the conduction time between the atrial event and depolarization of the ventricle.

6. The method of claim 1, further comprising applying a backup pacing impulse to the ventricle when the time between application of the impulse and onset of the measured response is greater than the first delay.

7. The method of claim 1, further comprising, in response to the backup pacing counter exceeding a threshold value, recalibrating the stimulation device.

8. The method of claim 1, further comprising, in response to the backup pacing counter exceeding a threshold value, initiating the capture threshold test.

9. A cardiac stimulation system adapted to deliver impulses for pacing a HIS bundle of a patient heart and for backup pacing of a ventricle of the patient heart, the cardiac stimulation system comprising:
  a pulse generator adapted to generate electrical impulses for each of pacing the HIS bundle and providing backup pacing of the ventricle;
  a processor communicatively coupled to the pulse generator and adapted to receive response characteristics from one or more sensing electrodes in response to pacing the HIS bundle; and
  a memory communicatively coupled to the processor, the memory including instructions executable by the processor that, when executed by the processor, cause the processor to:
  measure a conduction time between the HIS bundle and the ventricle;
  set a first delay of the pulse generator between pacing of the HIS bundle and backup pacing of the ventricle (HP-VP) to be greater than the conduction time between the HIS bundle and the ventricle;
  apply, using the pulse generator, an impulse through the stimulating electrode;
  measure, using the one or more sensing electrodes, a response of the patient heart to application of the impulse;
  inhibit backup pacing of the ventricle when the time between application of the impulse and onset of the measured response is less than the first delay;
  increment a backup pacing counter in response to the pulse generator generating the backup pacing impulse; and
  in response to the backup pacing counter exceeding a threshold value, at least one of recalibrate the stimulation device or initiate a capture threshold test.

10. The cardiac stimulation system of claim 9, wherein the instructions further cause the processor to measure the conduction time between the HIS bundle and the ventricle for multiple capture types.

11. The cardiac stimulation system of claim 9, wherein the instructions further cause the process to set a second delay for the pulse generator between sensing an event of an atrium and pacing of the HIS bundle (A-HP) to be less than a conduction time between the atrium and HIS bundle.

12. The cardiac stimulation system of claim 11, wherein to set the second delay includes calculating the conduction time between the atrium and HIS bundle based on each of the conduction time between the HIS bundle and the ventricle and a conduction time between an atrial event and depolarization of the ventricle.

13. The cardiac stimulation system of claim 12, wherein to set the second delay further includes measuring each of the conduction time between the HIS bundle and the ventricle and the conduction time between the atrial event and depolarization of the ventricle.

14. The cardiac stimulation system of claim 9, wherein the instructions further cause the process to cause the pulse generator to generate a backup pacing impulse when the time between application of the impulse and onset of the measured response is greater than the first delay.

15. The cardiac stimulation system of claim 9, wherein the instructions further cause the processor to recalibrate the stimulation device in response to the backup pacing counter exceeding the threshold value.

16. The cardiac stimulation system of claim 9, wherein the instructions further cause the processor to initiate the capture threshold test.

\* \* \* \* \*